(12) United States Patent
Palucki et al.

(10) Patent No.: US 6,458,790 B2
(45) Date of Patent: Oct. 1, 2002

(54) SUBSTITUTED PIPERIDINES AS MELANOCORTIN RECEPTOR AGONISTS

(75) Inventors: Brenda L. Palucki, Hillsborough, NJ (US); Khaled J. Barakat, Brooklyn, NY (US); Liangqin Guo; Yingjie Lai, both of Edison, NJ (US); Ravi P. Nargund, East Brunswick, NJ (US); Min K. Park, Whippany, NJ (US); Patrick G. Pollard, Oakhurst, NJ (US); Iyassu K. Sebhat, Hoboken, NJ (US); Zhixiong Ye, Princeton, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/812,965

(22) Filed: Mar. 20, 2001

Related U.S. Application Data

(60) Provisional application No. 60/191,442, filed on Mar. 23, 2000, and provisional application No. 60/242,265, filed on Oct. 20, 2000.

(51) Int. Cl.⁷ .................... C07D 401/12; C07D 413/12; A61K 31/453; A61K 31/4545
(52) U.S. Cl. .................... 514/237.2; 514/227.8; 514/232.2; 514/253.09; 514/253.1; 514/253.13; 544/60; 544/61; 544/96; 544/120; 544/122; 544/130; 544/360; 544/364; 544/365
(58) Field of Search .................... 544/365, 364, 544/357, 355, 130, 60; 514/253.13, 252.11, 253.1, 249, 237.2, 227.8

(56) References Cited

U.S. PATENT DOCUMENTS

| 5,492,920 A | 2/1996 | Chen et al. |
| 5,536,716 A | 7/1996 | Chen et al. |
| 5,721,251 A | 2/1998 | Chen et al. |
| 5,767,118 A | 6/1998 | Nargund et al. |

FOREIGN PATENT DOCUMENTS

| WO | WO 97/34604 | 9/1997 |
| WO | WO 98/10653 | 3/1998 |
| WO | WO 99/64002 | 12/1999 |
| WO | WO 00/74679 A1 | 12/2000 |

*Primary Examiner*—Deepak R. Rao
(74) *Attorney, Agent, or Firm*—Philippe L. Durette; Melvin Winokur

(57) ABSTRACT

Certain novel substituted piperidine compounds are agonists of the human melanocortin receptor(s) and, in particular, are selective agonists of the human melanocortin-4 receptor (MC-4R). They are therefore useful for the treatment and control of obesity, diabetes, and sexual dysfunction, including erectile dysfunction and female sexual dysfunction.

29 Claims, No Drawings

SUBSTITUTED PIPERIDINES AS MELANOCORTIN RECEPTOR AGONISTS

CROSS-REFERENCE TO RELATED APPLICATIONS

The present invention is related to U.S. provisional applications Ser. No. 60/191,442, filed Mar. 23, 2000, and Ser. No. 242,265, filed Oct. 20, 2000, the contents of each of which are hereby incorporated by reference in their entirety.

FIELD OF THE INVENTION

The present invention relates to piperidine derivatives, their synthesis, and their use as melanocortin receptor (MC-R) agonists. More particularly, the compounds of the present invention are selective agonists of the melanocortin-4 receptor (MC-4R) and are thereby useful for the treatment of disorders responsive to the activation of MC-4R, such as obesity, diabetes, male sexual dysfunction, and female sexual dysfunction.

BACKGROUND OF THE INVENTION

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism. A specific single MC-R that may be targeted for the control of obesity has not yet been identified, although evidence has been presented that MC-4R signalling is important in mediating feed behavior (S. Q. Giraudo et al., "Feeding effects of hypothalamic injection of melanocortin-4 receptor ligands," Brain Research, 80: 302–306 (1998)).

Evidence for the involvement of MC-R's in obesity includes: i) the agouti ($A^{vy}$) mouse which ectopically expresses an antagonist of the MC-1R, MC-3R and -4R is obese, indicating that blocking the action of these three MC-R's can lead to hyperphagia and metabolic disorders; ii) MC-4R knockout mice (D. Huszar et al., Cell, 88: 131–141 (1997)) recapitulate the phenotype of the agouti mouse and these mice are obese; iii) the cyclic heptapeptide MT-II (a non-selective MC-1R, -3R, -4R, and -5R agonist) injected intracerebroventricularly (ICV) in rodents, reduces food intake in several animal feeding models (NPY, ob/ob, agouti, fasted) while ICV injected SHU-9119 (MC-3R and 4R antagonist; MC-1R and -5R agonist) reverses this effect and can induce hyperphagia; iv) chronic intraperitoneal treatment of Zucker fatty rats with an α-NDP-MSH derivative (HP228) has been reported to activate MC-1R, -3R, -4R, and -5R and to attenuate food intake and body weight gain over a 12-week period (I. Corcos et al., "HP228 is a potent agonist of melanocortin receptor-4 and significantly attenuates obesity and diabetes in Zucker fatty rats," Society for Neuroscience abstracts, 23: 673 (1997)).

Five distinct MC-R's have thus far been identified, and these are expressed in different tissues. MC-1R was initially characterized by dominant gain of function mutations at the Extension locus, affecting coat color by controlling phaeomelanin to eumelanin conversion through control of tyrosinase. MC-1R is mainly expressed in melanocytes. MC-2R is expressed in the adrenal gland and represents the ACTH receptor. MC-3R is expressed in the brain, gut, and placenta and may be involved in the control of food intake and thermogenesis. MC-4R is uniquely expressed in the brain, and its inactivation was shown to cause obesity (A. Kask, et al., "Selective antagonist for the melanocortin-4 receptor (HS014) increases food intake in free-feeding rats," Biochem. Biophys. Res. Commun., 245: 90–93 (1998)). MC-5R is expressed in many tissues, including white fat, placenta and exocrine glands. A low level of expression is also observed in the brain. MC-5R knockout mice reveal reduced sebaceous gland lipid production (Chen et al., Cell, 91: 789–798 (1997)).

Erectile dysfunction denotes the medical condition of inability to achieve penile erection sufficient for successful sexual intercourse. The term "impotence" is oftentimes employed to describe this prevalent condition. Approximately 140 million men worldwide, and, according to a National Institutes of Health study, about 30 million American men suffer from impotency or erectile dysfunction. It has been estimated that the latter number could rise to 47 million men by the year 2000. Erectile dysfunction can arise from either organic or psychogenic causes, with about 20% of such cases being purely psychogenic in origin. Erectile dysfunction increases from 40% at age 40, to 67% at age 75, with over 75% occurring in men over the age of 50. In spite of the frequent occurrence of this condition, only a small number of patients have received treatment because existing treatment alternatives, such as injection therapies, penile prosthesis implantation, and vacuum pumps, have been uniformly disagreeable [for a discussion, see "ABC of sexual health—erectile dysfunction," Brit. Med. J. 318: 387–390 (1999)]. Only more recently have more viable treatment modalities become available, in particular orally active agents, such as sildenafil citrate, marketed by Pfizer under the brand name of Viagra®. Sildenafil is a selective inhibitor of type V phosphodiesterase (PDE-V), a cyclic-GMP-specific phosphodiesterase isozyme [see R. B. Moreland et al., "Sildenafil: A Novel Inhibitor of Phosphodiesterase Type 5 in Human Corpus Cavernosum Smooth Muscle Cells," Life Sci., 62: 309–318 (1998)]. Prior to the introduction of Viagra on the market, less than 10% of patients suffering from erectile dysfunction received treatment. Sildenafil is also being evaluated in the clinic for the treatment of female sexual dysfunction.

The regulatory approval of Viagra® for the oral treatment of erectile dysfunction has invigorated efforts to discover even more effective methods to treat erectile dysfunction. Several additional selective PDE-V inhibitors are in clinical trials. UK-114542 is a sildenafil backup from Pfizer with supposedly improved properties. IC-351 (ICOS Corp.) is claimed to have greater selectivity for PDE-V over PDE-VI than sildenafil. Other PDE-V inhibitors include M-54033 and M-54018 from Mochida Pharmaceutical Co. and E-4010 from Eisai Co., Ltd.

Other pharmacological approaches to the treatment of erectile dysfunction have been described [see, e.g., "Latest Findings on the Diagnosis and Treatment of Erectile Dysfunction," Drug News & Perspectives, 9: 572–575 (1996); "Oral Pharmacotherapy in Erectile Dysfunction," Current Opinion in Urology, 7: 349–353 (1997)]. A product under clinical development by Zonagen is an oral formulation of the alpha-adrenoceptor antagonist phentolamine mesylate under the brand name of Vasomax®. Vasomax® is also being evaluated for the treatment of female sexual dysfunction.

Drugs to treat erectile dysfunction act either peripherally or centrally. They are also classified according to whether they initiate a sexual response or "facilitate" a sexual response to prior stimulation [for a discussion, see "A Therapeutic Taxonomy of Treatments for Erectile Dysfunction: An Evolutionary Imperative," *Int. J. Impotence Res.*, 9: 115–121(1997)]. While sildenafil and phentolamine act peripherally and are considered to be "enhancers" or "facilitators" of the sexual response to erotic stimulation, sildenafil appears to be efficacious in both mild organic and psychogenic erectile dysfunction. Sildenafil has an onset of action of 30–60 minutes after an oral dose with the effect lasting about 4 hours, whereas phentolamine requires 5–30 minutes for onset with a duration of 2 hours. Although sildenafil is effective in a majority of patients, it takes a relatively long time for the compound to show the desired effects. The faster-acting phentolamine appears to be less effective and to have a shorter duration of action than sildenafil. Oral sildenafil is effective in about 70% of men who take it, whereas an adequate response with phentolamine is observed in only 35–40% of patients. Both compounds require erotic stimulation for efficacy. Since sildenafil indirectly increases blood flow in the systemic circulation by enhancing the smooth muscle relaxation effects of nitric oxide, it is contraindicated for patients with unstable heart conditions or cardiovascular disease, in particular patients taking nitrates, such as nitroglycerin, to treat angina. Other adverse effects associated with the clinical use of sildenafil include headache, flushing, dyspepsia, and "abnormal vision," the latter the result of inhibition of the type VI phosphodiesterase isozyme (PDE-VI), a cyclic-GMP-specific phosphodiesterase that is concentrated in the retina. "Abnormal vision" is defined as a mild and transient "bluish" tinge to vision, but also an increased sensitivity to light or blurred vision.

Synthetic melanocortin receptor agonists (melanotropic peptides) have been found to initiate erections in men with psychogenic erectile dysfunction [See H. Wessells et al., "Synthetic Melanotropic Peptide Initiates Erections in Men With Psychogenic Erectile Dysfunction: Double-Blind, Placebo Controlled Crossover Study," *J. Urol.*, 160: 389–393 (1998); *Fifteenth American Peptide Symposium,* Jun. 14–19, 1997 (Nashville, Tenn.)]. Activation of melanocortin receptors of the brain appears to cause normal stimulation of sexual arousal. In the above study, the centrally acting α-melanocyte-stimulating hormone analog, melanotan-II (MT-II), exhibited a 75% response rate, similar to results obtained with apomorphine, when injected intramuscularly or subcutaneously to males with psychogenic erectile dysfunction. MT-II is a synthetic cyclic heptapeptide, Ac-Nle-c[Asp-His-DPhe-Arg-Trp-Lys]-NH$_2$, which contains the 4–10 melanocortin receptor binding region common to α-MSH and adrenocorticotropin, but with a lactam bridge. It is a non-selective MC-1R, -3R, -4R, and -5R agonist (Dorr et al., *Life Sciences,* Vol. 58, 1777–1784, 1996). MT-II (also referred to as PT-14) (Erectide®) is presently in clinical development by Palatin Technologies, Inc. and TheraTech, Inc. as a non-penile subcutaneous injection formulation. It is considered to be an "initiator" of the sexual response. The time to onset of erection with this drug is relatively short (10–20 minutes) with a duration of action approximately 2.5 hours. Adverse reactions observed with MT-II include nausea, flushing, loss of appetite, stretching, and yawning and may be the result of activation of MC-1R, MC-2R, MC-3R, and/or MC-5R. MT-II must be administered parenterally, such as by subcutaneous, intravenous, or intramuscular route, since it is not absorbed into the systemic circulation when given by the oral route.

MT-II's erectogenic properties apparently are not limited to cases of psychogenic erectile dysfunction in that men with a variety of organic risk factors developed penile erections upon subcutaneous injection of the compound; moreover, the level of sexual desire was significantly higher after MT-II administration than after placebo [see H. Wessells, "Effect of an Alpha-Melanocyte Stimulating Hormone Analog on Penile Erection and Sexual Desire in Men with Organic Erectile Dysfunction," *Urology,* 56: 641–646 (2000)].

Compositions of melanotropic peptides and methods for the treatment of psychogenic erectile dysfunction are disclosed in U.S. Pat. No. 5,576,290, assigned to Competitive Technologies. Methods of stimulating sexual response in females using melanotropic peptides have been disclosed in U.S. Pat. No. 6,051,555.

Spiropiperidine and piperidine derivatives have been disclosed in WO 99/64002 (Dec. 16, 1999) and WO 00/74679 (Dec. 14, 2000), respectively, as agonists of the melanocortin receptor(s) and thereby useful for the treatment of diseases and disorders, such as obesity, diabetes, and sexual dysfunction, including erectile dysfunction and female sexual dysfunction.

Because of the unresolved deficiencies of the various pharmacological agents discussed above, there is a continuing need in the medical arts for improved methods and compositions to treat individuals suffering from psychogenic and/or organic erectile dysfunction. Such methods and compositions should have wider applicability, enhanced convenience and ease of compliance, short onset of action, reasonably long duration of action, and minimal side effects with few contraindications, as compared to agents now available.

It is therefore an object of the present invention to provide novel piperidine derivatives which are useful as melanocortin receptor agonists and thereby useful to treat obesity, diabetes, and male and female sexual dysfunction.

It is another object of the present invention to provide novel piperidine derivatives which are selective agonists of the melanocortin-4 (MC-4R) receptor.

It is another object of the present invention to provide pharmaceutical compositions comprising melanocortin receptor agonists of the present invention with a pharmaceutically acceptable carrier.

It is another object of the present invention to provide methods for the treatment or prevention of disorders, diseases, or conditions responsive to the activation of the melanocortin receptor in a subject in need thereof by administering the compounds and pharmaceutical compositions of the present invention.

It is another object of the present invention to provide methods for the treatment or prevention of obesity, diabetes mellitus, male sexual dysfunction, and female sexual dysfunction by administering the compounds and pharmaceutical compositions of the present invention to a subject in need thereof.

It is another object of the present invention to provide methods for the treatment of erectile dysfunction by administering the compounds and pharmaceutical compositions of the present invention to a subject in need thereof.

These and other objects will become readily apparent from the detailed description that follows.

SUMMARY OF THE INVENTION

The present invention relates to novel substituted piperidines of structural formula (I):

(I)

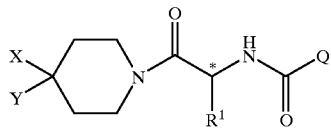

These piperidine derivatives are effective as melanocortin receptor agonists and are particularly effective as selective melanocortin-4 receptor (MC-4R) agonists. They are therefore useful for the treatment and/or prevention of disorders responsive to the activation of MC-4R, such as obesity, diabetes as well as male and female sexual dysfunction, in particular, male erectile dysfunction.

The present invention also relates to pharmaceutical compositions comprising the compounds of the present invention and a pharmaceutically acceptable carrier.

The present invention also relates to methods for the treatment or prevention of disorders, diseases, or conditions responsive to the activation of the melanocortin receptor in a mammal in need thereof by administering the compounds and pharmaceutical compositions of the present invention.

The present invention also relates to methods for the treatment or prevention of obesity, diabetes mellitus, male sexual dysfunction, and female sexual dysfunction by administering the compounds and pharmaceutical compositions of the present invention.

The present invention also relates to methods for treating erectile dysfunction by administering the compounds and pharmaceutical compositions of the present invention.

The present invention also relates to methods for treating erectile dysfunction by administering the compounds of the present invention in combination with a therapeutically effective amount of another agent known to be useful to treat the condition.

The present invention also relates to methods for treating or preventing obesity by administering the compounds of the present invention in combination with a therapeutically effective amount of another agent known to be useful to treat the condition.

DETAILED DESCRIPTION OF THE INVENTION

The present invention relates to substituted piperidines useful as melanocortin receptor agonists. Representative compounds of the present invention are described by structural formula (I):

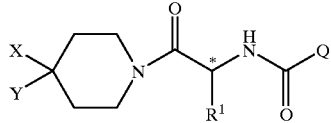

(I)

or a pharmaceutically acceptable salt thereof;

wherein Q is

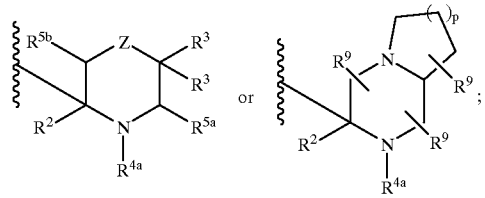

or $Z$ is O, S, or $NR^{4b}$;
each p is independently 1 or 2;
each n is independently 0, 1, or 2;
$R^1$ is selected from the group consisting of
  hydrogen,
  $C_{1-8}$ alkyl,
  $(CHR^7)_n$—$C_{3-6}$ cycloalkyl,
  $(CHR^7)_n$—$O(CHR^7)$aryl,
  $(CHR^7)_n$-aryl, and
  $(CHR^7)_n$-heteroaryl;
  in which aryl and heteroaryl are unsubstituted or substituted with one to three groups independently selected from $R^6$; and alkyl and cycloalkyl are unsubstituted or substituted with one to three groups independently selected from $R^6$ and oxo;
$R^2$ is selected from the group consisting of
  hydrogen,
  $C_{1-8}$ alkyl,
  $(CH_2)_nC_{3-6}$ cycloalkyl, and
  $(CH_2)_n$-aryl;
each $R^3$ is independently selected from the group consisting of
  hydrogen,
  $C_{1-8}$ alkyl,
  $(CH_2)_n$-aryl,
  $(CH_2)_nC_{3-6}$ cycloalkyl,
  $(CH_2)_n$-heteroaryl, and
  $(CH_2)_n$-heterocyclyl;
  in which aryl and heteroaryl are unsubstituted or substituted with one to three groups independently selected from $R^6$; and alkyl, cycloalkyl, and heterocyclyl are unsubstituted or substituted with one to three groups independently selected from $R^6$ and oxo;
  or $R^3$ and $R^{5a}$ and the carbons to which they are attached form a 5- to 7-membered ring optionally containing an additional heteroatom selected from O, S, and $NR^7$;
$R^{4a}$ and $R^{4b}$ are each independently selected from the group consisting of
  hydrogen,
  $C_{1-8}$ alkyl,
  $(CH_2)_n$-aryl,
  $(CH_2)_nC_{3-6}$ cycloalkyl,
  $(CH_2)_n$-heteroaryl,
  $(CH_2)_n$-heterocyclyl,
  $COC(R^7)_2NH_2$,
  $COR^7$,
  $(CH_2)_nOR^7$,
  $(CH_2)_nCO_2R^7$,
  $CH_2C\equiv CH$,
  $CO_2R^7$,
  $CH_2CHF_2$,
  $CONR^7R^7$, and
  $SO_2R^7$;
  in which aryl and heteroaryl are unsubstituted or substituted with one to three groups independently selected from $R^6$; and alkyl, cycloalkyl, and heterocyclyl are unsubstituted or substituted with one to three groups independently selected from $R^6$ and oxo;

or $R^{4a}$ and $R^2$ and the carbons to which they are attached form a 5- to 7-membered ring optionally containing an additional heteroatom selected from O, S, and $NR^7$; or $R^{4a}$ and $R^{4b}$ and the atoms to which they are attached form a 5- to 7-membered ring;

$R^{5a}$ and $R^{5b}$ are each independently selected from the group consisting of
  hydrogen,
  $C_{1-8}$ alkyl,
  $(CH_2)_n$-aryl, and
  $C_{3-8}$ cycloalkyl;
  wherein alkyl and cycloalkyl are unsubstituted or substituted with one to three groups independently selected from $R^6$ and oxo; aryl is unsubstituted or substituted with one to three groups independently selected from $R^6$;

or $R^{5a}$ and $R^{5b}$ together with the carbons to which they are attached form a 5- to 7-membered ring;

$R^6$ is selected from the group consisting of
  hydrogen,
  $C_{1-8}$ alkyl,
  $(CH_2)_n$-aryl,
  $(CH_2)_nC_{3-7}$ cycloalkyl,
  $(CH_2)_n$-heteroaryl,
  halogen,
  $OR^7$,
  $NHSO_2R^7$,
  $N(R^7)_2$,
  $C\equiv N$,
  $CO_2R^7$,
  $C(R^7)(R^7)N(R^7)_2$,
  $NO_2$,
  $SO_2N(R^7)_2$,
  $S(O)_{0-2}R^7$,
  $CF_3$, and
  $OCF_3$;
  or two R6 substituents, when on the same carbon atom, can be taken together with the carbon atom to which they are attached to form a cyclopropyl group;

each $R^7$ is independently selected from the group consisting of
  hydrogen,
  $C_{1-8}$ alkyl,
  $(CH_2)_n$-aryl, and
  $(CH_2)_nC_{3-7}$ cycloalkyl;

each $R^8$ is independently selected from the group consisting of
  hydrogen,
  $C_{1-8}$ alkyl,
  $(CH_2)_n$-aryl,
  $(CH_2)_n$-heteroaryl,
  $(CH_2)_n$-heterocyclyl, and
  $(CH_2)_nC_{3-7}$ cycloalkyl;
  wherein aryl and heteroaryl are unsubstituted or substituted with one to three groups independently selected from $R^6$; and alkyl, cycloalkyl, heterocyclyl, and $(CH_2)_n$ are unsubstituted or substituted with one to three groups independently selected from $R^6$ and oxo;
  or two $R^8$ groups together with the atoms to which they are attached form a 5- to 8-membered mono- or bi-cyclic ring system optionally containing an additional heteroatom selected from O, S, $NR^7$, NBoc, and NCbz;

each $R^9$ is independently selected from the group consisting of
  hydrogen,
  $C_{1-8}$ alkyl,
  $(CH_2)_n$-aryl,
  $(CH_2)_nC_{3-6}$ cycloalkyl,
  $(CH_2)_n$-heteroaryl,
  halogen,
  $OR^7$,
  $NHSO_2R^7$,
  $N(R^7)_2$,
  $C\equiv N$,
  $CO_2R^7$,
  $C(R^7)(R^7)N(R^7)_2$,
  $NO_2$,
  $SO_2N(R^7)_2$,
  $S(O)_{0-2}R^7$,
  $CF_3$, and
  $OCF_3$;

X is selected from the group consisting of
  $C_{1-8}$ alkyl,
  $(CH_2)_nC_{3-8}$ cycloalkyl,
  $(CH_2)_n$aryl,
  $(CH_2)_n$heteroaryl,
  $(CH_2)_n$heterocyclyl,
  $(CH_2)_nC\equiv N$,
  $(CH_2)_nCONR^8R^8$,
  $(CH_2)_nCO_2R^8$,
  $(CH_2)_nCOR^8$,
  $(CH_2)_nNR^8C(O)R^8$,
  $(CH_2)_nNR^8CO_2R^8$,
  $(CH_2)_nNR^8C(O)N(R^8)_2$,
  $(CH_2)_nNR^8SO_2R^8$,
  $(CH_2)_nS(O)_{0-2}R^8$,
  $(CH_2)_nSO_2N(R^8)(R^8)$,
  $(CH_2)_nOR^8$,
  $(CH_2)_nOC(O)R^8$,
  $(CH_2)_nOC(O)OR^8$,
  $(CH_2)_nOC(O)N(R^8)_2$,
  $(CH_2)_nN(R^8)(R^8)$, and
  $(CH_2)_nNR^8SO_2N(R^8)(R^8)$;
  wherein aryl and heteroaryl are unsubstituted or substituted with one to three groups selected from $R^6$; and alkyl, $(CH_2)_n$, cycloalkyl, and heterocyclyl are unsubstituted or substituted with one to three groups independently selected from $R^6$ and oxo;

Y is selected from the group consisting of
  hydrogen,
  $C_{1-8}$ alkyl,
  $(CH_2)_nC_{3-8}$ cycloalkyl,
  $(CH_2)_n$aryl,
  $(CH_2)_n$heterocyclyl, and
  $(CH_2)_n$heteroaryl;
  wherein aryl and heteroaryl are unsubstituted or substituted with one to three groups selected from $R^6$; and alkyl, $(CH_2)_n$, cycloalkyl, and heterocyclyl are optionally substituted with one to three groups selected from $R^6$ and oxo.

In one embodiment of the compounds of formula I, Q is

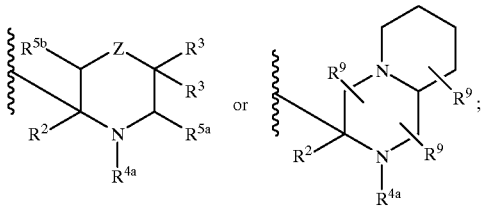

wherein Z is O or $NR^{4b}$; and $R^2$, $R^3$, $R^{4a}$, $R^{4b}$, $R^{5a}$, $R^{5b}$, and $R^9$ are as defined above.

In a second embodiment of the compounds of formula I, Q is

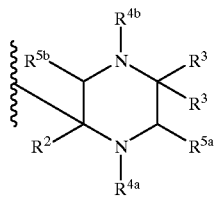

wherein $R^2$, $R^3$, $R^{4a}$, $R^{4b}$, $R^{5a}$, and $R^{5b}$ are as defined above.

In a class of this second embodiment, $R^{4a}$ and $R^{4b}$ are each independently selected from the group consisting of
hydrogen,
$C_{1-8}$ alkyl,
$(CH_2)_n$-aryl,
$(CH_2)_n$-heteroaryl,
$(CH_2)_n$-heterocyclyl,
$(CH_2)_n C_{3-6}$ cycloalkyl,
$(CH_2)_n CO_2 R^7$
$(CH_2)_n OR^7$,
$COC(R^7)NH_2$,
$CH_2C\equiv CH$, and
$CH_2CHF_2$;
or $R^{4a}$ and $R^{4b}$ and the atoms to which they are attached form a 6-membered ring;
$R^3$, $R^{5a}$, and $R^{5b}$ are each independently hydrogen, $C_{1-4}$ alkyl, $C_{3-6}$ cycloalkyl, or aryl; wherein aryl is unsubstituted or substituted with one to three groups independently selected from $R^6$; or $R^3$ and $R^{5a}$ and the carbons to which they are attached form a 6-membered ring optionally containing an additional heteroatom selected from O, S, and $NR^7$.

In a subclass of this class, $R^{4a}$ and $R^{4b}$ are each independently selected from the group consisting of
hydrogen,
$C_{1-4}$ alkyl,
$CH_2$-aryl,
$CH_2$-heteroaryl,
$CH_2$-heterocyclyl,
$(CH_2)_{0-1} C_{3-6}$ cycloalkyl,
$CH_2CO_2R^7$
$(CH_2)_2OR^7$,
$COC(R^7)NH_2$,
$CH_2C\equiv CH$, and
$CH_2CHF_2$;
or $R^4a$ and $R^{4b}$ and the atoms to which they are attached form a 6-membered ring;

$R^3$, $R^{5a}$, and $R^{5b}$ are each independently hydrogen, $C_{1-4}$ alkyl, $C_{3-6}$ cycloalkyl, or phenyl; wherein phenyl is unsubstituted or substituted with one to three groups independently selected from $R^6$; or $R^3$ and $R^{5a}$ and the carbons to which they are attached form a 6-membered ring optionally containing an additional heteroatom selected from O, S, and $NR^7$.

In a third embodiment of the compounds of formula I, $R^1$ is $CHR^7$-aryl, $CHR^7OCHR^7$-aryl, or $CHR^7$-heteroaryl wherein aryl and heteroaryl are optionally substituted with one or two $R^6$ groups. In a class of this embodiment, $R^1$ is benzyl optionally substituted with one or two groups selected from halogen, $C_{1-4}$ alkyl, $C_{1-4}$ alkoxy, CN, $CF_3$, and $OCF_3$. In a subclass of this class, $R^1$ is 4-chlorobenzyl; 4-fluorobenzyl; 3,4-difluorobenzyl; 3,5-difluorobenzyl; 2-cyano-4-fluorobenzyl; or 4-methoxybenzyl.

In a fourth embodiment of compounds of formula I, $R^2$ is H or $CH_3$.

In a fifth embodiment of compounds of formula I, X is $C_{1-6}$ alkyl, $(CH_2)_n$-aryl, $(CH_2)_n$-heteroaryl, $(CH_2)_n$-heterocyclyl, $(CH_2)_nC(O)N(R^8)(R^8)$, $(CH_2)_nCO_2R^8$, $(CH_2)_nOR^8$, $(CH_2)_nS(O)_{0-2}R^8$, $(CH_2)_nNHC(O)R^8$, $(CH_2)_nOC(O)NR^8R^8$, or $(CH_2)_nNR^8SO_2R^8$; wherein aryl and heteroaryl are optionally substituted with one to three groups selected from $R^6$; heterocyclyl is optionally substituted with one to three groups selected from $R^6$ and oxo; the $(CH_2)_n$ group is optionally substituted with one to three groups selected from $R^7$, halogen, $S(O)_{0-2}R^7$, $N(R^7)_2$, and $OR^7$; and $R^8$ is each independently selected from H, $C_{1-8}$ alkyl, and $C_{3-6}$ cycloalkyl optionally substituted with one to three groups selected from $R^6$ and oxo; or two $R^8$ groups together with the atoms to which they are attached form a 5- to 8-membered mono- or bi-cyclic ring system optionally containing an additional heteroatom selected from O, S, $NR^7$, NBoc, and NCbz.

In a class of this embodiment, X is $C_{1-6}$ alkyl, $(CH_2)_{0-1}$-heteroaryl, $CH_2$-heterocyclyl, $CO_2R^8$, $CH_2OR^8$, $CH_2S(O)_{0-2}R^8$, $NHC(O)R^8$, $CH_2NR^8SO_2R^8$, $CH_2OC(O)NR^8R^8$, $CH_2NR^8SO_2R^8$, or $C(O)N(R^8)(R^8)$; wherein heteroaryl is optionally substituted with one to three groups selected from $R^6$; heterocyclyl is optionally substituted with one to three groups selected from $R^6$ and oxo; and $R^8$ is each independently selected from H, $C_{1-8}$ alkyl, and $C_{3-6}$ cycloalkyl optionally substituted with one to three groups selected from $R^6$ and oxo; or two $R^8$ groups together with the atoms to which they are attached form a 5- to 8-membered mono- or bi-cyclic ring system optionally containing an additional heteroatom selected from O, S, $NR^7$, NBoc, and NCbz.

In a sixth embodiment of compounds of formula I, Y is $C_{1-8}$ alkyl, $(CH_2)_nC_{3-7}$ cycloalkyl, $(CH_2)_n$-aryl, $(CH_2)_n$-heterocyclyl, or $(CH_2)_n$-heteroaryl; wherein aryl and heteroaryl are optionally substituted with one to three groups selected from $R^6$; and $(CH_2)_n$, alkyl, cycloalkyl, and heterocyclyl are optionally substituted with one to three groups selected from $R^6$ and oxo. In a class of this embodiment, Y is cyclohexyl, cycloheptyl, cyclopentyl, or $C_{1-6}$ alkyl, unsubstituted or substituted with one to three groups selected from $R^6$ and oxo. In a subclass of this class, Y is cyclohexyl or $C_{1-6}$ alkyl, wherein the cyclohexyl and alkyl groups are unsubstituted or substituted with one to three groups selected from $R^6$ and oxo.

In yet a further embodiment of compounds of formula I, the carbon atom marked with * has the R configuration.

In yet a further embodiment of compounds of formula I, X is selected from the group consisting of:

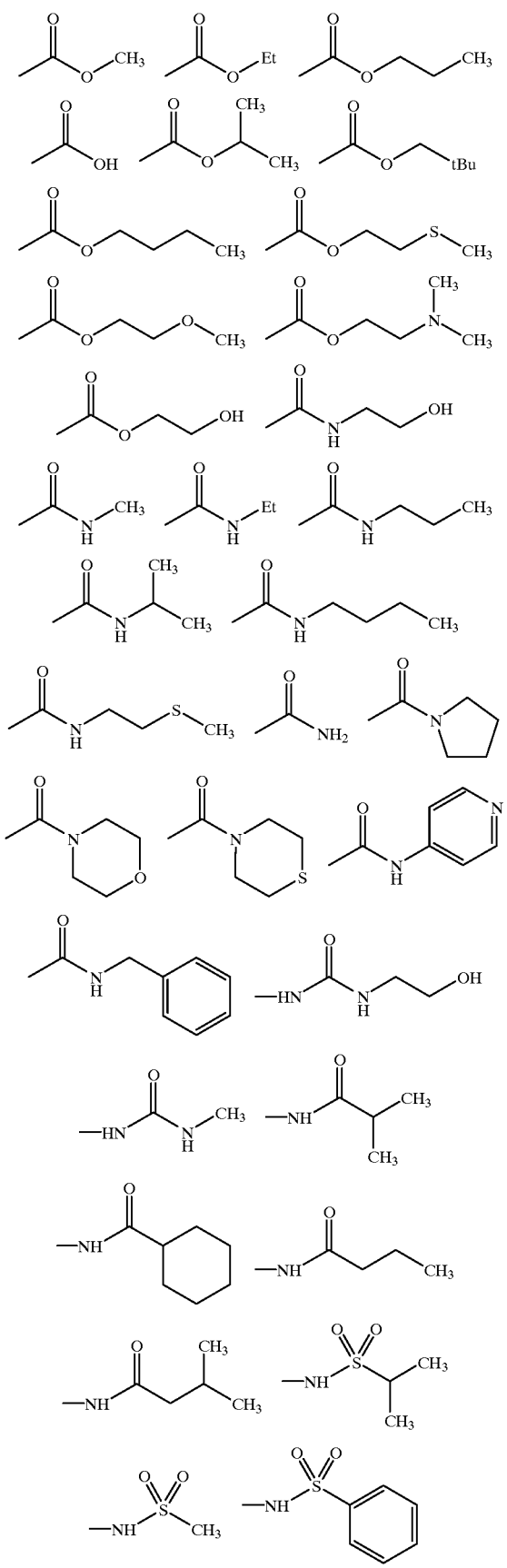
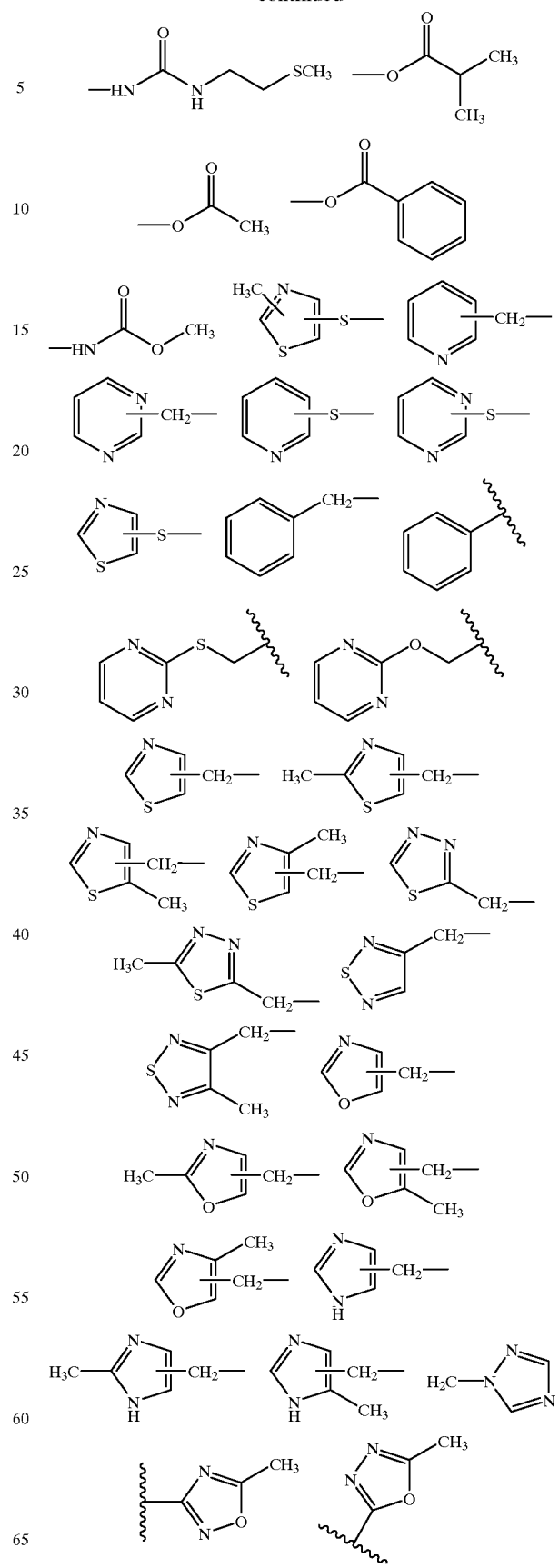

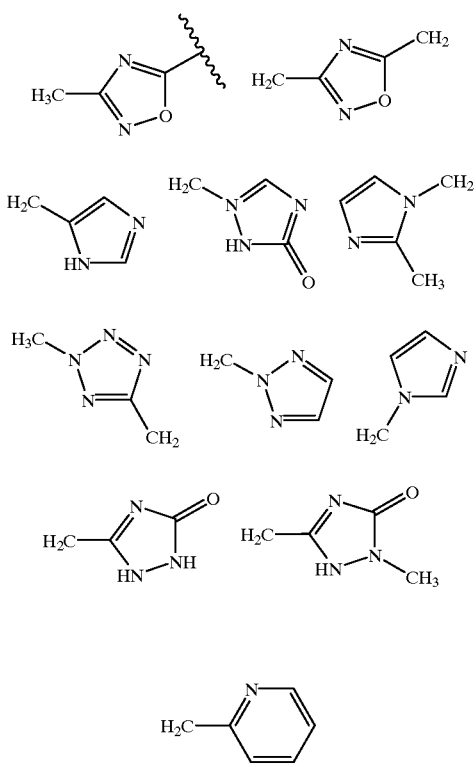
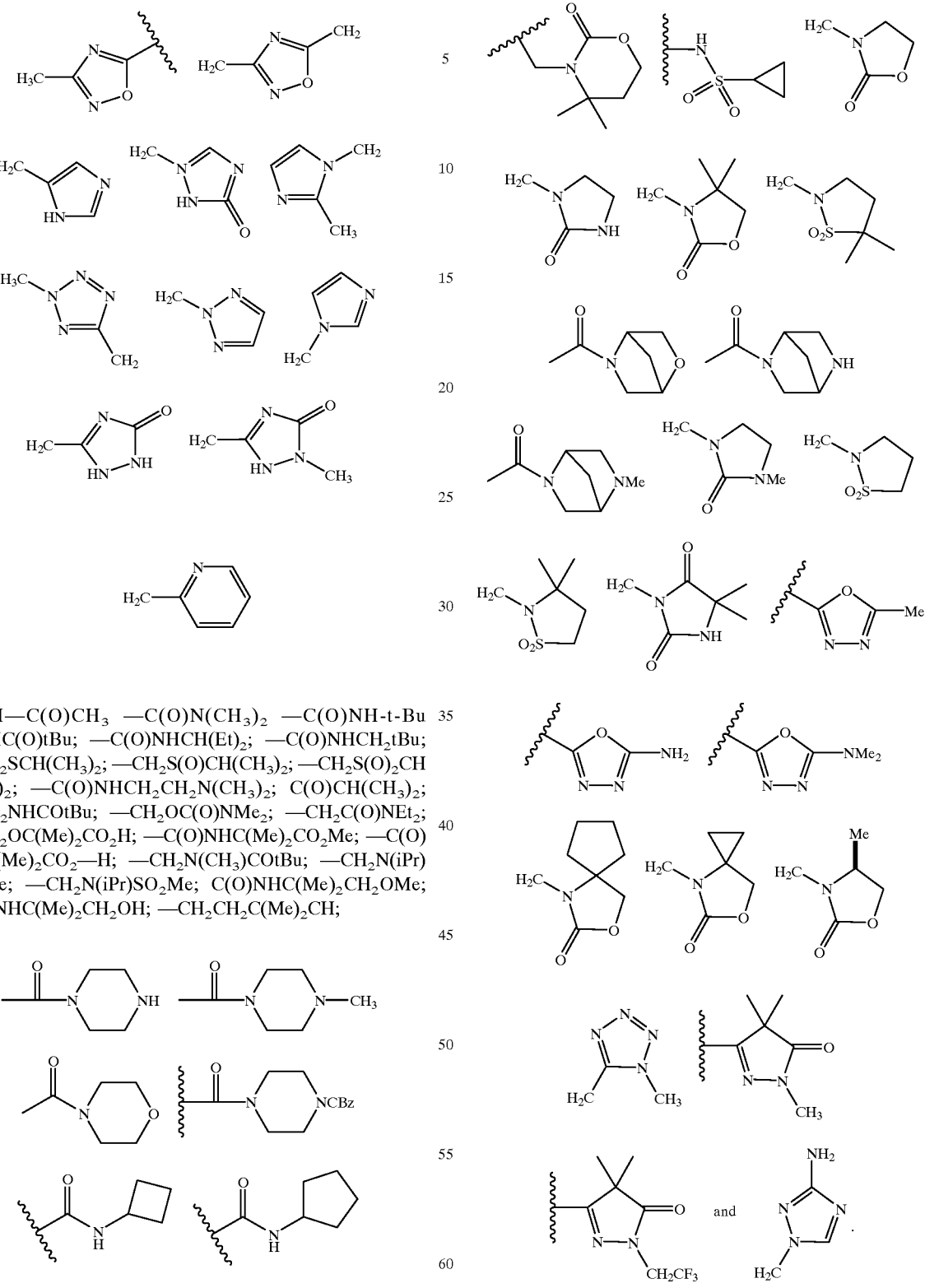

—NH—C(O)CH₃   —C(O)N(CH₃)₂   —C(O)NH-t-Bu
—NHC(O)tBu;   —C(O)NHCH(Et)₂;   —C(O)NHCH₂tBu;
—CH₂SCH(CH₃)₂;   —CH₂S(O)CH(CH₃)₂;   —CH₂S(O)₂CH(CH₃)₂;   —C(O)NHCH₂CH₂N(CH₃)₂;   C(O)CH(CH₃)₂;
—CH₂NHCOtBu;   —CH₂OC(O)NMe₂;   —CH₂C(O)NEt₂;
—CH₂OC(Me)₂CO₂H;   —C(O)NHC(Me)₂CO₂Me;   —C(O)NHC(Me)₂CO₂—H;   —CH₂N(CH₃)COtBu;   —CH₂N(iPr)COMe;   —CH₂N(iPr)SO₂Me;   C(O)NHC(Me)₂CH₂OMe;   C(O)NHC(Me)₂CH₂OH;   —CH₂CH₂C(Me)₂CH;

Representative compounds of the present invention of structural formula Ia or Ib with the indicated stereochemistry at the stereogenic center marked with ** are as follows:

| | | R⁶ | ** | R⁴ᵃ | R⁴ᵇ |
|---|---|---|---|---|---|
| cyclohexyl | –C(O)NH-tBu | Cl | (R) | H | CH₃ |
| cyclohexyl | –C(O)NH-tBu | Cl | (S) | H | H |
| cyclohexyl | –C(O)O-Et | F | (R) | H | H |
| cyclohexyl | –C(O)NH-tBu | F | (R) | H | H |
| cyclohexyl | –C(O)NH-tBu | F | (S) | H | H |
| cyclohexyl | –C(O)NH-iPr | Cl | (S) | H | H |
| cyclohexyl | –C(O)NH-cyclopentyl | Cl | (S) | H | H |

-continued
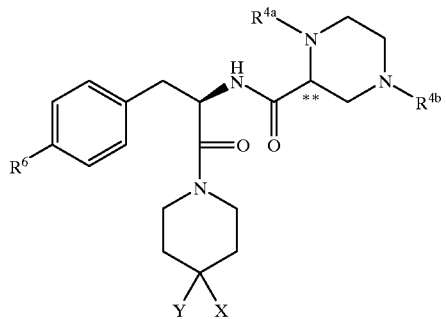
| Y | X | R⁶ | ** | R⁴ᵃ | R⁴ᵇ |
|---|---|---|---|---|---|
| cyclohexyl | -C(O)NH-cyclopentyl | Cl | (R) | H | H |
| cyclohexyl | -C(O)NH-CH(Et)₂ | Cl | (S) | H | H |
| cyclohexyl | -C(O)NH-CH(Et)₂ | Cl | (R) | H | H |
| cyclohexyl | -C(O)NH-CH₂C(CH₃)₃ | Cl | (R) | H | H |
| cyclohexyl | -C(O)NH-(2-pyridyl) | Cl | (S) | H | H |
| cyclohexyl | -C(O)NH-CH₂CF₃ | Cl | (S) | H | H |
| cyclohexyl | -C(O)-N(piperazine)NH | F | (S) | H | H |

-continued
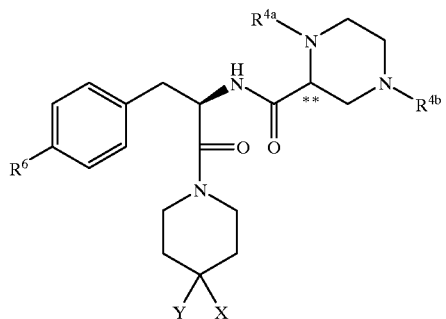
| Y | X | R⁶ | ** | R⁴ᵃ | R⁴ᵇ |
|---|---|---|---|---|---|
| cyclohexyl | N-methylpiperazinylcarbonyl | F | (S) | H | H |
| cyclohexyl | NH-C(O)-C(CH₃)₃ | Cl | (S) | H | H |
| cyclohexyl | NH-C(O)-C(CH₃)₃ | Cl | (R) | H | H |
| cyclohexyl | 4,4-dimethyloxazolidin-2-on-3-ylmethyl | F | (S) | H | H |
| cyclohexyl | 4,4-dimethyloxazolidin-2-on-3-ylmethyl | F | (R) | H | H |
| cyclohexyl | CH₂-O-C(O)-N(CH₃)₂ | Cl | (S) | H | H |
| cyclohexyl | NH-C(O)-C(CH₃)₃ | Cl | (S) | CH₃ | H |

-continued
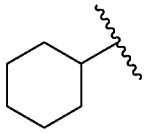
| Y | X | R⁶ | ** | R⁴ᵃ | R⁴ᵇ |
|---|---|---|---|---|---|
| 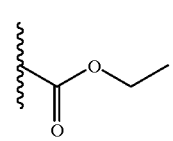 | 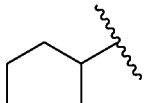 | F | (R) | CH₃ | H |
| 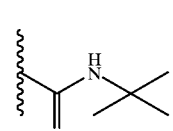 | 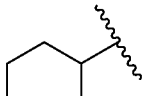 | Cl | (S) | CH₃ | H |
| 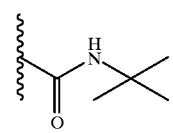 | 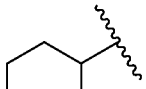 | F | (S) | CH₃ | H |
| 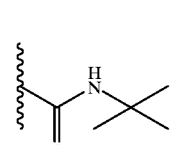 | 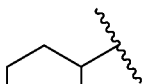 | Cl | (R) | CH₃ | H |
| 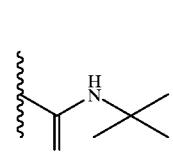 | 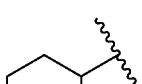 | F | (R) | CH₃ | H |
| 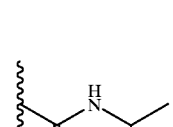 | 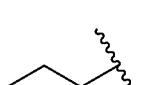 | Cl | (S) | CH₃ | H |
| 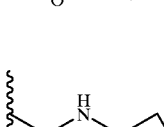 | | Cl | (S) | CH₃ | H |

-continued

| Y | X | R⁶ | ** | R⁴ᵃ | R⁴ᵇ |
|---|---|---|---|---|---|
| cyclohexyl | C(O)NH-cyclobutyl | Cl | (R) | CH₃ | H |
| cyclohexyl | C(O)NH-cyclopentyl | Cl | (S) | CH₃ | H |
| cyclohexyl | C(O)NH-cyclopentyl | Cl | (R) | CH₃ | H |
| cyclohexyl | C(O)NH-CH(Et)₂ | Cl | (S) | CH₃ | H |
| cyclohexyl | C(O)NH-CH(Et)₂ | Cl | (R) | CH₃ | H |
| cyclohexyl | C(O)NH-CH₂C(CH₃)₃ | Cl | (R) | CH₃ | H |
| cyclohexyl | C(O)NH-(2-pyridyl) | Cl | (S) | CH₃ | H |

-continued
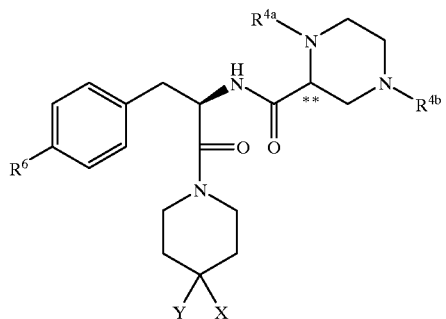
| Y | X | R⁶ | ** | R⁴ᵃ | R⁴ᵇ |
|---|---|---|---|---|---|
| cyclohexyl | -C(O)NH-CH₂CF₃ | Cl | (S) | CH₃ | H |
| cyclohexyl | -C(O)-piperazinyl-NH | F | (S) | CH₃ | H |
| cyclohexyl | -C(O)-(4-methylpiperazinyl) | F | (S) | CH₃ | H |
| cyclohexyl | -NHC(O)C(CH₃)₃ | Cl | (S) | CH₃ | H |
| cyclohexyl | -NHC(O)C(CH₃)₃ | Cl | (R) | CH₃ | H |
| cyclohexyl | 4,4-dimethyl-2-oxo-oxazolidin-3-yl-methyl | Cl | (S) | CH₃ | H |
| cyclohexyl | 4,4-dimethyl-2-oxo-oxazolidin-3-yl-methyl | F | (S) | CH₃ | H |

-continued

*Structure 1a*: A compound with a para-R⁶-substituted benzyl group attached to a chiral carbon (marked with stereochemistry) bearing an NH-C(=O) linkage to a piperazine ring (with R⁴ᵃ on one nitrogen and R⁴ᵇ on the other, ** marking the chiral center on the piperazine). The chiral carbon also bears a C(=O) connected to a 4,4-disubstituted piperidine nitrogen, where the 4-position substituents are Y and X.

| Y | X | R⁶ | ** | R⁴ᵃ | R⁴ᵇ |
|---|---|---|---|---|---|
| cyclohexyl | 4,4-dimethyl-2-oxo-oxazolidin-3-ylmethyl | Cl | (R) | CH₃ | H |
| cyclohexyl | 4,4-dimethyl-2-oxo-oxazolidin-3-ylmethyl | F | (R) | CH₃ | H |
| cyclohexyl | -CH₂-O-C(=O)-N(CH₃)₂ | Cl | (S) | CH₃ | H |
| cyclohexyl | -CH₂-C(=O)-NH-C(CH₃)₃ | Cl | (S) | CH₃ | CH₃ |
| cyclohexyl | -CH₂-C(=O)-O-CH₂CH₃ | Cl | (S) | CH₃ | CH₃ |
| cyclohexyl | -C(=O)-NH-C(CH₃)₃ | Cl | (S) | CH₃ | CH₃ |
| cyclohexyl | -C(=O)-NH-C(CH₃)₃ | Cl | (R) | CH₃ | CH₃ |

-continued

1a

| Y | X | R⁶ | ** | R⁴ᵃ | R⁴ᵇ |
|---|---|----|----|-----|-----|
| cyclohexyl | -C(O)NH-cyclopentyl | Cl | (R) | CH₃ | CH₃ |
| cyclohexyl | -C(O)NH-CH(Et)₂ | Cl | (R) | CH₃ | CH₃ |
| cyclohexyl | -C(O)NH-C(CH₃)₃ | Cl | (S) | CH₃ | CH₃ |
| cyclohexyl | -C(O)NH-C(CH₃)₃ | Cl | (S) | H | CH₃ |
| cyclohexyl | -C(O)O-ethyl | Cl | (S) | H | i-Pr |
| cyclohexyl | -C(O)O-ethyl | F | (S) | H | 2-hydroxyethyl |
| cyclohexyl | -C(O)O-ethyl | F | (S) | H | 2-methoxyethyl |

-continued

1a

[Structure: phenyl(R6)-CH2-CH(NH-C(O)-[piperazine with R4a, R4b])-C(O)-N(piperidine with Y,X at 4-position)]

| Y | X | R⁶ | ** | R⁴ᵃ | R⁴ᵇ |
|---|---|---|---|---|---|
| cyclohexyl | -C(O)O-Et | F | (S) | H | CH₂CO₂Et |
| cyclohexyl | -C(O)O-Et | F | (R) | H | CH₃ |
| cyclohexyl | -C(O)O-Et | F | (R) | H | 2-methoxyethyl |
| cyclohexyl | -C(O)NH-tBu | Cl | (S) | H | CH₃ |
| cyclohexyl | -C(O)NH-tBu | Cl | (S) | H | i-Pr |
| cyclohexyl | -C(O)NH-tBu | Cl | (S) | H | 2,2-difluoroethyl |
| cyclohexyl | -C(O)NH-tBu | F | (S) | H | CH₃ |

-continued
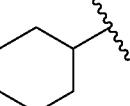
1a
| Y | X | R⁶ | ** | R⁴ᵃ | R⁴ᵇ |
|---|---|---|---|---|---|
| 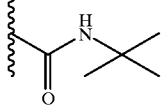 | 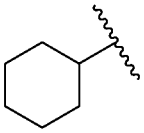 | F | (S) | H | i-Pr |
| 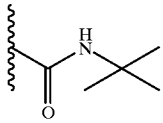 | 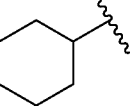 | F | (S) | H | 2,2-difluoroethyl |
| 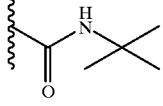 | 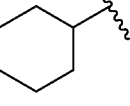 | Cl | (R) | H | CH₃ |
| 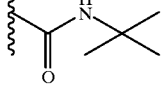 | 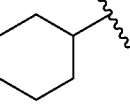 | Cl | (R) | H | i-Pr |
| 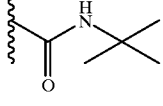 | 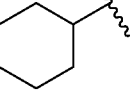 | Cl | (R) | H | cyclopropyl-methyl |
| 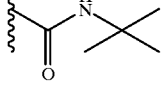 | 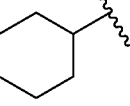 | Cl | (R) | H | benzyl |
| 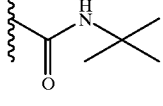 | | Cl | (R) | H | 2-propynyl |

-continued
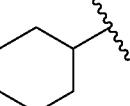
1a
| Y | X | R⁶ | ** | R⁴ᵃ | R⁴ᵇ |
|---|---|---|---|---|---|
| 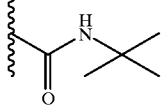 | 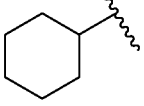 | Cl | (R) | H | cyclobutyl |
| 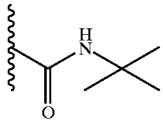 | 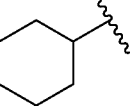 | Cl | (R) | H | 2,2-difluoroethyl |
| 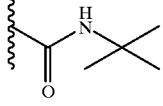 | 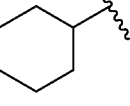 | F | (R) | H | CH₃ |
| 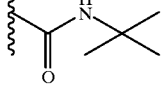 | 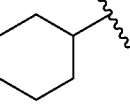 | F | (R) | H | i-Pr |
| 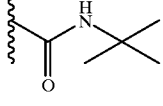 | 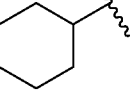 | F | (R) | H | cyclopropyl-methyl |
| 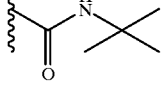 | 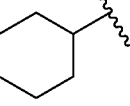 | F | (R) | H | 2,2-difluoroethyl |
| 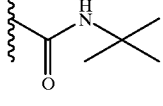 | | Cl | (S) | H | CH₃ |

-continued
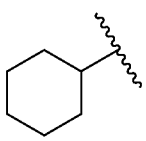
| Y | X | R⁶ | ** | R⁴ᵃ | R⁴ᵇ |
|---|---|---|---|---|---|
| 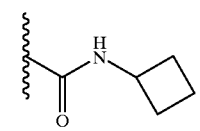 | 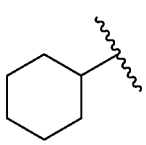 | Cl | (S) | H | CH₃ |
| 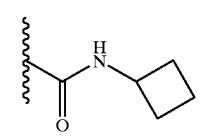 | 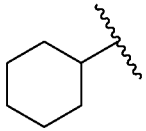 | Cl | (R) | H | CH₃ |
| 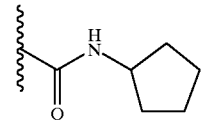 | 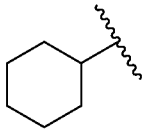 | Cl | (S) | H | CH₃ |
| 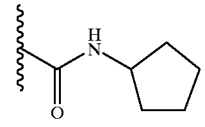 | 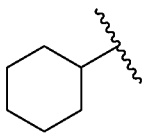 | Cl | (R) | H | CH₃ |
| 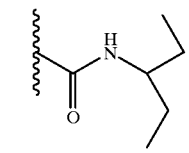 | 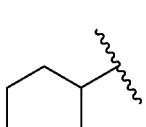 | Cl | (S) | H | CH₃ |
| 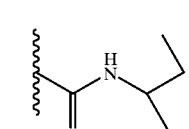 | 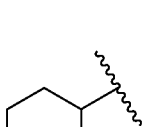 | Cl | (R) | H | CH₃ |
| 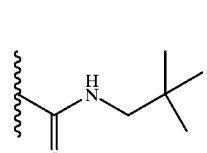 | | Cl | (R) | H | CH₃ |

-continued
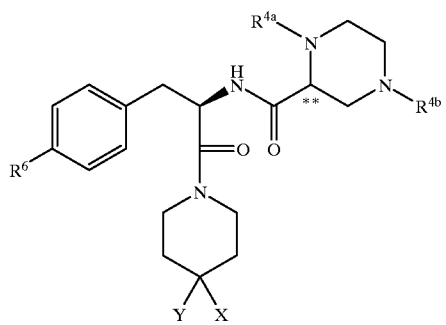
| Y | X | R⁶ | ** | R⁴ᵃ | R⁴ᵇ |
|---|---|---|---|---|---|
| cyclohexyl | -C(=O)NH-(2-pyridyl) | Cl | (S) | H | CH₃ |
| cyclohexyl | -C(=O)-N(4-methylpiperazinyl) | F | (S) | H | CH₃ |
| cyclohexyl | -C(=O)NH-C(CH₃)₃ | Cl | (S) | H | CH₃ |
| cyclohexyl | -C(=O)NH-C(CH₃)₃ | Cl | (R) | H | CH₃ |
| cyclohexyl | -CH₂-(4,4-dimethyl-2-oxo-oxazolidin-3-yl) | Cl | (S) | H | CH₃ |
| cyclohexyl | -CH₂-(4,4-dimethyl-2-oxo-oxazolidin-3-yl) | Cl | (R) | H | CH₃ |
| cyclohexyl | -CH₂-(4,4-dimethyl-2-oxo-oxazolidin-3-yl) | F | (S) | H | CH₃ |

-continued
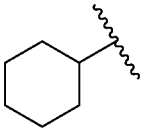
| Y | X | R⁶ | ** | R⁴ᵃ | R⁴ᵇ |
|---|---|---|---|---|---|
| 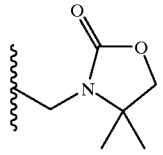 | 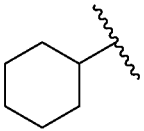 | F | (R) | H | CH₃ |
| 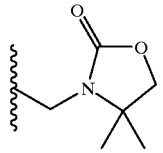 | 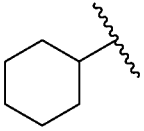 | F | (R) | H | i-Pr |
| 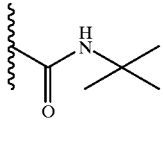 | 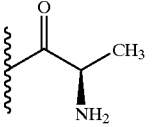 | F | (S) | H | 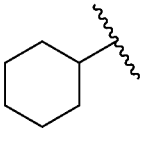 |
| 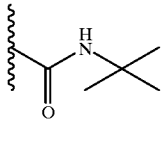 | 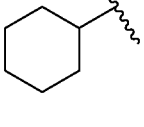 | Cl | (S) | CH₃ | i-Pr |
| 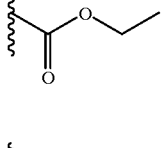 | 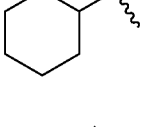 | Cl | (S) | CH₃ | i-Pr |
| 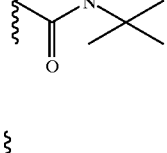 | 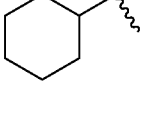 | F | (S) | H | Et |
| 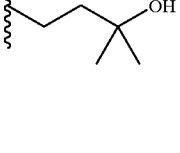 | | F | (R) | H | H |

-continued
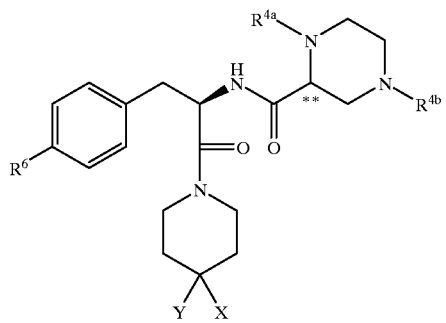
1a
| Y | X | R⁶ | ** | R⁴ᵃ | R⁴ᵇ |
|---|---|---|---|---|---|
| 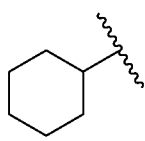 | 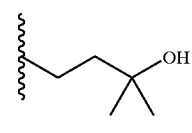 | F | (S) | H | H |
| 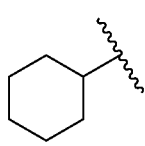 | 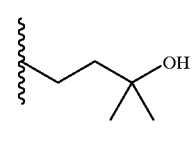 | F | (R) | H | Me |
| 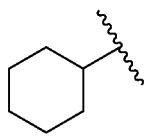 | 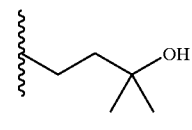 | F | (S) | H | Me |
| 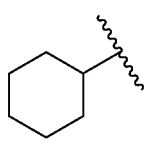 | 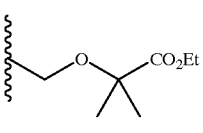 | F | (S) | H | Me |
| 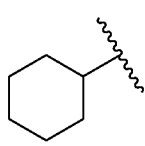 | 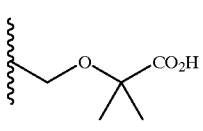 | F | (S) | H | Me |
| | 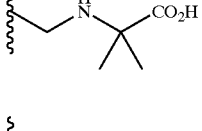 | | | | |
|  | 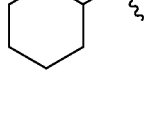 | F | (S) | H | Me |
| | 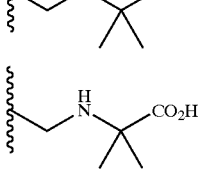 | | | | |

-continued

| Y | X | R⁶ | ** | R⁴ᵃ | R⁴ᵇ |
|---|---|---|---|---|---|
| cyclohexyl | -C(=O)NH-C(Me)₂-CO₂Me | F | (S) | H | Me |
| cyclohexyl | -NH-S(O)₂-cyclopropyl | F | (S) | H | Me |
| cyclohexyl | -CH₂-N(3-oxo-gem-dimethyl-morpholine) | F | (S) | H | Me |
| cyclohexyl | -C(=O)NH-tBu | F | (S) | H | Me |
| 1,1-dimethylpropyl | -C(=O)NH-tBu | F | (S) | H | Me |
| 4,4-dimethylcyclohexyl | -C(=O)NH-tBu | F | (S) | H | Me |
| 4,4-dimethylcyclohexyl | -C(=O)NH-tBu | F | (S) | H | H |

-continued

1a

| Y | X | R⁶ | ** | R⁴ᵃ | R⁴ᵇ |
|---|---|---|---|---|---|
| 4,4-difluorocyclohexylmethyl | CH₂C(O)NH-tBu | F | (S) | H | Me |
| 4-methylcyclohexylmethyl | CH₂C(O)NH-tBu | F | (S) | H | Me |
| 4-methylcyclohexylmethyl | CH₂C(O)NH-tBu | F | (S) | H | H |
| cyclopropylmethyl | CH₂C(O)NH-tBu | F | (S) | H | Me |
| cyclobutylmethyl | CH₂C(O)NH-tBu | F | (S) | H | Me |
| cyclopropylmethyl | CH₂S-iPr | F | (S) | H | H |
| cyclohexyl | CH₂CH₂N(iPr)SO₂Me | Cl | (R) | H | Me |

-continued
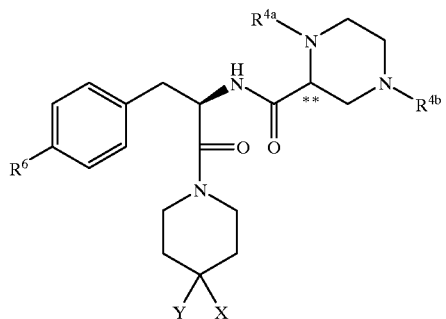
1a
| Y | X | R⁶ | ** | R⁴ᵃ | R⁴ᵇ |
|---|---|----|----|-----|-----|
| cyclohexyl | 5-methyl-1,3,4-oxadiazol-2-yl | Cl | (S) | H | H |
| cyclohexyl | 4,4-dimethyl-2-oxo-oxazolidin-3-ylmethyl | F | (S) | iPr | Me |
| cyclohexyl | CH₂C(O)NEt₂ | F | (S) | H | Me |
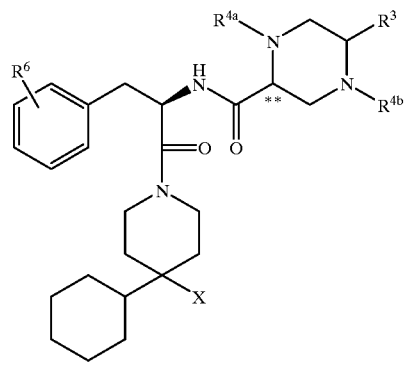
Ib
| R⁶ | ** | X | R³ | R⁴ᵃ | R⁴ᵇ | Diastereomer |
|----|----|---|----|-----|-----|--------------|
| 4-fluoro | (R) | C(O)NH-tBu | iPr | H | H | D₁ + D₂ |

-continued
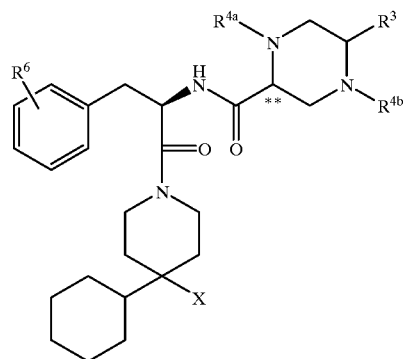
| $R^6$ | ** | X | $R^3$ | $R^{4a}$ | $R^{4b}$ | Diastereomer |
|---|---|---|---|---|---|---|
| 4-fluoro | (R) | -C(O)NH-tBu | iPr | H | H | $D_1$ |
| 4-fluoro | (R) | -C(O)NH-tBu | iPr | H | H | $D_2$ |
| 4-chloro | (R) | -C(O)NH-tBu | iPr | H | H | $D_1 + D_2$ |
| 4-chloro | (R) | -C(O)NH-tBu | iPr | H | H | $D_1$ |
| 4-chloro | (R) | -C(O)NH-tBu | iPr | H | H | $D_2$ |
| 4-fluoro | (R) | 4,4-dimethyl-oxazolidinon-3-yl-methyl | iPr | H | H | $D_1 + D_2$ |
| 4-fluoro | (R) | -C(O)OEt | iPr | H | H | $D_1 + D_2$ |

-continued
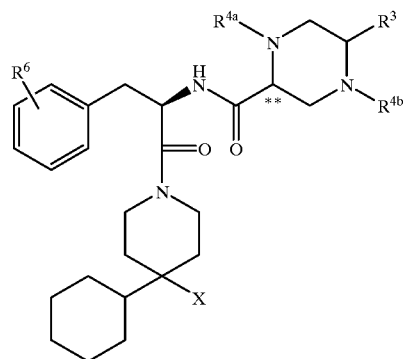
Ib
| R[6] | ** | X | R[3] | R[4a] | R[4b] | Diastereomer |
|---|---|---|---|---|---|---|
| 4-fluoro | (R) | —CH2—S—iPr | iBu | H | H | D1 + D2 |
| 4-fluoro | (R) | —CH2—S(O)—iPr | iBu | H | H |  |
| 4-chloro | (R) | —C(O)NH—tBu | Ph | H | H | D1 + D2 |
| 4-fluoro | (R) | —C(O)NH—tBu | Ph | H | H | D1 + D2 |
| 4-fluoro | (R) | —CH2-(4,4-dimethyloxazolidin-2-one-3-yl) | Ph | H | H | D1 + D2 |
| 4-fluoro | (S) | —C(O)NH—tBu | iBu | H | H | D1 + D2 |
| 4-fluoro | (S) | —C(O)NH—tBu | iBu | H | H | D1 |

-continued
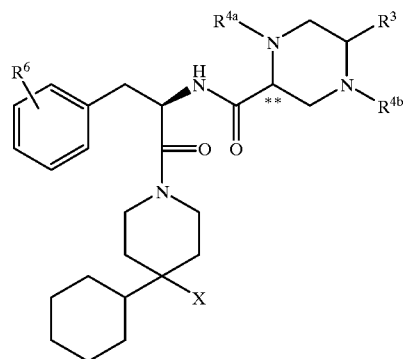
| R⁶ | ** | X | R³ | R⁴ᵃ | R⁴ᵇ | Diastereomer |
|---|---|---|---|---|---|---|
| 4-fluoro | (S) | —C(O)NH-tBu | iPr | H | H | D₂ |
| 4-fluoro | (S) | —C(O)NH-tBu | cyclopropyl | H | H | D₁ + D₂ |
| 4-fluoro | (S) | —C(O)NH-tBu | cyclopropyl | H | H | D₁ |
| 4-fluoro | (S) | —C(O)NH-tBu | cyclopropyl | H | H | D₂ |
| 4-fluoro | (R) | —C(O)NH-tBu | cyclopropyl | H | H | D₁ + D₂ |
| 4-fluoro | (R) | —C(O)NH-tBu | cyclopropyl | H | H | D₁ |
| 4-fluoro | (R) | —C(O)NH-tBu | cyclopropyl | H | H | D₂ |

-continued
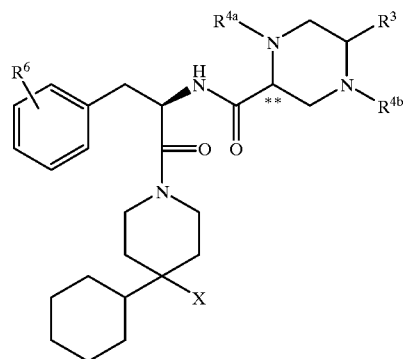
Ib
| R⁶ | ** | X | R³ | R⁴ᵃ | R⁴ᵇ | Diastereomer |
|---|---|---|---|---|---|---|
| 4-fluoro | (S) | -C(O)NH-tBu | tBu | H | H | D₁ + D₂ |
| 4-fluoro | (S) | -C(O)NH-tBu | tBu | H | H | D₁ |
| 4-fluoro | (S) | -C(O)NH-tBu | tBu | H | H | D₂ |
| 4-fluoro | (R) | -C(O)NH-tBu | tBu | H | H | D₁ + D₂ |
| 4-fluoro | (R) | -C(O)NH-tBu | tBu | H | H | D₁ |
| 4-fluoro | (R) | -C(O)NH-tBu | tBu | H | H | D₂ |
| 4-fluoro | (S) | -C(O)NH-tBu | cyclopropyl | H | H | D₁ + D₂ |

-continued
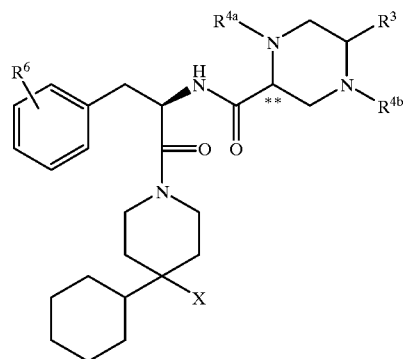
| R⁶ | ** | X | R³ | R⁴ᵃ | R⁴ᵇ | Diastereomer |
|---|---|---|---|---|---|---|
| 4-fluoro | (S) | -C(O)NH-C(CH₃)₃ | 1-methylcyclopropyl | H | H | D₁ |
| 4-fluoro | (S) | -C(O)NH-C(CH₃)₃ | 1-methylcyclopropyl | H | H | D₂ |
| 4-fluoro | (R) | -C(O)NH-C(CH₃)₃ | 1-methylcyclopropyl | H | H | D₁ + D₂ |
| 4-fluoro | (R) | -C(O)NH-C(CH₃)₃ | 1-methylcyclopropyl | H | H | D₁ |
| 4-fluoro | (R) | -C(O)NH-C(CH₃)₃ | 1-methylcyclopropyl | H | H | D₂ |
| 4-chloro | (R) | -C(O)NH-C(CH₃)₃ | 1-methylcyclopropyl | H | H | D₁ + D₂ |
| 4-chloro | (R) | -C(O)NH-C(CH₃)₃ | 1-methylcyclopropyl | H | H | D₁ |

-continued
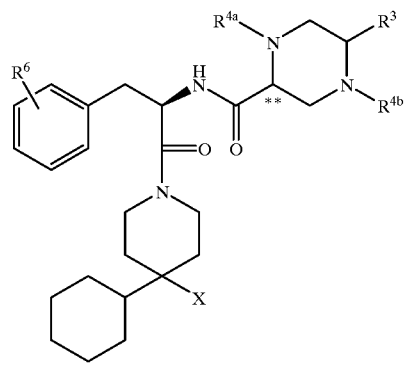
| R⁶ | ** | X | R³ | R⁴ᵃ | R⁴ᵇ | Diastereomer |
|---|---|---|---|---|---|---|
| 4-chloro | (R) | -C(O)NH-tBu | 1-methylcyclopropyl | H | H | D₂ |
| 4-chloro | (S) | -C(O)NH-tBu | Ph | H | H | D₁ + D₂ |
| 4-fluoro | (S) | -C(O)NH-tBu | Ph | H | H | D₁ + D₂ |
| 4-fluoro | (S) | (4,4-dimethyl-2-oxo-oxazolidin-3-yl)methyl | Ph | H | H | D₁ + D₂ |
| 4-chloro | (S) | -C(O)NH-tBu | Ph | Me | Me | D₁ |
| 4-chloro | (S) | -C(O)NH-tBu | Ph | Me | Me | D₂ |
| 4-fluoro | (S) | -C(O)NH-tBu | Ph | Me | Me | D₁ |

-continued
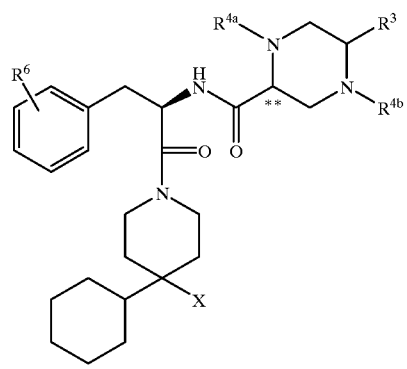
Ib
| R⁶ | ** | X | R³ | R⁴ᵃ | R⁴ᵇ | Diastereomer |
|---|---|---|---|---|---|---|
| 4-fluoro | (S) | -C(O)NH-tBu | Ph | Me | Me | D₂ |
| 4-fluoro | (S) | -CH₂-(4,4-dimethyl-oxazolidin-2-one-3-yl) | Ph | Me | Me | D₁ |
| 4-chloro | (R) | -C(O)NH-tBu | Ph | Me | Me | D₁ |
| 4-chloro | (R) | -C(O)NH-tBu | Ph | Me | Me | D₂ |
| 4-fluoro | (R) | -C(O)NH-tBu | Ph | Me | Me | D₁ |
| 4-fluoro | (R) | -C(O)NH-tBu | Ph | Me | Me | D₂ |
| 4-fluoro | (R) | -CH₂-(4,4-dimethyl-oxazolidin-2-one-3-yl) | Ph | Me | Me | D₁ |

-continued
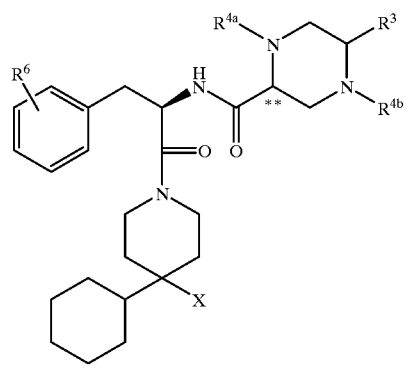
Ib
| R⁶ | ** | X | R³ | R⁴ᵃ | R⁴ᵇ | Diastereomer |
|---|---|---|---|---|---|---|
| 3,4-difluoro | (S) | -C(O)NH-tBu | H | H | H | |
| 3,4-difluoro | (S) | -C(O)NH-tBu | H | H | Me | |
| 3,4-difluoro | (S) | -C(O)NH-tBu | iPr | H | H | D₁ + D₂ |
| 3,4-difluoro | (S) | -C(O)NH-tBu | iPr | H | H | D₁ |
| 3,4-difluoro | (S) | -C(O)NH-tBu | iPr | H | H | D₂ |
| 3,5-difluoro | (S) | -C(O)NH-tBu | H | H | Me | |
| 3,5-difluoro | (S) | -C(O)NH-tBu | iPr | H | H | |

-continued
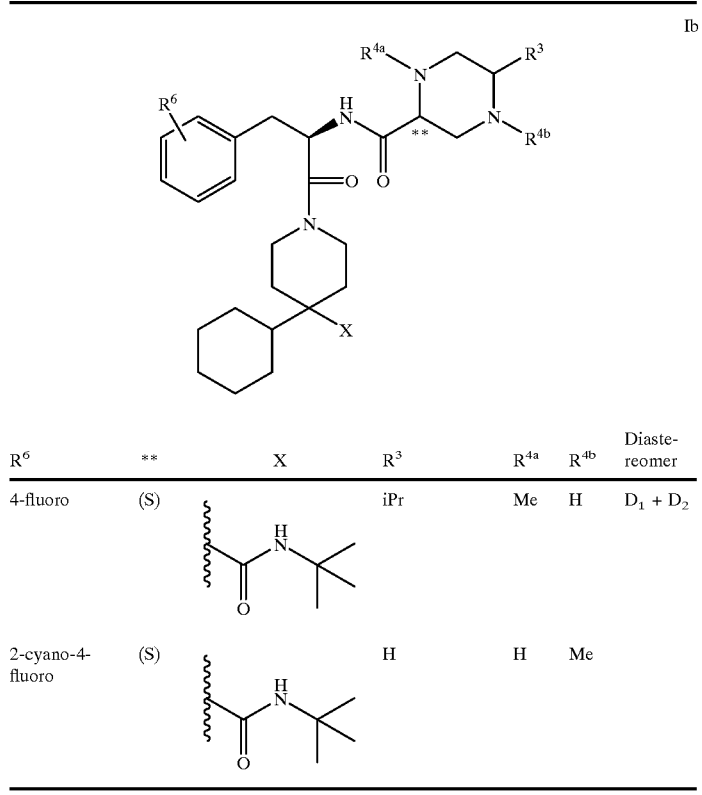
| $R^6$ | ** | X | $R^3$ | $R^{4a}$ | $R^{4b}$ | Diastereomer |
|---|---|---|---|---|---|---|
| 4-fluoro | (S) | | iPr | Me | H | $D_1 + D_2$ |
| 2-cyano-4-fluoro | (S) | | H | H | Me | |
Further illustrative but nonlimiting examples of compounds of the present invention that are useful as melanocortin receptor agonists are the following:
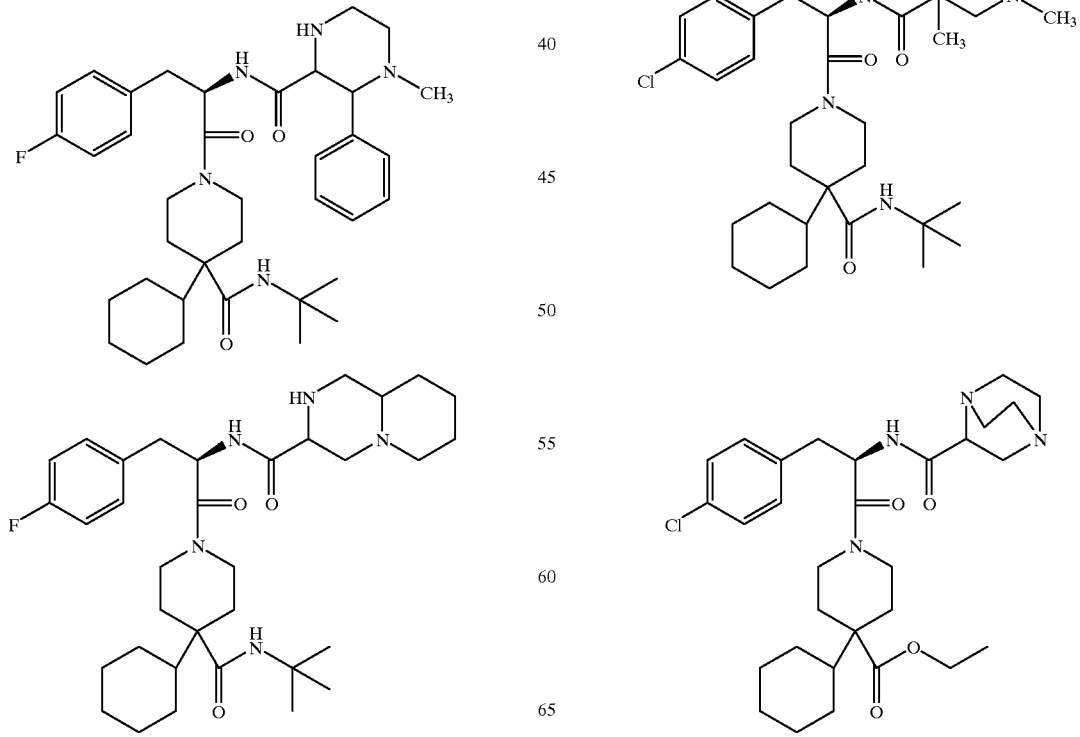

69
-continued
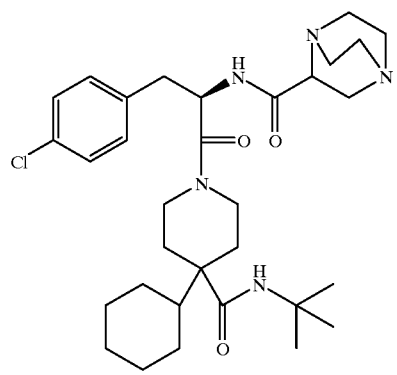
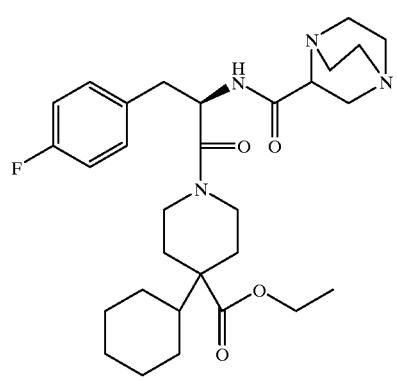
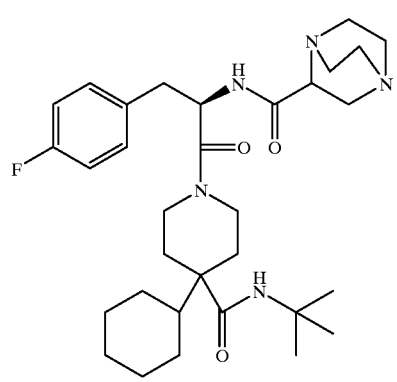
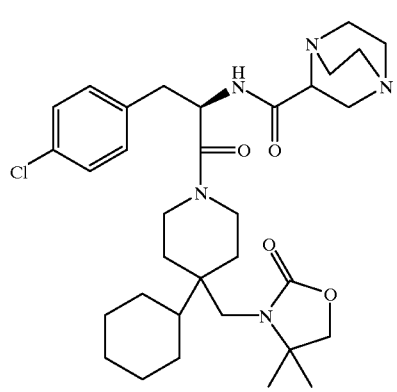
70
-continued
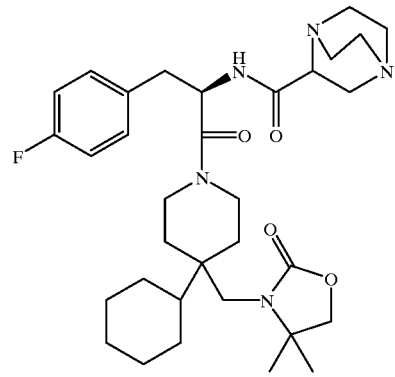
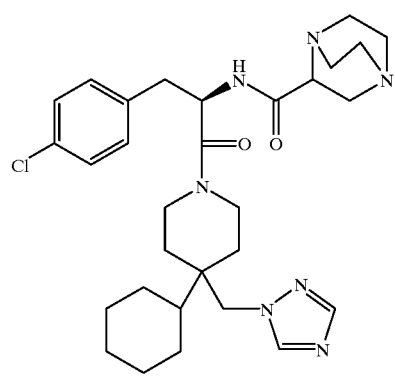
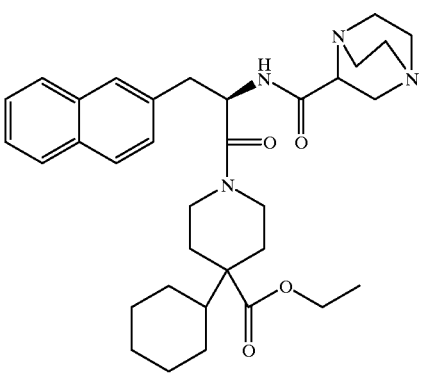
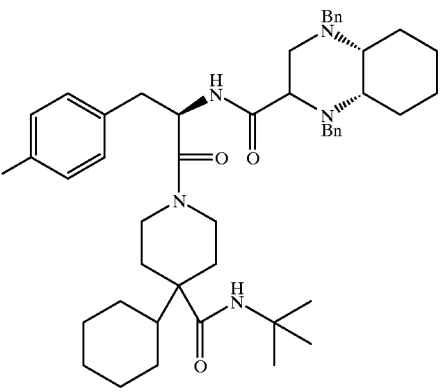

71
-continued
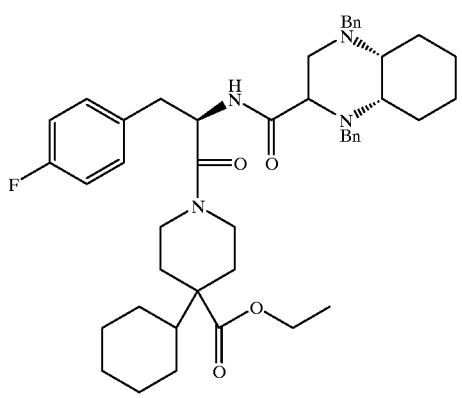
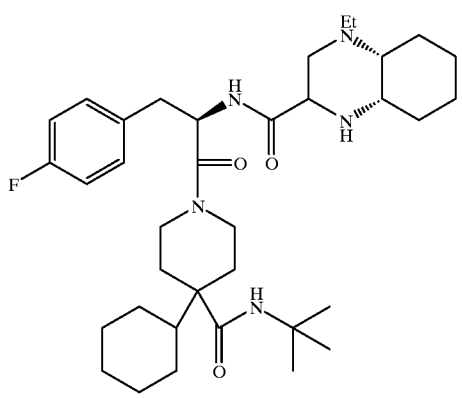
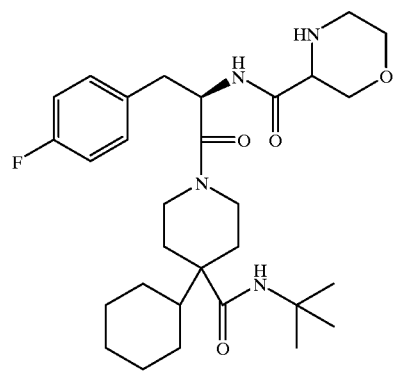
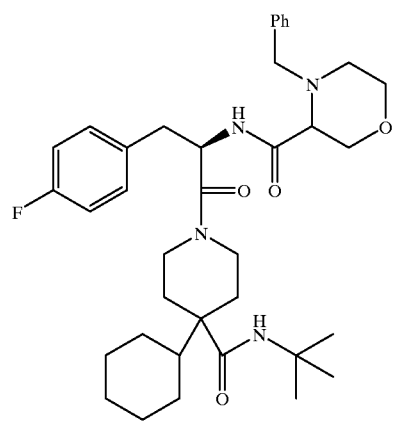
72
-continued
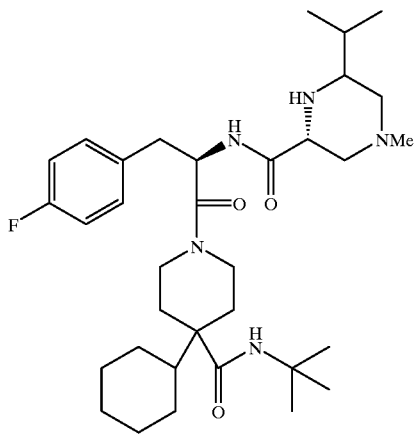
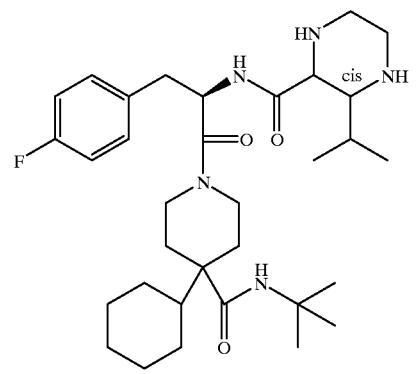
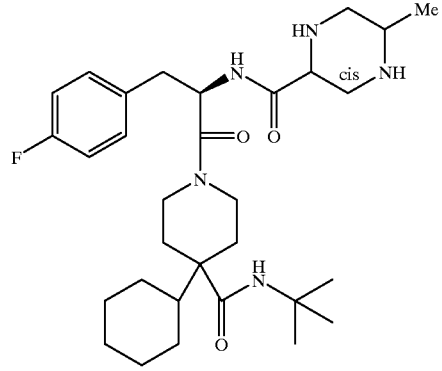
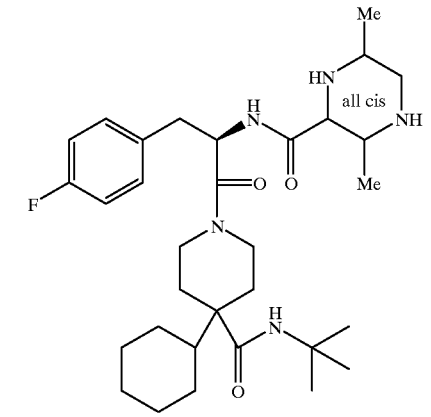

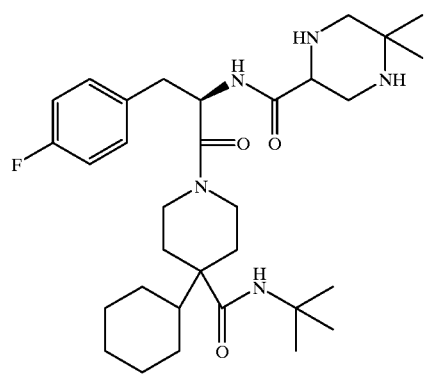
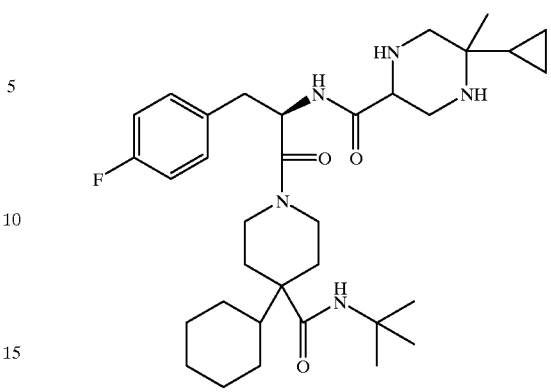
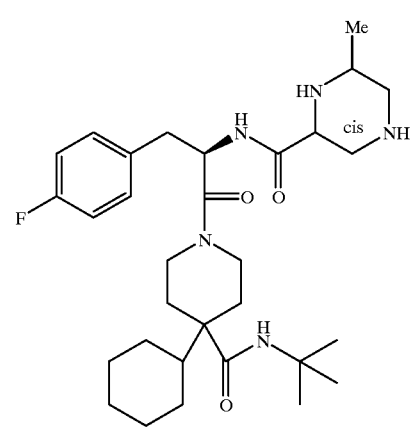
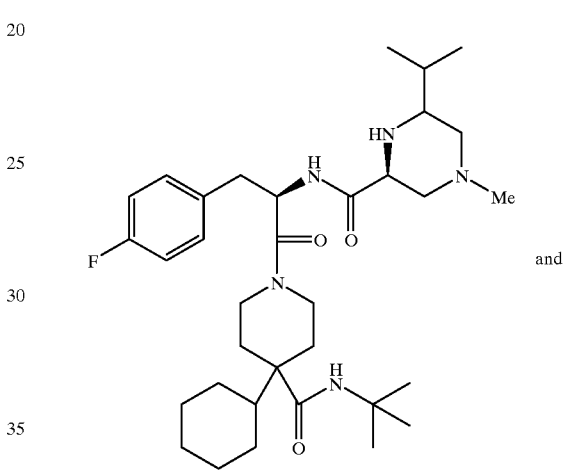
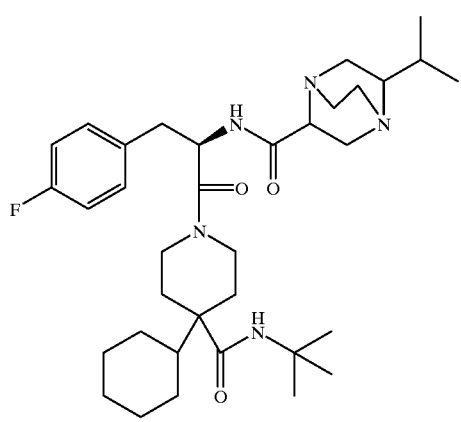
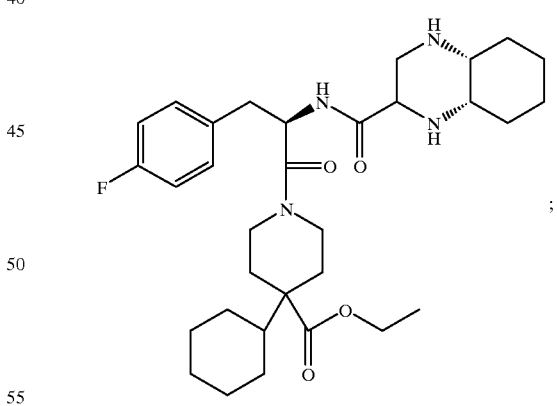
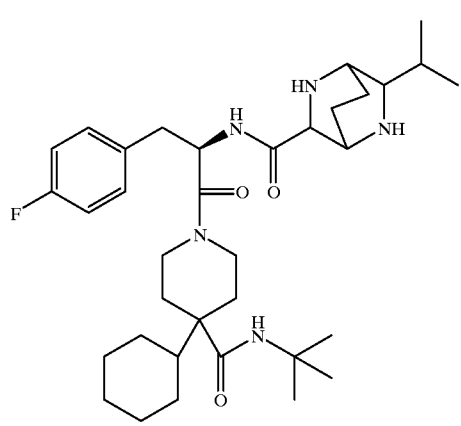
or a pharmaceutically acceptable salt thereof.
Even further illustrative of the compounds of the present invention are those of structural formula Ic with the indicated stereochemistry at the stereogenic center marked with ** selected from the group consisting of:

Ic

| Y | X | R⁶ | ** | R³ | R⁴ᵇ |
|---|---|---|---|---|---|
| cyclohexyl | -C(O)NH-tBu | F | (S) | H | CH₃ |
| cyclohexyl | -C(O)OEt | F | (S) | H | CH₃ |
| cyclohexyl | -CH₂C(O)NEt₂ | F | (S) | H | CH₃ |
| cyclohexyl | -CH₂-(4,4-dimethyl-2-oxo-oxazolidin-3-yl) | F | (R) | H | CH₃ |
| 4-methylcyclohexyl | -C(O)NH-tBu | F | (S) | H | CH₃ |
| cyclohexyl | -C(O)NH-tBu | Cl | (R) | H | CH₃ |
| cyclohexyl | -C(O)NH-tBu | F | (S) | cyclopropyl | H |

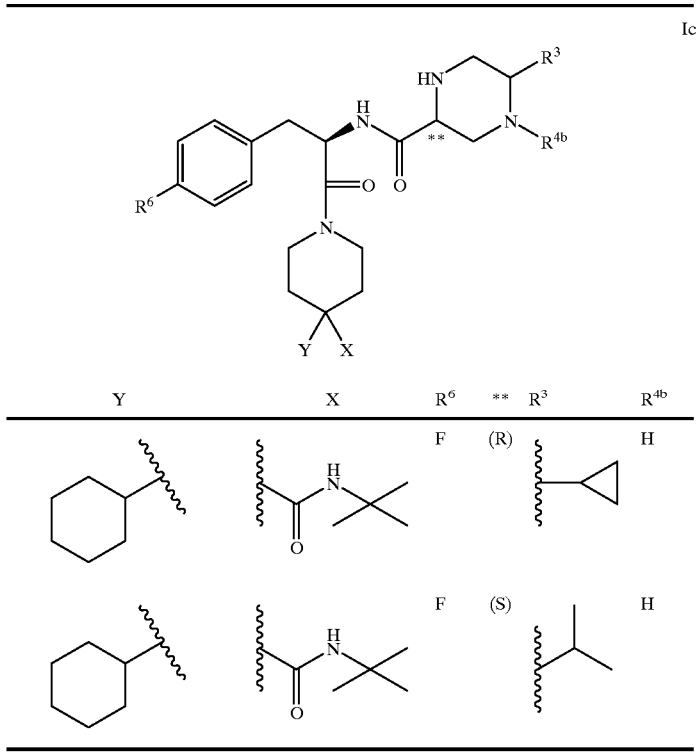

The compounds of structural Formula I are effective as melanocortin receptor agonists and are particularly effective as selective agonists of the MC-4R. They are therefore useful for the treatment and/or prevention of disorders responsive to the activation of MC-4R, such as obesity, diabetes as well as male and/or female sexual dysfunction, in particular, erectile dysfunction, and further in particular, male erectile dysfunction.

Another aspect of the present invention provides a method for the treatment or prevention of obesity or diabetes in a mammal which comprises administering to said mammal an effective amount of a compound of formula I.

Another aspect of the present invention provides a method for the treatment or prevention of male or female sexual dysfunction including erectile dysfunction which comprises administering to a patient in need of such treatment or prevention an effective amount of a compound of formula I.

Yet another aspect of the present invention provides a pharmaceutical composition comprising a compound of formula I and a pharmaceutically acceptable carrier.

Throughout the instant application, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The term "halogen" is intended to include the halogen atoms fluorine, chlorine, bromine and iodine.

The term "aryl" includes phenyl and naphthyl.

The term "heteroaryl" includes mono- and bicyclic aromatic rings containing from 1 to 4 heteroatoms selected from nitrogen, oxygen and sulfur. "5- or 6-membered heteroaryl" are monocyclic heteroaromatic rings, examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

The term "5- or 6-membered carbocyclyl" is intended to include non-aromatic rings containing only carbon atoms such as cyclopentyl and cyclohexyl.

The term "5 and 6-membered heterocyclyl" is intended to include non-aromatic heterocycles containing one to four heteroatoms selected from nitrogen, oxygen and sulfur. Examples of a 5 or 6-membered heterocyclyl include piperidine, morpholine, thiamorpholine, pyrrolidine, imidazolidine, tetrahydrofuran, piperazine, and the like.

Certain of the above defined terms may occur more than once in the above formula and upon such occurrence each term shall be defined independently of the other; thus for example, $NR^7R^7$ may represent $NH_2$, $NHCH_3$, $N(CH_3)CH_2CH_3$, and the like.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

"Erectile dysfunction" is a disorder involving the failure of a male mammal to achieve erection, ejaculation, or both.

Symptoms of erectile dysfunction include an inability to achieve or maintain an erection, ejaculatory failure, premature ejaculation, or inability to achieve an orgasm. An increase in erectile dysfunction is often associated with age and is generally caused by a physical disease or as a side-effect of drug treatment.

By a melanocortin receptor "agonist" is meant an endogenous or drug substance or compound that can interact with a melanocortin receptor and initiate a pharmacological response characteristic of the melanocortin receptor. By a melanocortin receptor "antagonist" is meant a drug or a compound that opposes the melanocortin receptor-associated responses normally induced by another bioactive agent. The "agonistic" properties of the compounds of the present invention were measured in the functional assay described below. The functional assay discriminates a melanocortin receptor agonist from a melanocortin receptor antagonist.

By "binding affinity" is meant the ability of a compound/drug to bind to its biological target, in the the present instance, the ability of a compound of formula I to bind to a melanocortin receptor. Binding affinities for the compounds of the present invention were measured in the binding assay described below and are expressed as IC50's.

"Efficacy" describes the relative intensity with which agonists vary in the response they produce even when they occupy the same number of receptors and with the same affinity. Efficacy is the property that enables drugs to produce responses. Properties of compounds/drugs can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events, which, from the binding of the drug to the receptor, leads to the desired biological effect.

The functional activities expressed as $EC_{50}$'s and the "agonist efficacy" for the compounds of the present invention at a particular concentration were measured in the functional assay described below.

Optical Isomers-Diastereomers-Geometric Isomers-Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixtures thereof are encompassed with compounds of Formula I.

Compounds of the Formula I may be separated into their individual diastereoisomers by, for example, fractional crystallization from a suitable solvent, for example methanol or ethyl acetate or a mixture thereof, or via chiral chromatography using an optically active stationary phase.

Alternatively, any diastereomer of a compound of the general Formula I or Ia may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

It will be understood that, as used herein, references to the compounds of Formula I are meant to also include the pharmaceutically acceptable salts.

Utility

Compounds of formula I are melanocortin receptor agonists and as such are useful in the treatment, control or prevention of diseases, disorders or conditions responsive to the activation of one or more of the melanocortin receptors including, but are not limited to, MC-1, MC-2, MC-3, MC-4, or MC-5. Such diseases, disorders or conditions include, but are not limited to, obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction (including impotence, loss of libido and erectile dysfunction), fever, inflammation, immunemodulation, rheumatoid arthritis, skin tanning, acne and other skin disorders, neuroprotective and cognitive and memory enhancement including the treatment of Alzheimer's disease. Some compounds encompassed by formula I show highly selective affinity for the melanocortin-4 receptor relative to MC-1R, MC-2R, MC-3R, and MC-5R, which makes them especially useful in the prevention and treatment of obesity, as well as male and/or female sexual dysfunction, including erectile dysfunction.

"Male sexual dysfunction" includes impotence, loss of libido, and erectile dysfunction.

"Erectile dysfunction" is a disorder involving the failure of a male mammal to achieve erection, ejaculation, or both.

Symptoms of erectile dysfunction include an inability to achieve or maintain an erection, ejaculatory failure, premature ejaculation, or inability to achieve an orgasm. An increase in erectile dysfunction and sexual dysfunction can have numerous underlying causes, including but not limited to (1) aging, (b) an underlying physical dysfunction, such as trauma, surgery, and peripheral vascular disease, and (3) side-effects resulting from drug treatment, depression, and other CNS disorders.

"Female sexual dysfunction" can be seen as resulting from multiple components including dysfunction in desire, sexual arousal, sexual receptivity, and orgasm related to disturbances in the clitoris, vagina, periurethral glans, and other trigger points of sexual function. In particular, anatomic and functional modification of such trigger points may diminish the orgasmic potential in breast cancer and gynecologic cancer patients. Treatment of female sexual dysfunction with an MC-4 receptor agonist can result in improved blood flow, improved lubrication, improved sensation, facilitation of reaching orgasm, reduction in the refractory period between orgasms, and improvements in arousal and desire. In a broader sense, "female sexual dysfunction" also incorporates sexual pain, premature labor, and dysmenorrhea.

Administration and Dose Ranges

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally or topically.

The effective dosage of active ingredient employed may vary depending on the particular compound employed, the mode of administration, the condition being treated and the severity of the condition being treated. Such dosage may be ascertained readily by a person skilled in the art.

When treating obesity, in conjunction with diabetes and/or hyperglycemia, or alone, generally satisfactory results are obtained when the compounds of the present invention are administered at a daily dosage of from about 0.001 milligram to about 100 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

When treating diabetes mellitus and/or hyperglycemia, as well as other diseases or disorders for which compounds of formula I are useful, generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

For the treatment of sexual dysfunction compounds of the present invention are given in a dose range of 0.001 milligram to about 100 milligram per kilogram of body weight, preferably as a single dose orally or as a nasal spray.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to:

(a) insulin sensitizers including (i) PPARγ agonists such as the glitazones (e.g. troglitazone, pioglitazone, englitazone, MCC-555, BR-49653 and the like), and compounds disclosed in WO97/27857, 97/28115, 97/28137 and 97/27847; (ii) biguanides such as metformin and phenformin;

(b) insulin or insulin mimetics;

(c) sulfonylureas, such as tolbutamide and glipizide;

(d) α-glucosidase inhibitors (such as acarbose), (e) cholesterol lowering agents such as (i) HMG-CoA reductase inhibitors (lovastatin, simvastatin, pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activater receptor α agonists such as fenofibric acid derivatives (gemfibrozil, clofibrate, fenofibrate and benzafibrate), (iv) inhibitors of cholesterol absorption for example beta-sitosterol and (acyl CoA:cholesterol acyltransferase) inhibitors for example melinamide, (v) probucol, (vi) vitamin E, and (vii) thyromimetics;

(f) PPARδ agonists, such as those disclosed in WO97/28149;

(g) antiobesity compounds, such as fenfluramine, dexfenfluramine, phentermine, sibutramine, orlistat, or $β_3$ adrenergic receptor agonists;

(h) feeding behavior modifying agents, such as neuropeptide Y antagonists (e.g. neuropeptide Y5) such as those disclosed in WO 97/19682, WO 97/20820, WO 97/20821, WO 97/20822 and WO 97/20823;

(i) PPARα agonists such as described in WO 97/36579 by Glaxo;

(j) PPARγ antagonists as described in WO97/10813;

(k) serotonin reuptake inhibitors such as fluoxetine and sertraline;

(l) growth hormone secretagogues such as MK-0677; and (m) agents useful in the treatment of male and/or female sexual dysfunction, such as type V cyclic-GMP-specific phosphodiesterase (PDE-V) inhibitors, including sildenafil and IC-351; alpha-adrenergic receptor antagonists, including phentolamine and yohimbine and pharmaceutically acceptable salts thereof; and dopamine receptor agonists, such as apomorphine.

In one embodiment of a combination for the treatment of male or female sexual dysfunction, the second ingredient to be combined with a compound of Formula I can be a type V cyclic-GMP-specific phosphodiesterase (PDE-V) inhibitor, such as sildenafil and IC-351 or a pharmaceutically acceptable salt thereof; an alpha-adrenergic receptor antagonist, such as phentolamine and yohimbine or a pharmaceutically acceptable salt thereof; or a dopamine receptor agonist, such as apomorphine or a pharmaceutically acceptable salt thereof.

Pharmaceutical Compositions

Another aspect of the present invention provides pharmaceutical compositions which comprises a compound of Formula I and a pharmaceutically acceptable carrier. The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

In the Schemes and Examples below, various reagent symbols and abbreviations have the following meanings:

| | |
|---|---|
| BOC | t-butyloxycarbonyl |
| Bu | butyl |
| calc. | calculated |
| CBZ | benzyloxycarbonyl |
| DCM | dichloromethane |
| DEAD | diethyl azodicarboxylate |
| DIEA | diisopropylethylamine |
| DMAP | 4-dimethylamino-pyridine |
| DMF | N,N-dimethylformamide |
| EDC | 1-(3-dimethylaminopropyl)3-ethylcarbodiimide HCl |
| eq. | equivalent(s) |
| ESI-MS | electron spray ion-mass spectroscopy |
| Et | ethyl |
| EtOAc | ethyl acetate |
| HOAt | 1-hydroxy-7-azabenzotriazole |
| HOBt | 1-hydroxybenzotriazole hydrate |
| HPLC | high performance liquid chromatography |
| LC-MS | liquid chromatography-mass spectroscopy |
| LDA | lithium diisopropylamide |
| MC-xR | melanocortin receptor (x being a number) |
| Me | methyl |
| MF | molecular formula |
| Ms | methanesulfonyl |
| NMM | N-methylmorpholine |
| OIC | octahydroindole-2-carboxylic acid |
| Ph | phenyl |
| Phe | phenylalanine |
| Pr | propyl |
| prep. | prepared |
| PyBrop | bromo-tris-pyrrolidino-phosphonium hexafluorophosphate |
| TFA | trifluoroacetic acid |
| THF | tetrahydrofuran |
| Tic | 1,2,3,4-tetrahydroisoquinoline-3-carboxylic acid |
| TLC | thin-layer chromatography |

PREPARATION OF COMPOUNDS OF THE INVENTION

The novel compounds of the present invention can be prepared according to the procedure of the following schemes and examples, using appropriate starting materials and are further exemplified by the following specific examples. The compounds illustrated in the examples are not, however, to be construed as forming the only genus that is considered as the invention. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

The following Schemes and Examples describe procedures for making representative compounds of the present invention. Moreover, by utilizing the procedures described in detail in PCT International Applications WO 99/64002 (Dec. 16, 1999) and WO 00/74679 (Dec. 14, 2000), which are incorporated by reference herein in their entirety, in conjunction with the disclosure contained herein, one of ordinary skill in the art can readily prepare additional compounds of the present invention claimed herein.

The phrase standard peptide coupling reaction conditions means coupling a carboxylic acid with an amine using an acid activating agent such as EDC, DCC, and BOP in a inert solvent such as dichloromethane in the presence of a catalyst such as HOBT. The use of protecting groups for amine and carboxylic acid to facilitate the desired reaction and minimize undesired reactions is well documented. Conditions required to remove protecting groups are found in standard textbooks such as Greene, T, and Wuts, P. G. M., *Protective Groups in Organic Synthesis,* John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation with hydrogen in the presence of a noble metal or its oxide such as palladium on activated carbon in a protic solvent such as ethanol. In cases where catalytic hydrogenation is contraindicated due to the presence of other potentially reactive functionality, removal of CBZ groups can also be achieved by treatment with a solution of hydrogen bromide in acetic acid, or by treatment with a mixture of TFA and dimethylsulfide. Removal of BOC protecting groups is carried out in a solvent such as methylene chloride or methanol or ethyl acetate, with a strong acid, such as trifluoroacetic acid or hydrochloric acid or hydrogen chloride gas.

It is understood that in some cases the order of carrying out the reaction schemes below may be varied to facilitate the reaction or to avoid unwanted reaction products.

PREPARATION OF 4-SUBSTITUTED PIPERIDINE INTERMEDIATES

The preparation of 4-substituted piperidine intermediates for coupling with the appropriate carboxylic acid intermediates is disclosed in PCT International Application WO 00/74679 (Dec. 14, 2000), which is incorporated by reference herein in its entirety. The synthesis of additional 4-substituted piperidine intermediates needed to prepare the compounds of the present invention is provided below.

Piperidine Intermediate 1

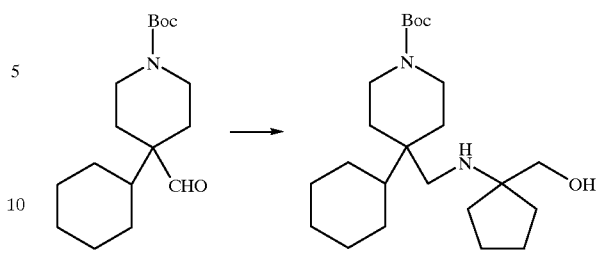

To a solution of 4-cyclohexyl 4-formyl-N-(tertbutyloxycarbonyl)piperidine (2.56 g, 8.68 mmol) in toluene (100 ml) was added acetic acid (2 ml) and 1-amino-1-cyclopentanemethanol (1.0 g, 8.68 mmol). After refluxing by using a Dean-Stark apparatus for 11 hours, the reaction mixture was concentrated. The residue was dissolved in acetic acid (70 ml) and hydrogenated overnight in the presence of platinum oxide (500 mg) under a balloon atmosphere of hydrogen gas. The catalyst was filtered off and solvent was removed to give a colorless oil, which was dissolved in methanol and made basic by addition of NaOH (5N, 4 ml) and concentrated. The residue was partitioned between water and $CH_2Cl_2$, the two layers separated, and the aqueous layer extracted with $CH_2Cl_2$. The combined organic extracts were washed with brine, dried over $MgSO_4$ and concentrated to give the title compound as a colorless oil (2.1 g).

MS: calc.for $C_{23}H_{42}N_2O_3$: 394.3; Found: 395 (M+1), 417 (M+Na).

Piperidine Intermediate 2

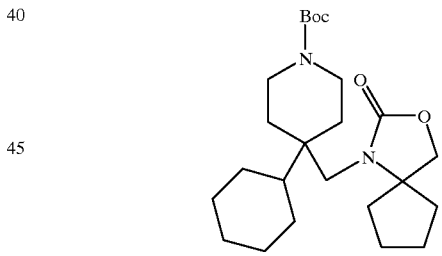

To a solution of Intermediate 1 (2.1 g, 5.33 mmol) in $CH_2Cl_2$ (70 ml) at 0° was added DMAP (0.65 g, 5.33 mmol), DIEA (3.76 ml, 21.3 mmol) followed by slow addition of phosgene (4.1 ml, 8.0 mmol). After stirring the reaction mixture for one hour at 0° C., the ice-water bath was removed and the reaction mixture was continued to stir at room temperature overnight. The mixture was diluted with $CH_2Cl_2$, washed with water and brine, dried over $MgSO_4$ and concentrated to give crude product, which was purified by column chromatography on silica gel (2% EtOAc/$CH_2Cl_2$ to 5% EtOAc/$CH_2Cl_2$) to give the title compound as a white solid (1.2g).

MS: calc. for $C_{24}H_{40}N_2O_4$: 420.3; Found: (M+1), (M+Na).

Piperidine Intermediate 3

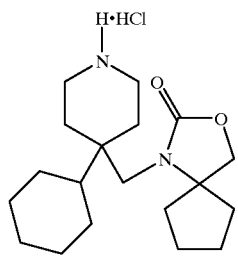

To the Intermediate 2 (1.2 g) was added hydrogen chloride (4.0 M in dioxane). The reaction mixture was stirred at room temperature for 30 minutes and the solvent was removed in vacuo to afford the title compound (1.2 g).

MS: calc.for $C_{19}H_{32}N_2O_2$: 320.3; Found: 321.1 (M+H).

Piperidine Intermediate 4

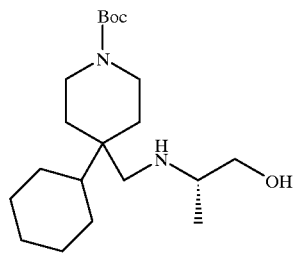

Intermediate 4 was prepared from (S)-(+)-2-amino-1-propanol in an analogous manner to the one described for the preparation of Intermediate 1.

MS: calc.for $C_{20}H_{38}N_2O_3$: 354; Found: 355 (M+H).

Piperidine Intermediate 5

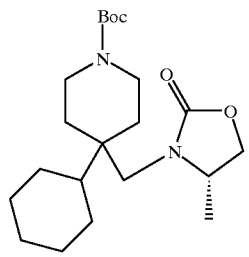

Intermediate 5 was prepared from Intermediate 4 in an analogous manner to the one described for the preparation of Intermediate 2.

MS: calc. for $C_{21}H_{36}N_2O_4$: 380.3; Found: 381 (M+H).

Piperidine Intermediate 6

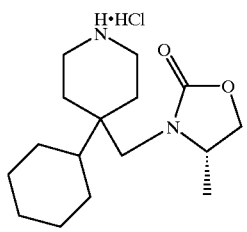

Intermediate 6 was prepared from Intermediate 5 in an analogous manner to the one described for the preparation of Intermediate 3.

MS: calc. for $C_{16}H_{28}N_2O_2$: 280.3; Found: 281 (M+H).

Piperidine Intermediate 7

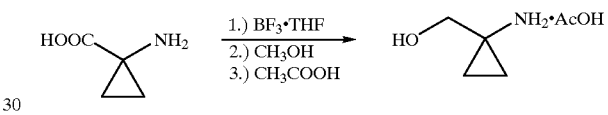

To a suspension of 1-aminocyclopropane-1-carboxylic acid (2.8 g, 27.7 mmol) in THF (20 ml) was added borane-tetrahydrofuran complex (100 ml, 100 mmol) slowly under nitrogen at room temperature. The reaction mixture was stirred at 70° C. overnight, then cooled to 0° C. After addition of methanol (12.2 ml, 300 mmol), the mixture was allowed to stir for 30 minutes. Then acetic acid (1.6 ml, 27.7 mmol) was added. The reaction mixture was concentrated to provide the title compound as a colorless oil (3.0 g).

Piperidine Intermediate 8

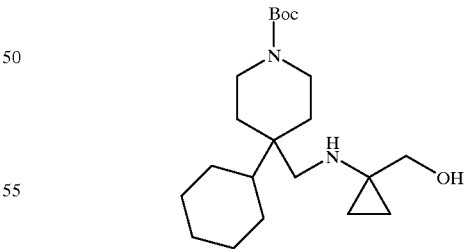

Intermediate 8 was prepared from Intermediate 7 in an analogous manner to the one described for the preparation of Intermediate 1.

MS: calc. for $C_{21}H_{38}N_2O_3$: 366.3; Found: 367 (M+H).

Piperidine Intermediate 9

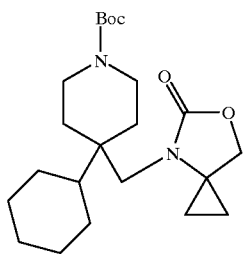

To a solution of Intermediate 8 (0.8 g, 2.18 mmol) in CH$_2$Cl$_2$ (40 ml) at 0° was added DMAP (0.266 g, 2.18 mmol), DIEA (1.52 ml, 8.74 mmol) and triphosgene (0.648 g, 2.18 mmol). After stirring the reaction mixture for one hour at 0° C., the ice-water bath was removed and the reaction mixture was allowed to stir at r.t. overnight. The mixture was diluted with CH$_2$Cl$_2$, washed with water and brine, dried over MgSO$_4$ and concentrated to give crude product, which was purified by column chromatography on silica gel (10% CH$_2$Cl$_2$/EtOAc) to give the title compound as a colorless oil (0.13 g).

ESI-MS: calc. for C$_{22}$H$_{36}$N$_2$O$_4$: 392; Found: 393 (M+1).

Piperidine Intermediate 10

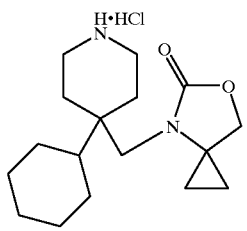

Intermediate 10 was prepared from Intermediate 9 in an analogous manner to the one described for the preparation of Intermediate 3.

MS: calc. for C$_{17}$H$_{28}$N$_2$O$_2$: 292.2; Found: 293 (M+H).

Piperidine Intermediate 11

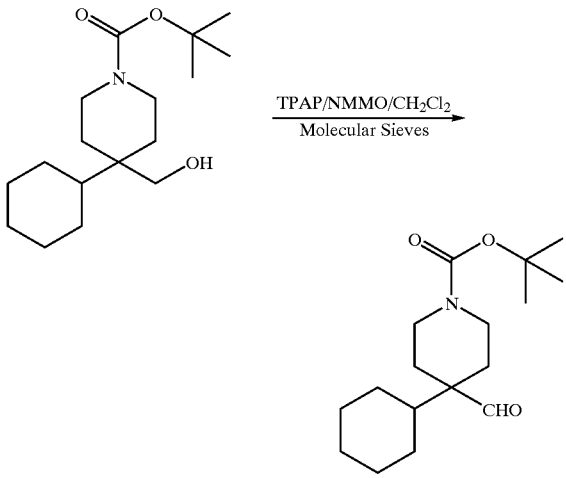

To a solution of the alcohol (9.41 g, 31.6 mmol) in CH$_2$Cl$_2$ (100 ml) at 0° C. containing molecular sieves (2 g) and 4-methylmorpholine N-oxide (NMMO) (4.449 g, 37.98 mmol) was added TPAP (1.12 g, 3.16 mmol). After stirring the reaction mixture at 0° C. for 0.5 h, the reaction mixture was warmed to room temperature and stirred further for 5 hrs. The reaction mixture was concentrated to half the volume, diluted with hexane (250 ml), filtered through a silica gel pad and concentrated to give pure title compound (9.4 g).

Piperidine Intermediate 12

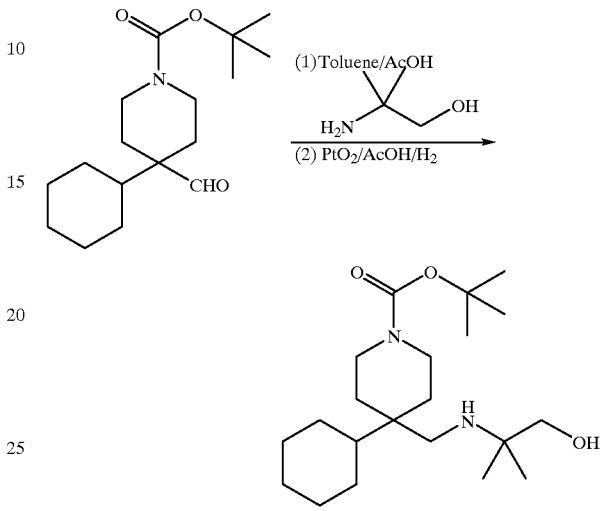

To a solution of the aldehyde (2 g, 6.7 mmol) in toluene (50 ml) was added acetic acid (500 µl). After stirring the reaction mixture at reflux temperature using Dean Stark apparatus for 8 hrs, the mixture was concentrated and dissolved in acetic acid (30 ml). To the mixture was added PtO$_2$ (500 mg) which was stirred under an atmosphere of H$_2$ overnight. The rection mixture was flushed with nitrogen, filtered and concentrated to give the title compound (2 g).

Piperidine Intermediate 13

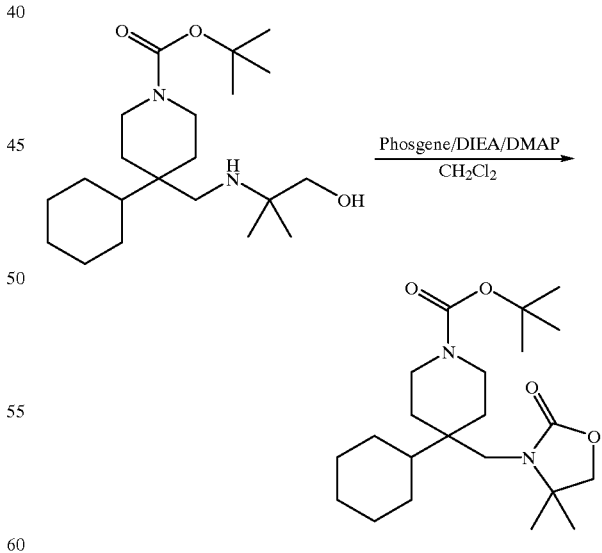

To a solution of the amino alcohol (4.96 g, 13.47 mmol) in CH$_2$Cl$_2$ at 0° C. containing DIEA (6.98 g, 53.9 mmol), DMAP (1.64 g, 13.47 mmol) was added slowly a toluene solution of phosgene (1.93M, 10.47 ml, 20.21 mmol). After stirring the reaction mixture for 1 hr at 0° C., the temperature was raised to room temperarure and stirred further for 2 hrs.

The reaction mixture was diluted with CH$_2$Cl$_2$, washed with water, brine, dried and concentrated. The residue was purified by column chromatography over silica gel (5% EtOAc/CH$_2$Cl$_2$) to give pure product (3.95 g).

Piperidine Intermediate 14

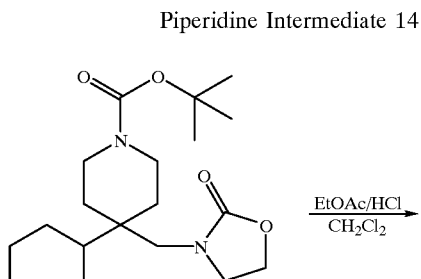

To a solution of Intermediate 13 (3.95 g) in CH$_2$Cl$_2$ was added 5 ml of a saturated HCl solution of EtOAc. After stirring the reaction mixture for 30 minutes at room temperature, the solvent was removed and the residue lyophilized from a benzene/methanol solution to afford the title compound (3.85 g).

Piperidine Intermediate 15

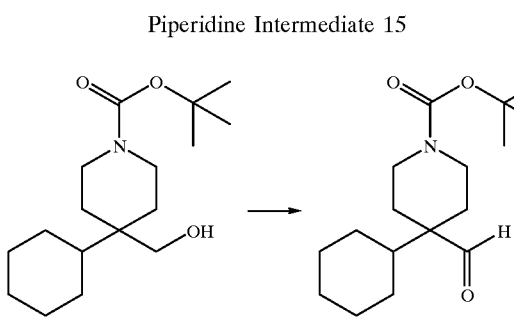

To a suspension of the alcohol (29 g, 97.5 mmol), 4-methylmorpholine-N-oxide (15.8 g, 134.6 mmol), and molecular sieves (15.0 gm) in DCM (500 mL) was added tetrapropylammonium perruthenate (TPAP, 1.03 g, 2.92 mmol) portionwise at room temperature. The mixture was stirred at room temperature for 30 min and TLC showed the reaction was completed. The mixture was filtered through a pad of silica gel, washed with DCM and 2:1 hexane/EtOAc. The mixture was then concentrated to give the aldehyde as a light yellow oil (28.5 g, 99%).

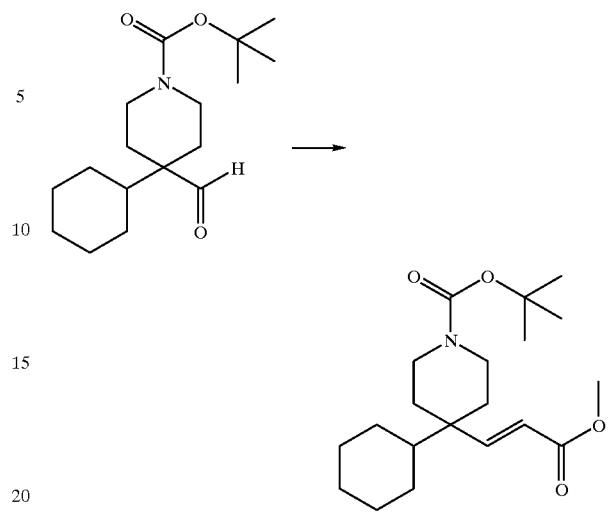

To a solution of methyl diethylphosphonoacetate (24.8 g, 117.8 mmol) in THF (400 mL) was add LDA (2.0 N, 58.9 mL, 117.8 mmol) at 0° C. After 30 min, a solution of the aldehyde from the previous step (28.5 g, 98.2 mmol) in THF (100 mL) was added, and the mixture was stirred at room temperature for two days and was then brought to reflux temperature overnight. The solvent was removed by rotary evaporation. The mixture was quenched with saturated NH$_4$Cl and extracted with EtOAc. The combined organic layers were washed with brine, dried, filtered, concentrated, and purified by medium pressure-liquid chromatography to give the unsaturated ester (31.3 g, 90.7%).

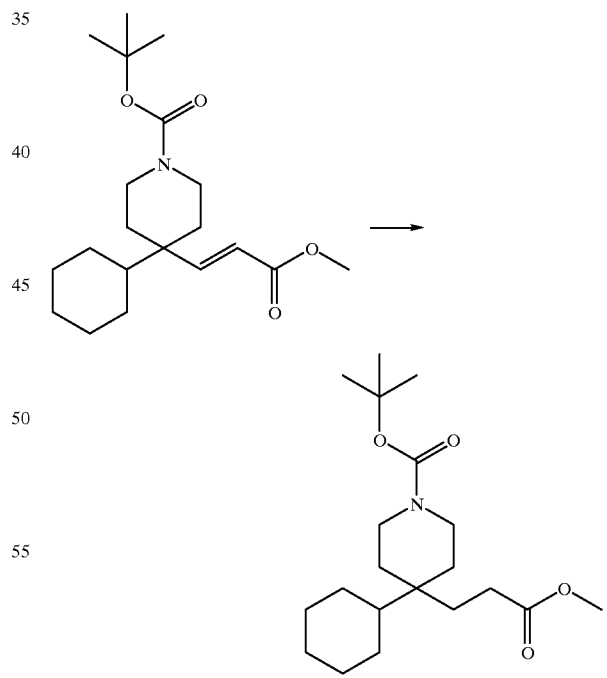

To a solution of the unsaturated ester (20 g, 56.9 mmol) in MeOH (200 mL) was added Pd/C (10%, 6.05 g), and the suspension was placed on a shaker under a hydrogen gas atmosphere (50 psi) overnight. The solid was filtered and washed with MeOH, and solvents were removed to give the product (19.3 g, 96%).

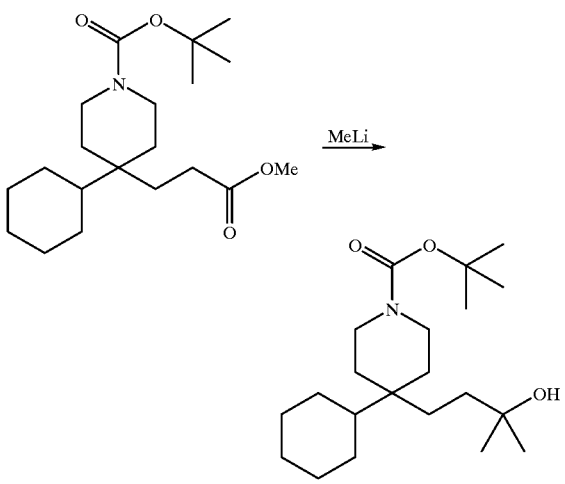

To a solution of the ester (2.9 g, 8.2 mmol) in dry THF (100 mL) was added MeLi (1.4 N in THF, 29.3 mL, 41.0 mmol) at −78° C. The mixture was stirred at −78° C. for 3 h and quenched with HCl (4.0 N in dioxane, 10.0 mL). The solvent was removed and the residue was washed with ether. The ether solution was concentrated to give the product (2.85 g, 98%) as an oil.

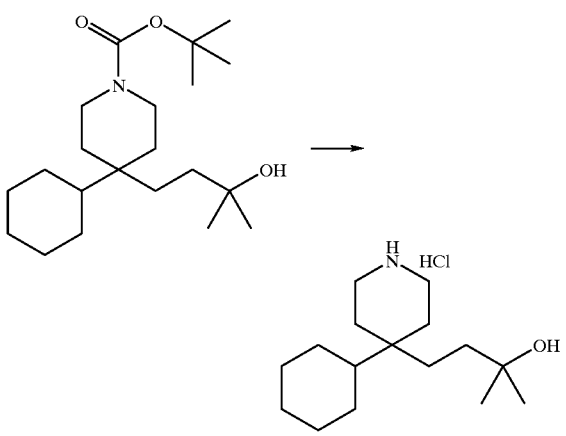

To a solution of HCl in dioxane (4 N, 14.1 mL, 56.6 mmol) was added the N-Boc-protected alcohol (2.0 g, 5.66 mmol) at room temperature. The mixture was stirred for 1 h and then the solution was evaporated to give Intermediate 15 (1.34 g, 81.7%) as a white solid.

Piperidine Intermediate 16

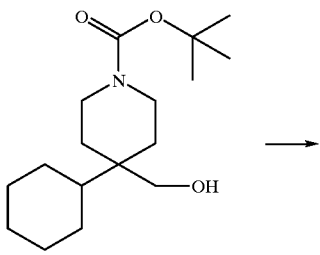

A dry flask was charged with NaH (60% in oil, 960 mg, 24 mmol) and anhydrous THF (40 mL). Added the alcohol starting material (5.95 g, 20 mmol) in dry THF (20 ml) through a two-ended needle under nitrogen atmosphere. Stirred at room temperature for about 60 min or until bubbling ceased, then added ethyl 2-bromoisopropionate (3.12 ml, 24 mmol). The mixture was stirred at room temperature overnight under nitrogen atmosphere. Quenched the reaction by adding the reaction mixture in portions to EtOAc (200 ml)/ice water (50 ml) with stirring. Transferred the mixture to a separatory funnel and added 1N HCl (30 ml). Extracted the aqueous solution with EtOAc (3×150 ml). Combined the organic phases which were dried over MgSO$_4$. Concentrated in vacuo and purified by flash column chromatography on silica gel using 20% EtOAc in hexane as eluent to give the desired product (1.0 g, 13%). LC-MS: M+1=398.5.

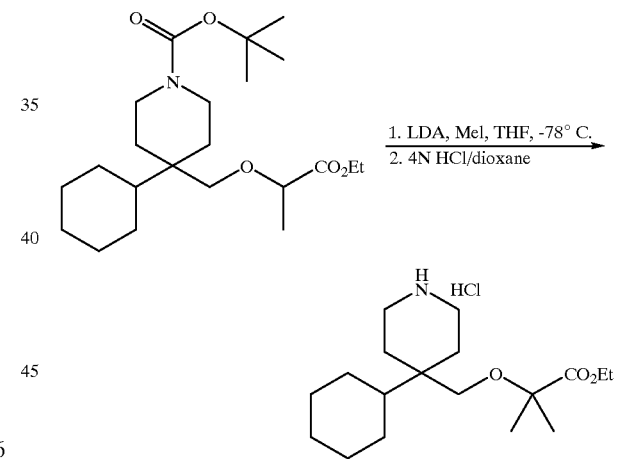

To the stirred solution of the Boc-derivative (1.0 g, 2.5 mmol) in dry THF (50 ml) was added LDA (1.5 M in cyclohexane, 2.0 ml, 3 mmol) dropwise at −78° C. The mixture was stirred at −78° C. for 30 min, then MeI (784 μl, 12.5 mmol) was added. Slowly warmed up to room temperature and stirred at room temperature overnight. Quenched the reaction by adding the reaction mixture in portions to EtOAc (200 ml)/ice water (50 ml) with stirring. Transferred the mixture to a separatory funnel and added 1N HCl (30 ml). Extracted the aqueous solution with EtOAc (3×150 ml). Combined the organic phases and dried over MgSO$_4$. Concentrated in vacuo and purified by flash column chromatography on silica gel using 20% EtOAc in hexane as eluent to give the desired product as a thick oil (681.8 mg). LC-MS: M+1=412.

$^1$H NMR (400 MHz, CDCl$_3$): δ 4.13 (q, J=7.2, 2 H), 3.52 (br, 2H), 3.25 (s, 2H), 3.18–3.12 (m, 2H), 1.75–1.61 (m,

5H), 1.53–1.388 (m, 4H), 1.42 (s, 9H), 1.35 (s, 6H), 1.27 (t, J=7.2, 3H), 1.10 (m, 6H).

Dissolved the above resulting compound in 4N HCl in dioxane (20 ml). Stirred at room temperature for about 60 min. Evaporated to dryness to give Intermediate 16 as a white solid (541 mg). LC-MS: M+1=312.

Piperidine Intermediate 17

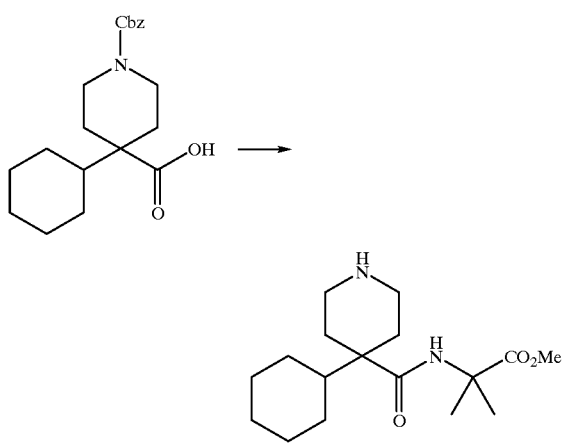

To the stirred solution of N-Cbz-4-cyclohexyl-piperidine-4-carboxylic acid (1.0 g, 2.9 mmol) in DCM (20 ml) was added oxalyl chloride (2.0M in DCM, 1.6 ml, 3.19 mmol) dropwise. Then added 3 drops of DMF. Stirred at room temperature for 1 hour and then evaporated to give the desired product. The crude mixture was used in the next step without further purification.

To the stirred solution of the acid chloride (2.9 mmol) in 1,2-dichloroethane (30 ml) was added α-methylalanine methyl ester (446 mg, 2.9 mmol) and DIEA (1.01 ml, 5.8 mmol). Stirred at 75° C. for 1 hour, and then at 60° C. overnight. Cooled to room temperature and diluted the mixture with DCM. Washed with 1N HCl, satd. NaHCO₃ and then satd. NaCl. Dried over Na₂SO₄ and concentrated in vacuo to give the crude desired product (1.2 g). LC-MS: 445 (M+1).

Dissolved intermediate from previous step (1.2 g, 2.7 mmol) in ethanol (50 ml). Added Pd-C (10%, 200 mg) and stirred at room temperature in the presence of hydrogen gas for two hours. Filtered off the catalyst, and concentrated in vacuo to give Intermediate 17 (663 mg). LC-MS: 312 (M+1).

Piperidine Intermediate 18

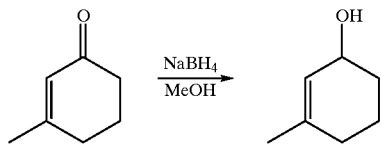

To a solution of the enone (6 mmol, 0.7 mL) in MeOH (20 mL) at 0° C. was added NaBH₄ (3 mmol, 113 mg). The reaction was stirred at room temp for 1 hr. Volatiles were removed and the residue partitioned between CH₂Cl₂ and 0.5M HCl. Organic phase was dried over MgSO₄ and concentrated to afford a clear colorless oil which was used in the next step without further purification.

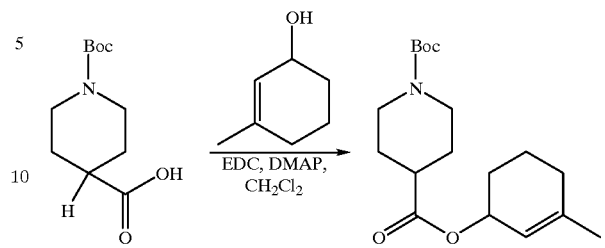

A solution of the acid (6 mmol, 1.38 g), EDC (12 mmol, 2.3 g), DMAP (ca.50 mg) and enol (ca. 6 mmol) in CH₂Cl₂ (25 mL) was stirred at room temp for 72 hours. Reaction mixture was poured into EtOAc (200 mL) and washed successively with 0.5M HCl, 1M NaOH, H₂O and brine, dried over Na₂SO₄ and concentrated. Chromatography over silica gel eluting with 500 mL of 5–10% EtOAc/hexane afforded a clear colorless oil (1.9 g).

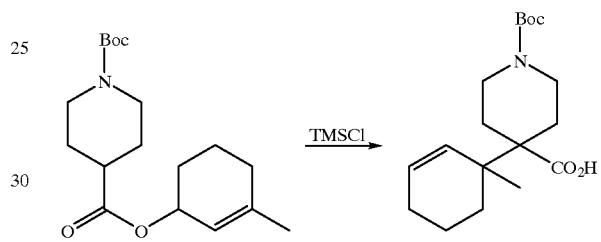

To a solution of LDA (2M in THF) (4.38 mmol, 2.2 mL) in THF (10 mL) at −78° C. was added the ester from the previous step (3.98 mmol, 1.3 g) in THF (2 mL) followed 30 min later by TMSCl (4.38 mmol, 0.6 mL). Resultant solution was allowed to warm to room temperature and then heated at reflux for 16 hr. After cooling to room temp, 2M HCl (5 mL) was added and stirring continued for 5 min. Resultant solution was partitioned between Et₂O (40 mL) and 2M HCl. The organic phase was washed with H₂O and brine, dried over Na₂SO₄ and concentrated. Chromatography over silica eluting with 20–30% EtOAc/hexane afforded the desired acid as an off-white solid (653 mg).

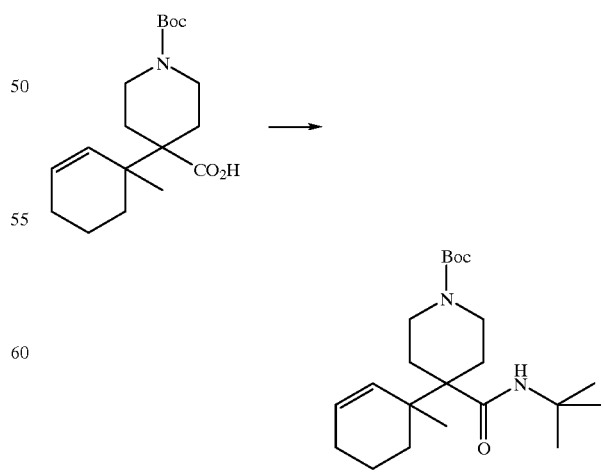

To a solution of the acid from the previous step (1.46 mmol, 474 mg) in CH₂Cl₂ (5 mL) at 0° C. was added oxalyl chloride (2M in CH$_2$Cl$_2$) (1.61 mmol, 0.81 mL) and DMF (0.05 mL) and the reaction stirred at 0° C. for 1 hr. Volatiles were removed, azeotroping with toluene and finally under high vacuum for 3 hr to afford the acid chloride. The acid chloride was dissolved in t-butylamine (5 mL) and the resultant cloudy solution was stirred at room temperature overnight. The reaction mixture was concentrated to afford a yellow solid. Chromatography over silica gel eluting with 50 mL of 5% then 100 mL of 10–20% EtOAc/hexane afforded the desired tert-butyl amide as a white solid (282 mg).

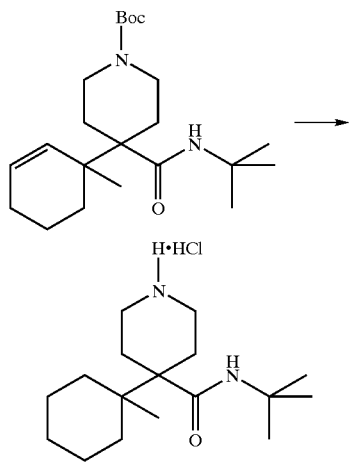

A suspension of Pd (10% on activated charcoal) (10 mol %, 79 mg) in a solution of the N-Boc derivative from the previous step (0.75 mmol, 282 mg) in MeOH containing 4M HCl (4M in dioxane) (1.5 mmol, 0.37 mL) was shaken under 45 psi of hydrogen gas for 60 hours. After work-up, the hydrochloride salt was used without further purification in the peptide coupling reaction.

Piperidine Intermediate 19

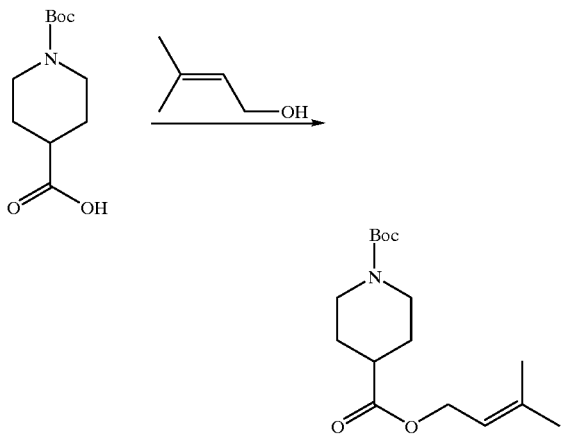

To a solution of the acid (10 mmol, 2.29 g) in CH$_2$Cl$_2$ (40 mL) at room temp was added EDC (20 mmol, 3.8 g) and DMAP (ca.50 mg) followed by 3-methyl-2-buten-1-ol (15 mmol, 1.52 mL). Resultant solution was stirred at room temp overnight. Reaction mixture was poured into EtOAc (200 mL) and washed successively with 0.5M HCl, 1M NaOH, H$_2$O and brine, dried over Na$_2$SO$_4$ and concentrated. Chromatography over silica gel eluting with 500 mL of 5% then 250 mL of 10% EtOAc/hexane afforded the ester as a clear colorless oil (2.97 g).

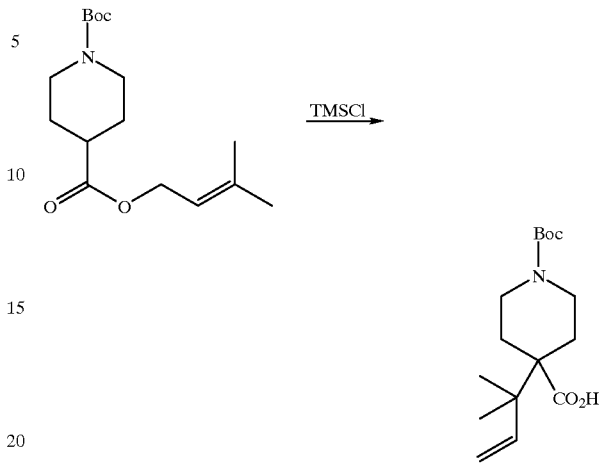

To a solution of LDA (2M in THF) (7.46 mmol, 3.73 mL) in THF (15 mL) at –78° C. was added the ester from the previous step (6.78 mmol, 2.02 g) in THF (3 mL) followed 30 min later by TMSCl (7.46 mmol, 0.95 mL). Resultant solution was allowed to warm to room temp and heated at reflux for 24 hr. After cooling to room temp, 2M HCl (5 mL) was added and stirring continued for 5 min. Resultant solution was partitioned between Et$_2$O (40 mL) and 2M HCl. The organic phase was washed with H$_2$O and brine, dried over Na$_2$SO$_4$ and concentrated. Chromatography over silica eluting with 10–20% EtOAc/hexane afforded the desired acid as a white solid (1.23 g).

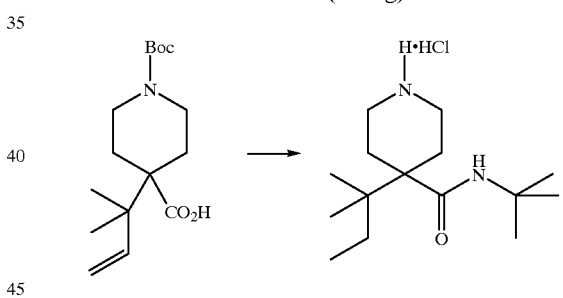

To a solution of the acid from the previous step (4.14 mmol, 1.23 g) in CH$_2$Cl$_2$ (10 mL) at 0° C. was added oxalyl chloride (2M in CH$_2$Cl$_2$) (4.55 mmol, 2.27 mL) and DMF (0.15 mL) and the reaction stirred at 0° C. for 1 hr. Volatiles were removed, azeotroping with toluene and finally under high vacuum for 3 hr to afford the acid chloride. The acid chloride was dissolved in t-butylamine (10 mL) and the resultant cloudy solution was left to stir at room temperature overnight. The reaction mixture was concentrated and partitioned between CH$_2$Cl$_2$ and 2M HCl. Organics were dried over Na$_2$SO$_4$ and concentrated. Chromatography over silica gel eluting with 10–30% EtOAc/hexane afforded a white solid (1.07 g).

A suspension of Pd (10% on activated charcoal) (10 mol %, 322 mg) in a solution of the compound from the previous step (3.03 mmol, 1.07 g) in MeOH (60 mL) containing 4M HCl in dioxane (6.06 mmol, 1.5 mL) was shaken under 45 psi of hydrogen gas for 5 hr. Reaction was filtered through a short pad of celite and concentrated. Residue was dissolved in EtOAc (20 mL) and HCl (4M in dioxane) (20 mL). Resultant solution was left to stir at room temp for 1 hr.

Volatiles were removed and the residue precipitated from a CH₂Cl₂ solution with Et₂O/hexane to afford Intermediate 19 as a white solid.

Piperidine Intermediate 20

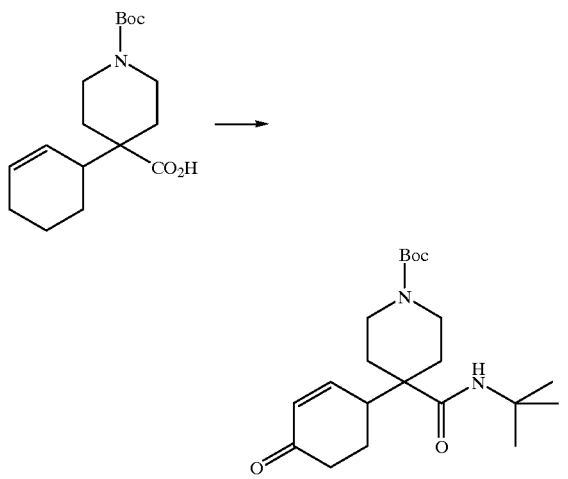

To a solution of CrO₃ (15.8 mmol, 1.59 g) in dry CH₂Cl₂ (20 mL) at −20° C. was added 3,5-dimethylpyrazole (15.8 mmol, 1.52 mg) in one portion. The resultant solution was stirred at −20° C. for 15 min before the addition of the cyclohexene intermediate (0.79 mmol, 289 mg) in CH₂Cl₂ (2.5 mL) over 3 min. The reaction mixture was warmed to −15° C. and stirred for a further 5 hr. 5N NaOH (51.5 mmol, 10.3 mL) was added and the emulsion stirred at 0° C. for 1 hr then at rt overnight. Aqueous phase was extracted with CH₂Cl₂, and the combined organics were washed with 1N HCl, water, satd NaHCO₃ and brine, dried over Na₂SO₄ and concentrated. Chromatography over silica gel eluting with 50 mL of 0, 2.5, 5, and 10% EtOAc/hexane afforded the cyclohexenone as a white solid (135 mg).

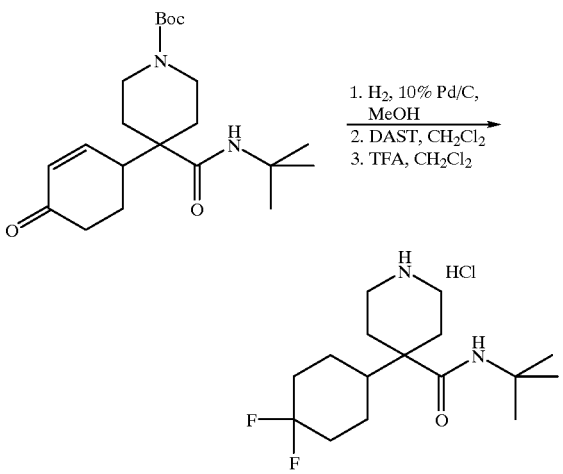

A suspension of Pd (10% on activated charcoal) (20 mol %, 76 mg) in a solution of the cyclohexenone (0.36 mmol, 135 mg) in MeOH was shaken under 45 psi of hydrogen gas for 60 hr. The reaction mixture was filtered through a short pad of celite and concentrated to afford a clear colorless gum. Chromatography over silica gel eluting with 50 mL of 0, 2.5, 5, 10, and 20% Me₂CO/CH₂Cl₂ afforded the cyclohexanone as a white solid (111 mg).

To a solution of the cyclohexanone (0.29 mmol, 111 mg) in CH₂Cl₂ was added (diethylamino)sulfur trifluoride (0.73 mmol, 0.1 mL). Resultant solution was left to stir at room temp for 24 hours. Reaction mixture was poured into saturated NaHCO₃. Organic phase was washed with NaHCO₃, dried over Na₂SO₄ and concentrated. Chromatography over silica gel eluting with 10–30% EtOAc/hexane afforded the difluorocyclohexane intermediate as a white solid (84 mg)

A solution of the difluorocyclohexane intermediate from the previous step (0.2 mmol, 80 mg) in CH₂Cl₂ and TFA was stirred at room temp for 1 hr. Volatiles were removed and the residue partitioned between NaOH and EtOAc. Organic phase was dried over Na₂SO₄ and concentrated to give Intermediate 20.

Piperidine Intermediate 21

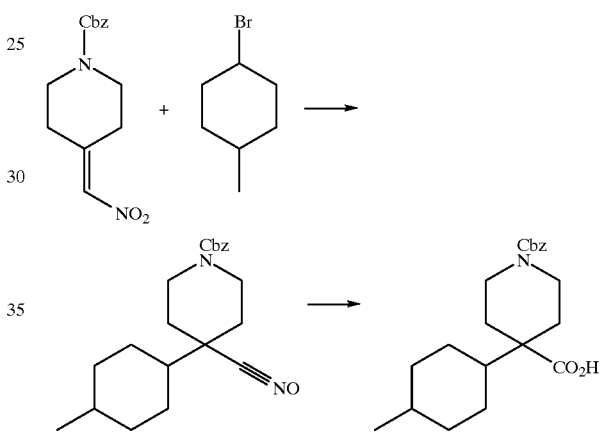

To a suspension of Reike Mg (5 g/200 mL THF) (6 mmol, 6 mL) at 0° C. was added a solution of 4-methyl-1-bromocyclohexane (4 mmol, 708 mg) in THF (4 mL) over a period of about 5 min. The resultant slurry was stirred at room temp for 5 min then cooled to −20° C. A solution of the Cbz-piperidine derivative (1 mmol, 276 mg) in THF (10 mL) was then added. The reaction was stirred at −20° C. for 15 min then poured into ice-cold 50% H₂SO₄ (25 mL) and stirred for a further 30 min. The emulsion was poured into H₂O (100 mL) and extracted with CH₂Cl₂ (2×25 mL). The combined organic phases were dried over Na₂SO₄ and concentrated to afford a green oil. To a solution of this oil in DMSO (2 mL) was added NaNO₂ (3 mmol, 207 mg) and AcOH (10 mmol, 0.6 mL). The resultant orange solution was stirred at 40° C. for 24 hr. After cooling to room temperature, 1N HCl (2.5 mL) was added and stirring continued for a further 15 min. The mixture was extracted with CH₂Cl₂ (3×5 mL). The combined organic layers were dried over Na₂SO₄ and concentrated. Chromatography over silica gel eluting with 100 mL of 10% and 50 mL of 20–30% EtOAc/hexane afforded the desired acid as an off-white solid (100 mg).

101

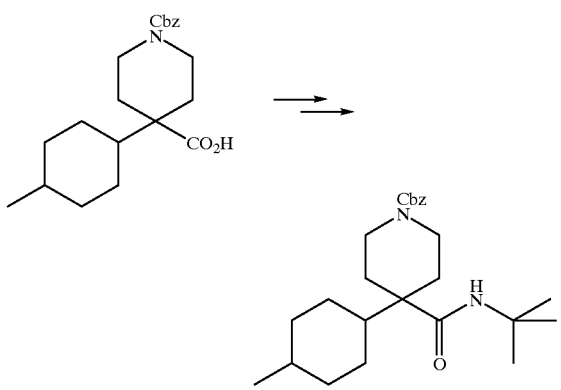

To a solution of the acid (0.42 mmol, 151 mg) in $CH_2Cl_2$ (2.5 mL) at 0° C. was added oxalyl chloride (2M in $CH_2Cl_2$) (0.46 mmol, 0.23 mL) and DMF (4 drops) and the reaction stirred at 0° C. for 1 hr. Volatiles were removed, azeotroping with toluene and finally under high vacuum for 3 hr to afford the acid chloride. The acid chloride was dissolved in $CH_2Cl_2$ (2.5 mL) and cooled to 0° C. t-Butylamine (1.26 mmol, 0.13 mL) was added and the resultant cloudy solution was left to stir at room temperature overnight. The reaction mixture was poured into $CH_2Cl_2$ (ca. 3 mL) and washed with brine, dried over $Na_2SO_4$ and concentrated. Chromatography over silica gel eluting with 250 mL of 20, 25, 30, and 40% EtOAc/hexane afforded the Cbz-protected t-butyl amide as a white foam (174 mg). A mixture of the Cbz-protected t-butyl amide (0.1 mmol, 174 mg) and catalytic Pd (10% on activated C) (20 mg) in methanol was stirred under an atmosphere of hydrogen gas at room temp for 1 hr. The solution was filtered through a short pad of celite and concentrated to give Intermediate 21.

Piperidine Intermediate 22

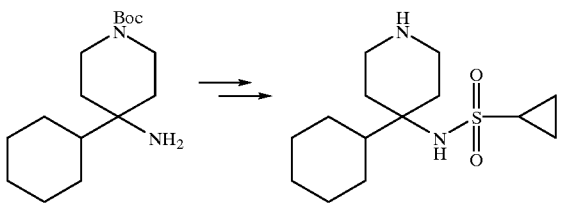

A solution of the amine (400 mg, 1.42 mmol), cyclopropylsulfonyl chloride (600 mg, 4.26 mmol), DIEA (1.47 g, 11.36 mmol) and DMAP (100 mg, 0.8 mmol) in toluene (50 mL) was heated to reflux overnight. A solution of NaOH (5N, 10 mL) was added and allowed the reaction to reflux for an additional 4 h. The reaction mixture was cooled to rt and diluted with EtOAc (200 mL). The combined organics were washed with 0.5N HCl, satd $NaHCO_3$, and brine, dried over $Na_2SO_4$ and concentrated. Chromatography over silica gel eluting with 50 mL of 10, 20, 15, 25, 40, and 50% EtOAc/hexane afforded the Boc-protected intermediate as a white solid (615 mg). A solution of this intermediate in $CH_2Cl_2$ (4mL) and HCl (4M in dioxane) (4 mL) was stirred at room temp for 1 hr. Volatiles were removed and the product precipitated from a $CH_2Cl_2$ solution with $Et_2O$/hexane to give Intermediate 22 (615 mg).

102

Piperidine Intermediate 23

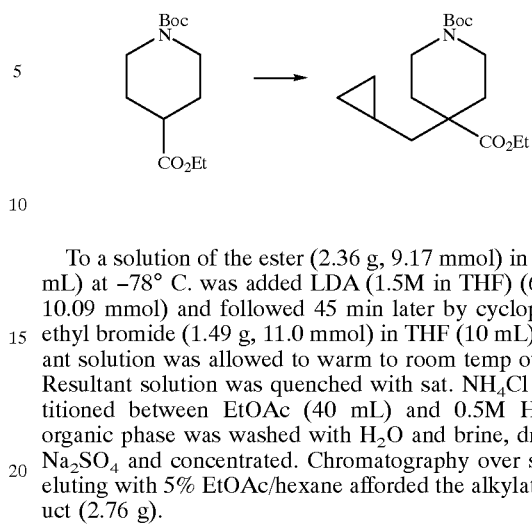

To a solution of the ester (2.36 g, 9.17 mmol) in THF (50 mL) at −78° C. was added LDA (1.5M in THF) (6.72 mL, 10.09 mmol) and followed 45 min later by cyclopropylmethyl bromide (1.49 g, 11.0 mmol) in THF (10 mL). Resultant solution was allowed to warm to room temp overnight. Resultant solution was quenched with sat. $NH_4Cl$ and partitioned between EtOAc (40 mL) and 0.5M HCl. The organic phase was washed with $H_2O$ and brine, dried over $Na_2SO_4$ and concentrated. Chromatography over silica gel eluting with 5% EtOAc/hexane afforded the alkylated product (2.76 g).

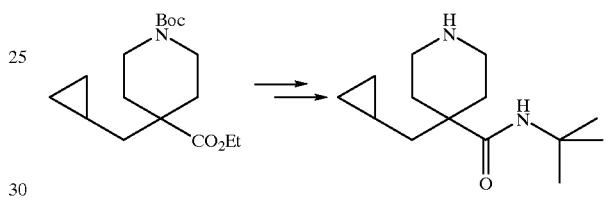

A solution of intermediate from the previous step (2.76 g, 8.86 mmol) and LiOH (1.1 g, 44.3 mmol) in $MeOH/H_2O$ (70 mL) was heated to reflux overnight. More MeOH was added to the reaction mixture to make the solution homogeneous. The reaction mixture was concentrated to about 10 mL and acidified with 2N HCl to pH about 2. The aqueous solution was extracted with EtOAc (3×100 mL). The organics were washed successively with $H_2O$ and brine, dried over $Na_2SO_4$ and concentrated. Chromatography over silica gel eluting with 20–70% EtOAc/hexane afforded the Boc-protected acid as a white solid (1.69 g). To a solution of the acid (2.5 g, 8.82 mmol) in $CH_2Cl_2$ (5 mL) at 0° C. was added oxalyl chloride (2M in $CH_2Cl_2$) (4.85 mL, 9.70 mmol) and DMF (0.05 mL) and the reaction stirred at 0° C. for 1 hr. Volatiles were removed, azeotroping with toluene and finally under high vacuum for 3 hr to afford the acid chloride. The acid chloride was dissolved in t-butylamine (2.8 mL), and the resultant cloudy solution was left to stir at room temp overnight. The reaction mixture was concentrated and partitioned between $CH_2Cl_2$ and 2M HCl. Organics were dried over $Na_2SO_4$ and concentrated. A solution of the Boc-protected amide in $CH_2Cl_2$ (4 mL) and 4.0 M HCl/dioxane (4 mL) was stirred at room temp for 1 hr. Volatiles were removed and Intermediate 23 was precipitated from a $CH_2Cl_2$ solution with $Et_2O$/hexane (1.9 g).

Piperidine Intermediate 24

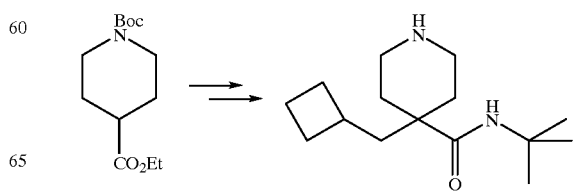

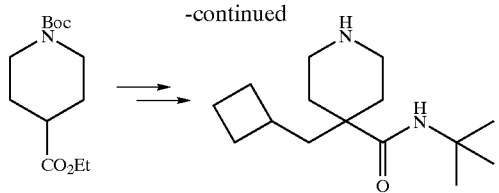

This intermediate was prepared in the same manner as Intermediate 23 but using cyclobutylmethyl bromide in place of cyclopropylmethyl bromide in the alkylation step.

Piperidine Intermediate 25

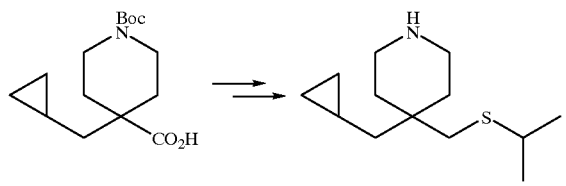

To a solution of the acid (600 mg, 2.117 mmol) in THF (5 mL) at 0° C. was added $BH_3.Me_2S$ (10 M in THF) (0.85 mL, 8.47 mmol) and the solution was left to stir at room temperature for 3 h. The reaction mixture was then cooled to 0° C., and $H_2O_2$ (30% aqueous, 2.5 mL) was added dropwise and then 1M NaOH (10 mL). The resultant solution was stirred for 10 min at 0° C. and then a further 30 min at rt. The reaction mixture was poured into EtOAc (100 mL), and washed successively with water, sat. $NH_4Cl$, saturated $NaHCO_3$, and brine, dried over $Na_2SO_4$ and concentrated. Chromatography over silica gel eluting with 40% EtOAc/hexane afforded the alcohol intermediate (611 mg). To a solution of the alcohol (611 mg, 2.268 mmol) and $Et_3N$ (0.63 mL, 4.5 mmol) in $CH_2Cl_2$ (5 mL) at 0° C. was added methanesulfonyl chloride (10 M in THF) (0.35 mL, 4.53 mmol) at 0° C. and the solution was left to stir at room temp 45 min. The reaction was concentrated and was poured into water (100 mL), and extracted with EtOAc (3×100 mL). The organics were dried over $Na_2SO_4$ and concentrated. Chromatography over silica gel eluting with 5–30% EtOAc/hexane afforded the mesylate as a solid. To a solution of the mesylate (596 mg, 1.7 mmol) in DMF (5 mL) at rt was added sodium isopropylsulfide (842 mg, 8.57 mmol) and the solution was left to stir at room temp overnight. The reaction was concentrated and was poured into water (100 mL), and extracted with EtOAc (3×100 mL). The organics were dried over $Na_2SO_4$ and concentrated. Chromatography over silica gel eluting with 5–30% EtOAc/hexane afforded a solid. A solution of the Boc-protected isopropyl sulfide in $CH_2Cl_2$ (4 mL) and 4.0 M HCl/dioxane (4 mL) was stirred at room temp for 1 hr. Volatiles were removed and Intermediate 25 was precipitated from a $CH_2Cl_2$ solution with $Et_2O$/hexane (400 mg).

Piperidine Intermediate 26

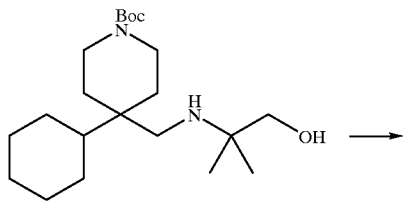

To a solution of the amino alcohol (177 mg, 0.48 mmol), NaOH (192 mg, 4.8 mmol) in $CHCl_3$ (5 mL) and water (2 mL) at 0° C. was added dropwise a solution of $BrCH_2COBr$ (263 mg, 1.3 mmol) in $CHCl_3$ (1 mL) over a period of 5 min., and the solution was left to stir at 0° C. for 1 h and then at rt overnight. The reaction was concentrated and was poured into water (100 mL), and extracted with EtOAc (3×100 mL). The organics were washed successively with water, 1N HCl and brine and dried over $Na_2SO_4$ and concentrated. Chromatography over silica gel eluting with 25% EtOAc/hexane afforded a solid. A solution of this solid in $CH_2Cl_2$ (4 mL) and 4.0 M HCl/dioxane (4 mL) was stirred at room temp for 1 hr. Volatiles were removed and Intermediate 26 precipitated from a $CH_2Cl_2$ solution with $Et_2O$/hexane (100 mg).

SCHEME 1

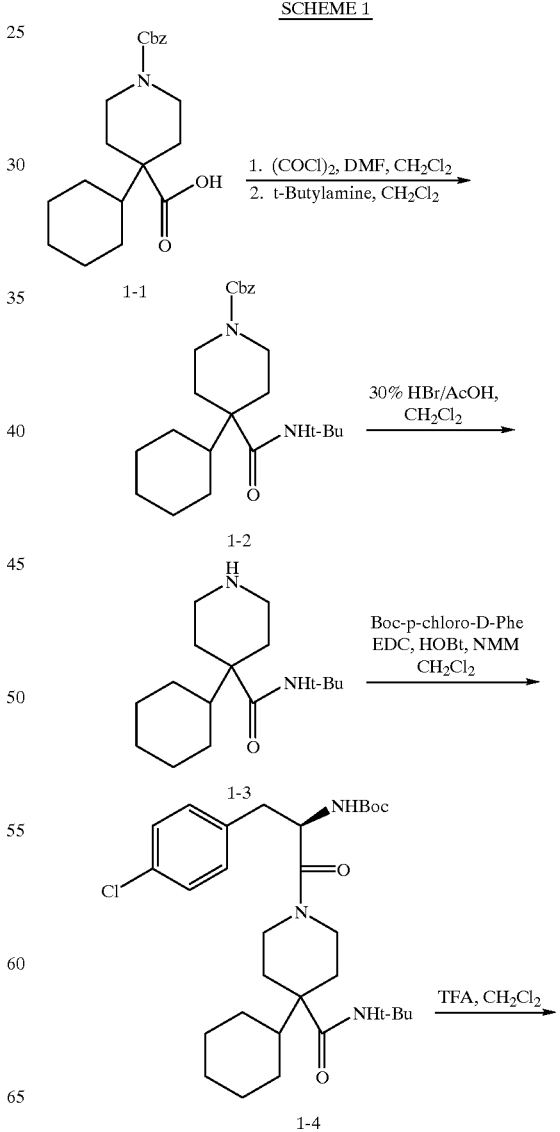

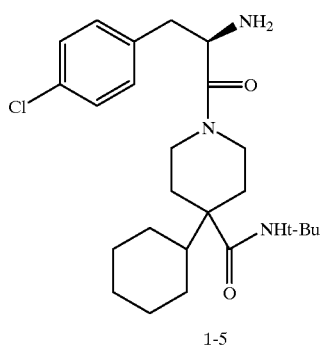

1-5

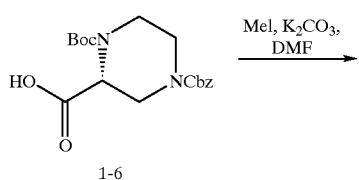

1-6

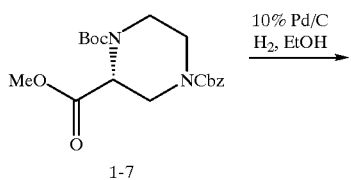

1-7

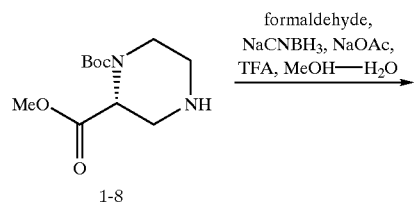

1-8

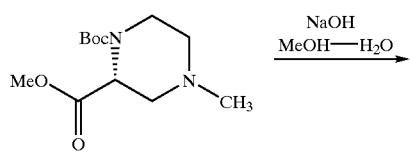

1-9

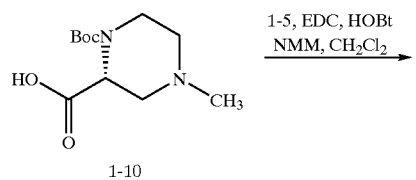

1-10

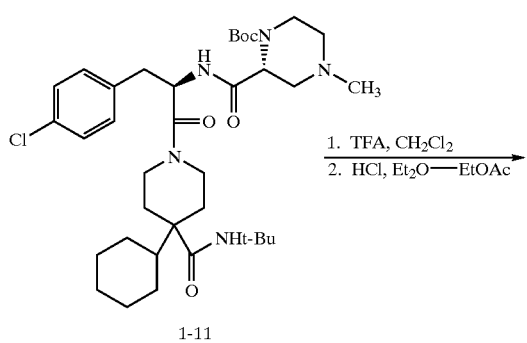

1-11

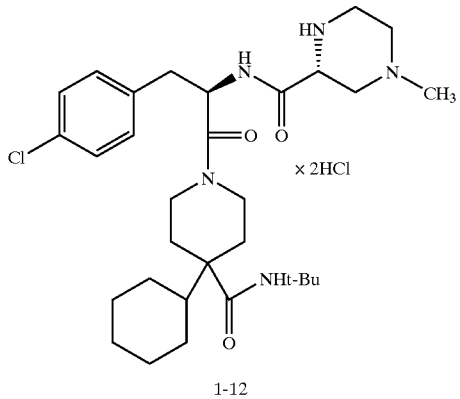

1-12

EXAMPLE 1

Step A

N-(Benzyloxycarbonyl)-4-cyclohexyl-piperidine-4-carboxylic acid (1—1) (2.5 g, 7.24 mmol) was dissolved in 36 mL of $CH_2Cl_2$ and cooled at 0° C. in an ice-$H_2O$ bath. Oxalyl chloride (2.0 M solution in $CH_2Cl_2$, 3.98 mL, 7.96 mmol) was then added dropwise followed by the addition of 1–2 drops of DMF. This mixture was stirred at 0° C. for 2 h and then concentrated with toluene. The residue was dissolved in $CH_2Cl_2$ and cooled at 0° C. in an ice-$H_2O$ bath, and then t-butylamine (2.28 mL, 21.72 mmol) was added dropwise. The reaction mixture was then stirred at 0° C. for 2 h, warmed to room temperature, and stirred at room temperature overnight. The resulting mixture was then diluted with $CH_2Cl_2$ and washed with brine, dried over $MgSO_4$, filtered, and concentrated to give 1–2 as a solid (2.92 g). Mass spectrum: Calcd for $C_{24}H_{36}N_2O_3$: 400.27; Found: 401 ($M^+$+1).

Step B

Compound 1–2 (7.24 mmol) was dissolved in 30 mL of $CH_2Cl_2$ and then 30% HBr in acetic acid (7.2 mL, 36.15 mmol) was added. The mixture was stirred at room temperature for 45 min (reaction monitored by TLC), and then diethyl ether was added. The resulting precipitate was filtered and washed with ether. The solid was dissolved in ethyl acetate and washed with IN NaOH solution, and the aqueous layer was extracted with EtOAc. The combined organic phases were dried over $K_2CO_3$, filtered, and concentrated to give 1–3 as a white solid (1.362 g). Mass spectrum: Calcd for $C_{16}H_{30}N_2O$: 266.24; Found: 267 ($M^+$+1).

Step C

N-Boc-(D)-4-chlorophenylalanine (0.935 g, 3.12 mmol) was dissolved in 14.2 mL of methylene chloride, and then amine 1–3 (0.755 g, 2.84 mmol), NMM (1.20 mL, 11.36 mmol), EDC (0.598 g, 3.12 mmol), and HOBt (0.422 g, 3.12 mmol) were added. The resulting mixture was stirred at room temperature overnight, and then diluted with 20 mL of $CH_2Cl_2$ and washed with 20 mL of 1N HCl solution, 20 mL of saturated $NaHCO_3$ solution, 20 mL of $H_2O$, and 20 mL of saturated NaCl solution. The organic phase was dried over $MgSO_4$, filtered, and concentrated to give a white, foamy-solid. The crude product was purified by column chromatography (30:1 to 9:1 methylene chloride-acetone) to give 1–4 as a white solid (1.34 g). Mass spectrum: Calcd for $C_{30}H_{46}N_3O_4Cl$: 547.32; Found: 548 ($M^+$+1).

Step D

Compound 1–4 (1.33 g, 2.43 mmol) was dissolved in 6.1 mL of methylene chloride and 6.1 mL of trifluoroacetic acid, and this solution was stirred at room temperature for 30 min. The mixture was then concentrated with two 8-mL portions of toluene and two 8-mL portions of diethyl ether to give a white solid. The solid was dissolved in EtOAc and washed with 1N NaOH solution, and the aqueous layer was extracted with EtOAc. The combined organic phases were dried over $K_2CO_3$, filtered, and concentrated to give 1–5 as a foamy-solid (1.08 g). Mass spectrum: Calcd for $C_{25}H_{38}N_3O_2Cl$: 447.27; Found: 448 ($M^+$+1).

Step E

A 25-mL, round-bottomed flask was purged under nitrogen and charged with (R)-4-(benzyloxycarbonyl)-1-(tert-butoxycarbonyl)-piperazine-2-carboxylic acid (1–6) (0.5 g, 1.37 mmol) (the preparation of this intermediate from commercially available 2(R)-piperazine carboxylic acid was achieved via modifications to the procedures described by Bigge and coworkers in *Tetrahedron Lett.* 1989, 30, 5193) and 7 mL of DMF. Potassium carbonate (0.228 g, 1.65 mmol) was then added followed by the addition of methyl iodide (0.43 mL, 6.86 mmol), and the resulting mixture was stirred at room temperature overnight. The cloudy yellow mixture was diluted with $H_2O$ and EtOAc, and the layers were separated. The aqueous layer was extracted with EtOAc, and the combined organic phases were washed with brine, dried over $Na_2SO_4$, filtered, and concentrated. Purification by column chromatography (30% ethyl acetate-hexane) provided 1–7 (0.52 g). Mass spectrum: Calcd for $C_{19}H_{26}N_2O_6$: 378.18; Found: 279 ($M^+$+1-Boc).

Step F

Intermediate 1–7 (0.52 g, 1.37 mmol) was charged with 6.8 mL of EtOH, and 10% Pd/C (0.052 g). A $H_2$ balloon was placed on the top of the flask via a 3-way stopcock and the system was evacuated and purged with $H_2$ three times. The mixture was then stirred at room temperature under $H_2$ overnight. The flask was evacuated and purged with $N_2$ three times, and then the reaction mixture was filtered through a pad of Celite and concentrated to give 1–8 as a clear oil (0.328 g). Mass spectrum: Calcd for $C_{11}H_{20}N_2O_4$: 244.14; Found: 245 ($M^+$+1).

Step G

Compound 1–8 (0.205 g, 0.84 mmol) was dissolved in 4.2 mL of methanol, and then sodium acetate (0.345 g, 4.20 mmol), trifluoroacetic acid (0.065 mL, 0.84 mmol), and 37% aqueous formaldehyde solution (0.30 mL, 4.03 mmol) were added. The mixture was stirred at room temperature for 30 min, and then sodium cyanoborohydride (1.0 M in THF, 2.7 mL, 2.7 mmol) was added. The reaction mixture was stirred at room temperature overnight and then concentrated to give a white sludge. The crude mixture was dissolved in EtOAc and 1N NaOH, and the layers were separated. The organic phase was washed with 1N NaOH solution, $H_2O$, and brine, dried over $MgSO_4$, filtered, and concentrated. Purification by column chromatography (10% methanol-methylene chloride) provided 1–9 (0.14 g). Mass spectrum: Calcd for $C_{12}H_{22}N_2O_4$: 258.16; Found: 259 ($M^+$+1).

Step H

Ester 1–9 (0.14 g, 0.56 mmol) was dissolved in 2.7 mL of methanol, and then 1N NaOH solution (1.12 mL, 1.12 mmol) was added. The mixture was stirred at room temperature overnight, and then concentrated. The residue was dissolved in water and then the pH was adjusted to pH=6. The solution was then concentrated twice with toluene to give 1–10 (0.217 g, 63% purity). Mass spectrum: Calcd for $C_{11}H_{20}N_2O_4$: 244.14; Found: 245 ($M^+$+1).

Step I (R)-4-Methyl-1-(tert-butoxycarbonyl)piperazine-2-carboxylic acid 1–10 (63% purity, 0.063 g, 0.172 mmol) was dissolved in 0.78 mL of methylene chloride, and then amine intermediate 1–5 (0.07 g, 0.156 mmol), NMM (0.07 mL, 0.624 mmol), EDC (0.033 g, 0.172 mmol), and HOBt (0.023 g, 0.172 mmol) were added. The resulting mixture was stirred at room temperature overnight, and then diluted with 10 mL of $CH_2Cl_2$ and washed with 5 mL of 1N HCl solution, 5 mL of saturated $NaHCO_3$ solution, 5 mL of $H_2O$, and 5 mL of saturated NaCl solution. The organic phase was dried over $MgSO_4$, filtered, and concentrated to give a yellow oil. The crude product was purified by column chromatography (9:1 to 1:1 methylene chloride-acetone) to give 1–11 as a white solid (0.080 g). Mass spectrum: Calcd for $C_{36}H_{56}N_5O_5Cl$: 673.40; Found: 674 ($M^+$+1).

Step J

Compound 1–11 (0.078 g, 0.116 mmol) was dissolved in 0.30 mL of methylene chloride and 0.30 mL of trifluoroacetic acid. This solution was stirred at room temperature for 30 min, and then concentrated with two 5-mL portions of toluene and two 5-mL portions diethyl ether to give a white, foamy-solid. The solid was dissolved in EtOAc and washed with 1N NaOH solution, and the aqueous layer was extracted with EtOAc. The combined organic phases were dried over $K_2CO_3$, filtered, and concentrated, and the residue was purified by column chromatography (5–10% methanol-methylene chloride) to give a white, foamy-solid. The solid was dissolved in EtOAc and 1.0 M HCl solution in $Et_2O$ (0.28 mL, 0.28 mmol) was added. The precipitate was filtered under $N_2$ and dried under vacuum to give 1–12 as a white solid (0.046 g). Mass spectrum: Calcd for $C_{31}H_{48}N_5O_3Cl$: 573.34; Found: 574 ($M^+$+1).

$^1$H NMR ($CD_3OD$): δ 7.28–7.13 (m, 4 H), 5.02 (m, 1 H), 4.26 (m, 2 H), 3.66–3.50 (m, 2 H), 3.26–3.45 (m, 3 H), 3.00–2.87 (m, 4 H), 2.78 (s, 3 H), 2.43 (m, 2 H), 1.94 (m, 2 H), 1.71 (m, 3 H), 1.58 (d, J=10.7 Hz, 1 H), 1.47 (d, J=11.7 Hz, 1 H), 1.25 (d, J=16.2 Hz, 9 H), 1.25–0.75 (m, 7 H), 0.11 (m, 1 H)

SCHEME 2

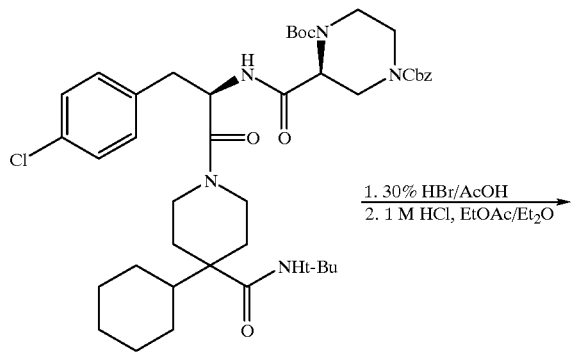

2-1

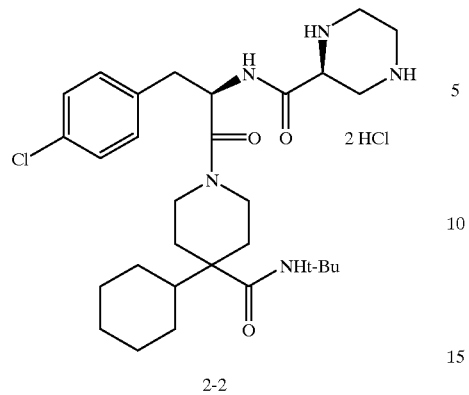

2-2

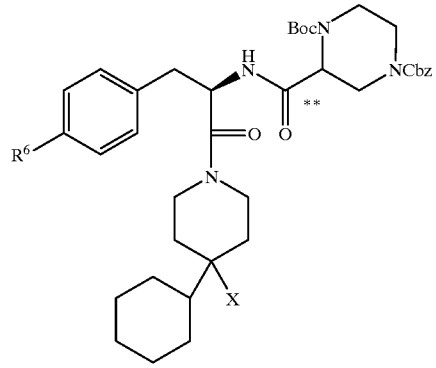

EXAMPLE 2

Step A

The bis-protected (S)-piperazine-2-carboxamide intermediate (2–1) was prepared by coupling amine 1–5 with (S)-4-(benzyloxycarbonyl)-1-(tert-butoxycarbonyl)-piperazine-2-carboxylic acid in place of (S)-4-methyl-1-(tert-butoxycarbonyl)-piperazine-2-carboxylic acid in Step I of Example 1.

Step B

Compound 2–1 (0.164 g, 0.206 mmol) was dissolved in 0.6 mL of methylene chloride and 30% HBr in acetic acid (0.409 mL, 2.06 mmol) was added. The mixture was stirred at room temperature for 45 min (TLC showed no starting material). To this orange solution, diethyl ether (5 mL) was added, and the precipitate was filtered and washed with ether. The solid was dissolved in ethyl acetate and washed with 1N NaOH and the aqueous layer was extracted with EtOAc. The combined organics were dried over $K_2CO_3$, filtered and concentrated to give a white solid (0.1096 g). A portion of the white solid (0.050 g, 0.089 mmol) was dissolved in EtOAc and 1.0 M HCl in $Et_2O$ (0.22 mL, 0.22 mmol) was added. The precipitate was filtered under $N_2$ and dried under vacuum to give 2–2 as a white solid (0.047 g); mass spectrum: 560 (M+1); 582 (M+Na).

SCHEME 3

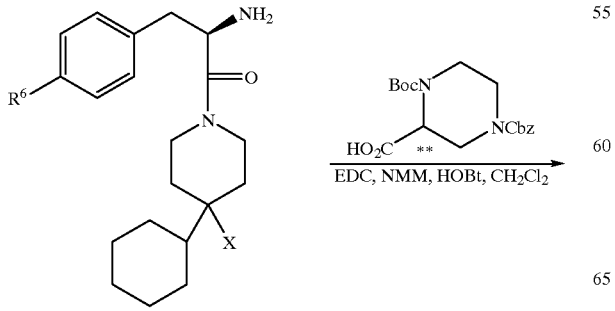

The intermediates shown in Table 1 below having bis-protected piperazine-2-carboxylic acid residues and variable X groups at the 4-position of the piperidine ring were prepared as shown in Scheme 3 above with the indicated stereochemistry at the stereogenic center marked with **.

TABLE 1

| X | $R^6$ | ** | Exact Mass | Mass Spec. |
|---|---|---|---|---|
| ~~~O~~~ ethyl ester | F | (R) | 750.40 | 751 (M⁺ + 1) |
| ~~~NH-tBu amide | Cl | (S) | 793.42 | 794 (M⁺ + 1), 816 (M⁺ + Na) |
| ~~~NH-tBu amide | F | (R) | 777.55 | 778 (M⁺ + 1) |
| ~~~NH-tBu amide | F | (S) | 777.55 | 778 (M⁺ + 1), 800 (M⁺ + Na) |
| ~~~NH-tBu amide | Cl | (R) | 793.42 | 794 (M⁺ + 1) |
| ~~~NH-tBu amide | F | (R) | 777.55 | 778 (M⁺ + 1) |

TABLE 1-continued

| X | R⁶ | ** | Exact Mass | Mass Spec. |
|---|---|---|---|---|
| *-C(O)NH-iPr | Cl | (S) | 779.40 | 780 (M⁺ + 1), 802 (M⁺ + Na) |
| *-C(O)NH-cyclobutyl | Cl | (S) | 791.40 | 792 (M⁺ + 1) |
| *-C(O)NH-cyclobutyl | Cl | (R) | 791.40 | 792 (M⁺ + 1) |
| *-C(O)NH-cyclopentyl | Cl | (S) | 805.42 | 806 (M⁺ + 1) |
| *-C(O)NH-cyclopentyl | Cl | (R) | 805.42 | 806 (M⁺ + 1) |
| *-C(O)NH-CH(Et)₂ | Cl | (S) | 807.43 | 808 (M⁺ + 1) |
| *-C(O)NH-CH(Et)₂ | Cl | (R) | 807.43 | 808 (M⁺ + 1) |
| *-C(O)NH-CH₂C(CH₃)₃ | Cl | (R) | 807.43 | 808 (M⁺ + 1) |
| *-C(O)NH-(2-pyridyl) | Cl | (S) | 814.38 | 815 (M⁺ + 1), 837 (M⁺ + Na) |
| *-C(O)NH-CH₂CF₃ | Cl | (S) | 819.36 | 820 (M⁺ + 1) |
| *-C(O)-N(piperazine)-NCbz | F | (S) | 924.48 | 925 (M⁺ + 1), 947 (M⁺ + Na) |
| *-C(O)-N(piperazine)-NMe | F | (S) | 804.46 | 805 (M⁺ + 1), 827 (M⁺ + Na) |
| *-C(O)NH-C(CH₃)₃ | Cl | (S) | 793.42 | 794 (M⁺ + 1), 816 (M⁺ + Na) |
| *-C(O)NH-C(CH₃)₃ | Cl | (R) | 793.42 | 794 (M⁺ + 1), 816 (M⁺ + Na) |
| *-CH₂-(4,4-dimethyl-oxazolidin-2-one) | Cl | (S) | 821.41 | 822 (M⁺ + 1), 844 (M⁺ + Na), 722 (M⁺ − Boc) |
| *-CH₂-(4,4-dimethyl-oxazolidin-2-one) | F | (S) | 805.44 | 806 (M⁺ + 1), 828 (M⁺ + Na), 706 (M⁺ − Boc) |
| *-CH₂-(4,4-dimethyl-oxazolidin-2-one) | Cl | (R) | 821.41 | 822 (M⁺ + 1), 844 (M⁺ + Na), 722 (M⁺ − Boc) |
| *-CH₂-(4,4-dimethyl-oxazolidin-2-one) | F | (R) | 805.44 | 806 (M⁺ + 1), 828 (M⁺ + Na), 706 (M⁺ − Boc) |
| *-CH₂-O-C(O)-N(CH₃)₂ | Cl | (S) | 795.4 | 796 (M⁺ + 1), 818 (M⁺ + Na) |

The following $N^{\alpha,\beta}$-unsubstituted piperazine examples shown in Table 2 below above with the indicated stereochemistry at the stereogenic center marked with ** were prepared from the intermediates in Table 1 by treatment with 30% HBr in acetic acid to afford the hydrobromide salt, which upon neutralization and subsequent treatment with HCl in diethyl ether afforded the hydrochloride salt.

TABLE 2
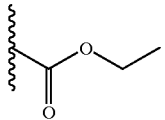
| Example | X | R⁶ | ** | Exact Mass | Mass Spec. |
|---|---|---|---|---|---|
| 3 | 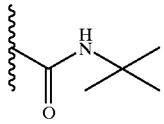 | F | (R) | 516.31 | 517 (M⁺ + 1), 539 (M⁺ + Na) |
| 4 | 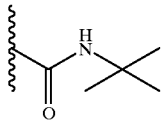 | Cl | (S) | 559.23 | 560 (M⁺ + 1), 582 (M⁺ + Na) |
| 5 | 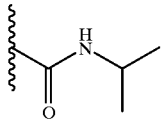 | F | (S) | 543.36 | 544 (M⁺ + 1), 566 (M⁺ + Na) |
| 6 | 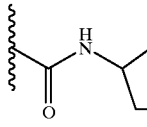 | Cl | (S) | 545.31 | 546 (M⁺ + 1), 568 (M⁺ + Na) |
| 7 | 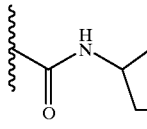 | Cl | (S) | 571.33 | 572 (M⁺ + 1), 594 (M⁺ + Na) |
| 8 | 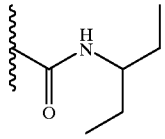 | Cl | (R) | 571.33 | 572 (M⁺ + 1) |
| 9 |  | Cl | (S) | 573.34 | 574 (M⁺ + 1), 596 (M⁺ + Na) |

TABLE 2-continued

| Example | X | R[6] | ** | Exact Mass | Mass Spec. |
|---|---|---|---|---|---|
| 10 | -C(O)NH-CH(Et)(Et) | Cl | (R) | 573.34 | 574 (M[+] + 1) |
| 11 | -C(O)NH-CH2-C(CH3)3 | Cl | (R) | 573.34 | 574 (M[+] + 1) |
| 12 | -C(O)NH-(2-pyridyl) | Cl | (S) | 580.29 | 581 (M[+] + 1), 603 (M[+] + Na) |
| 13 | -C(O)NH-CH2-CF3 | Cl | (S) | 585.27 | 586 (M[+] + 1), 608 (M[+] + Na) |
| 14 | -C(O)-piperazinyl | F | (S) | 556.35 | 557 (M[+] + 1), 579 (M[+] + Na) |
| 15 | -C(O)-(4-methylpiperazinyl) | F | (S) | 570.37 | 571 (M[+] + 1), 593 (M[+] + Na) |
| 16 | -NH-C(O)-C(CH3)3 | Cl | (S) | 559.33 | 560 (M[+] + 1), 582 (M[+] + Na) |

TABLE 2-continued

| Example | X | R⁶ | ** | Exact Mass | Mass Spec. |
|---|---|---|---|---|---|
| 17 | -NH-C(=O)-C(CH₃)₃ | Cl | (R) | 559.33 | 560 (M⁺ + 1), 582 (M⁺ + Na) |
| 18 | -CH₂-N(4,4-dimethyloxazolidin-2-one) | F | (S) | 571.35 | 572 (M⁺ + 1), 594 (M⁺ + Na) |
| 19 | -CH₂-N(4,4-dimethyloxazolidin-2-one) | F | (R) | 571.35 | 572 (M⁺ + 1) |
| 20 | -CH₂-O-C(=O)-N(CH₃)₂ | Cl | (S) | 561.31 | 562 (M⁺ + 1), 584 (M⁺ + Na) |
| 21 | -C(=O)-NH-C(CH₃)₃ | F | (R) | 543.66 | 544 (M⁺ + 1) |
| 22 | -CH₂CH₂-C(CH₃)₂-OH | F | (R) |  | 531 (M⁺ + 1) |
| 23 | -CH₂CH₂-C(CH₃)₂-OH | F | (S) |  | 531 (M⁺ + 1) |

SCHEME 4

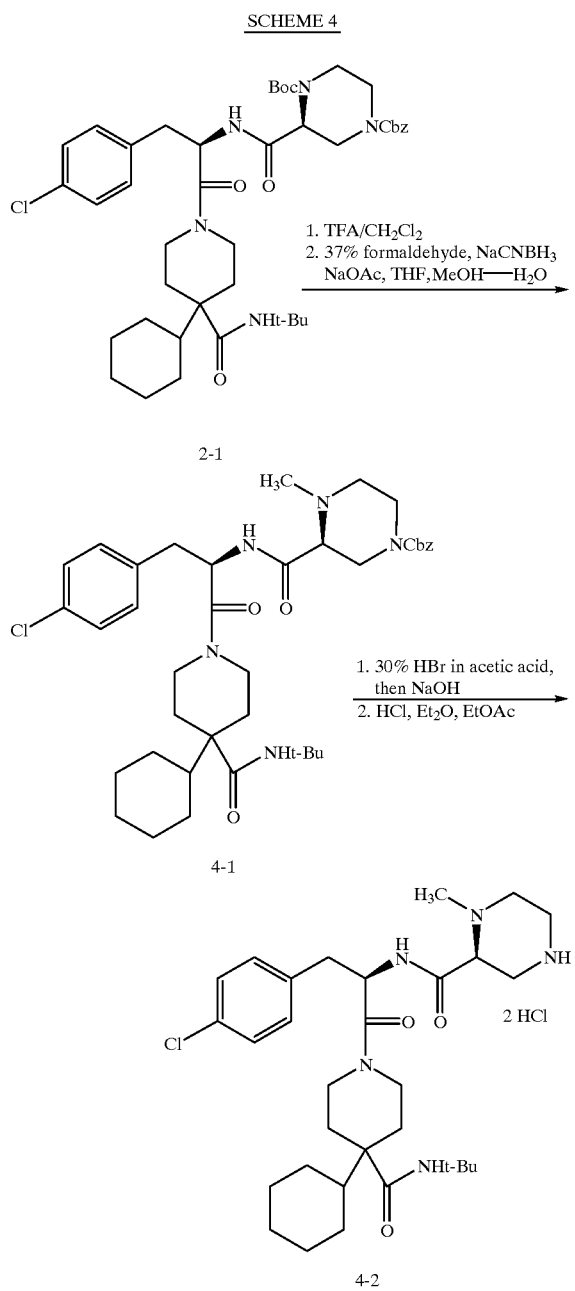

EXAMPLE 24

Step A

Compound 2–1 (0.090 g, 0.113 mmol) was dissolved in 0.30 mL of methylene chloride and 0.30 mL of trifluoroacetic acid. This solution was stirred for 30 min at room temperature. The mixture was then concentrated with toluene (3 mL×2) and diethyl ether (3 mL×2) to give a white solid. The solid was dissolved in 0.6 mL of methanol, and then sodium acetate (0.046 g, 0.565 mmol) and 37% aqueous formaldehyde solution (0.041 mL, 0.542 mmol) were added. The reaction mixture was stirred at room temperature for 30 min, and then sodium cyanoborohydride (1.0 M in THF, 0.36 mL, 0.36 mmol) was added. The mixture was stirred at room temperature overnight. The solution was concentrated to give a white sludge, and then dissolved in EtOAc (10 mL) and 1N NaOH (5 mL) and the layers were separated. The organic phase was washed with 1N NaOH (5 mL), H$_2$O (5 mL), and brine (5 mL), dried over MgSO$_4$, filtered, and concentrated to give an oil. Purification by column chromatography using 10% methanol in methylene chloride afforded 4–1 as a white, foamy-solid (0.080 g); mass spectrum: 708 (M+1); 730 (M+Na).

Step B

Compound 4–1 (0.080 g, 0.113 mmol) was dissolved in 0.5 mL of methylene chloride and 30% HBr in acetic acid (0.112 mL, 0.565 mmol) was added. The mixture was stirred at room temperature for 45 min (TLC showed no starting material). To this orange solution, diethyl ether was added and the precipitate was filtered and washed with ether. The solid was dissolved in EtOAc and washed with 1N NaOH, and the aqueous layer was extracted with EtOAc. The combined organics were dried over K$_2$CO$_3$, filtered and concentrated to give a foamy solid. Purification by column chromatography (5% –20% methanol in methylene chloride) provided a solid. The solid was dissolved in EtOAc and 1M HCl in Et$_2$O (0.27 mL, 0.27 mmol) was added whereupon a precipitate formed. The precipitate was filtered under N$_2$ and dried under vacuum to give 4–2 as a white solid (0.044 g).

SCHEME 5

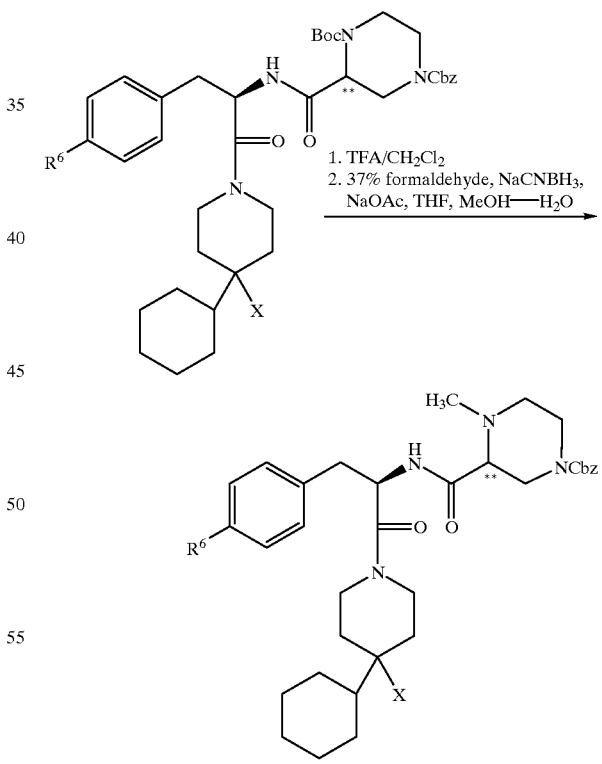

The following N$^\alpha$-methyl-N$^\beta$-(Cbz) intermediates shown in Table 3 below above with the indicated stereochemistry at the stereogenic center marked with ** having variable X groups at the 4-position of the piperidine ring were prepared as shown in Scheme 5 above.

TABLE 3
| X | R⁶ | ** | Exact Mass | Mass Spec. |
|---|---|---|---|---|
| 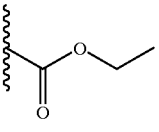 | F | (R) | 750.40 | 751 (M⁺ + 1) |
| 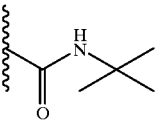 | Cl | (S) | 707.37 | 708 (M⁺ + 1), 730 (M⁺ + Na) |
| 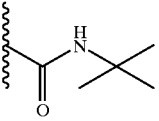 | F | (S) | 691.41 | 692 (M⁺ + 1), 714 (M⁺ + Na) |
| 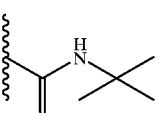 | Cl | (R) | 707.38 | 708 (M⁺ + 1) |
| 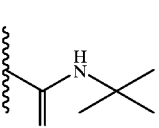 | F | (R) | 691.41 | 692 (M⁺ + 1) |
| 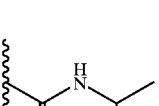 | Cl | (S) | 693.37 | 694 (M⁺ + 1), 716 (M⁺ + Na) |
| 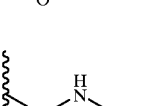 | Cl | (S) | 705.37 | 706 (M⁺ + 1) |
| 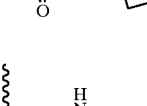 | Cl | (R) | 705.37 | 706 (M⁺ + 1) |
| 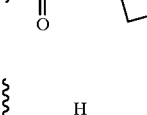 | Cl | (S) | 719.38 | 720 (M⁺ + 1), 742 (M⁺ + Na) |
| 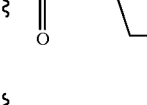 | Cl | (R) | 719.38 | 720 (M⁺ + 1) |
TABLE 3-continued
| X | R⁶ | ** | Exact Mass | Mass Spec. |
|---|---|---|---|---|
| 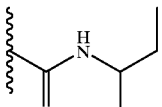 | Cl | (S) | 721.40 | 722 (M⁺ + 1), 742 (M⁺ + Na) |
| 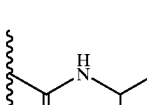 | Cl | (R) | 721.40 | 722 (M⁺ + 1) |
| 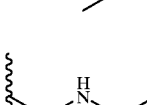 | Cl | (R) | 721.40 | 722 (M⁺ + 1) |
| 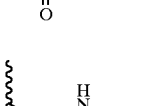 | Cl | (S) | 728.35 | 729 (M⁺ + 1), 751 (M⁺ + Na) |
| 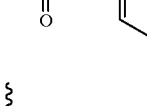 | Cl | (S) | 733.32 | 734 (M⁺ + 1), 717 (M⁺ + Na) |
| 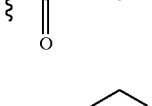 | F | (S) | 838.44 | 839 (M⁺ + 1), 861 (M⁺ + Na) |
| 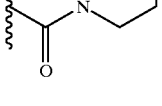 | F | (S) | 718.42 | 719 (M⁺ + 1), 741 (M⁺ + Na) |
| 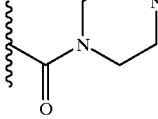 | Cl | (S) | 707.38 | 708 (M⁺ + 1), 730 (M⁺ + Na) |
| 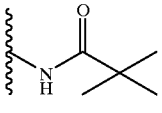 | Cl | (R) | 707.38 | 708 (M⁺ + 1), 730 (M⁺ + Na) |
| 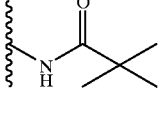 | Cl | (S) | 735.38 | 736 (M⁺ + 1), 758 (M⁺ + Na) |

TABLE 3-continued

| X | R⁶ | ** | Exact Mass | Mass Spec. |
|---|----|----|------------|------------|
| (oxazolidinone-CH₂, 4,4-dimethyl) | F | (S) | 719.41 | 720 (M⁺ + 1) |
| (oxazolidinone-CH₂, 4,4-dimethyl) | Cl | (R) | 735.38 | 736 (M⁺ + 1), 758 (M⁺ + Na) |
| (oxazolidinone-CH₂, 4,4-dimethyl) | F | (R) | 719.41 | 720 (M⁺ + 1) |
| (CH₂-O-C(O)-N(CH₃)₂) | Cl | (S) | 709.36 | 710 (M⁺ + 1), 732 (M⁺ + Na) |

The following N^α-methyl-N^β-unsubstituted piperazine Examples shown in Table 4 below above with the indicated stereochemistry at the stereogenic center marked with ** were prepared from the intermediates in Table 3 by treatment with 30% HBr in acetic acid to afford the hydrobromide salt, which upon neutralization and subsequent treatment with HCl in diethyl ether afforded the hydrochloride salt.

TABLE 4

| Ex. | X | R⁶ | ** | Exact Mass | Mass Spec. |
|-----|---|----|----|------------|------------|
| 25 | ethyl ester (-C(O)-O-CH₂CH₃) | F | (R) | 530.33 | 531 (M⁺ + 1), 553 (M⁺ + Na) |
| 26 | -C(O)-NH-C(CH₃)₃ | Cl | (S) | 573.34 | 574 (M⁺ + 1), 596 (M⁺ + Na) |
| 27 | -C(O)-NH-C(CH₃)₃ | F | (S) | 557.37 | 558 (M⁺ + 1), 580 (M⁺ + Na) |
| 28 | -C(O)-NH-C(CH₃)₃ | Cl | (R) | 573.34 | 574 (M⁺ + 1), 596 (M⁺ + Na) |
| 29 | -C(O)-NH-C(CH₃)₃ | F | (R) | 557.37 | 558 (M⁺ + 1) |
| 30 | -C(O)-NH-CH(CH₃)₂ | Cl | (S) | 559.33 | 560 (M⁺ + 1), 682 (M⁺ + Na) |
| 31 | -C(O)-NH-cyclobutyl | Cl | (S) | 571.33 | 572 (M⁺ + 1) |
| 32 | -C(O)-NH-cyclobutyl | Cl | (R) | 571.33 | 572 (M⁺ + 1) |
| 33 | -C(O)-NH-cyclopentyl | Cl | (S) | 585.34 | 586 (M⁺ + 1), 608 (M⁺ + Na) |

TABLE 4-continued

[Structure: A compound with H₃C-N-piperazine-NH group, connected via NH-C(=O) to a chiral center bearing a CH₂-phenyl (with R⁶ para substituent), linked through C(=O)-N to a piperidine bearing cyclohexyl and X at the 4-position; shown as 2 HX salt, with ** marking stereocenter]

| Ex. | X | R⁶ | ** | Exact Mass | Mass Spec. |
|---|---|---|---|---|---|
| 34 | -C(=O)NH-cyclopentyl | Cl | (R) | 585.34 | 586 (M⁺ + 1) |
| 35 | -C(=O)NH-CH(CH₂CH₃)₂ (3-pentyl) | Cl | (S) | 587.36 | 588 (M⁺ + 1), 610 (M⁺ + Na) |
| 36 | -C(=O)NH-CH(CH₂CH₃)₂ (3-pentyl) | Cl | (R) | 587.36 | 588 (M⁺ + 1) |
| 37 | -C(=O)NH-CH₂C(CH₃)₃ (neopentyl) | Cl | (R) | 587.36 | 588 (M⁺ + 1) |
| 38 | -C(=O)NH-(2-pyridyl) | Cl | (S) | 594.31 | 595 (M⁺ + 1), 617 (M⁺ + Na) |
| 39 | -C(=O)NH-CH₂CF₃ | Cl | (S) | 599.29 | 600 (M⁺ + 1) |
| 40 | -C(=O)-piperazinyl (NH) | F | (S) | 570.37 | 571 (M⁺ + 1), 593 (M⁺ + Na) |
| 41 | -C(=O)-(4-methylpiperazinyl) | F | (S) | 584.39 | 585 (M⁺ + 1), 607 (M⁺ + Na) |
| 42 | -NH-C(=O)-C(CH₃)₃ | Cl | (S) | 573.34 | 574 (M⁺ + 1), 596 (M⁺ + Na) |
| 43 | -NH-C(=O)-C(CH₃)₃ | Cl | (R) | 573.34 | 574 (M⁺ + 1), 596 (M⁺ + Na) |
| 44 | -CH₂-N(4,4-dimethyl-2-oxo-oxazolidinyl) | Cl | (S) | 601.34 | 602 (M⁺ + 1), 624 (M⁺ + Na) |
| 45 | -CH₂-N(4,4-dimethyl-2-oxo-oxazolidinyl) | F | (S) | 585.37 | 586 (M⁺ + 1) |
| 46 | -CH₂-N(4,4-dimethyl-2-oxo-oxazolidinyl) | Cl | (R) | 601.34 | 602 (M⁺ + 1), 624 (M⁺ + Na) |
| 47 | -CH₂-N(4,4-dimethyl-2-oxo-oxazolidinyl) | F | (R) | 585.37 | 586 (M⁺ + 1) |

TABLE 4-continued

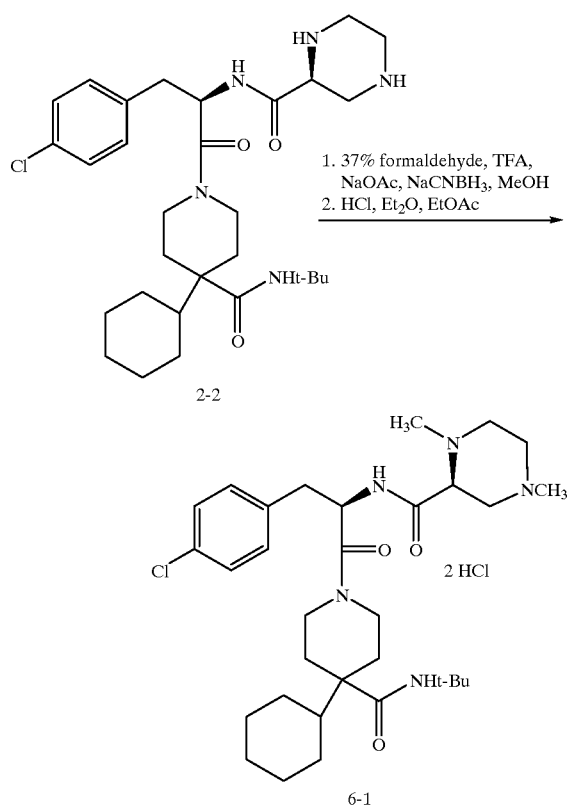

| Ex. | X | R[6] | ** | Exact Mass | Mass Spec. |
|---|---|---|---|---|---|
| 48 | (structure: -CH2-O-C(O)-N(CH3)2) | Cl | (S) | 575.32 | 576 (M[+] + 1), 598 (M[+] + Na) |

SCHEME 6 mmol), trifluoroacetic acid (0.016 mL, 0.210 mmol), and 37% aqueous formaldehyde solution (0.093 mL, 1.008 mmol) were added. The reaction mixture was stirred at room temperature for 30 min, and then sodium cyanoborohydride (1.0 M in THF, 0.67 mL, 0.67 mmol) was added. The mixture was stirred at room temperature overnight, and then concentrated to give a white sludge. This was dissolved in EtOAc (10 mL) and 1N NaOH (5 mL) and the layers were separated. The organic phase was washed with 1N NaOH (5 mL), H₂O (5 mL), and brine (5 mL), dried over MgSO₄, filtered, and concentrated to give a white foamy solid. Purification by column chromatography on silica gel using 10% methanol in methylene chloride provided a white foamy solid (0.044 g).

Step B

The compound from Step A (0.040 g, 0.067 mmol) was dissolved in EtOAc, and 1.0 M HCl in Et₂O (0.16 mL, 0.16 mmol) was added. The precipitate was filtered under N₂ and dried under vacuum to give 6–1 as a white solid (0.031 g); mass spectrum: 588 (M+1); 610 (M+Na).

The following N[α,β]-dimethyl-piperazine Examples shown in Table 5 below above with the indicated stereochemistry at the stereogenic center marked with ** were prepared by reductive methylation of the corresponding N[α,β]-unsubstituted-piperazine intermediates, neutralization, and subsequent treatment with HCl in diethyl ether.

TABLE 5

| Ex. | X | R[6] | ** | Exact Mass | Mass Spec. |
|---|---|---|---|---|---|
| 50 | (ethyl ester) | Cl | (S) | 560.31 | 561 (M[+] + 1), 583 (M[+] + Na) |
| 51 | (-CH2-C(O)-NH-t-Bu) | Cl | (S) | 587.36 | 588 (M[+] + 1), 610 (M[+] + Na) |
| 52 | (-CH2-C(O)-NH-t-Bu) | Cl | (R) | 587.36 | 588 (M[+] + 1) |

EXAMPLE 49

Step A

Compound 2–2 (0.059 g, 0.105 mmol) was dissolved in 0.5 mL of methanol, and then sodium acetate (0.046 g, 0.565

TABLE 5-continued

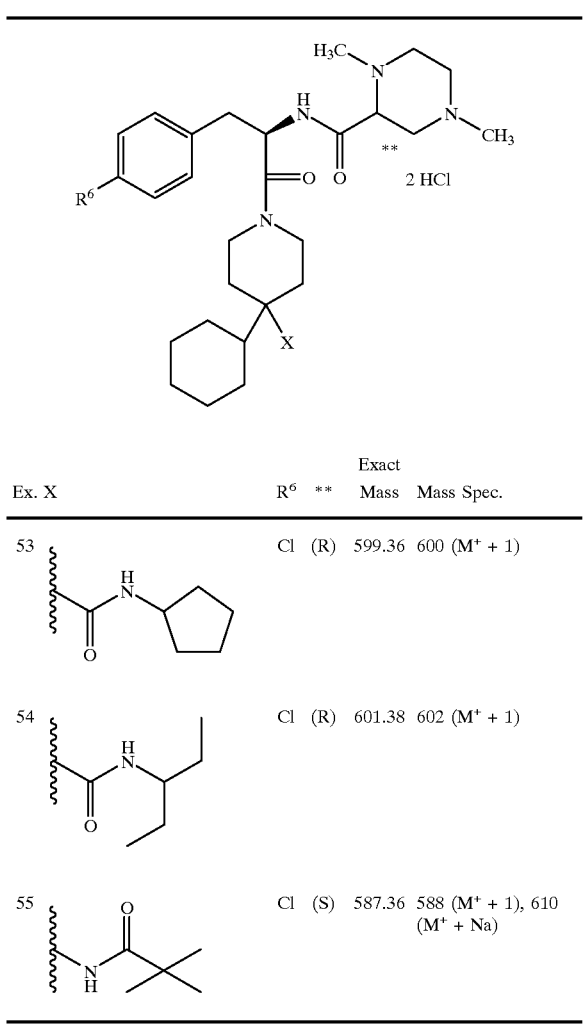

| Ex. | X | R⁶ | ** | Exact Mass | Mass Spec. |
|---|---|---|---|---|---|
| 53 | (cyclopentyl amide group) | Cl | (R) | 599.36 | 600 (M⁺ + 1) |
| 54 | (pentan-3-yl amide group) | Cl | (R) | 601.38 | 602 (M⁺ + 1) |
| 55 | (tert-butyl amide group) | Cl | (S) | 587.36 | 588 (M⁺ + 1), 610 (M⁺ + Na) |

SCHEME 7

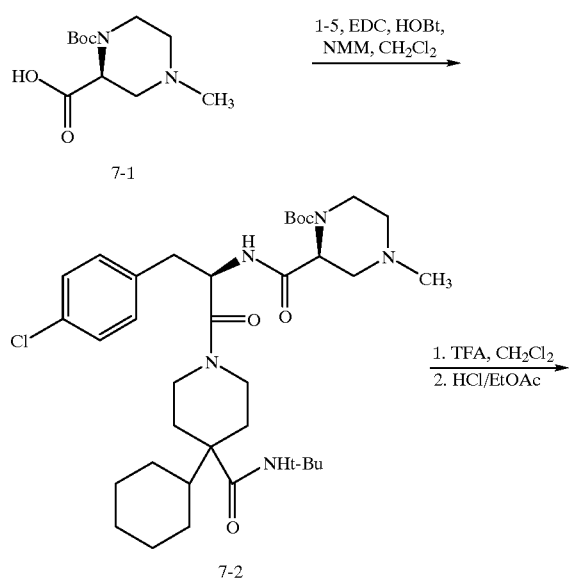

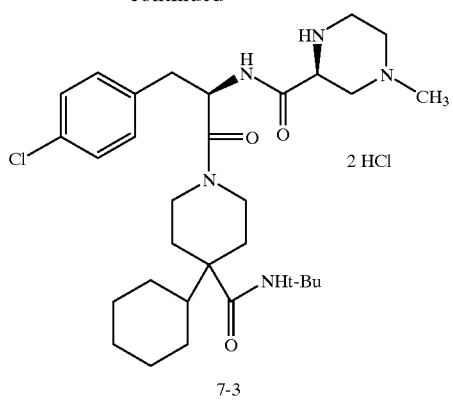

7-3

EXAMPLE 56

Step A

Intermediate 7-2 was prepared in a similar fashion as 1-11 but using (S)-4-methyl-1-(tert-butoxycarbonyl)-piperazine-2-carboxylic acid (7-1) in the coupling reaction with amine 1-5. (S)-4-Methyl-1-(tert-butoxycarbonyl)-piperazine-2-carboxylic acid (7-1) (61.0% purity, 0.162 g, 0.405 mmol) was dissolved in 1.8 mL of methylene chloride, and then the amine intermediate 1-5 (0.165 g, 0.368 mmol), NMM (0.16 mL, 1.472 mmol), EDC (0.078 g, 0.405 mmol), and HOBt (0.055 g, 0.405 mmol) were added. The resulting mixture was stirred at room temperature overnight, and then diluted with 10 mL of CH$_2$Cl$_2$ and washed with 5 mL of 1N HCl, 5 mL of saturated NaHCO$_3$, 5 mL of H$_2$O, and 5 mL of saturated NaCl solution, dried over MgSO$_4$, filtered and concentrated to give a yellow oil. The crude product was purified by column chromatography on silica gel (9:1 to 1:1 methylene chloride-acetone) to give 7-2 as a white solid (0.219 g).

Step B

Compound 7-2 (0.219 g, 0.324 mmol) was dissolved in 0.80 mL of methylene chloride and 0.80 ml of trifluoroacetic acid. This solution was stirred for 30 min at room temperature, and then concentrated with toluene (5 mL×2) and diethyl ether (5 mL×2) to give a white foamy solid. The solid was dissolved in EtOAc and washed with 1N NaOH, and the aqueous layer was extracted with EtOAc. The combined organics were dried over K$_2$CO$_3$, filtered and concentrated. Purification by column chromatography (5% -10% methanol in methylene chloride) provided a white foamy solid. The solid was dissolved in EtOAc and 1.0 M HCl in Et$_2$O (0.78 mL, 0.78 mmol) was added. The precipitate was filtered under N$_2$ and dried under vacuum to give 7-3 as a white solid (0.083 g); mass spectrum: 574 (M+1); 596 (M+Na).

The N$^\alpha$-(tert-butoxycarbonyl)-N$^\beta$-substituted-piperazine-2-carboxylic acid amide intermediates shown in Table 6 below were prepared by reductive alkylation of N$^\alpha$-(tert-butoxycarbonyl)-piperazine-2-carboxylic acid methyl ester with the appropriate aldehyde or nucleophilic displacement of an alkyl halide with N$^\alpha$-(tert-butoxycarbonyl)-piperazine-2-carboxylic acid methyl ester, followed by saponification, and coupling with the appropriate substituted N-piperidinyl-Phe amine intermediate. Alternatively, N$^\alpha$-(tert-butoxycarbonyl)-N$^\beta$-(Cbz)-piperazine-2-carboxylic acid was EDC-coupled with the substituted N-piperidinyl-4-halo-Phe amine intermediate, the Cbz group cleaved by hydrogenolysis (H$_2$, Pd/C), and then either reductive alkylation of the β-piperazine nitrogen with the appropriate aldehyde or nucleophilic displacement of an alkyl halide.

TABLE 6
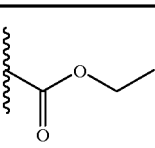
| X | R⁶ | ** | R⁴ᵇ | Exact Mass | Mass Spec. |
|---|---|---|---|---|---|
| 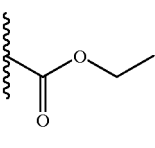 | Cl | (S) | i-Pr | 674.38 | 675 ($M^+ + 1$) |
| 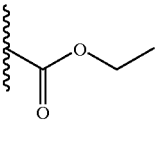 | F | (S) | 2-hydroxyethyl | 660.39 | 661 ($M^+ + 1$) |
| 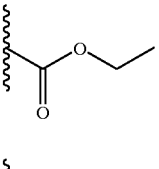 | F | (S) | 2-methoxyethyl | 674.41 | 675 ($M^+ + 1$), 697 ($M^+ + Na$) |
| 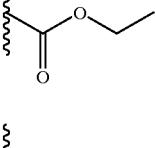 | F | (S) | $CH_2CO_2Et$ | 702.40 | 703 ($M^+ + 1$), 725 ($M^+ + Na$) |
| 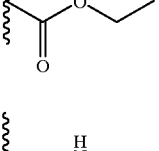 | F | (R) | Me | 630.38 | 631 ($M^+ + 1$), 653 ($M^+ + Na$) |
| 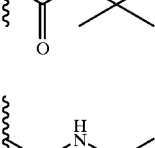 | F | (R) | 2-methoxyethyl | 674.41 | 675 ($M^+ + 1$), 697 ($M^+ + Na$) |
| 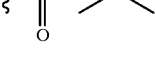 | Cl | (S) | i-Pr | 701.43 | 702 ($M^+ + 1$) |
| 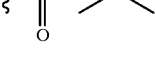 | Cl | (S) | 2,2-difluoroethyl | 723.39 | 724 ($M^+ + 1$) |

TABLE 6-continued

| X | R⁶ | ** | R⁴ᵇ | Exact Mass | Mass Spec. |
|---|---|---|---|---|---|
| -C(O)NH-C(CH₃)₃ | F | (S) | Me | 657.43 | 658 (M⁺ + 1) |
| -C(O)NH-C(CH₃)₃ | F | (S) | i-Pr | 685.46 | 686 (M⁺ + 1) |
| -C(O)NH-C(CH₃)₃ | F | (S) | 2,2-difluoroethyl | 707.42 | 708 (M⁺ + 1) |
| -C(O)NH-C(CH₃)₃ | Cl | (R) | Me | 673.40 | 674 (M⁺ + 1), 696 (M⁺ + Na) |
| -C(O)NH-C(CH₃)₃ | Cl | (R) | i-Pr | 701.43 | 702 (M⁺ + 1) |
| -C(O)NH-C(CH₃)₃ | Cl | (R) | cyclopropylmethyl | 713.43 | 714 (M⁺ + 1) |
| -C(O)NH-C(CH₃)₃ | Cl | (R) | benzyl | 749.43 | 750 (M⁺ + 1) |
| -C(O)NH-C(CH₃)₃ | Cl | (R) | 2-propynyl | 697.40 | 698 (M⁺ + 1) |

TABLE 6-continued

| X | R⁶ | ** | R⁴ᵇ | Exact Mass | Mass Spec. |
|---|---|---|---|---|---|
| ~C(O)NH-C(CH₃)₃ | Cl | (R) | cyclobutyl | 713.43 | 714 (M⁺ + 1) |
| ~C(O)NH-C(CH₃)₃ | Cl | (R) | 2,2-difluoroethyl | 723.39 | 724 (M⁺ + 1) |
| ~C(O)NH-C(CH₃)₃ | F | (R) | Me | 657.43 | 658 (M⁺ + 1) |
| ~C(O)NH-C(CH₃)₃ | F | (R) | i-Pr | 685.46 | 686 (M⁺ + 1) |
| ~C(O)NH-C(CH₃)₃ | F | (R) | cyclopropylmethyl | 697.46 | 698 (M⁺ + 1) |
| ~C(O)NH-C(CH₃)₃ | F | (R) | 2,2-difluoroethyl | 707.42 | 708 (M⁺ + 1) |
| ~C(O)NH-iPr | Cl | (S) | Me | 659.38 | 660 (M⁺ + 1) |
| ~C(O)NH-cyclobutyl | Cl | (S) | Me | 671.38 | 672 (M⁺ + 1) |

TABLE 6-continued

| X | R⁶ | ** | R⁴ᵇ | Exact Mass | Mass Spec. |
|---|---|---|---|---|---|
| ⌇C(O)NH-cyclobutyl | Cl | (R) | Me | 671.38 | 672 (M⁺ + 1) |
| ⌇C(O)NH-cyclopentyl | Cl | (S) | Me | 685.40 | 686 (M⁺ + 1) |
| ⌇C(O)NH-cyclopentyl | Cl | (R) | Me | 685.40 | 686 (M⁺ + 1) |
| ⌇C(O)NH-CH(Et)₂ | Cl | (S) | Me | 687.41 | 688 (M⁺ + 1) |
| ⌇C(O)NH-CH(Et)₂ | Cl | (R) | Me | 687.41 | 688 (M⁺ + 1) |
| ⌇C(O)NH-CH₂C(CH₃)₃ | Cl | (R) | Me | 687.41 | 688 (M⁺ + 1) |
| ⌇C(O)NH-(2-pyridyl) | Cl | (S) | Me | 694.36 | 695 (M⁺ + 1), 717 (M⁺ + Na) |

TABLE 6-continued

| X | R⁶ | ** | R⁴ᵇ | Exact Mass | Mass Spec. |
|---|---|---|---|---|---|
| N-methylpiperazine carbonyl | F | (S) | Me | 684.44 | 685 (M⁺ + 1), 707 (M⁺ + Na) |
| NH-C(O)-t-Bu | Cl | (S) | Me | 673.40 | 674 (M⁺ + 1), 696 (M⁺ + Na) |
| NH-C(O)-t-Bu | Cl | (R) | Me | 673.40 | 674 (M⁺ + 1), 696 (M⁺ + Na) |
| 4,4-dimethyl-oxazolidinone-CH₂ | F | (S) | Me | 685.42 | 686 (M⁺ + 1) |
| 4,4-dimethyl-oxazolidinone-CH₂ | F | (R) | Me | 685.42 | 686 (M⁺ + 1) |
| 4,4-dimethyl-oxazolidinone-CH₂ | F | (R) | i-Pr | 713.45 | 714 (M⁺ + 1) |
| NH-C(O)-t-Bu | F | (S) | Et | | 672 (M⁺ + 1) |

TABLE 6-continued

| X | R⁶ | ** | R⁴ᵇ | Exact Mass | Mass Spec. |
|---|----|----|-----|------------|------------|
| (oxazolidinone-CH₂ group) | F | (R) | H | | 672 (M⁺ + 1) |

The following N^α-unsubstituted-N^β-(R^{4b})-piperazine Examples shown in Table 7 below above with the indicated stereochemistry at the stereogenic center marked with ** were prepared as their bis-hydrochloride salts by cleavage of the N^α-(Boc) group in the corresponding compounds in Table 6 to afford the trifluoroacetate salt, which upon neutralization and subsequent treatment with HCl in diethyl ether afforded the hydrochloride salt.

TABLE 7

| Ex. | X | R⁶ | ** | R⁴ᵇ | | Mass Spec. |
|-----|---|----|----|-----|--|-----------|
| 57 | ethyl ester-CH₂ | Cl | (S) | i-Pr | 574.33 | 575 (M⁺ + 1), 597 (M⁺ + Na) |
| 58 | ethyl ester-CH₂ | F | (S) | 2-hydroxyethyl | 560.34 | 561 (M⁺ + 1), 583 (M⁺ + Na) |

TABLE 7-continued

| Ex. | X | R⁶ | ** | R⁴ᵇ | Mass Spec. | |
|---|---|---|---|---|---|---|
| 59 | ethyl ester (–C(O)OEt) | F | (S) | 2-methoxyethyl | 574.35 | 575 (M⁺ + 1), 597 (M⁺ + Na) |
| 60 | ethyl ester | F | (S) | CH₂CO₂Et | 602.35 | 603 (M⁺ + 1), 625 (M⁺ + Na) |
| 61 | ethyl ester | F | (R) | Me | 530.33 | 531 (M⁺ + 1), 553 (M⁺ + Na) |
| 62 | ethyl ester | F | (R) | 2-methoxyethyl | 574.35 | 575 (M⁺ + 1), 597 (M⁺ + Na) |
| 63 | t-butyl amide | Cl | (S) | Me | 573.34 | 574 (M⁺ + 1), 596 (M⁺ + Na) |
| 64 | t-butyl amide | Cl | (S) | i-Pr | 601.38 | 602 (M⁺ + 1), 624 (M⁺ + Na) |
| 65 | t-butyl amide | Cl | (S) | 2,2-difluoroethyl | 623.34 | 624 (M⁺ + 1) |
| 66 | t-butyl amide | F | (S) | Me | 557.37 | 558 (M⁺ + 1), 580 (M⁺ + Na) |

TABLE 7-continued

| Ex. | X | R[6] | ** | R[4b] | Mass Spec. |
|---|---|---|---|---|---|
| 67 | ~C(O)NH-C(CH3)3 | F | (S) | i-Pr | 585.41 586 (M+ + 1) |
| 68 | ~C(O)NH-C(CH3)3 | F | (S) | 2,2-difluoroethyl | 607.37 608 (M+ + 1) |
| 69 | ~C(O)NH-C(CH3)3 | Cl | (R) | Me | 573.34 574 (M+ + 1), 596 (M+ + Na) |
| 70 | ~C(O)NH-C(CH3)3 | Cl | (R) | i-Pr | 601.38 602 (M+ + 1) |
| 71 | ~C(O)NH-C(CH3)3 | Cl | (R) | cyclopropylmethyl | 613.38 614 (M+ + 1) |
| 72 | ~C(O)NH-C(CH3)3 | Cl | (R) | benzyl | 649.38 650 (M+ + 1) |
| 73 | ~C(O)NH-C(CH3)3 | Cl | (R) | 2-propynyl | 597.34 598 (M+ + 1) |
| 74 | ~C(O)NH-C(CH3)3 | Cl | (R) | cyclobutyl | 613.38 614 (M+ + 1) |

TABLE 7-continued

| Ex. | X | R⁶ | ** | R⁴ᵇ | Mass Spec. |
|---|---|---|---|---|---|
| 75 | ~C(O)NH-C(CH₃)₃ | Cl | (R) | 2,2-difluoroethyl | 623.34 624 (M⁺ + 1) |
| 76 | ~C(O)NH-C(CH₃)₃ | F | (R) | Me | 557.37 558 (M⁺ + 1), 580 (M⁺ + Na) |
| 77 | ~C(O)NH-C(CH₃)₃ | F | (R) | i-Pr | 585.41 586 (M⁺ + 1) |
| 78 | ~C(O)NH-C(CH₃)₃ | F | (R) | cyclopropylmethyl | 597.41 598 (M⁺ + 1) |
| 79 | ~C(O)NH-C(CH₃)₃ | F | (R) | 2,2-difluoroethyl | 607.37 608 (M⁺ + 1) |
| 80 | ~C(O)NH-CH(CH₃)₂ | Cl | (S) | Me | 559.33 560 (M⁺ + 1), 682 (M⁺ + Na) |
| 81 | ~C(O)NH-cyclobutyl | Cl | (S) | Me | 571.33 572 (M⁺ + 1) |
| 82 | ~C(O)NH-cyclobutyl | Cl | (R) | Me | 571.33 572 (M⁺ + 1) |

TABLE 7-continued
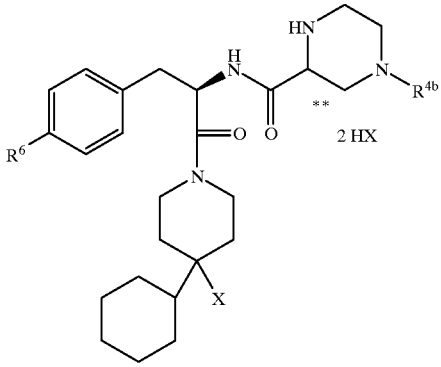
| Ex. | X | R[6] | ** | R[4b] | Mass Spec. |
|---|---|---|---|---|---|
| 83 | ![cyclopentyl amide] | Cl | (S) | Me | 585.34  586 (M[+] + 1) |
| 84 | ![cyclopentyl amide] | Cl | (R) | Me | 585.34  586 (M[+] + 1) |
| 85 | ![pentan-3-yl amide] | Cl | (S) | Me | 587.36  588 (M[+] + 1) |
| 86 | ![pentan-3-yl amide] | Cl | (R) | Me | 587.36  588 (M[+] + 1) |
| 87 | ![neopentyl amide] | Cl | (R) | Me | 587.36  588 (M[+] + 1) |
| 88 | ![2-pyridyl amide] | Cl | (S) | Me | 594.31  595 (M[+] + 1), 617 (M[+] + Na) |
| 89 | ![4-methylpiperazinyl amide] | F | (S) | Me | 584.39  585 (M[+] + 1), 607 (M[+] + Na) |

TABLE 7-continued
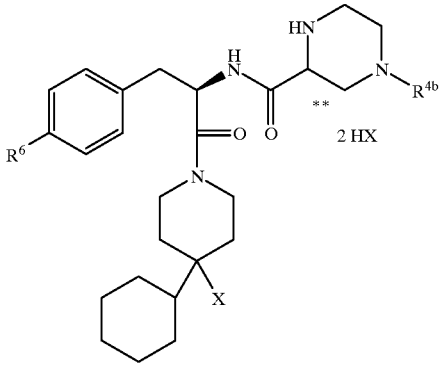
| Ex. | X | R⁶ | ** | R⁴ᵇ | | Mass Spec. |
|---|---|---|---|---|---|---|
| 90 | 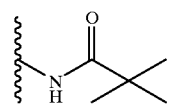 | Cl | (S) | Me | 573.34 | 574 (M⁺ + 1), 596 (M⁺ + Na) |
| 91 | 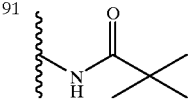 | Cl | (R) | Me | 573.34 | 574 (M⁺ + 1), 596 (M⁺ + Na) |
| 92 | 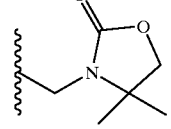 | Cl | (S) | Me | 601.34 | 602 (M⁺ + 1), 624 (M⁺ + Na) |
| 93 | 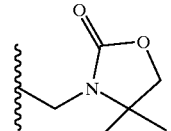 | Cl | (R) | Me | 601.34 | 602 (M⁺ + 1), 624 (M⁺ + Na) |
| 94 | 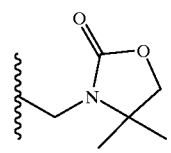 | F | (S) | Me | 585.37 | 586 (M⁺ + 1) |
| 95 | 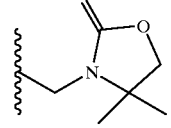 | F | (R) | Me | 585.37 | 586 (M⁺ + 1) |
| 96 | 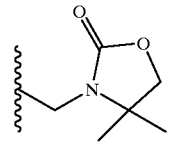 | F | (R) | i-Pr | 613.40 | 614 (M⁺ + 1) |

TABLE 7-continued
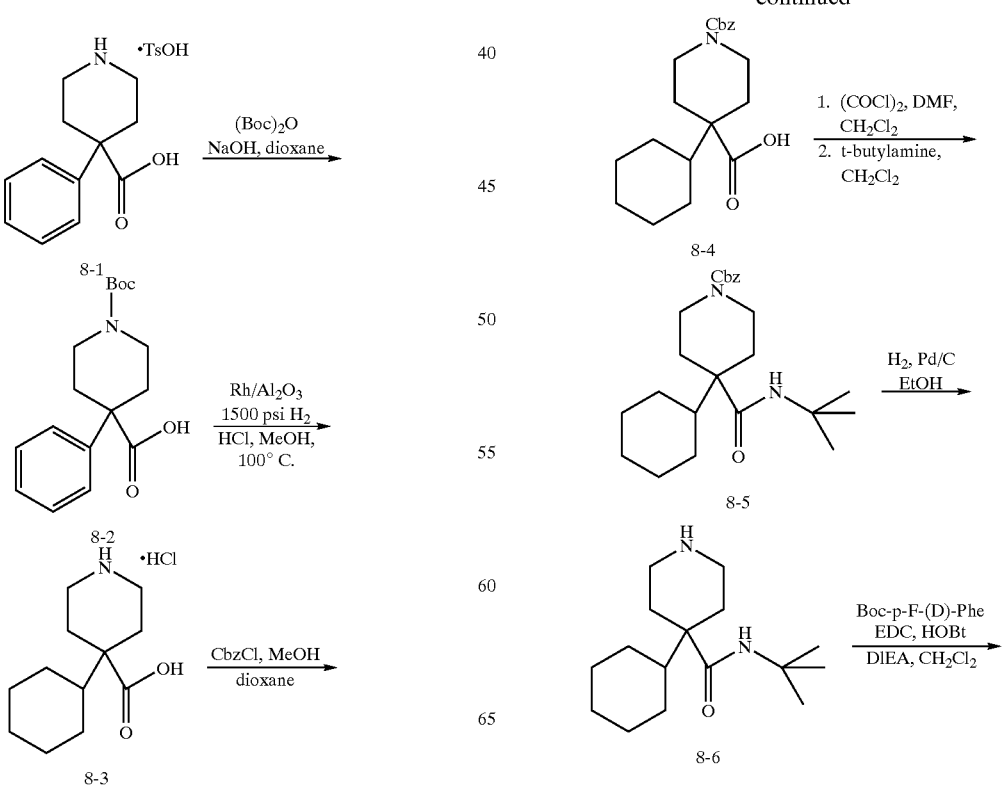
| Ex. | X | R⁶ | ** | R⁴ᵇ | Mass Spec. |
|---|---|---|---|---|---|
| 97 | ⸺NH-C(CH₃)₃ (amide) | F | (S) | Et | 572 (M⁺ + 1) |
| 98 | ⸺CH₂CH₂C(CH₃)₂OH | F | (R) | Me | 545 (M⁺ + 1) |
| 99 | ⸺CH₂CH₂C(CH₃)₂OH | F | (S) | Me | 545 (M⁺ + 1) |

-continued

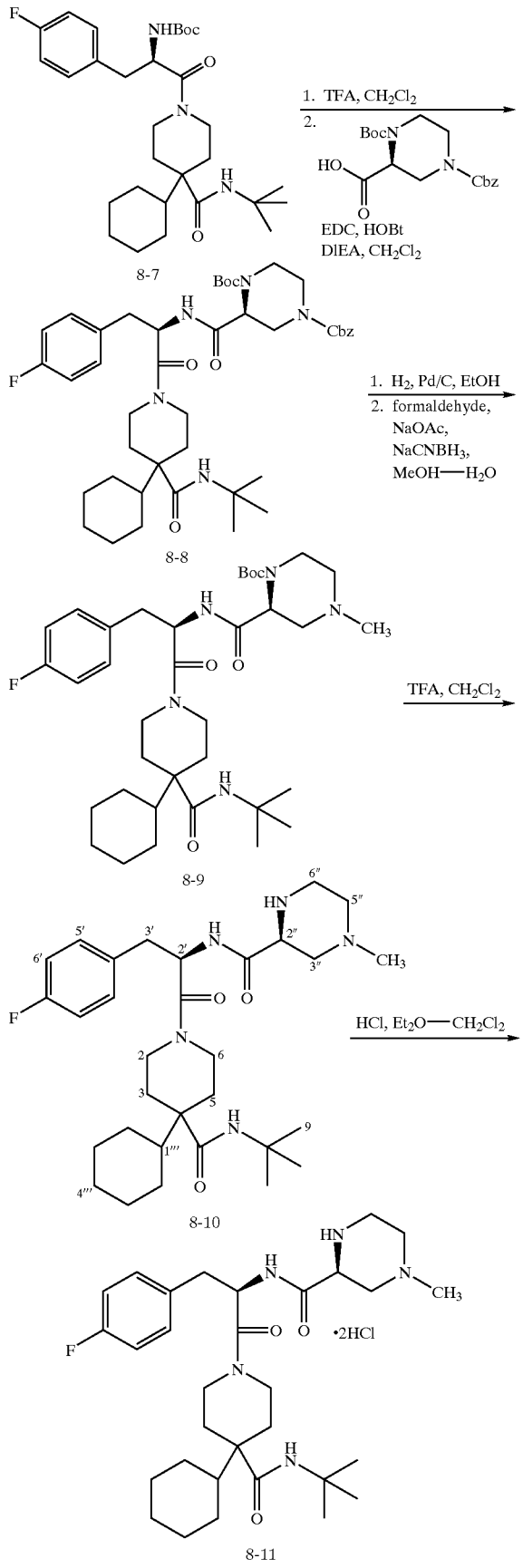

EXAMPLE 100

Step A: 4-Phenyl-1,4-piperidinedicarboxylic Acid 1-(1,1-dimethylethyl) Ester (8–2)

A 12-L, three-necked, round-bottomed flask equipped with a mechanical stirrer was charged with commercially available 4-phenyl-4-piperidinecarboxylic acid p-methylbenzenesulfonate (8–1) (500 g, 1.32 mol), di-tert-butyl dicarbonate (318 g, 1.46 mol), 3000 mL of 1 N NaOH solution (3.0 mol), and 3000 mL of dioxane. After addition, the pH was adjusted to 11–12 using 5 N NaOH solution, and the resulting mixture was stirred at room temperature overnight. The mixture was then concentrated and acidified using 2 N HCl solution to about pH 1. The precipitate was filtered using 2 L of water to wash and dried to give 418 g of title compound 8–2 as a white solid.

Step B: 4-Cyclohexyl-4-piperidinecarboxylic Acid Hydrochloride (8–3)

4-Phenyl-1,4-piperidinedicarboxylic acid 1-(1,1-dimethylethyl) ester (8–2) (202 g, 0.662 mol) was dissolved in 1700 mL of 10% HCl in methanol and rhodium on alumina (25 g) was added. The mixture was placed on a high pressure hydrogenator using 1500 psi of hydrogen at 100° C. for 17 h. The resulting mixture was filtered through Celite using methanol to rinse and concentrated. The resulting solid was triturated with diethyl ether and filtered to afford title compound 8–3 as an off-white solid.

Step C: 4-Cyclohexyl-1,4-piperidinedicarboxylic Acid 1-(phenylmethyl) Ester (8–4)

A 2-L, three-necked, round-bottomed flask equipped with a mechanical stirrer and two addition funnels was charged with 4-cyclohexyl-4-piperidinecarboxylic acid hydrochloride (8–3) (157.9 g, 0.637 mol), 1 L of dioxane, and 255 mL of 5 N NaOH solution. The mixture was cooled at about 5° C., and then benzyl chloroformate (92 mL, 0.643 mmol) and 127 mL of 5 N NaOH solution were added dropwise simultaneously via two separate addition funnels while maintaining the temperature at or below 10° C. The reaction was monitored by TLC and, upon completion, the resulting mixture was diluted with 1 L of water and concentrated. The residue was diluted with 2 L of water and the pH was adjusted to about 12 using 5 N NaOH solution. The mixture was then extracted with 1 L of ethyl acetate. The aqueous layer was acidified to pH 1.5–2.0 using 2 N HCl solution, and extracted with three 1-L portions of ethyl acetate. The combined organic layers were washed with 1 L of saturated sodium chloride solution, dried over sodium sulfate, filtered and concentrated to give 165 g of title compound 8–4 as a white solid.

Step D: 4-Cyclohexyl-4-[[(1,1-dimethylethyl)amino]carbonyl]-1-piperidinecarboxylic Acid Phenylmethyl Ester (8–5)

4-Cyclohexyl-1,4-piperidinedicarboxylic acid 1-(phenylmethyl) ester (8–4) (2.50 g, 7.24 mmol) was dissolved in 36 mL of methylene chloride and cooled at 0° C. in an ice-water bath. Oxalyl chloride (2.0 M solution in $CH_2Cl_2$, 3.98 mL, 7.96 mmol) was then added dropwise followed by the addition of 1–2 drops of DMF. This mixture was stirred at 0° C. for 2 h and then concentrated with toluene. The residue was dissolved in 36 mL of methylene chloride and cooled at 0° C. in an ice-water bath. tert-Butylamine (2.28 mL, 21.7 mmol) was then added dropwise, and the reaction mixture was stirred at 0° C. for 2 h, warmed to room temperature, and stirred at room temperature overnight. The resulting mixture was diluted with methylene chloride, washed with brine, dried over $MgSO_4$, filtered, and concentrated to give 2.92 g of title compound 8–5 as a solid. LCMS (ESI): m/z 401 (M$^+$+1).

Step E: 4-Cyclohexyl-N-(1,1-dimethylethyl)-4-piperidinecarboxamide (8–6)

4-Cyclohexyl-4-[[(1,1-dimethylethyl)amino]carbonyl]-1-piperidinecarboxylic acid phenylmethyl ester (8–5) (10.0 g, 25.0 mmol) was dissolved in 130 mL of ethyl alcohol and 10% palladium on carbon (1 g) was added. The mixture was evacuated and purged with hydrogen three times and then stirred at room temperature overnight. The resulting mixture was filtered through Celite using methylene chloride to rinse and concentrated to afford 6.22 g of title compound 876 as a white solid. This crude product was used in the next reaction without further purification. LCMS (ESI): m/z 267 (M$^+$+1). $^1$H NMR (500 MHz, CDCl$_3$) δ 2.99 (d, J=12.6 Hz, 2H), 2.71 (dd, J=12.3, 11.5 Hz, 2H), 1.93 (d, J=12.8 Hz, 2H), 1.79–1.73 (m, 3H), 1.65, (d, J=12.1 Hz, 1H), 1.51–1.45 (m, 2H), 1.36 (s, 9H), 1.33–0.94 (m, 7H).

Step F: [(1R)-2-[4-Cyclohexyl-4-[[(1,1-dimethylethyl)amino]carbonyl]-1-piperidinyl]-1-[(4-fluorophenyl)methyl]-2-oxoethyl]carbamic Acid 1,1-dimethylethyl Ester (8–7)

N-Boc-(D)-4-fluorophenylalanine (7.26 g, 25.63 mmol) was dissolved in 116.5 mL of methylene chloride, and amine 8–6 (6.21 g, 23.3 mmol), DIEA (16.2 mL, 93.2 mmol), EDC.HCl (4.91 g, 25.6 mmol), and HOBt (3.46 g, 25.6 mmol) were added. The resulting mixture was stirred at room temperature overnight and then diluted with 100 mL of methylene chloride. The mixture was washed with 100 mL of 1 N HCl solution, 100 mL of saturated NaHCO$_3$ solution, 100 mL of water, and 100 mL of saturated NaCl solution, dried over MgSO$_4$, filtered, and concentrated to give a white foamy-solid. The crude product was purified by column chromatography (30:1 to 9:1 methylene chloride-acetone) to give 10.1 g (81%) of title compound 8–7 as a white solid. LCMS (ESI): m/z 532 (M$^+$+1). $^1$H NMR (500 MHz, CDCl$_3$) (mixture of two rotamers) δ 7.20–6.90 (m), 5.45 (d, J=8.7 Hz), 5.36 (d, J=8.5 Hz), 5.20 (d, J=5.8 Hz), 4.84–4.77 (m), 4.42 (d, J=12.9 Hz), 3.56 (m), 3.04 (dd, J=12.8, 12.3 Hz), 2.95 (d, J=7.3 Hz), 2.89 (d, J=6.9 Hz), 2.61–2.54 (m), 1.87–1.54, (m), 1.41 (s), 1.35 (s), 1.32 (s), 1.28–0.80 (m), 0.33–0.28 (m).

Steps G and H: (2S)-2-[[[(1R)-2-[4-cyclohexyl-4-[[(1,1-dimethylethyl)amino]carbonyl]-1-piperidinyl]-1-[(4-fluorophenyl)methyl]-2-oxoethyl]amino]carbonyl]-1,4-piperazinedicarboxylic Acid 1-(1,1-dimethylethyl) 4-(phenylmethyl) Ester (8–8)

Step G

Compound 8–7 (5.33 g, 10.0 mmol) was dissolved in 25.1 mL of methylene chloride and 25.1 mL of trifluoroacetic acid. This solution was stirred at room temperature for 30 min. The mixture was then concentrated with four 30-mL portions of methylene chloride to give a white foamy solid. The solid was dissolved in ethyl acetate and washed with 1 N NaOH solution, and the aqueous layer was extracted with ethyl acetate. The combined organics were dried over K$_2$CO$_3$, filtered, and concentrated to give 4.04 g of a white foamy-solid. This crude product was used in the next reaction without further purification. LCMS (ESI): m/z 432 (M$^+$+1). $^1$H NMR (500 MHz, CDCl$_3$) (mixture of two rotamers) δ 7.28–6.24 (m), 5.25 (d, J=8.2 Hz), 4.51 (d, J=13.5 Hz), 3.96–3.90 (m), 3.62 (d, J=13.5 Hz), 3.55 (d, J=13.7 Hz), 3.10–3.05 (m), 2.93–2.81 (m), 2.74–2.69 (m), 2.62–2.57 (m), 2.00 (d, J=13.5 Hz), 1.85–1.47 (m), 1.37 (s), 1.35 (s), 1.33–0.81 (m), 0.41–0.35 (m).

Step H (2S)-1,2,4-piperazinetricarboxylic acid 1-(1,1-dimethylethyl) 4-(phenylmethyl) ester (the preparation of this intermediate from commercially available 2-(S)-piperazine carboxylic acid was achieved via modifications to the procedures described by Bigge and coworkers in *Tetrahedron Lett.* 1989, 30, 5193) (3.73 g, 10.3 mmol) was dissolved in 47 mL of methylene chloride, and the crude amine intermediate (4.02 g, 9.31 mmol), DIEA (6.49 mL, 37.2 mmol), EDC.HCl (1.97 g, 10.3 mmol), and HOBt (1.385 g, 10.3 mmol) were added. The resulting mixture was stirred at room temperature overnight and then diluted with 100 mL of methylene chloride. The mixture was washed with 100 mL of 1 N HCl solution, 100 mL of saturated NaHCO$_3$ solution, 100 mL of water, and 100 mL of saturated NaCl solution, dried over MgSO$_4$, filtered, and concentrated to give an off-white, foamy solid. The crude product was purified by column chromatography (30:1 to 3:1 methylene chloride-acetone) to give 5.77 g (80%) of title compound 8–8 as a white solid. LCMS (ESI): m/z 778 (M$^+$+1). $^1$H NMR (500 MHz, CDCl$_3$) (mixture of two rotamers) δ 7.37–6.79 (m), 5.30–5.00 (m), 4.71–4.50 (m), 4.40 (d, J=10.5 Hz), 4.04–3.79 (br s), 3.53 (d, J=12.6 Hz), 3.13–2.79 (m), 2.60–2.55 (m), 1.88–1.57 (m), 1.47 (s), 1.35 (s), 1.33 (s), 1.17–0.81 (m), 0.41–0.23 (m).

Steps I and J: (2S)-2-[[[(R)-2-[4-Cyclohexyl-4-[[(1,1-dimethylethyl)amino]carbonyl]-1-piperidinyl]-1-[(4-fluorophenyl)methyl]-2-oxoethyl]amino]carbonyl]-4-methyl-1-piperazinecarboxylic Acid 1,1-dimethylethyl Ester (8–9)

Step I

Compound 8–8 (5.77 g, 7.41 mmol) was dissolved in 37 mL of ethyl alcohol and 10% palladium on carbon (0.577 g) was added. The mixture was then evacuated and purged with hydrogen three times and stirred at room temperature overnight. The resulting mixture was filtered through Celite using methylene chloride to rinse and concentrated to give 4.28 g of a white solid. This crude product was used in the next reaction without further purification. LCMS (ESI): m/z 644 (M$^+$+1). $^1$H NMR (500 MHz, CDCl$_3$) (mixture of two rotamers) δ 7.19–6.92 (m), 5.21 (d, J=5.1 Hz), 5.17–5.10 (m), 4.60–4.46 (m), 4.41 (d, J=9.4 Hz), 3.98–3.85 (m), 3.60–3.46 (m), 3.06 (app t, J=13.2 Hz), 2.97–2.91 (m), 2.78 (d, J=12.8 Hz), 2.68–2.57 (m), 1.90–1.58 (m), 1.48 (s), 1.42–1.33 (m), 1.2–0.82 (m), 0.44–0.38 (m).

Step J

The crude amine intermediate from Step I (3.28 g, 5.10 mmol) was dissolved in 25.5 mL of methanol, and sodium acetate (2.09 g, 25.5 mmol), trifluoroacetic acid (0.39 mL, 5.10 mmol), and 37% aqueous formaldehyde solution (1.83 mL, 24.5 mmol) were added. The reaction mixture was stirred at room temperature for 20 min and then sodium cyanoborohydride (1.0 M in THF, 16.3 mL, 16.3 mmol) was added. The resulting mixture was stirred at room temperature overnight and then concentrated to give a white sludge. The crude mixture was dissolved in 30 mL of ethyl acetate and 15 mL of 1 N NaOH solution, and the layers were separated. The organic phase was washed with 15 mL of 1 N NaOH solution, 15 mL of water, and 15 mL of brine, dried over MgSO$_4$, filtered, and concentrated to give a solid. Purification by column chromatography (3% methanol in methylene chloride) afforded 2.84 g of title compound 8–9 as a white solid. LCMS (ESI): m/z 658 (M$^+$+1). $^1$H NMR (500 MHz, CDCl$_3$) (mixture of two rotamers) δ 7.18–6.91 m), 5.21 (d, J=7.3 Hz), 5.18–5.12 (m), 4.73–4.35 (m), 4.05–3.92 (m), 3.61–3.29 (m), 3.08–2.99 (m), 2.96–2.91

(m), 2.80–2.56 (m), 2.26 (s), 2.25 (s), 2.05–2.02 (m), 1.93–1.53 (m), 1.48 (s), 1.44–1.32 (m), 1.21–0.83 (m), 0.49–0.38 (m).

Steps K and L: (2S)-N-[(1R)-2-[4-Cyclohexyl-4-[[(1,1-dimethylethyl)amino]carbonyl]-1-piperidinyl]-1-[(4-fluorophenyl)methyl]-2-oxoethyl]-4-methyl-2-piperazinecarboxamide Dihydrochloride (8–11)

Step K

Compound 8–9 (2.82 g, 4.29 mmol) was dissolved in 10.7 mL of methylene chloride and 10.7 mL of trifluoroacetic acid. This solution was stirred at room temperature for 30 min. The mixture was then concentrated with four 30-mL portions of methylene chloride to give a white foamy solid. The solid was dissolved in ethyl acetate and washed with 1 N NaOH solution, and the aqueous layer was extracted with ethyl acetate. The combined organics were dried over $K_2CO_3$, filtered, and concentrated to give 2.18 g of 8–10 as a white foamy-solid. This crude product was used in the next reaction without further purification. LCMS (ESI): m/z 558 ($M^++1$); $^1H$ NMR (600 MHz, $CD_3CN$) (mixture of two rotamers) δ 2.53; 2.51 (H-2ax); 4.28; 4.26 (H-2eq); 1.28; 1.11 (H-3ax); 1.93; 1.27 (H-3eq); 1.31; 0.68 (H-5ax); 1.90; 1.83 (H-5eq); 2.75; 2.97 (H-6ax); 3.72; 3.66 (H-6eq); 5.74; 5.72 (7NH); 1.30 (H-9); 4.99 (H-2'); 7.55; 7.63 (2'NH); 2.91 (H-3'a); 2.84 (H-3'b); 7.18; 7.12 (H-5'); 7.01; 6.96 (H-6'); 3.22 (H-2''); 2.50 (H-3''a); 2.08 (H-3''b); 2.32 (H-5''a); 2.00 (H-5''b); 2.80 (H-6''a); 2.69 (H-6''b); 2.13 (NMe); 1.20 (H-1'''); 1.61 (H-2'''a); 0.90 (H-2'''b); 1.72 (H-3''', H-4'''a); 1.14 (H-3'''; H-4'''b); 1.04 (H-4''', H-3'''a); and 0.91 (H-4'''; H-3'''b).

Step L

The crude amine from Step K (1.89 g, 3.39 mmol) was dissolved in 8 mL of methylene chloride and 1.0 M HCl in ethyl ether (8.13 mL, 8.13 mmol) was added. The precipitate was filtered and dried under vacuum to give 2.09 g as a white solid. LCMS (ESI): m/z 558 ($M^++1$).

SCHEME 9

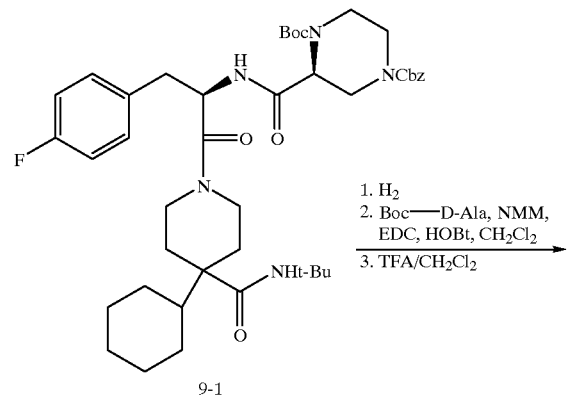

9-1

-continued

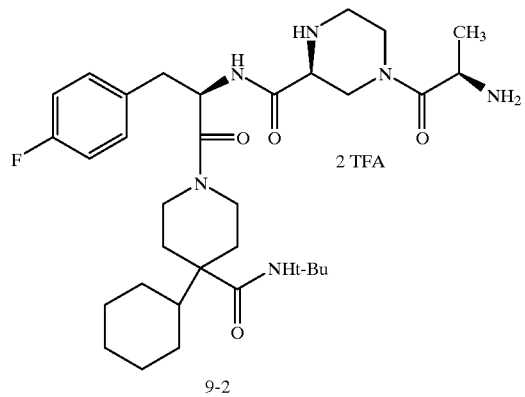

9-2

EXAMPLE 101

Step A

Compound 9–1 was hydrogenated to remove the Cbz group. N-tert-Butoxycarbonyl-(D)-alanine (0.050 g, 0.263 mmol) was dissolved in 1.2 mL of methylene chloride, and then the piperazine intermediate obtained after cleavage of the Cbz group above (0.154 g, 0.239 mmol), NMM (0.11 mL, 0.956 mmol), EDC (0.050 g, 0.263 mmol), and HOBt (0.036 g, 0.263 mmol) were added. The resulting mixture was stirred at room temperature overnight, and then diluted with 10 mL of $CH_2Cl_2$ and washed with 5 mL of 1N HCl, 5 mL of saturated $NaHCO_3$, 5 mL of $H_2O$, and 5 mL of saturated NaCl solution, dried over $MgSO_4$, filtered and concentrated to give a yellow oil. The crude product was purified by column chromatography (30:1 to 9:1 methylene chloride-acetone) to give a white solid (0.18 g). Mass spectrum: Calcd for $C_{43}H_{67}N_6O_8F$: 814.5; Found: 815 ($M^+$+1), 715 ($M^+$-Boc).

Step B

The bis-Boc intermediate was dissolved in 0.54 mL of methylene chloride and 0.54 mL of trifluoroacetic acid. This solution was stirred for 30 min at room temperature, and then concentrated with toluene (3 mL×2) and diethyl ether (3 mL×2) to give 9–2 as a TFA salt (0.22 g). Mass spectrum: Calcd for $C_{33}H_{51}N_6O_4F$: 614.40; Found: 615 ($M^++1$).

SCHEME 10

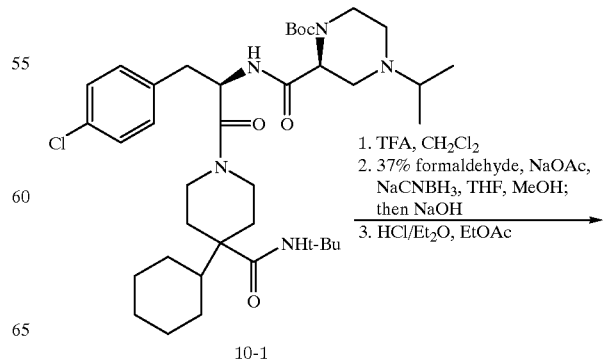

10-1

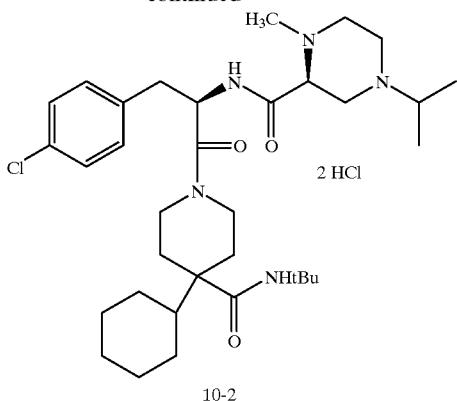

10-2

EXAMPLE 102

Intermediate 10–1 (0.066 g, 0.093 mmol) was dissolved in 0.24 mL of methylene chloride and 0.24 ml of trifluoroacetic acid. This solution was stirred for 30 min at room temperature, and then concentrated with toluene (5 mL×2) and diethyl ether (5 mL×2). The resulting foam was dissolved in 0.5 mL of methanol, and then sodium acetate (0.038 g, 0.465 mmol) and 37% aqueous formaldehyde solution (0.033 mL, 0.446 mmol) were added. The mixture was stirred at room temperature for 30 min, and then sodium cyanoborohydride (1.0 M in THF, 0.30 mL, 0.30 mmol) was added. The reaction mixture was stirred at room temperature overnight, and then concentrated to give a white sludge. The crude mixture was dissolved in EtOAc (10 mL) and 1N NaOH (5 mL), and the layers were separated. The organic phase was washed with 1N NaOH (5 mL), H$_2$O (5 mL), and brine (5 mL), dried over MgSO$_4$, filtered, and concentrated. Purification by column chromatography using 10% methanol in methylene chloride provided a white foamy solid. The solid was dissolved in EtOAc, and 1.0 M HCl in Et$_2$O (0.23 mL, 0.23 mmol) was added. The precipitate was filtered under N$_2$ and dried under vacuum to give 10–2 as a white solid (0.043 g); mass spectrum: Calcd for C$_{33}$H$_{54}$N$_5$O$_3$Cl: 615.39; Found: 616 (M$^+$+1).

EXAMPLE 103

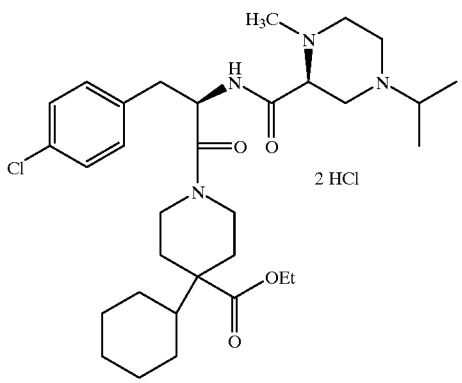

Example 103 was prepared in a similar fashion as Example 102, but using the 4-cyclohexyl-4-(ethoxycarbonyl)-piperidine intermediate instead; mass spectrum: Calcd for C$_{32}$H$_{49}$N$_4$O$_4$Cl: 588.34; Found: 589 (M$^+$+1).

SCHEME 11

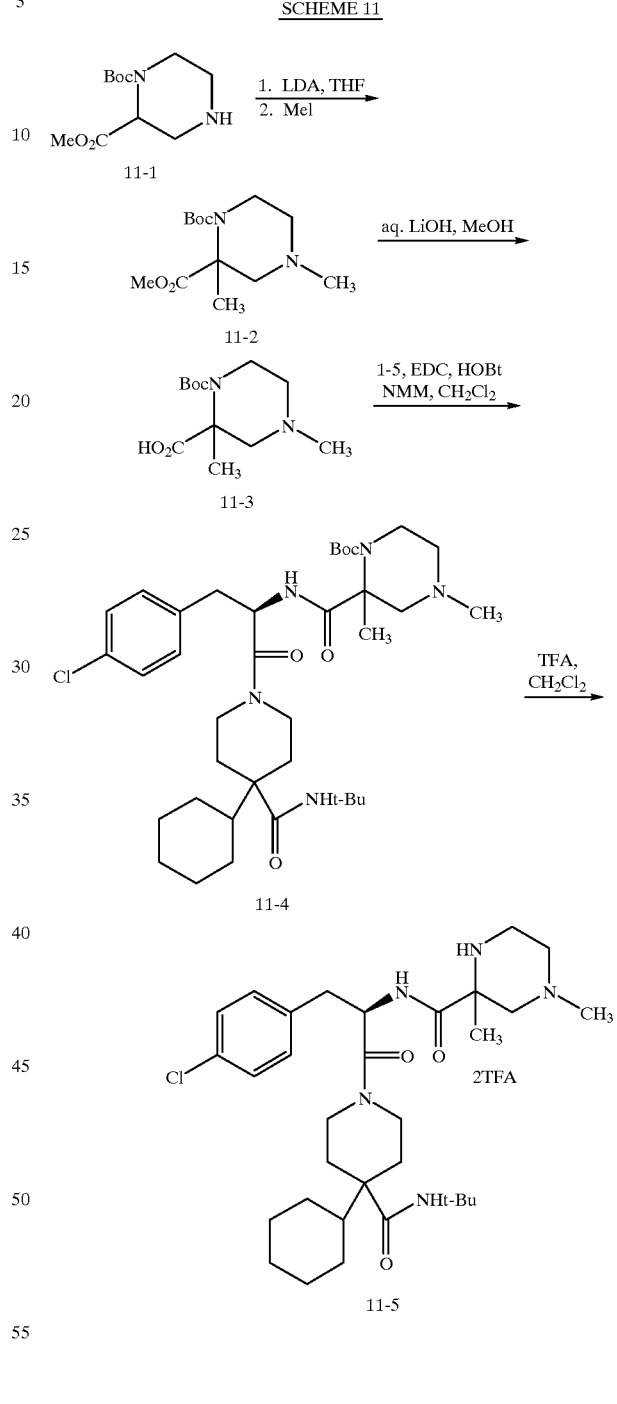

EXAMPLE 104

Step A

A solution of methyl (R)-1-(tert-butoxycarbonyl) piperazine-2-carboxylate (11–1) (0.37 g, 1.52 mmol) in 5 mL of anhydrous THF was treated with a solution of LDA (1.5 M in cyclohexane, 2.02 mL, 3.04 mmol) at −78° C. under $N_2$. After 0.5 h, a solution of methyl iodide (0.28 mL, 4.56 mmol) in THF was added. The mixture was stirred at −78° C. for 2.5 h, warmed up to room temperature, and stirred for 3 days. The resulting mixture was diluted with EtOAc and washed with sat. $NH_4Cl$ solution and brine. The organic phase was dried over $MgSO_4$, filtered and concentrated. Purification by column chromatography (30% ethyl acetate-hexane) provided 11–2 (0.024 g). Mass spectrum: Calcd for $C_{13}H_{24}N_2O_4$: 272.17; Found: 273 ($M^++1$).

Step B

Ester 11–2 (0.022 g, 0.081 mmol) was dissolved in 0.5 mL of methanol and lithium hydroxide in 0.5 mL of water was added. The mixture was stirred at 50° C. overnight, and then concentrated. The residue was dissolved in water and then the pH was adjusted to about 6. The solution was then concentrated twice with toluene to give 11–3 as a solid. Mass spectrum: Calcd for $C_{12}H_{22}N_2O_4$: 258.16; Found: 259 ($M^++1$).

Step C

The crude acid 11–3 (0.081 mmol) was dissolved in 0.4 mL of methylene chloride, and then the amine intermediate 1–5 (0.033 g, 0.074 mmol), NMM (0.033 mL, 0.296 mmol), EDC (0.016 g, 0.074 mmol), and HOBt (0.011 g, 0.074 mmol) were added. The resulting mixture was stirred at room temperature overnight, and then diluted with 5 mL of $CH_2Cl_2$ and washed with 2 mL of 1N HCl, 2 mL of saturated $NaHCO_3$, 2 mL of $H_2O$, and 2 mL of saturated NaCl solution, dried over $MgSO_4$, filtered and concentrated to give a yellow oil. The crude product was purified by column chromatography (30:1 to 9:1 methylene chloride-acetone) to give 11–4 as a white solid (0.012 g). Mass spectrum: Calcd for $C_{37}H_{58}N_5O_5Cl$: 687.41; Found: 688 ($M^++1$), 710 ($M^++Na$).

Step D

Intermediate 11–4 was dissolved in 0.05 mL of methylene chloride and 0.05 mL of trifluoroacetic acid, and the solution was stirred for 30 min at room temperature. The resulting mixture was then concentrated with toluene (2 mL×2) and diethyl ether (2 mL×2) to give 11–5 as a bis-TFA salt (0.012 g). Mass spectrum: Calcd for $C_{32}H_{50}N_5O_3Cl$: 587.36; Found: 588 ($M^++1$), 610 ($M^++Na$).

SCHEME 12

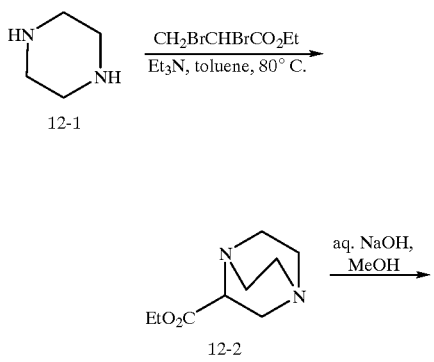

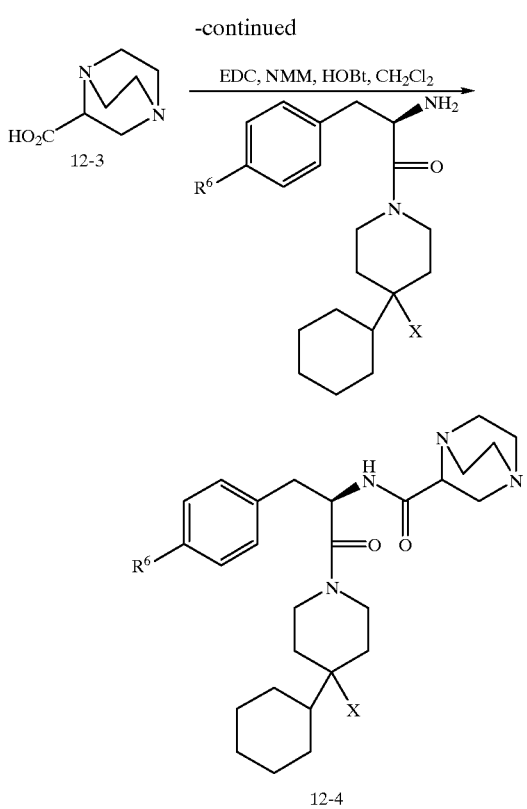

EXAMPLES 105–111

Examples 105–111 were prepared according to Scheme 12 above. The required bridged piperazine intermediate 12–3 was prepared as follows:

Step A

Piperazine (1.0 g, 11.61 mmol) was charged with 50 mL of toluene, triethylamine (3.24 mL, 23.22 mmol), and ethyl dibromopropionate (1.69 mL,11.61 mmol). The mixture was then heated at 80° C. and stirred overnight. The resulting white precipitate was filtered and the filtrate was concentrated to give an oil. Purification by column chromatography (3–10% methanol in methylene chloride) provided the bridged piperazine ester 12–2 (1.20 g). Mass spectrum: Calcd for $C_9H_{16}N_2O_2$: 184.12; Found: 185 ($M^++1$).

Step B

Ester 12–2 was dissolved in methanol and 1N NaOH solution was added. The mixture was stirred at room temperature overnight, and then concentrated. The residue was dissolved in water and then the pH was adjusted to 6. The solution was then concentrated twice with toluene to give the bridged piperazine acid 12–3 (1.81 g, 50.2% purity). Mass spectrum: Calcd for $C_7H_{12}N_2O_2$: 156.09; Found: 157 ($M^++1$).

Step C

Bridged piperazine acid 12–3 was coupled with the appropriate amine, and the isolated product was treated with HCl in diethyl ether to afford Examples 105–111 as their bishydrochloride salts.

TABLE 8
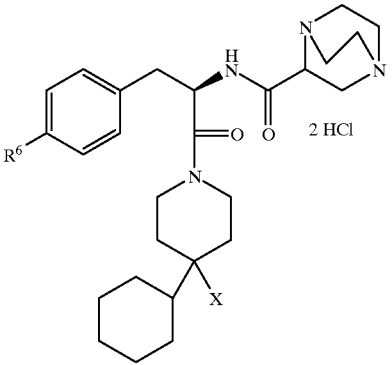
| Example | X | R⁶ | Exact mass | Mass Spec |
|---|---|---|---|---|
| 105 | 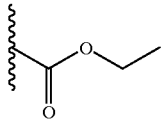 | Cl | 558.30 | 559 (M⁺ + 1) |
| 106 | 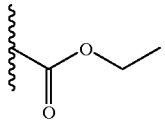 | F | 542.33 | 543 (M⁺ + 1) |
| 107 | 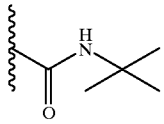 | Cl | 585.34 | 586 (M⁺ + 1) |
| 108 | 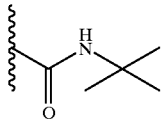 | F | 569.37 | 570 (M⁺ + 1) |
| 109 | 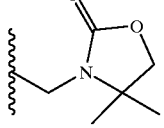 | Cl | 613.34 | 614 (M⁺ + 1) |
| 110 | 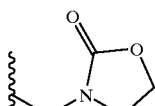 | F | 597.37 | 598 (M⁺ + 1) |
| 111 | 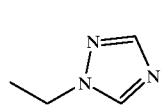 | Cl | 567.31 | 568 (M⁺ + 1), 590 (M⁺ + Na) |

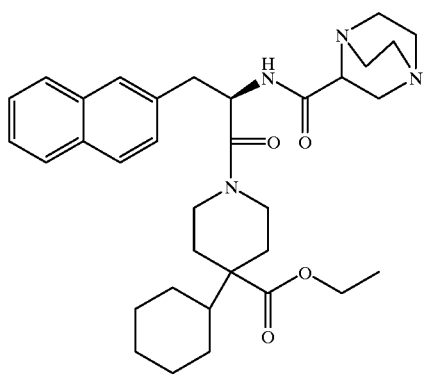

Example 112 was prepared in a similar fashion as Examples 105–111 but using the D-3-(2-naphthyl)alanine-derived amine intermediate for the coupling reaction. Mass spectrum: Calcd for $C_{34}H_{46}N_4O_4$: 574.35; Found: 575 ($M^+$+1).

SCHEME 13

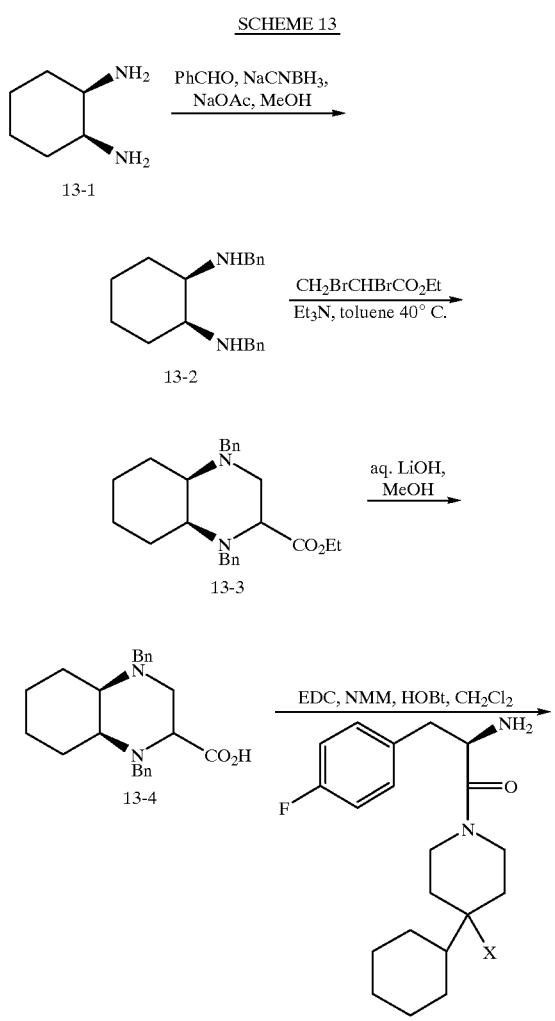

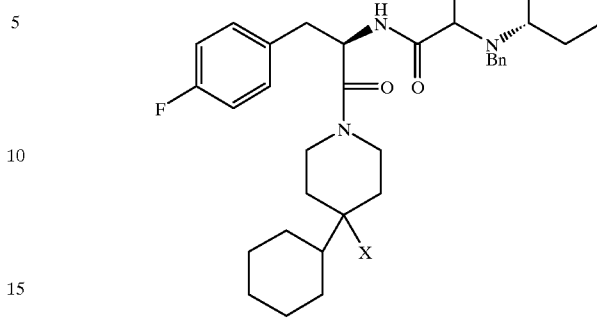

EXAMPLES 113–114

Examples 113 and 114 were prepared according to Scheme 12 above. The required saturated quinoxaline intermediate 13–4 was prepared as follows:

Step A

Cis-1,2-diaminocyclohexane (13–1) (2.95 g, 25.87 mmol) was charged with 45 mL of THF, benzaldehyde (5.78 mL, 56.91 mmol) and $MgSO_4$ (1.61 g), and stirred at room temperature for 2 h. The mixture was filtered and the solution was concentrated. The residue was dissolved in methanol (129.35 mL) and sodium acetate was added. After 20 min, sodium cyanoborohydride (1.0 M in THF, 77.6 mL, 77.6 mmol) was added, and the reaction mixture was stirred at room temperature overnight. The mixture was then concentrated, diluted with ethyl acetate, and washed with 1N aq. NaOH solution and brine, dried over $MgSO_4$, filtered and concentrated. Purification by column chromatography (9:1 $CH_2Cl_2$/acetone) afforded 13–2 as a yellow oil (0.51 g). Mass spectrum: Calcd for $C_{20}H_{26}N_2$: 294.21; Found: 295 ($M^+$+1).

Step B

Dibenzylamine 13–2 (0.498 g, 1.693 mmol) was charged with 8.5 mL of toluene and triethylamine (0.47 mL, 3.386 mmol). The mixture was heated at 40° C. and then ethyl 2,3-dibromopropionate (0.25 mL, 1.693 mmol) was added. The reaction mixture was then stirred at 80° C. overnight, filtered, and concentrated. Purification by column chromatography (30:1 $CH_2Cl_2$/acetone) provided 13–3 as a yellow solid (0.215 g). Mass spectrum: Calcd for $C_{25}H_{32}N_2O_2$: 392.25; Found: 393 ($M^+$+1).

Step C

Ester 13–3 (0.215 g, 0.55 mmol) was charged with 2.75 mL of methanol and a solution of lithium hydroxide (0.026 g, 1.10 mmol) in 0.5 mL of water. The mixture was stirred at 50° C. for 2 days and concentrated. The residue was dissolved in water and the pH was adjusted to 6. The mixture was then concentrated with toluene twice to give 13–4 as a solid (0.351 g, 57% purity). Mass spectrum: Calcd for $C_{23}H_{28}N_2O_2$: 364.22; Found: 365 ($M^+$+1).

TABLE 9

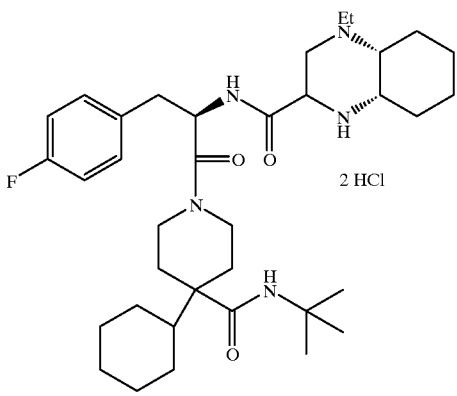

| Example | X | Exact mass | Mass Spec |
|---|---|---|---|
| 113 | (amide with NHtBu) | 777.50 | 778 (M+ + 1) |
| 114 | (ethyl ester) | 750.45 | 751 (M+ + 1) |

EXAMPLE 115

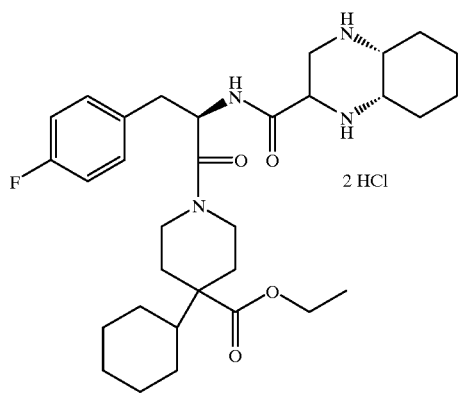

2 HCl

Example 113 (0.021 g, 0.027 mmol) was charged with 0.14 mL of EtOH and 10% Pd/C (0.0063 g). A $H_2$ balloon was placed on the top of the condenser via a 3-way stopcock, and the system was evacuated and purged with $H_2$ three times. The mixture was then stirred at 60° C. under $H_2$ overnight. The oil bath was removed and the flask was evacuated and purged with $N_2$ three times. The reaction mixture was filtered through a pad of Celite and concentrated to give a foamy solid. The solid was dissolved in $CH_2Cl_2$ and 1.0 M HCl in diethyl ether was added. The mixture was then concentrated to give Example 115 as a solid (0.017 g). Mass spectrum: Calcd for $C_{36}H_{56}N_5O_3F$: 625.44; Found: 626 (M++1).

EXAMPLE 116

2 HCl

Example 114 (0.021 g, 0.027 mmol) was charged with 0.14 mL of EtOH, 3.0 M HCl (0.12 mL, 0.122 mmol), and 10% Pd/C (0.0063 g). A $H_2$ balloon was placed on the top of the condenser via 3-way stop-cock and the system was evacuated and purged with $H_2$ three times. The mixture was then stirred at room temperature under $H_2$ for 5 h. The flask was evacuated and purged with $N_2$ three times, and then the reaction mixture was filtered through a pad of Celite and concentrated to give Example 116 as a solid (0.010 g). Mass spectrum: Calcd for $C_{32}H_7N_4O_3F$: 570.36; Found: 571 (M++1).

SCHEME 14

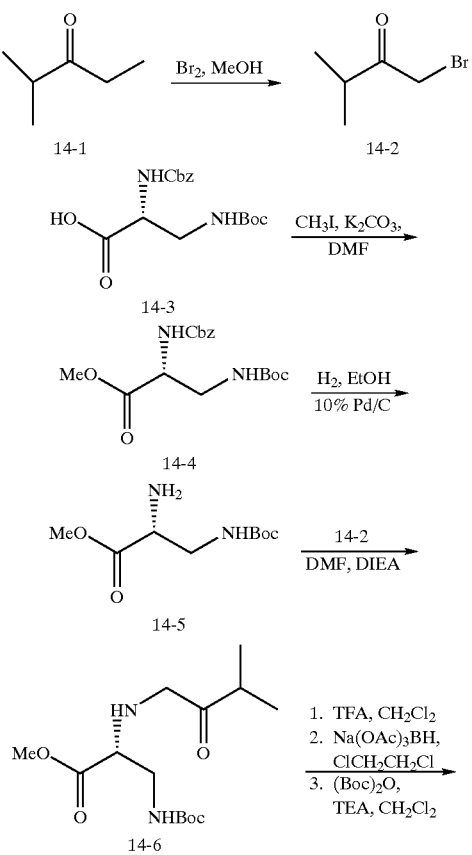

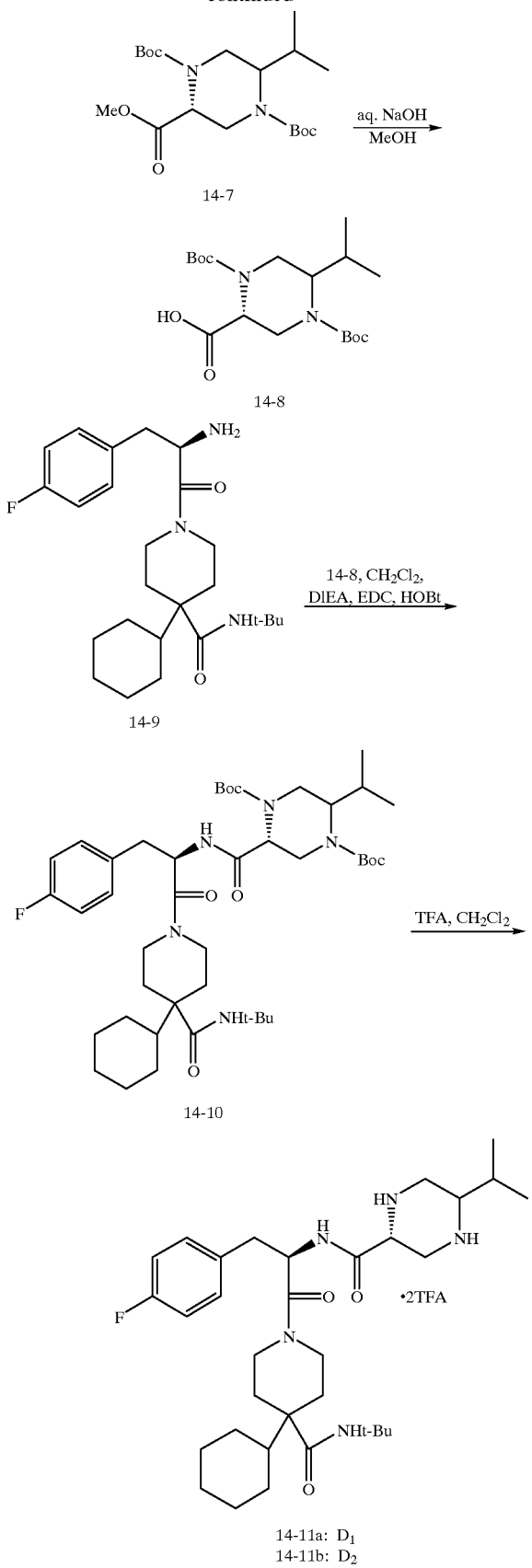

EXAMPLE 117

Step A

A 100-mL, three-necked, round-bottomed flask equipped with a condenser was charged with 3-methyl-2-butanone (14–1) (4.20 mL, 39.26 mmol) and 24 mL of methanol. The solution was stirred and cooled in an ice-H$_2$O bath at 0–5° C., and bromine (2.02 mL, 39.26 mmol) was added in a rapid, steady stream by syringe. The reaction temperature was maintained at 10° C. during the reaction time. The red color of the solution faded gradually in about 45 min and then 12 mL of H$_2$O was added, and the mixture was stirred at RT overnight. The resulting solution was diluted with 36 mL of H$_2$O and extracted with Et$_2$O (2×30 mL). The combined organic layers were washed with 40 mL of 10% potassium carbonate solution and H$_2$O, dried over MgSO$_4$, filtered, and concentrated to give 14–2 as a clear oil (5.23 g, 80%). $^1$H NMR (500 MHz, CDCl$_3$): δ 3.99 (s, 2H), 2.99 (m, 1H), 1.16 (d, 6H).

Step B

N-α-Cbz-N-β-Boc-(D)-diaminopropionic acid (14–3) (5.04 g, 14.91 mmol) was dissolved in 75 mL of DMF, and then K$_2$CO$_3$ (2.47 g, 17.89 mmol) and methyl iodide (4.64 mL, 74.55 mmol) were added. This mixture was stirred at RT overnight. The cloudy solution was diluted with EtOAc-H$_2$O, and the aqueous layer was extracted with EtOAc. The combined organics were washed with brine, dried over MgSO$_4$, filtered, and concentrated. Purification by chromatography on silica gel (30% EtOAc/hexane) gave 14–4 as a clear oil (5.21 g, 99%). LCMS (ESI): m/z 253 (M$^+$+1-Boc).

Step C

Compound 14–4 (5.20 g, 14.78 mmol) was dissolved in 74 mL of EtOH and 10% palladium on carbon (0.52 g) was added. The reaction mixture was stirred at RT under H$_2$ overnight. The reaction mixture was then filtered through Celite using CH$_2$Cl$_2$ and concentrated to give 14–5 as a clear oil (2.96 g, 91%). LCMS (ESI): m/z 219 (M$^+$+1).

Step D

Compound 14–5 (1.50 g, 6.87 mmol) was dissolved in 34.4 mL of DMF, and then DIEA (1.20 mL, 6.87 mmol) and compound 14–2 (1.13 g, 6.87 mmol) were added. Then the mixture was stirred at RT overnight. The reaction mixture was diluted with EtOAc and washed with brine and H$_2$O. The organic layer was dried over MgSO$_4$, filtered, and concentrated. Purification by chromatography on silica gel (30% and 50% EtOAc/hexane) gave 14–6 as a yellow oil (0.995 g, 48%). LCMS (ESI): m/z 303 (M$^+$+1), 247 (M$^+$-55).

Step E

Compound 14–6 (0.78 g, 2.59 mmol) was dissolved in 13.0 mL of 1:1 TFA-CH$_2$Cl$_2$ and stirred at RT for 30 min. Then the mixture was concentrated with CH$_2$Cl$_2$ two times. This TFA salt was dissolved in 32 mL of 1,2-dichloroethane, and sodium triacetoxyborohydride (0.77 g, 3.63 mmol) and acetic acid (0.15 mL, 2.59 mmol) were added. The reaction mixture was stirred at RT under N$_2$ overnight. To this reaction mixture, 16 mL of saturated aqueous NaHCO$_3$ solution was added, and the mixture was concentrated with toluene to give a yellow solid. The crude compound was dissolved in 13 mL of CH$_2$Cl$_2$ and then Boc-anhydride (1.24 g, 5.70 mmol) and TEA (1.08 mL, 7.77 mmol) were added. The resulting mixture was stirred at RT overnight, and then diluted with CH$_2$Cl$_2$. The organic phase was washed with 1N HCl and brine, dried over MgSO$_4$, filtered and concentrated. Purification by chromatography on silica gel (10% EtOAc/hexane) gave 14–7 as a white solid (0.51 g, 50%). LCMS (ESI): m/z 187 (M$^+$+1–2Boc).

Step F

Compound 14–7 (0.51 g, 1.31 mmol) was dissolved in 4 mL of MeOH and 1N aqueous NaOH solution (2.62 mL, 2.62 mmol) was added. This mixture was stirred at RT overnight, and then concentrated. Water was then added and the pH was adjusted to about 2 using 1N HCl solution. The acidic solution was then extracted with EtOAc, and the combined organics were washed with brine, dried over MgSO$_4$, filtered, and concentrated to give 14–8 as a white foamy-solid (0.40 g, 82%). LCMS (ESI): m/z 173 (M$^+$+ 1–2Boc).

Step G

N,N-Di-Boc-5-isopropyl-(R)-piperazine-2-carboxylic acid (14–8) (0.105 g, 0.281 mmol) was dissolved in 1.30 mL of methylene chloride, and then amine intermediate 14–9 (0.110 g, 0.255 mmol), DIEA (0.18 mL, 1.02 mmol), EDC (0.054 g, 0.255 mmol), and HOBt (0.038 g, 0.281 mmol) were added. The resulting mixture was stirred at room temperature overnight, and then diluted with 10 mL of CH$_2$Cl$_2$ and washed with 5 mL of 1N HCl solution, 5 mL of saturated NaHCO$_3$ solution, 5 mL of H$_2$O, and 5 mL of saturated NaCl solution. The organic phase was dried over MgSO$_4$, filtered, and concentrated to give a yellow oil. The crude product was purified by column chromatography on silica gel (30:1 to 9:1 methylene chloride-acetone) to give 14–10 as a white solid (0.148 g, 74%).

LCMS (ESI): m/z 786 (M$^+$+1).

Step H

Compound 14–10 (0.146 g, 0.185 mmol) was dissolved in 0.46 mL of methylene chloride and 0.46 mL of trifluoroacetic acid. This solution was stirred at room temperature for 1 h, and then concentrated with four, 2-mL portions of CH$_2$Cl$_2$ to give 14–11 as a white foamy-solid (0.142 g, 94%). LCMS (ESI): m/z 586 (M$^+$+1). This mixture of two diastereoisomers was separated into each diastereoisomer (D$_1$ and D$_2$) by preparative HPLC.

The following 5-substituted-piperazine Examples shown in Table 10 with the indicated stereochemistry at the stereogenic cneter marked with an ** were prepared in a similar manner as Example 117, but using the appropriate N,N-di-Boc-5-substituted-(R)-piperazine-2-carboxylic acids in place of 14–8 which are prepared in a similar manner as 14–8 from the ketone precursors corresponding to 14–1.

TABLE 10

| Ex. | R$^6$ | ** | X | R$^3$ | R$^{10}$, R$^{11}$ | Diastereomer | LCMS (ESI): m/z |
|---|---|---|---|---|---|---|---|
| 118 | F | (R) | —C(O)NH-tBu | isopropyl | H | D$_1$ + D$_2$ | 586 (M$^+$ + 1) |
| 119 | F | (R) | —C(O)NH-tBu | isopropyl | H | D$_1$ | 586 (M$^+$ + 1) |
| 120 | F | (R) | —C(O)NH-tBu | isopropyl | H | D$_2$ | 586 (M$^+$ + 1) |

TABLE 10-continued

| Ex. | R[6] | ** | X | R[3] | R[10], R[11] | Diastereomer | LCMS (ESI): m/z |
|---|---|---|---|---|---|---|---|
| 121 | Cl | (R) | -C(O)NH-tBu | -iPr | H | D$_1$ + D$_2$ | 602 (M$^+$ + 1) |
| 122 | Cl | (R) | -C(O)NH-tBu | -iPr | H | D$_1$ | 602 (M$^+$ + 1) |
| 123 | Cl | (R) | -C(O)NH-tBu | -iPr | H | D$_2$ | 602 (M$^+$ + 1) |
| 124 | F | (R) | -C(O)NH-tBu | -iPr | Me | D$_1$ + D$_2$ | 662 (M$^+$ + 1) |
| 125 | F | (R) | -CH$_2$-(4,4-dimethyl-2-oxo-oxazolidin-3-yl) | -iPr | H | D$_1$ + D$_2$ | 614 (M$^+$ + 1) |
| 126 | F | (R) | -C(O)OEt | -iPr | H | D$_1$ + D$_2$ | 559 (M$^+$ + 1) |
| 127 | F | (R) | -CH$_2$-S-iPr | -iPr | H | D$_1$ + D$_2$ | 575 (M$^+$ + 1) |

TABLE 10-continued
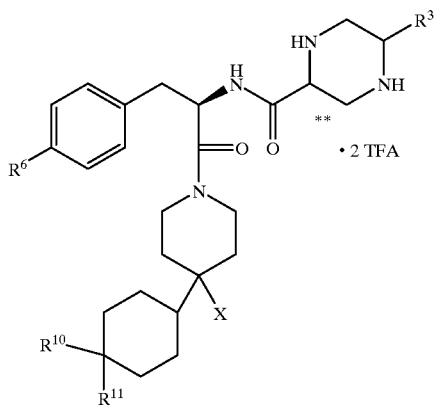
· 2 TFA
| Ex. | R6 | ** | X | R3 | R10, R11 | Diastereomer | LCMS (ESI): m/z |
|---|---|---|---|---|---|---|---|
| 128 | F | (R) | CH2-S(O)-iPr | iBu | H | | 591 (M+ + 1) |
| 129 | Cl | (R) | C(O)NH-tBu | Ph | H | D1 + D2 | 636 (M+ + 1) |
| 130 | F | (R) | C(O)NH-tBu | Ph | H | D1 + D2 | 620 (M+ + 1) |
| 131 | F | (R) | CH2-(4,4-dimethyl-oxazolidin-2-one-3-yl) | Ph | H | D1 + D2 | 648 (M+ + 1) |
| 132 | F | (S) | C(O)NH-tBu | iBu | H | D1 + D2 | 586 (M+ + 1) |
| 133 | F | (S) | C(O)NH-tBu | iBu | H | D1 | 586 (M+ + 1) |
| 134 | F | (S) | C(O)NH-tBu | iBu | H | D2 | 586 (M+ + 1) |

TABLE 10-continued
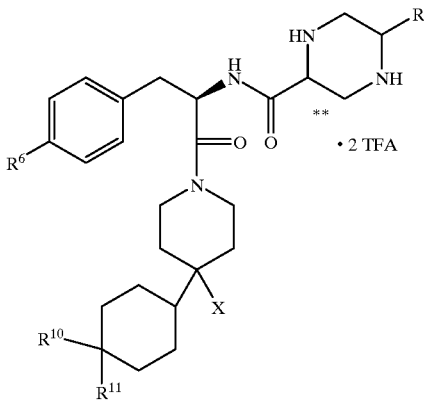
| Ex. | R⁶ | ** | X | R³ | R¹⁰, R¹¹ | Diastereomer | LCMS (ESI): m/z |
|---|---|---|---|---|---|---|---|
| 135 | F | (S) | 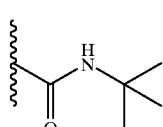 | 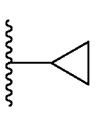 | H | D₁ + D₂ | 584 (M⁺ + 1) |
| 136 | F | (S) | 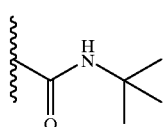 | 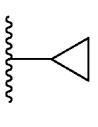 | H | D₁ | 584 (M⁺ + 1) |
| 137 | F | (S) | 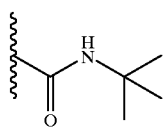 | 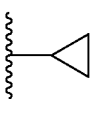 | H | D₂ | 584 (M⁺ + 1) |
| 138 | F | (R) | 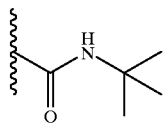 | 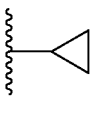 | H | D₁ + D₂ | 584 (M⁺ + 1) |
| 139 | F | (R) | 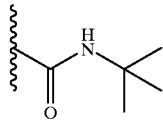 | 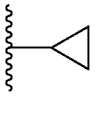 | H | D₁ | 584 (M⁺ + 1) |
| 140 | F | (R) | 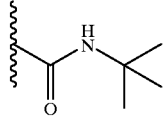 | 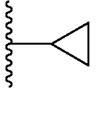 | H | D₁ + D₂ | 584 (M⁺ + 1) |
| 141 | F | (S) | 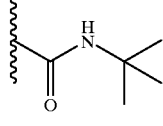 | 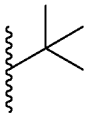 | H | D₁ + D₂ | 600 (M⁺ + 1) |

TABLE 10-continued
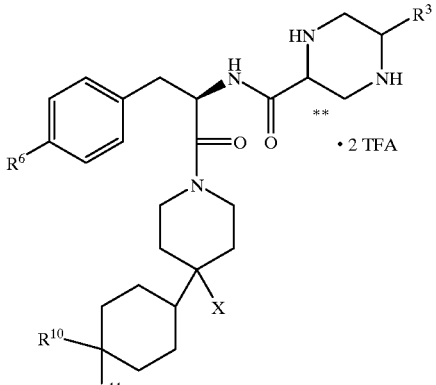
| Ex. | $R^6$ | ** | X | $R^3$ | $R^{10}, R^{11}$ | Diastereomer | LCMS (ESI): m/z |
|---|---|---|---|---|---|---|---|
| 142 | F | (S) | -C(O)NH-tBu | tBu | H | $D_1$ | 600 ($M^+ + 1$) |
| 143 | F | (S) | -C(O)NH-tBu | tBu | H | $D_2$ | 600 ($M^+ + 1$) |
| 144 | F | (R) | -C(O)NH-tBu | tBu | H | $D_1 + D_2$ | 600 ($M^+ + 1$) |
| 145 | F | (R) | -C(O)NH-tBu | tBu | H | $D_1$ | 600 ($M^+ + 1$) |
| 146 | F | (R) | -C(O)NH-tBu | tBu | H | $D_2$ | 600 ($M^+ + 1$) |
| 147 | F | (S) | -C(O)NH-tBu | cyclopropyl | H | $D_1 + D_2$ | 598 ($M^+ + 1$) |
| 148 | F | (S) | -C(O)NH-tBu | cyclopropyl | H | $D_1$ | 598 ($M^+ + 1$) |

TABLE 10-continued
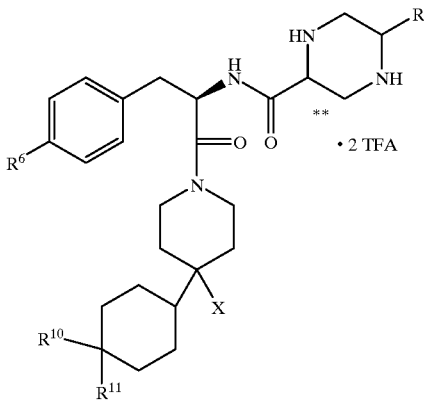
| Ex. | R[6] | ** | X | R[3] | R[10], R[11] | Diastereomer | LCMS (ESI): m/z |
|---|---|---|---|---|---|---|---|
| 149 | F | (S) | 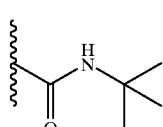 | 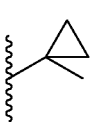 | H | D$_2$ | 598 (M$^+$ + 1) |
| 150 | F | (R) | 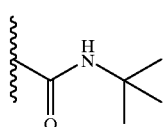 | 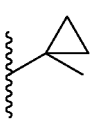 | H | D$_1$ + D$_2$ | 598 (M$^+$ + 1) |
| 151 | F | (R) | 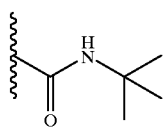 | 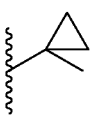 | H | D$_1$ | 598 (M$^+$ + 1) |
| 152 | F | (R) | 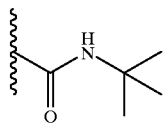 | 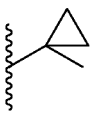 | H | D$_2$ | 598 (M$^+$ + 1) |
| 153 | Cl | (R) | 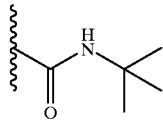 | 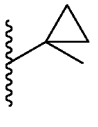 | H | D$_1$ + D$_2$ | 814 (M$^+$ + 1) |
| 154 | Cl | (R) | 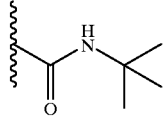 | 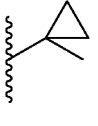 | H | D$_1$ | 814 (M$^+$ + 1) |
| 155 | Cl | (R) | 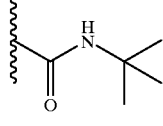 | 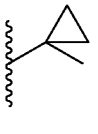 | H | D$_2$ | 814 (M$^+$ + 1) |

TABLE 10-continued
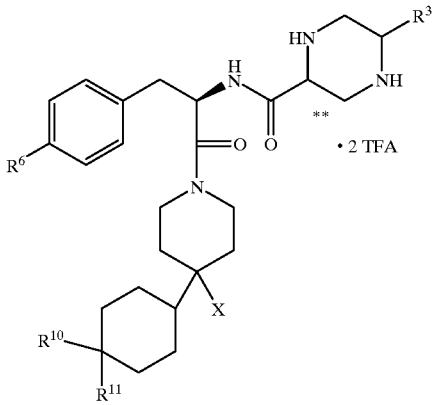
| Ex. | R[6] | ** | X | R[3] | R[10], R[11] | Diastereomer | LCMS (ESI): m/z |
|---|---|---|---|---|---|---|---|
| 156 | Cl | (S) | 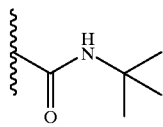 | Ph | H | D₁ + D₂ | 636 (M⁺ + 1) |
| 157 | F | (S) | 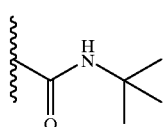 | Ph | H | D₁ + D₂ | 620 (M⁺ + 1) |
| 158 | F | (S) | 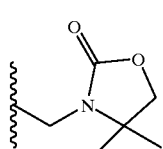 | Ph | H | D₁ + D₂ | 648 (M⁺ + 1) |
SCHEME 15
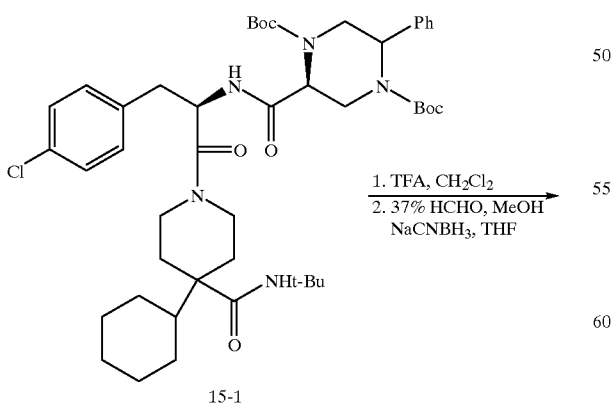
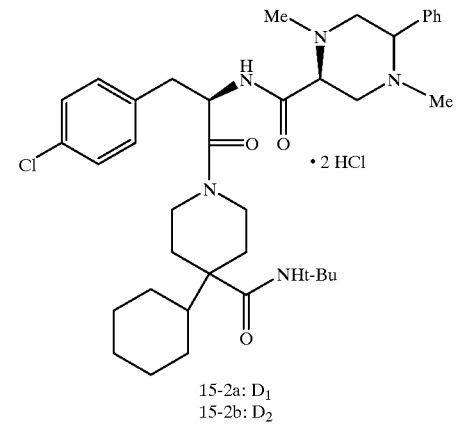

EXAMPLE 159

Intermediate 15-1 (0.0558 g, 0.068 mmol) was dissolved in 0.34 mL of 1:1 TFA-CH$_2$Cl$_2$ and stirred at RT for 1 h, and then the mixture was concentrated with CH$_2$Cl$_2$. The resulting TFA salt was dissolved in 0.34 mL of MeOH, and then sodium acetate (0.056 g, 0.68 mmol) and 37% aqueous formaldehyde solution (0.05 mL, 0.653 mmol) were added. After 20 min, sodium cyanoborohydride (1.0 M in THF, 0.44 mL, 0.44 mmol) was added. The reaction mixture was stirred at room temperature overnight and then concentrated. The crude mixture was dissolved in EtOAc and 1N NaOH, and the layers were separated. The organic phase was washed with 1N NaOH solution, H$_2$O, and brine, dried over MgSO$_4$, filtered, and concentrated. Purification by column chromatography (50–75% EtOAc/hexane, and then 1% TEA in EtOAc) provided two diastereoisomers as a white foamy solid [0.014 g (D$_1$) and 0.009 g (D$_2$)]. Each of these diastereoisomers [0.012 g, 0.019 mmol (D$_1$); and 0.007 g, 0.011 mmol (D$_2$)] was separately dissolved in CH$_2$Cl$_2$, and 1.0 M HCl solution in Et$_2$O (0.28 mL, 0.28 mmol; and 0.03 mL, 0.03 mmol, respectively) was added. The precipitates were filtered under N$_2$ and dried under vacuum to give white solids [0.012 g (D$_1$) and 0.0072 g (D$_2$)]. LCMS (ESI): m/z 664 (M$^+$+1).

The following N$^\alpha$-methyl-N$^\beta$-methyl-5-phenyl-piperazine Examples shown in Table 11 with the indicated stereochemistry at the stereogenic cneter marked with an ** were prepared in a similar manner as Example 159, but using the appropriate N,N-di-Boc-5-phenyl-(D)-piperazine-2-carboxamide intermediate in place of 15–1.

TABLE 11

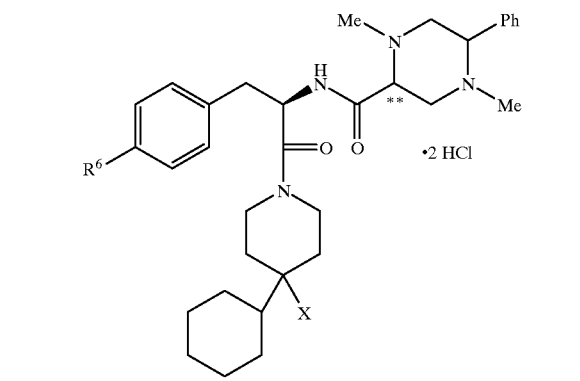

| Ex. | R$^6$ | ** | Diastereomer | X | LCMS (ESI): m/z |
|---|---|---|---|---|---|
| 160 | Cl | (S) | D$_1$ | ⸮–C(O)NH–tBu | 664 (M$^+$ + 1) |
| 161 | Cl | (S) | D$_2$ | ⸮–C(O)NH–tBu | 664 (M$^+$ + 1) |
| 162 | F | (S) | D$_1$ | ⸮–C(O)NH–tBu | 648 (M$^+$ + 1) |
| 163 | F | (S) | D2 | ⸮–C(O)NH–tBu | 648 (M$^+$ + 1) |
| 164 | F | (S) | D$_1$ | ⸮–CH$_2$–(4,4-dimethyl-oxazolidin-2-one) | 676 (M$^+$ + 1) |
| 165 | Cl | (R) | D$_1$ | ⸮–C(O)NH–tBu | 664 (M$^+$ + 1) |
| 166 | Cl | (R) | D$_2$ | ⸮–C(O)NH–tBu | 664 (M$^+$ + 1) |
| 167 | F | (R) | D$_1$ | ⸮–C(O)NH–tBu | 648 (M$^+$ + 1) |
| 168 | F | (R) | D$_2$ | ⸮–C(O)NH–tBu | 648 (M$^+$ + 1) |

TABLE 11-continued

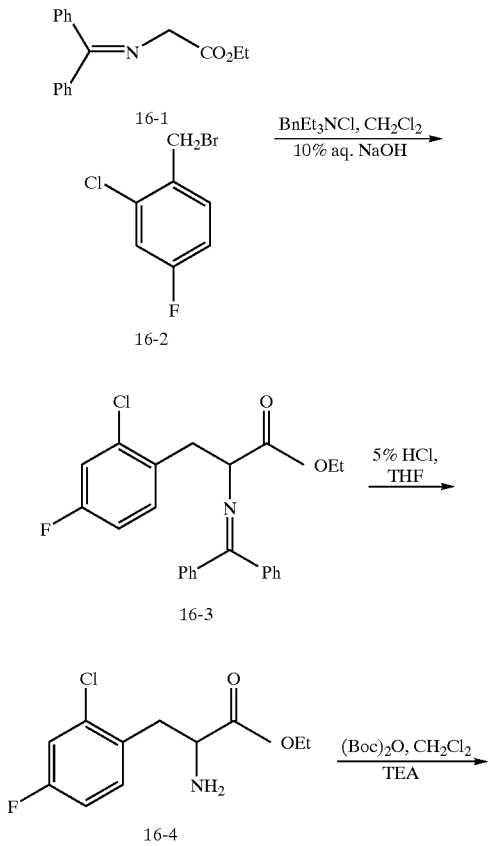

| Ex. | R⁶ | ** | Diastereomer | X | LCMS (ESI): m/z |
|---|---|---|---|---|---|
| 169 | F | (R) | $D_1$ | (oxazolidinone-methyl group) | 676 ($M^+ + 1$) |

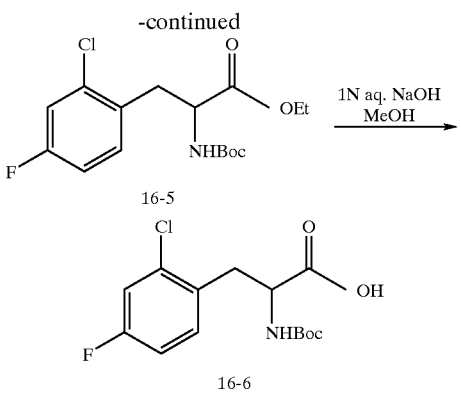

EXAMPLE 170

Step A

2-Chloro-4-fluorobenzyl bromide (16-2) (1.0 g, 4.47 mmol), N-(diphenylmethylene)glycine ethyl ester (1-1) (1.067 g, 3.99 mmol) and benzyl triethylammonium chloride (0.922 g, 4.05 mmol) were dissolved in $CH_2Cl_2$, and 10% aqueous NaOH solution was added. The resulting two-phase mixture was stirred at RT overnight. The organic layer was separated and concentrated. The residue was dissolved in ether, washed with $H_2O$, dried over $MgSO_4$, filtered, and concentrated to give 16-3 as a clear oil (1.445 g, 88%).

LCMS (ESI): m/z 410 ($M^+$+1).

Step B

Compound 16-3 was dissolved in THF and 5% aqueous HCl solution was added. The mixture was stirred at RT for 1 h. Saturated $NaHCO_3$ solution was then added slowly and the mixture was extracted with EtOAc. The combined organics were washed with $H_2O$ and brine, dried over $MgSO_4$, filtered, and concentrated. Purification by chromatography on silica gel (3–30% EtOAc/hexane) gave 16-4 as a clear oil (0.626 g, 75%). LCMS (ESI): m/z 246 ($M^+$+1).

Step C

Compound 16-4 (0.6238 g, 2.54 mmol) was dissolved in 12.7 mL of $CH_2Cl_2$, and then Boc-anhydride (0.61 g, 2.79 mmol) and TEA (0.53 mL, 3.81 mmol) were added. The resulting mixture was stirred at RT overnight and then diluted with $CH_2Cl_2$. The organic phase was washed with 1N HCl and brine, dried over $MgSO_4$, filtered and concentrated to give 16-5 as an oil (0.88 g).

LCMS (ESI): m/z 246 ($M^+$+1-Boc).

Step D

Compound 16-5 (0.88 g, 2.54 mmol) was dissolved in 8 mL of MeOH and 1N aqueous NaOH solution (5.08 mL, 5.08 mmol) was added. The resulting mixture was stirred at RT overnight and then concentrated. Water was added and the pH was adjusted to about 2 using 1N HCl solution. The acidic solution was extracted with EtOAc, and the combined organic layers were washed with brine, dried over $MgSO_4$, filtered, and concentrated to give intermediate 16-6 as a white solid (0.65 g, 81%).

LCMS (ESI): m/z 218 ($M^+$+1-Boc).

Step E

The following Examples shown in Table 12 were prepared following the procedures shown in Scheme 1 and detailed in Example 1 but using the appropriately substituted Boc-phenylalanine intermediate as prepared in Steps A-D above or commercially available Boc-phenylalanines and the appropriately protected piperazine-2-carboxylic acid intermediate.

TABLE 12

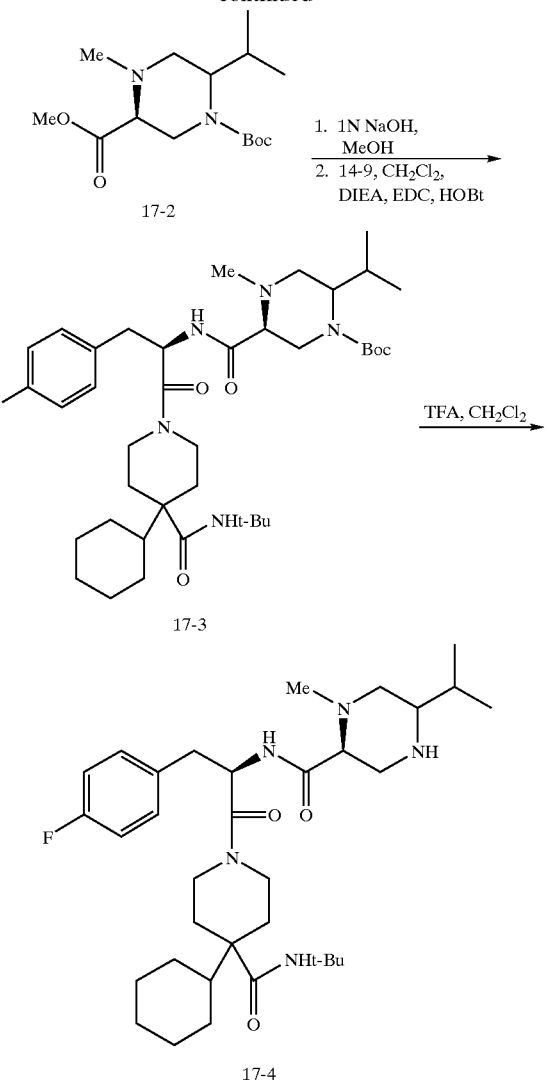

| Ex. | R⁶ | * | R³ | R⁴ᵇ | LCMS (ESI): m/z |
|---|---|---|---|---|---|
| 171 | 3,4-difluoro- | (R) | H | H | 562 (M⁺ + 1) |
| 172 | 3,4-difluoro- | (R) | H | Me | 576 (M⁺ + 1) |
| 173 | 3,4-difluoro- | (R) | i-Pr(D₁ + D₂) | H | 604 (M⁺ + 1) |
| 174 | 3,4-difluoro- | (R) | i-Pr(D₁) | H | 604 (M⁺ + 1) |
| 175 | 3,4-difluoro- | (R) | i-Pr(D₂) | H | 604 (M⁺ + 1) |
| 176 | 3,5-difluoro- | (R) | H | Me | 576 (M⁺ + 1) |
| 177 | 3,5-difluoro- | (R) | i-Pr | H | 604 (M⁺ + 1) |
| 178 | 2,4-difluoro | (RS) | H | H | 562 (M⁺ + 1) |
| 179 | 2,4-difluoro | (RS) | H | Me | 576 (M⁺ + 1) |
| 180 | 2-chloro-4-fluoro | (RS) | H | H | 578 (M⁺ + 1) |
| 181 | 2-chloro-4-fluoro | (RS) | H | Me | 592 (M⁺ + 1) |

SCHEME 17

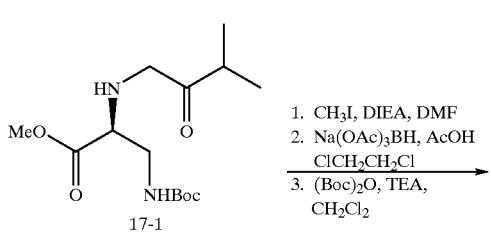

EXAMPLE 182

Step A

Intermediate 17–1 (0.28 g, 0.926 mmol) was dissolved in 4.6 mL of DMF, and then DIEA (0.16 mL, 0.926 mmol) and methyl iodide (0.12 mL, 1.852 mmol) were added. The resulting mixture was stirred at RT overnight. The reaction mixture was diluted with EtOAc and washed with brine and H₂O, and the organic layer was dried over MgSO₄, filtered, and concentrated to give a red oil which was treated with TFA in methylene chloride to remove the Boc-protecting group. After the usual work-up, the crude compound was dissolved in 18 mL of 1,2-dichloroethane, and then sodium triacetoxyborohydride (0.275 g, 1.30 mmol) and acetic acid (0.053 mL, 0.926 mmol) were added. The reaction mixture was stirred at RT under N₂ overnight. The reaction mixture was then diluted with 9 mL of saturated aqueous NaHCO₃ solution and then concentrated with toluene to give a yellow solid. The crude compound was dissolved in 4.6 mL of CH₂Cl₂, and then Boc-anhydride (0.22 g, 1.02 mmol) and TEA (0.19 mL, 1.39 mmol) were added. The reaction mixture was stirred at room temperature overnight and then diluted with CH₂Cl₂. The solution was washed with H₂O and brine, dried over MgSO₄, filtered and concentrated.

Purification by chromatography on silica gel (10% EtOAc/hexane) gave 17-2 as a white solid (0.02 g, 7%). LCMS (ESI): m/z 301 ($M^+$+1), 245 ($M^+$−55).

Step B

Compound 17-2 (0.020 g, 0.067 mmol) was dissolved in 0.2 mL of MeOH and 1N aqueous NaOH solution (0.14 mL, 0.14 mmol) was added. The mixture was stirred at RT overnight and then concentrated. Water was added and the pH was adjusted to about 7 using 1N HCl solution. The aqueous solution was then extracted with EtOAc, and the combined organic layers were washed with brine, dried over $MgSO_4$, filtered, and concentrated to give a white foamy solid. This acid was dissolved in 0.5 mL of methylene chloride, and then the amine intermediate 14-9 (0.027 g, 0.061 mmol), DIEA (0.04 mL, 0.244 mmol), EDC (0.013 g, 0.067 mmol), and HOBt (0.009 g, 0.067 mmol) were added. The resulting mixture was stirred at room temperature overnight. The resulting mixture was diluted with $CH_2Cl_2$ and washed with $H_2O$, and brine, and the organic phase was dried over $MgSO_4$, filtered, and concentrated. The crude product was purified by column chromatography on silica gel (9:1 methylene chloride-acetone, and then 3–10% MeOH in $CH_2Cl_2$) to give 17-3 as a white solid (0.006 g, 14%).

LCMS (ESI): m/z 700 ($M^+$+1).

Step C

Compound 17-3 (0.0058 g, 0.0083 mmol) was dissolved in 0.1 mL of methylene chloride and 0.1 mL of trifluoroacetic acid. This solution was stirred at room temperature for 30 min, and then concentrated with four, 2-mL portions of $CH_2Cl_2$ to give 17-4 as a white, foamy-solid (0.006 g, 92%). LCMS (ESI): m/z 600 ($M^+$+1).

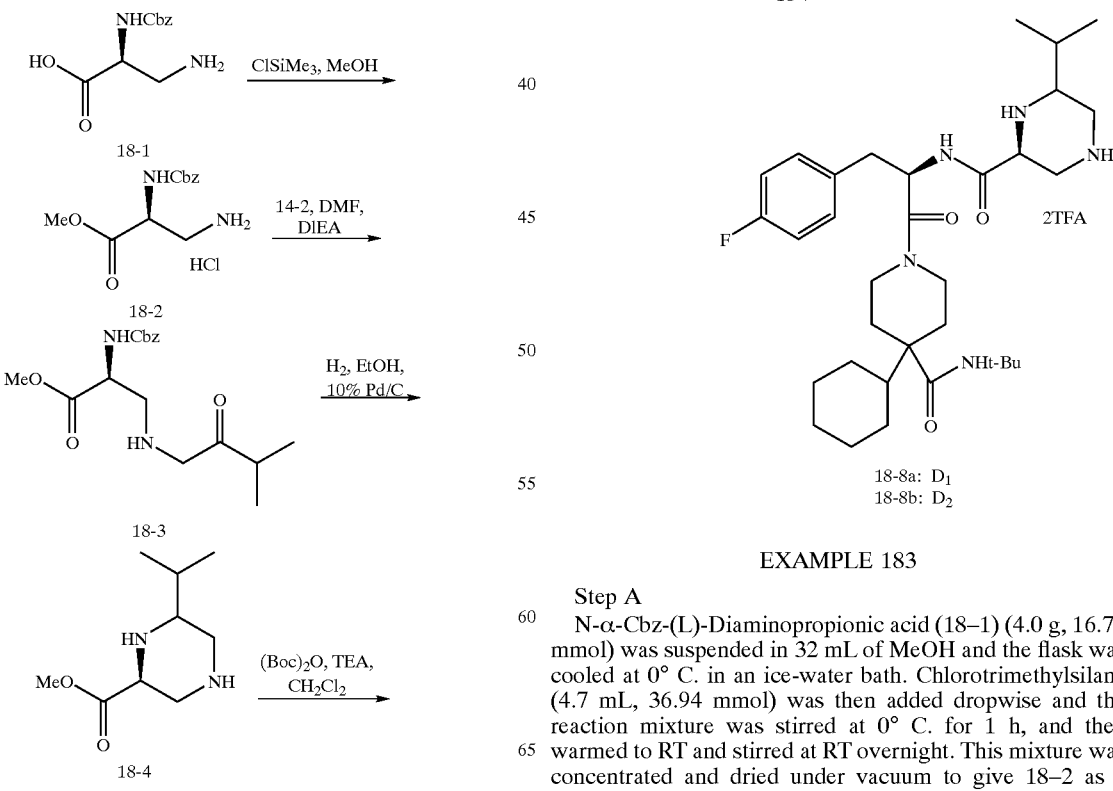

EXAMPLE 183

Step A

N-α-Cbz-(L)-Diaminopropionic acid (18-1) (4.0 g, 16.79 mmol) was suspended in 32 mL of MeOH and the flask was cooled at 0° C. in an ice-water bath. Chlorotrimethylsilane (4.7 mL, 36.94 mmol) was then added dropwise and the reaction mixture was stirred at 0° C. for 1 h, and then warmed to RT and stirred at RT overnight. This mixture was concentrated and dried under vacuum to give 18-2 as a white solid (4.77 g, 98%). LCMS (ESI): m/z 253 ($M^+$+1).

Step B

Compound 18–2 (2.50 g, 8.66 mmol) was dissolved in 34.4 mL of DMF, and then DIEA (3.02 mL, 17.32 mmol) and compound 14–2 (1.43 g, 8.66 mmol) were added. The resulting mixture was then stirred at RT overnight. The reaction mixture was diluted with EtOAc and washed with water and brine, and the organic layer was dried over MgSO$_4$, filtered, and concentrated. Purification by chromatography (30–40% EtOAc/hexane) gave 18–3 as a yellow oil (1.41 g, 49%).

LCMS (ESI): m/z 337 (M$^+$+1).

Step C

Compound 18–3 (1.26 g, 3.73 mmol) was dissolved in 70 mL of EtOH and 10% palladium on carbon (0.40 g) was then added. The resulting mixture was stirred at RT under H$_2$ overnight. This mixture was then filtered through Celite using CH$_2$Cl$_2$, and the filtrate was concentrated to give 18–4 as an orange oil (0.65 g, 94%).

LCMS (ESI): m/z 187 (M$^+$+1).

Step D

Compound 18–4 (0.643 g, 3.45 mmol) was dissolved in 17.3 mL of CH$_2$Cl$_2$, and then Boc-anhydride (1.66 g, 7.59 mmol) and TEA (1.44 mL, 10.35 mmol) were added. The resulting mixture was stirred at RT overnight. The reaction mixture was diluted with CH$_2$Cl$_2$ and washed with 1N HCl and brine, dried over MgSO$_4$, filtered, and concentrated. Purification by chromatography (10% EtOAc/hexane) gave 18–5 as a white solid (0.82 g, 62%). LCMS (ESI): m/z 231 (M$^+$-Boc-55).

Step E

Compound 18–5 (0.796 g, 0.16 mmol) was dissolved in 6.0 mL of MeOH and 1N aqueous NaOH solution (4.12 mL, 4.12 mmol) was added. This mixture was stirred at RT overnight. The solution was concentrated and resulting residue was diluted with water and the pH was adjusted to about 2 using 1N HCl solution. The aqueous solution was extracted with EtOAc, and the combined organic layers were washed with brine, dried over MgSO$_4$, filtered, and concentrated to give 18–6 as a white, foamy-solid (0.412 g, 54%). LCMS (ESI): m/z 217 (M$^+$-Boc-55).

Step F

N,N-Di-Boc-6-isopropyl-(S)-piperazine-2-carboxylic acid (18–6) (0.08 g, 0.215 mmol) was dissolved in 1.0 mL of methylene chloride, and then amine intermediate 14–9 (0.0843 g, 0.195 mmol), DIEA (0.14 mL, 0.78 mmol), EDC (0.041 g, 0.215 mmol), and HOBt (0.029 g, 0.215 mmol) were added. The resulting mixture was stirred at room temperature overnight, and then diluted with 10 mL of CH$_2$Cl$_2$ and washed with 5 mL of 1N HCl solution, 5 mL of saturated NaHCO$_3$ solution, 5 mL of H$_2$O, and 5 mL of saturated NaCl solution. The organic phase was dried over MgSO$_4$, filtered, and concentrated to give a yellow oil. The crude product was purified by column chromatography (30:1 to 3:1 methylene chloride-acetone) to give 18–7 as a white solid (0.0743 g, 49%). LCMS (ESI): m/z 786 (M$^+$+1).

Step G

Compound 18–7 (0.0729 g, 0.093 mmol) was dissolved in 0.23 mL of methylene chloride and 0.23 mL of trifluoroacetic acid. This solution was stirred at room temperature for 1 h, and then concentrated with four, 2-mL portions of CH$_2$Cl$_2$ to give 18–8 as a white foamy-solid (0.0732 g, 97%). LCMS (ESI): m/z 586 (M$^+$+1). This mixture of two diastereoisomers was separated into each diastereoisomer (D$_1$ and D$_2$) by preparative HPLC.

EXAMPLE 184

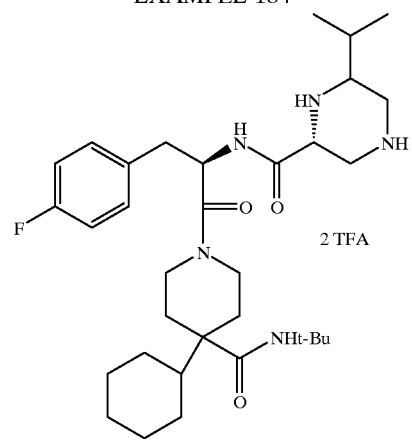

This example was prepared in the same manner as Example 183, but using N,N-di-Boc-6-isopropyl-(R)-piperazine-2-carboxylic acid in place of the corresponding (S)-isomer for the coupling reaction in Step F of Example 183. LCMS (ESI) m/z 586 (M$^+$+1).

SCHEME 19

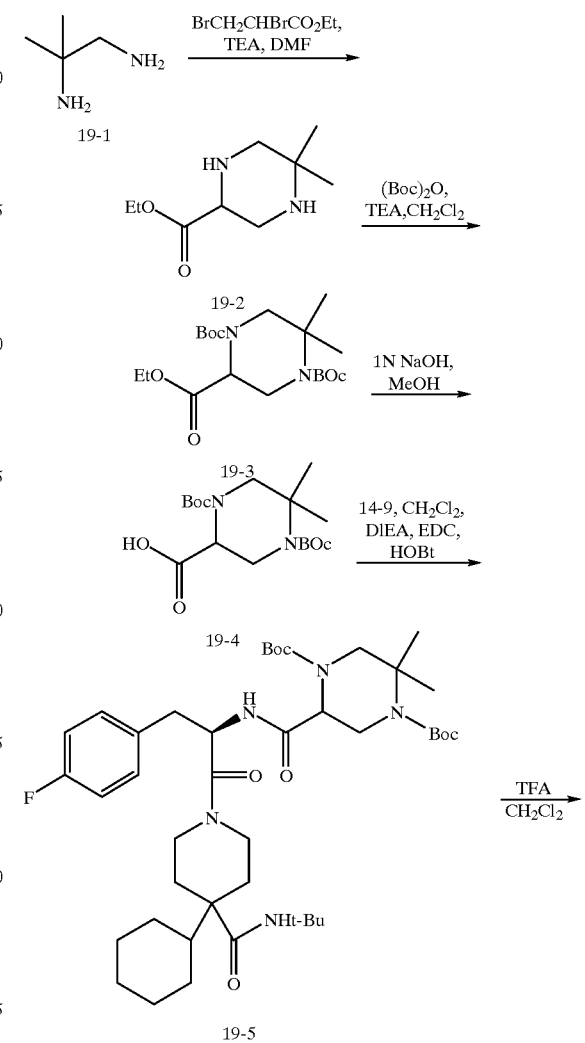

-continued

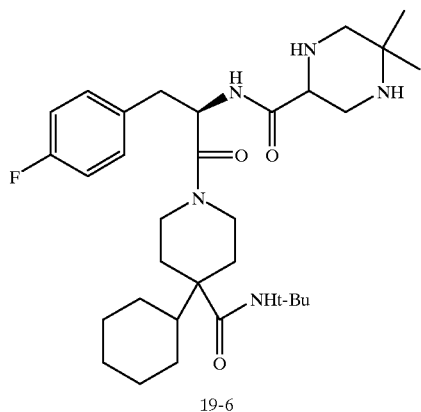

19-6

EXAMPLE 185

Step A 1,2-Diamino-2-methylpropane (19–1) (0.50 mL, 4.77 mmol) was dissolved in 20 ml of DMF, and then ethyl 2,3-dibromopropionate (0.70 mL, 4.77 mmol) and TEA (1.33 mL, 9.54 mmol) were added. This mixture was stirred at RT overnight, and then concentrated to give an oil. Purification by chromatography on silica gel (9:1 $CH_2Cl_2$/acetone, and then 3–10% MeOH in $CH_2Cl_2$) gave 19–2 as a yellow foamy-solid (0.76 g). LCMS (ESI): m/z 187 ($M^++1$).

Step B

Compound 19–2 (0.76 g, 4.06 mmol) was dissolved in 15.0 mL of $CH_2Cl_2$, and then Boc-anhydride (1.77 g, 8.12 mmol) and TEA (1.70 mL, 12.18 mmol) were added. The resulting mixture was stirred at RT overnight. The reaction mixture was then diluted with $CH_2Cl_2$ and washed with 1N HCl and brine, dried over $MgSO_4$, filtered, and concentrated. Purification by chromatography on silica gel (10% EtOAc/hexane) gave 19–3 as a white solid (0.065 g, 4%). LCMS (ESI): m/z 187 ($M^{+-2}Boc$).

Step C

Compound 19–3 (0.062 g, 0.16 mmol) was dissolved in 0.5 mL of MeOH and 1N aqueous NaOH solution (0.32 mL, 0.32 mmol) was added. This mixture was stirred at RT overnight. The solution was concentrated and resulting residue was diluted with water and the pH was adjusted to about 2 using 1N HCl solution. The aqueous solution was extracted with EtOAc and the combined organic layers were washed with brine, dried over $MgSO_4$, filtered, and concentrated to give acid 19–4 as a white, foamy-solid (0.053 g, 93%). LCMS (ESI): m/z 159 ($M^++1-2Boc$), 203 ($M^+-Boc-55$), 381 ($M^++Na$).

Step D

Acid 19–4 (0.51 g, 0.142 mmol) was dissolved in 0.65 mL of methylene chloride, and then amine intermediate 14–9 (0.058 g, 0.129 mmol), DIEA (0.09 mL, 0.516 mmol), EDC (0.027 g, 0.142 mmol), and HOBt (0.027 g, 0.142 mmol) were added. The resulting mixture was stirred at room temperature overnight, and then diluted with 10 mL of $CH_2Cl_2$ and washed with 5 mL of 1N HCl solution, 5 mL of saturated $NaHCO_3$ solution, 5 mL of $H_2O$, and 5 mL of saturated NaCl solution. The organic phase was dried over $MgSO_4$, filtered, and concentrated to give a yellow oil. The crude product was purified by column chromatography on silica gel (30:1 to 9:1 methylene chloride-acetone) to give 19–5 as a white solid (0.0724 g, 73%). LCMS (ESI): m/z 772 ($M^++1$), 672 ($M^+-Boc$).

Step E

Compound 19–5 (0.0692 g, 0.090 mmol) was dissolved in 0.22 mL of methylene chloride and 0.22 mL of trifluoroacetic acid. This solution was stirred at room temperature for 1 h, and then concentrated with four, 2-mL portions of $CH_2Cl_2$ to give 19–6 as a white foamy-solid (0.069 g, 96%). LCMS (ESI): m/z 572 ($M^++1$).

SCHEME 20

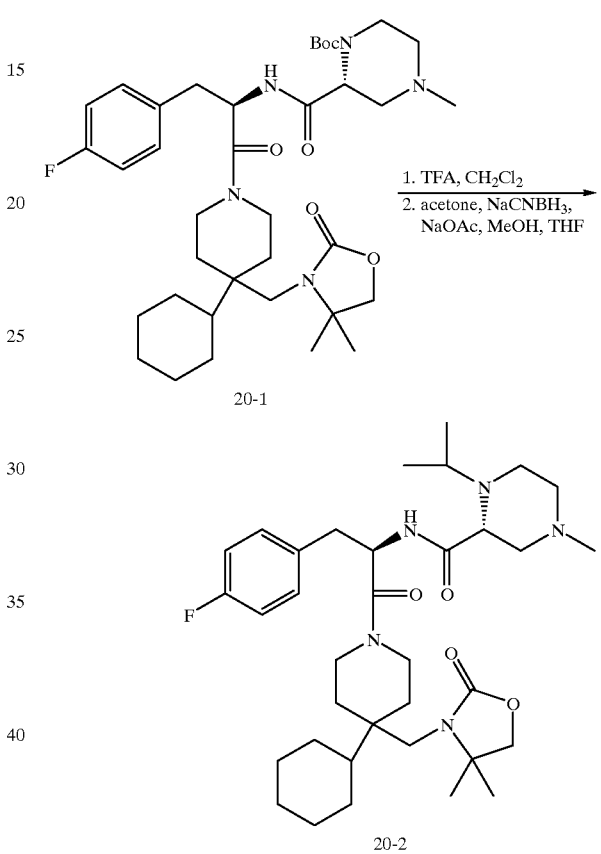

EXAMPLE 186

Intermediate 20–1 (0.14 g, 0.204 mmol) was dissolved in 0.51 mL of methylene chloride and 0.51 mL of trifluoroacetic acid. This solution was stirred for 30 min at room temperature. The mixture was then concentrated with methylene chloride (3mL×2) to give a white solid. The solid was dissolved in 1.0 mL of methanol, and then sodium acetate (0.084 g, 1.02 mmol) and acetone (0.072 mL, 0.98 mmol) were added. The reaction mixture was stirred at room temperature for 30 min, and then sodium cyanoborohydride (1.0 M in THF, 0.65 mL, 0.65 mmol) was added. The mixture was stirred at room temperature overnight. The solution was concentrated, and the residue was taken up in EtOAc (10 mL) and 1N NaOH (5 mL) and the layers were separated. The organic phase was washed with 1N NaOH (5 mL), $H_2O$ (5 mL), and brine (5 mL), dried over $MgSO_4$, filtered, and concentrated. Purification by column chromatography on silica gel (3% to 10% methanol in methylene chloride) gave 20–2 as a white foamy solid (0.088 g, 69%); mass spectrum: 628 (M+1).

SCHEME 21

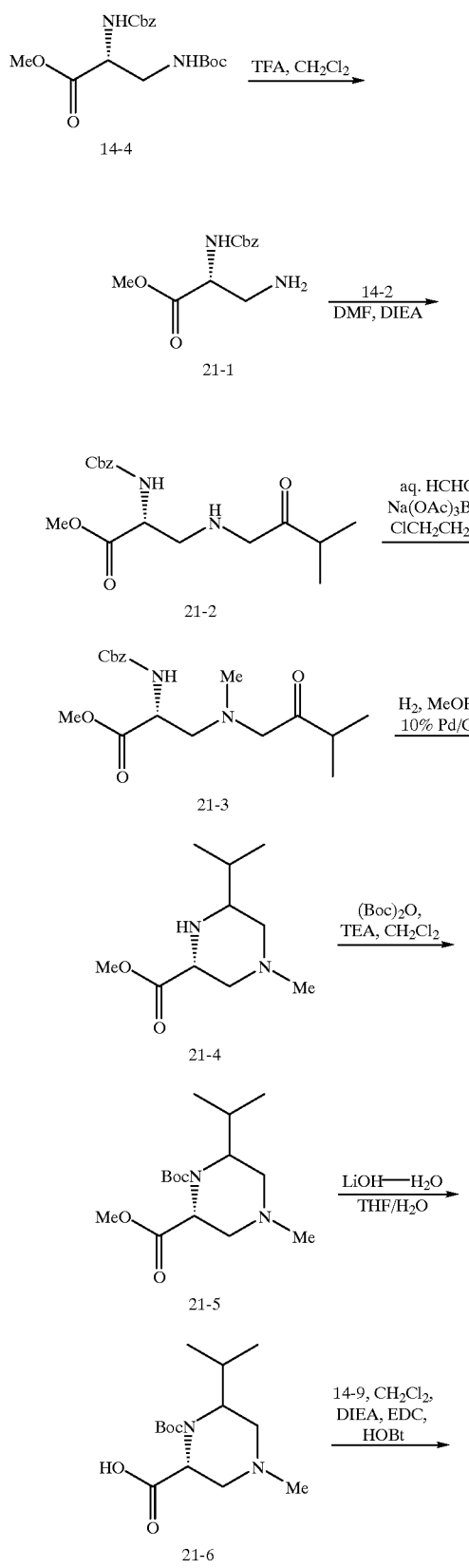

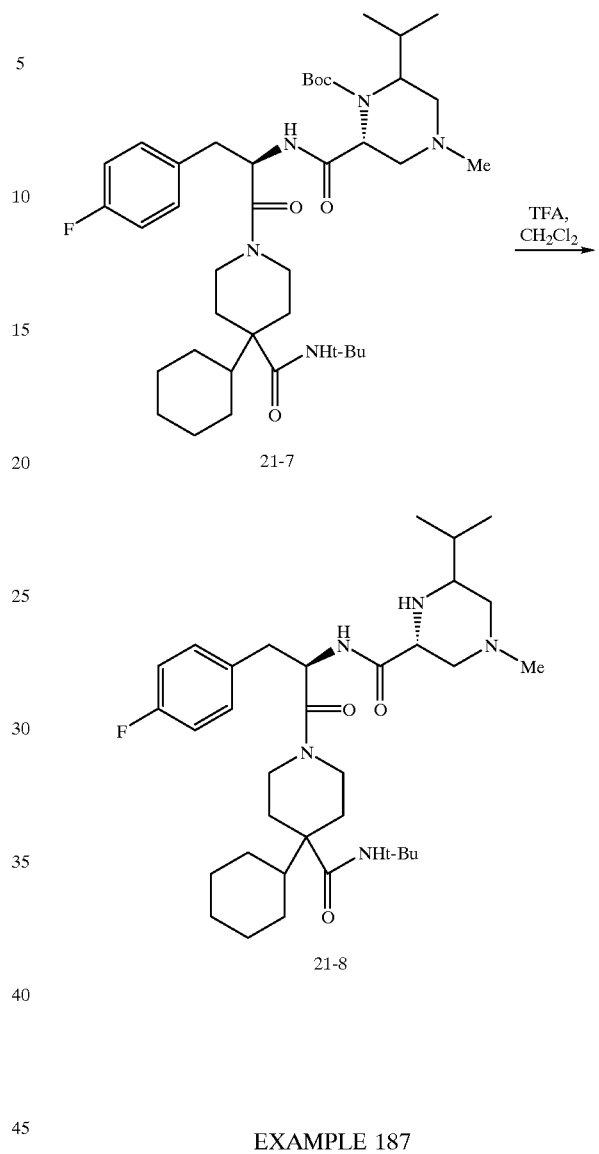

EXAMPLE 187

Step A

Intermediate 14–4 (2.19 g, 6.22 mmol) was dissolved in 16 mL of methylene chloride and 16 mL of trifluoroacetic acid. This solution was stirred at room temperature for 45 min, and then concentrated with two, 6-mL portions of $CH_2Cl_2$ to give an oil. The acid was then dissolved in ethyl acetate and washed twice with aqueous 1 N NaOH solution, dried over $K_2CO_3$, filtered and concentrated to give 21–1 as a clear oil (0.999 g, 64%). LCMS (ESI): m/z 253 ($M^+$+1).

Step B

Compound 21–1 (0.999 g, 3.96 mmol) was dissolved in 20 mL of DMF, and then DIEA (0.92 mL, 5.28 mmol) and compound 14–2 (0.436 g, 2.64 mmol) were added. The resulting mixture was then stirred at room temperature for 4.5 days. The reaction mixture was diluted with EtOAc and water, and the layers were separated. The aqueous phase was extracted with ethyl acetate, and the combined organic layers were washed with water and brine, dried over $Na_2SO_4$, filtered, and concentrated to give 21–2 as a golden yellow oil. Purification by chromatography on silica gel (20–50% EtOAc-hexane) gave a yellow oil (0.665 g, 75%). LCMS (ESI): m/z 337 (M++1).

Step C

Compound 21-2 (0.250 g, 0.743 mmol) was dissolved in 7 mL of 1,2-dichloroethane, and then 37% aqueous formaldehyde (0.36 mL, 4.46 mmol) and sodium triacetoxyborohydride (0.636 g, 2.97 mmol) were added. The reaction mixture was stirred at RT under N₂ overnight. The reaction mixture was then diluted with 6 mL of saturated aqueous NaHCO₃ solution and stirred at room temperature for 15 minutes. The layers were then separated and the aqueous phase was extracted with methylene chloride. The combined organic layers were washed with brine, dried over Na₂SO₄, filtered and concentrated to give a light yellow oil. Purification by chromatography on silica gel (20–50% EtOAc/hexane) gave 21-3 as a clear oil (0.144 g, 55%). LCMS (ESI): m/z 351 (M++1).

Step D

Compound 21-3 (0.144 g, 0.411 mmol) was dissolved in 8.5 mL of EtOH, and 10% palladium on carbon (0.044 g) was added. The resulting mixture was stirred at RT under H₂ overnight. This mixture was then diluted with MeOH and filtered through Celite using MeOH to wash the filter. The filtrate and washings were concentrated to give 21-4 as a yellow oil (0.077 g, 94%). LCMS (ESI): m/z 201 (M++1).

Step E

Compound 21-4 (0.077 g, 0.385 mmol) was dissolved in 2 mL of CH₂Cl₂, and then Boc-anhydride (0.092 g, 0.423 mmol) and TEA (0.08 mL, 0.578 mmol) were added. The resulting mixture was stirred at RT for 3.5 days. The reaction mixture was concentrated to give a yellow-brown oil. Purification by silica gel chromatography (20–50% EtOAc/hexane) gave 21-5 as a yellow oil (0.048 g, 41%). LCMS (ESI): m/z 301 (M++1).

Step F

Compound 21-5 (0.048 g, 0.160 mmol) was dissolved in 0.64 mL of THF, and then 0.16 mL of water and LiOH-H₂O (0.020 g, 0.479 mmol) were added. This mixture was stirred at RT overnight and then heated at 45° C. for 4 h. The solution was then diluted with 0.5 mL of 1N HCl solution (pH=4–5) and concentrated to give 21-6 as an oily solid. LCMS (ESI): ml/z 287 (M++1).

Step G

Acid 21-6 (0.160 mmol) was dissolved in 1.0 mL of methylene chloride, and then amine intermediate 14-9 (0.065 g, 0.145 mmol), DIEA (0.10 mL, 0.580 mmol), EDC (0.031 g, 0.160 mmol), and HOBt (0.022 g, 0.160 mmol) were added. The resulting mixture was stirred at room temperature overnight, and then diluted with 10 mL of CH₂Cl₂ and washed with 5 mL of saturated NaHCO₃ solution, 5 mL of H₂O, and 5 mL of saturated NaCl solution. The organic phase was dried over Na₂SO₄, filtered, and concentrated to give a yellow oil. The crude product was purified by column chromatography on silica gel (3:1 methylene chloride-acetone) to give 21-7 as a white solid (0.017 g, 16%). LCMS (ESI): m/z 716 (M++1).

Step H

Compound 21-7 (0.017 g, 0.024 mmol) was dissolved in 0.10 mL of methylene chloride and 0.10 mL of trifluoro-acetic acid. This solution was stirred at room temperature for 1 h, and then concentrated with four, 2-mL portions of CH₂Cl₂ to give 21-8 as an off-white solid (0.020 g). LCMS (ESI): m/z 616 (M++1).

EXAMPLE 188

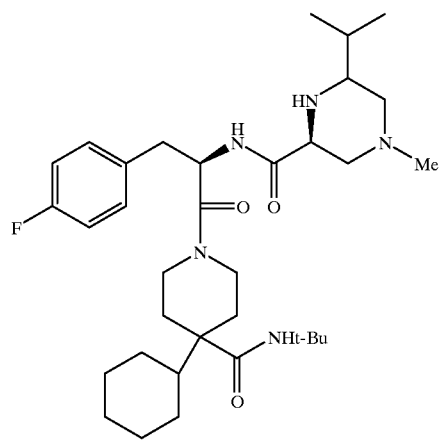

This Example was prepared in a similar fashion as Example 187, but using the protected D-piperazine-2-carboxylic acid for coupling with 14-9, in place of the L-piperazine 21-6.

SCHEME 22

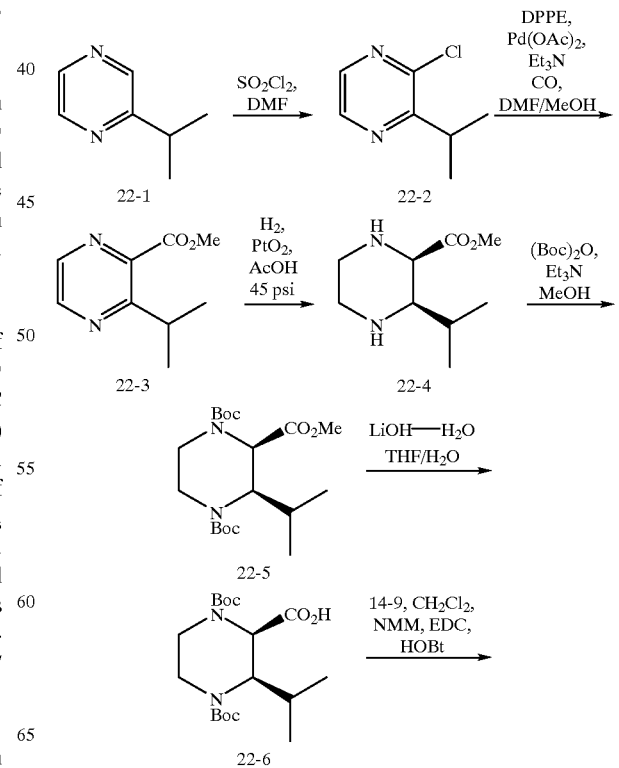

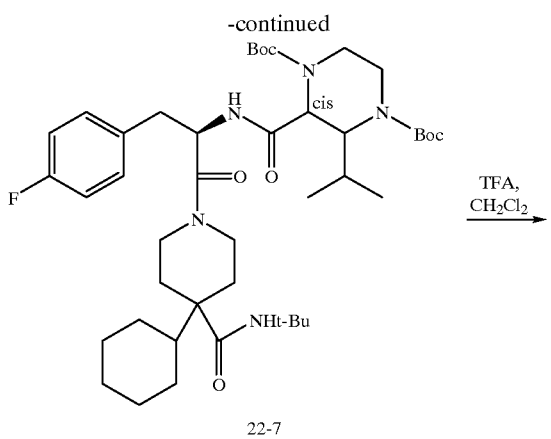

22-7

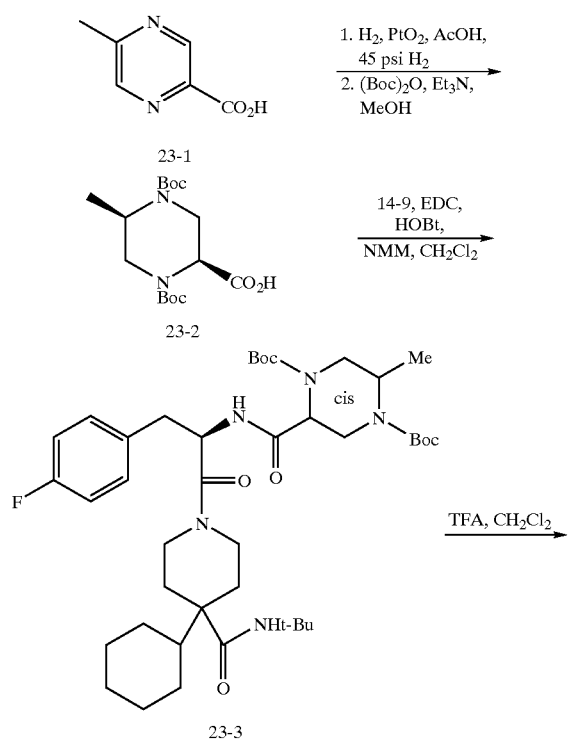

22-8a: D₁
22-8b: D₂

EXAMPLE 188

Step A

To a mixture of 2-isopropylpyrazine (22–1) (163.7 mmol, 20 mg) and DMF (188 mmol, 14.58 mL) was added sulfuryl chloride (163.7 mmol, 13.15 mL) slowly over 2 hr (syringe pump) maintaining the temperature below 40° C. Reaction was stirred at room temperature overnight. The mixture was cooled to 0° C. and H₂O (40 mL) was added cautiously followed by 5N NaOH (ca. 60 mL) to neutralize the solution. Water (600 mL) was added and the emulsion was distilled until no further oil condensed (about half the original volume). The emulsion was extracted with CH₂Cl₂ (4×200 mL). The combined organic layers were dried over Na₂SO₄ and concentrated to afford a clear colourless oil containing by NMR analysis a 1:1 mixture of starting material and desired product 22–2. This product was used without further purification in Step B.

Step B

A mixture of a 1:1 mix of isopropylpyrazine and 2-chloro-3-isopropylpyrazine from Step A (36 mmol), DPPE (0.9 mmol, 371 mg), Pd(OAc)₂ (0.9 mmol, 202 mg) and triethylamine (45 mmol, 6.3 mL) in DMF/MeOH (1:2) (18 mL) was stirred at 40 psi CO(g) at 60° C. overnight. The mixture was filtered through a short pad of celite, concentrated and partitioned between EtOAc/H₂O. Organic phase was washed with brine, dried over Na₂SO₄ and concentrated. Chromatography over silica gel eluting with 20% EtOAc/hexane afforded 22–3 as a clear colorless oil (1.38 g).

Step C

A suspension of PtO₂ (20 mol %, 45 mg) in a solution of 22–3 (1 mmol, 180 mg) in AcOH (20 mL) was shaken under 45 psi of hydrogen gas for 16 hr. Reaction mixture was filtered through a short pad of celite and concentrated to afford 22–4 as a white foam.

Step D

To a solution of 22–4 (1 mmol, 186 mg) in 10% Et₃N/MeOH was added Boc₂O (2.4 mmol, 765 mg) and the resultant solution was stirred at room temperature overnight to give a mixture of 2 products. Additional Boc₂O was added and the reaction heated to 50° C. for 5 hr. The volatiles were removed and the residue was partitioned between 0.5M HCl and EtOAc. Organic phase was washed with saturated NaHCO₃ and brine, dried over Na₂SO₄ and concentrated. Chromatography over silica gel eluting with 50 mL of 0, 2.5, 5, 10, 20, and 30% Me₂CO/CH₂Cl₂ afforded 22–5 which was hydrolyzed under basic conditions to give acid 22–6.

Step E

To a solution of 14–9 (0.1 mmol, 47 mg) in CH₂Cl₂ at room temperature was added the acid 22–6 (0.1 mmol, 46 mg) followed by HOBt (0.12 mmol, 16 mg), EDC (0.12 mmol, 23 mg) and NMM (0.45 mmol, 0.05 mL). Resultant solution was stirred at room temperature overnight. Reaction mixture was poured into EtOAc (20 mL) and washed successively with 0.5M HCl, saturated NaHCO₃, water and brine, dried over Na₂SO₄ and concentrated. Chromatography over silica gel eluting with 100 mL of 5 and 10%, then 50 mL of 20 and 30% Me₂CO/CH₂Cl₂ afforded two diastereoisomeric products D₁ and D₂ as white solids. Each diastereoisomer was deprotected with TFA in methylene chloride. Yield D₁: 20 mg; D₂: 16 mg.

SCHEME 23

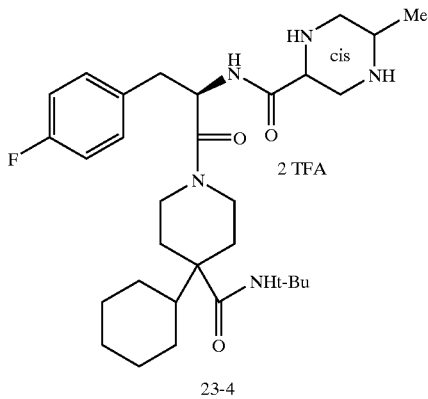

23-4

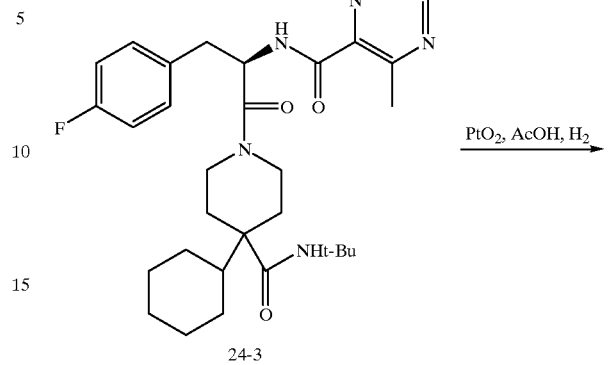

24-3

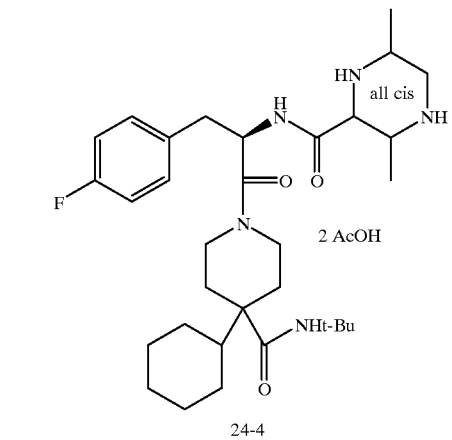

24-4

EXAMPLE 189

Step A

A suspension of PtO$_2$ (40 mol %, 330 mg) in a solution of 23–1 (3.62 mmol, 500 mg) in AcOH (36 mL) was shaken under 45 psi of hydrogen gas for 72 hours. Reaction mixture was filtered through a short pad of celite and concentrated to afford a white foam. To a solution of the resulting amino acid in 10% Et$_3$N/MeOH (15 mL) was added Boc$_2$O (8.69 mmol, 2.77 g), and the resultant solution was stirred at room temperature overnight. Volatiles were removed and the residue was partitioned between 0.5M HCl and EtOAc. Organic phase was washed with saturated NaHCO$_3$ and brine, dried over Na$_2$SO$_4$ and concentrated. Chromatography over silica gel eluting with 500 mL of 20–30% Me$_2$CO/CH$_2$Cl$_2$ afforded 23–2 (191 mg).

Step B

To a solution of amine 14–9 (0.11 mmol, 50 mg) in CH$_2$Cl$_2$ at room temperature was added the acid 23–2 (0.11 mmol, 37 mg) followed by HOBt (0.13 mmol, 17 mg), EDC (0.13 mmol, 25 mg) and NMM (4.5 mmol, 49 mg). Resultant solution was stirred at room temperature overnight. Reaction mixture was poured into EtOAc (20 mL) and washed successively with 0.5M HCl, saturated NaHCO$_3$, H$_2$O and brine, dried over Na$_2$SO$_4$ and concentrated. Chromatography over silica gel eluting with 50 mL of 0, 2.5, 5, 10, and 20% Me$_2$CO/CH$_2$Cl$_2$ afforded 23–3 as a white solid. A solution of 23–3 in CH$_2$Cl$_2$ and TFA was stirred at room temp for 1 hr. Volatiles were removed and the residue precipitated from a CH$_2$Cl$_2$ solution with Et$_2$O/hexane to give the desired compound 23–4.

SCHEME 24

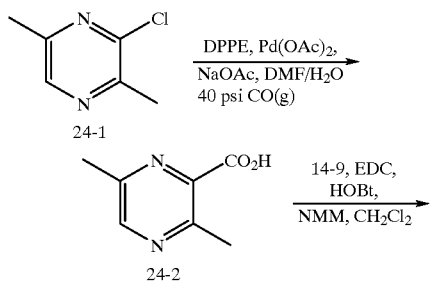

EXAMPLE 190

Step A

A mixture of 3-chloro-2,5-dimethylpyrazine (24–1) (100 mmol, 14.26 g), DPPE (5 mmol, 2.06 g), Pd(OAc)$_2$ (5 mmol, 1.22 g) and sodium acetate (100 mmol, 8.2 g) in DMF/H$_2$O (3:1) (80 mL) was stirred at 40 psi CO at 60° C. overnight. Mixture was filtered through a short pad of celite, concentrated and partitioned between CH$_2$Cl$_2$/1N NaOH. Aqueous phase was washed with CH$_2$Cl$_2$, acidified with 2N HCl and extracted wih EtOAc. Organic extracts were washed with brine, dried over Na$_2$SO$_4$ and evaporated to give 24–2 (1.6 g).

Step B

To a solution of amine 14–9 (0.1 mmol, 47 mg) in CH$_2$Cl$_2$ at room temp was added 24–2 (0.1 mmol, 15 mg) followed by HOBt (0.12 mmol, 16 mg), EDC (0.12 mmol, 23 mg) and NMM (0.45 mmol, 0.05 mL). Resultant solution was stirred at room temperature overnight. Reaction mixture was poured into EtOAc (10 mL) and washed successively with 0.5M HCl, saturated NaHCO$_3$, H$_2$O and brine, dried over Na$_2$SO$_4$ and concentrated. Chromatography over silica elut- ing with 50 mL of 0, 2.5, 5, 10, and 20% Me$_2$CO/CH$_2$Cl$_2$ afforded 24–3 as a white solid (50 mg).

Step C

A suspension of PtO$_2$ (40 mol %, 73 mg) in a solution of 24–3 (0.81 mmol, 456 mg) in AcOH (25 mL) was stirred for 1 hr under a balloon atmosphere of hydrogen gas. Reaction mixture was filtered through a short pad of celite and concentrated to afford the desired product 24–4 as a white foam.

SCHEME 25

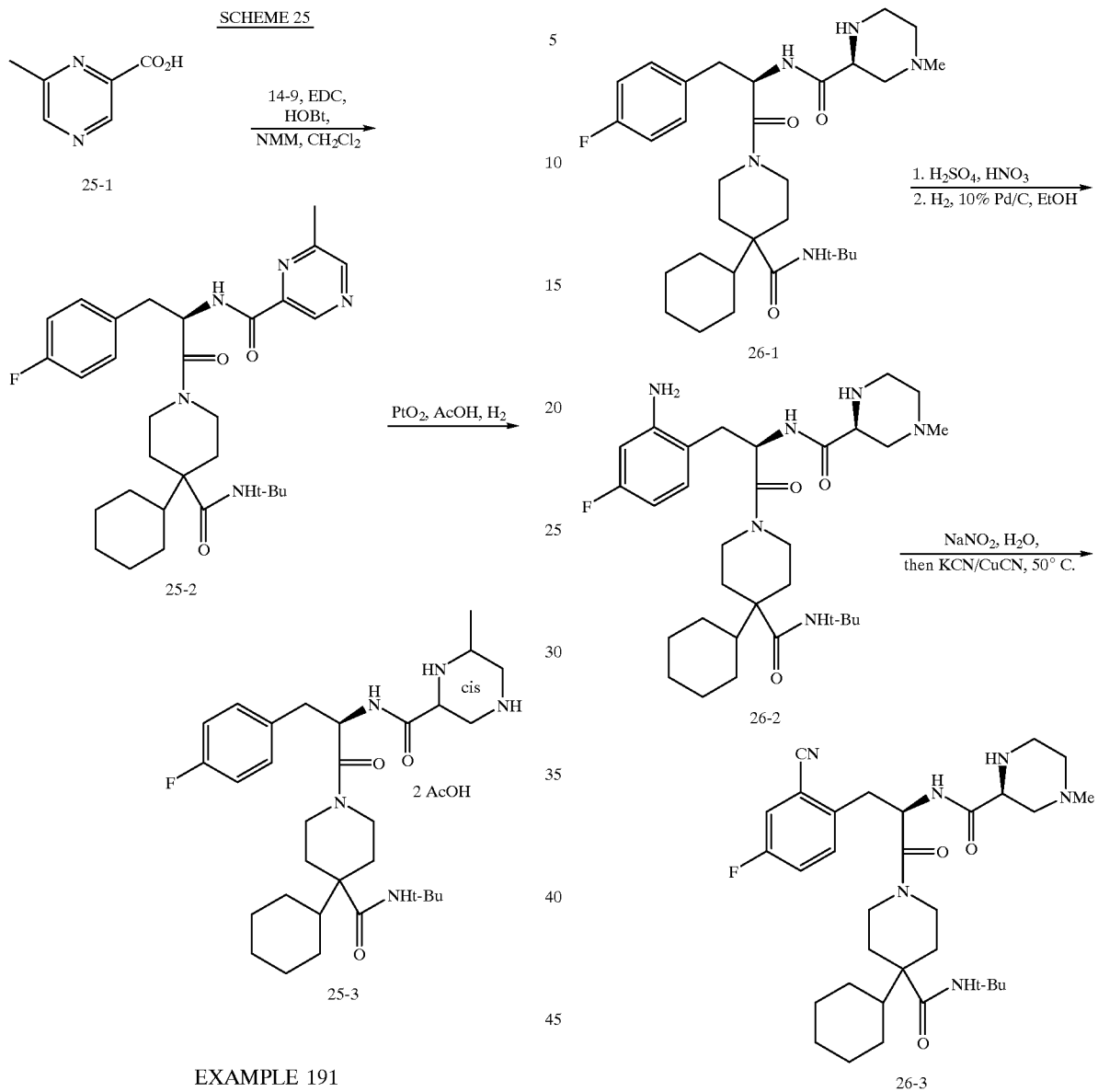

EXAMPLE 191

Step A

To a solution of amine 14–9 (0.1 mmol, 47 mg) in $CH_2Cl_2$ at room temperature was added 25–1 (0.11 mmol, 14 mg) followed by HOBt (0.12 mmol, 16 mg), EDC (0.12 mmol, 23 mg) and NMM (0.45 mmol, 0.05 mL). Resultant solution was stirred at room temperature overnight. Reaction mixture was poured into EtOAc (10 mL) and washed successively with 0.5M HCl, saturated $NaHCO_3$, $H_2O$ and brine, dried over $Na_2SO_4$ and concentrated. Chromatography over silica gel eluting with 50 mL of 0, 2.5, 5, 10, and 20% $Me_2CO/CH_2Cl_2$ afforded 25–2 as a white solid (43 mg).

Step B

A suspension of $PtO_2$ (40 mol %, 12 mg) in a solution of 25–2 (0.14 mmol, 75 mg) in AcOH (5 mL) was stirred for 1 hr under a balloon atmosphere of hydrogen gas. Reaction mixture was filtered through a short pad of celite and concentrated. The crude product was purified by prep HPLC to afford the title compound 25–3 (5 mg).

EXAMPLE 192

Step A

A solution of 26–1 (216 mg, 0.39 mmol) in $H_2SO_4$ (3 mL) was stirred at rt for 10 min. The resultant solution was placed in an ice-bath and fuming $HNO_3$ (0.03 mL) was added dropwise. After the addition was complete, the reaction was allowed to stir for 15 min at 0° C. The mixture was then poured into stirring ice-water (30 mL) and then allowed to warm to rt. Concentrated ammonia was added until pH 9 was obtained, and the resultant emulsion was extracted with EtOAc (3×100 mL). The organics were washed successively with 1N ammonia, water, and brine and dried over $Na_2SO_4$ and concentrated to give 26–2 (230 mg).

Step B

To an ice-cold solution of 26–2 (171 mg, 0.249 mmol) in water (2 mL) was added a solution of $NaNO_2$ (20 mg, 0.28 mmol) until the resultant solution tested positive for excess nitrous acid with KI-starch paper. The solution was neutralized with $Na_2CO_3$ and was added to a suspension of KCN and CuCN in water (4 mL) at rt. The mixture was gradually heated to 50° C. After being heated for 2 h, the mixture was extracted with $CHCl_3$ (4×25 mL). Organic phase was dried over $Na_2SO_4$ and concentrated. Chromatography over silica gel eluting with 5% $MeOH/CH_2Cl_2$ afforded the desired nitrile 26–3 (120 mg).

BIOLOGICAL ASSAYS

A. Binding Assay. The membrane binding assay was used to identify competitive inhibitors of $^{125}I$-NDP-alpha-MSH binding to cloned human MCRs expressed in L- or CHO-cells.

Cell lines expressing melanocortin receptors were grown in T-180 flasks containing selective medium of the composition: 1 L Dulbecco's modified Eagles Medium (DMEM) with 4.5 g L-glucose, 25 mM Hepes, without sodium pyruvate, (Gibco/BRl); 100 ml 10% heat-inactivated fetal bovine serum (Sigma); 10 ml 10,000 unit/ml penicillin & 10,000 ug/ml streptomycin (Gibco/BRl); 10 ml 200 mM L-glutamine (Gibco/BRl); 1 mg/ml Geneticin (G418) (Gibco/BRl). The cells were grown at 37° C. with $CO_2$ and humidity control until the desired cell density and cell number was obtained.

The medium was poured off and 10 mls/monolayer of enzyme-free dissociation media (Specialty Media Inc.) was added. The cells were incubated at 37° C. for 10 minutes or until cells sloughed off when flask was banged against hand.

The cells were harvested into 200 ml centrifuge tubes and spun at 1000 rpm, 4° C, for 10 min. The supernatant was discarded and the cells were resuspended in 5 mls/monolayer membrane preparation buffer having the composition: 10 mM Tris pH 7.2–7.4; 4 ug/ml Leupeptin (Sigma); 10 uM Phosphoramidon (Boehringer Mannheim); 40 ug/ml Bacitracin (Sigma); 5 ug/ml Aprotinin (Sigma); 10 mM Pefabloc (Boehringer Mannheim). The cells were homogenized with motor-driven dounce (Talboy setting 40), using 10 strokes and the homogenate centrifuged at 6,000 rpm, 4° C., for 15 minutes.

The pellets were resuspended in 0.2 mls/monolayer membrane prep buffer and aliquots were placed in tubes (500–1000 ul/tube) and quick frozen in liquid nitrogen and then stored at −80° C.

Test compounds or unlabelled NDP-α-MSH was added to 100 μL of membrane binding buffer to a final concentration of 1 μM. The membrane binding buffer had the composition: 50 mM Tris pH 7.2; 2 mM CaCl2; 1 mM MgCl2; 5 mM KCl; 0.2% BSA; 4 ug/ml Leupeptin (SIGMA); 10 uM Phosphoramidon (Boehringer Mannheim); 40 ug/ml Bacitracin (SIGMA); 5 ug/ml Aprotinin (SIGMA); and 10 mM Pefabloc (Boehringer Mannheim). One hundred μl of membrane binding buffer containing 10–40 ug membrane protein was added, followed by 100 μM 125I-NDP-α-MSH to final concentration of 100 pM. The resulting mixture was vortexed briefly and incubated for 90–120 min at room temp while shaking.

The mixture was filtered with Packard Microplate 196 filter apparatus using Packard Unifilter 96-well GF/C filter with 0.1% polyethyleneimine (Sigma). The filter was washed (5 times with a total of 10 ml per well) with room temperature of filter wash having the composition: 50 mM Tris-HCl pH 7.2 and 20 mM NaCl. The filter was dried, and the bottom sealed and 50 ul of Packard Microscint-20 was added to each well. The top was sealed and the radioactivity quantitated in a Packard Topcount Microplate Scintillation counter.

B. Functional assay. Functional cell based assays were developed to discriminate melanocortin receptor agonists from antagonists.

Cells (for example, CHO- or L-cells or other eukaryotic cells) expressing a human melanocortin receptor (see e.g. Yang-YK; Ollmann-MM; Wilson-BD; Dickinson-C; Yamada-T; Barsh-GS; Gantz-I; Mol-Endocrinol. 1997 Mar; 11(3): 274–80) were dissociated from tissue culture flasks by rinsing with Ca and Mg free phosphate buffered saline (14190–136, Life Technologies, Gaithersburg, Md.) and detached following 5 minutes incubation at 37° C. with enzyme free dissociation buffer (S-014-B, Specialty Media, Lavellette, N.J.). Cells were collected by centrifugation and resuspended in Earle's Balanced Salt Solution (14015–069, Life Technologies, Gaithersburg, Md.) with additions of 10 mM HEPES pH 7.5, 5 mM $MgCl_2$, 1 mM glutamine and 1 mg/ml bovine serum albumin. Cells were counted and diluted to 1 to $5\times10^6$/ml. The phosphodiesterase inhibitor 3-isobutyl-1-methylxanthine was added to cells to 0.6 mM.

Test compounds were diluted in dimethylsulfoxide (DMSO) ($10^{-5}$ to $10^{-10}$ M) and 0.1 volume of compound solution was added to 0.9 volumes of cell suspension; the final DMSO concentration was 1%. After room temperature incubation for 45 min., cells were lysed by incubation at 100° C. for 5 min. to release accumulated cAMP.

cAMP was measured in an aliquot of the cell lysate with the Amersham (Arlington Heights, Ill.) cAMP detection assay (RPA556). The amount of cAMP production which resulted from an unknown compound was compared to that amount of cAMP produced in response to alpha-MSH which was defined as a 100% agonist. The $EC_{50}$ is defined as the compound concentration which results in half maximal stimulation, when compared to its own maximal level of stimulation.

Antagonist assay: Antagonist activity was defined as the ability of a compound to block cAMP production in response to alpha-MSH. Solution of test compounds and suspension of receptor containing cells were prepared and mixed as described above; the mixture was incubated for 15 min., and an EC50 dose (approximately 10 nM alpha-MSH) was added to the cells. The assay was terminated at 45 min. and cAMP quantitated as above. Percent inhibition was determined by comparing the amount of cAMP produced in the presence to that produced in the absence of test compound.

C. In Vivo Food Intake Models

1) Overnight food intake. Sprague Dawley rats are injected intracerebroventricularly with a test compound in 400 mL of 50% propylene glycol/artificial cerebrospinal fluid one hour prior to onset of dark cycle (12 hours). Food intake is determined using a computerized system in which each rats food is placed on a computer monitored balance. Cumulative food intake for 16 hours post compound administration is measured.

2) Food intake in diet induced obese mice. Male C57/B16J mice maintained on a high fat diet (60% fat calories) for 6.5 months from 4 weeks of age are are dosed intraperitoneally with test compound. Food intake and body weight are measured over an eight day period. Biochemical parameters relating to obesity, including leptin, insulin, triglyceride, free fatty acid, cholesterol and serum glucose levels are determined.

D. Rat Ex Copula Assay

Sexually mature male Caesarian Derived Sprague Dawley (CD) rats (over 60 days old) are used with the suspensory ligament surgically removed to prevent retraction of the penis back into the penile sheath during the ex copula evaluations. Animals receive food and water ad lib and are kept on a normal light/dark cycle. Studies are conducted during the light cycle.

1) Conditioning to Supine Restraint for Ex Copula Reflex Tests. This conditioning takes ~4 days. Day 1, the animals are placed in a darkened restrainer and left for 15–30 minutes. Day 2, the animals are restrained in a supine position in the restrainer for 15–30 minutes. Day 3, the animals are restrained in the supine position with the penile sheath retracted for 15–30 minutes. Day 4, the animals are restrained in the supine position with the penile sheath retracted until penile responses are observed. Some animals require additional days of conditioning before they are completely acclimated to the procedures; non-responders are removed from further evaluation. After any handling or evaluation animals are given a treat to ensure positive reinforcement.

2) Ex Copula Reflex Tests. Rats are gently restrained in a supine position with their anterior torso placed inside a cylinder of adequate size to allow for normal head and paw grooming. For a 400–500 gram rat, the diameter of the cylinder is approximately 8 cm. The lower torso and hind limbs are restrained with a non-adhesive material (vetrap). An additional piece of vetrap with a hole in it, through which the glans penis will be passed, is fastened over the animal to maintain the preputial sheath in a retracted position. Penile responses will be observed, typically termed ex copula genital reflex tests. Typically, a series of penile erections will occur spontaneously within a few minutes after sheath retraction. The types of normal reflexogenic erectile responses include elongation, engorgement, cup and flip. An elongation is classified as an extension of the penile body. Engorgement is a dilation of the glans penis. A cup is defined as an intense erection where the distal margin of the glans penis momentarily flares open to form a cup. A flip is a dorsiflexion of the penile body.

Baseline and or vehicle evaluations are conducted to determine how and if an animal will respond. Some animals have a long duration until the first response while others are non-responders altogether. During this baseline evaluation latency to first response, number and type of responses are recorded. The testing time frame is 15 minutes after the first response.

After a minimum of 1 day between evaluations, these same animals are administered the test compound at 20 mg/kg and evaluated for penile reflexes. All evaluations are videotaped and scored later. Data are collected and analyzed using paired 2 tailed t-tests to compared baseline and/or vehicle evaluations to drug treated evaluations for individual animals. Groups of a minimum of 4 animals are utilized to reduce variability.

Positive reference controls are included in each study to assure the validity of the study. Animals can be dosed by a number of routes of administration depending on the nature of the study to be performed. The routes of administration includes intravenous (IV), intraperitoneal (IP), subcutaneous (SC) and intracerebral ventricular (ICV).

E. Models of Female Sexual Dysfunction

Rodent assays relevant to female sexual receptivity include the behavioral model of lordosis and direct observations of copulatory activity. There is also a urethrogenital reflex model in anesthetized spinally transected rats for measuring orgasm in both male and female rats. These and other established animal models of female sexual dysfunction are described in McKenna K E et al, *A Model For The Study of Sexual Function In Anesthetized Male And Female Rats*, Am. J. Physiol. (Regulatory Integrative Comp. Physiol 30): R1276–R1285, 1991; McKenna K E et al, *Modulation By Peripheral Serotonin of The Threshold For Sexual Reflexes In Female Rats*, Pharm. Bioch. Behav., 40:151–156, 1991; and Takahashi L K et al, *Dual Estradiol Action In The Diencephalon And The Regulation Of Sociosexual Behavior In Female Golden Hamsters*, Brain Res., 359:194–207, 1985.

EXAMPLES OF A PHARMACEUTICAL COMPOSITION

As a specific embodiment of an oral composition of a composition of the present invention, 5 mg of Example 2 is formulated with sufficient finely divided lactose to provide a total amount of 580 to 590 mg to fill a size O hard gelatin capsule.

As another specific embodiment of an oral composition of a compound of the present invention, 2.5 mg of Example 2 is formulated with sufficient finely divided lactose to provide a total amount of 580 to 590 mg to fill a size O hard gelatin capsule.

Representative compounds of the present invention were tested and found to bind to the melanocortin-4 receptor. These compounds were generally found to have $IC_{50}$ values less than 2 $\mu M$. Representative compounds of the present invention were also tested in the functional assay and found generally to activate the melanocortin-4 receptor with $EC_{50}$ values less than 1 $\mu M$.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for obesity, diabetes, or sexual dysfunction or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of structural formula I:

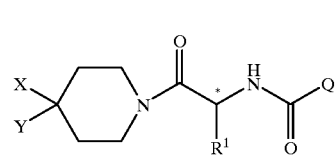

(I)

or a pharmaceutically acceptable salt thereof; wherein Q is

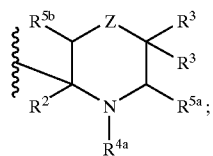

Z is O, S, or $NR^{4b}$;
each n is independently 0, 1, or 2;
$R^1$ is selected from the group consisting of
hydrogen,
$C_{1-8}$ alkyl,
$(CHR^7)_n$—$C_{3-6}$ cycloalkyl,
$(CHR^7)_n$—$O(CHR^7)$aryl,
$(CHR^7)_n$-aryl, and
$(CHR^7)_n$-heteroaryl;
in which aryl and heteroaryl are unsubstituted or substituted with one to three groups independently selected from $R^6$; and alkyl and cycloalkyl are unsubstituted or substituted with one to three groups independently selected from $R^6$ and oxo;
$R^2$ is selected from the group consisting of
hydrogen,
$C_{1-8}$ alkyl,
$(CH_2)_n C_{3-6}$ cycloalkyl, and
$(CH_2)_n$-aryl;
each $R^3$ is independently selected from the group consisting of
hydrogen,
$C_{1-8}$ alkyl,
$(CH_2)_n$-aryl,
$(CH_2)_n C_{3-6}$ cycloalkyl,
$(CH_2)_n$-heteroaryl, and
$(CH_2)_n$-heterocyclyl;
in which aryl and heteroaryl are unsubstituted or substituted with one to three groups independently selected from $R^6$; and alkyl, cycloalkyl, and heterocyclyl are unsubstituted or substituted with one to three groups independently selected from $R^6$ and oxo;
$R^{4a}$ and $R^{4b}$ are each independently selected from the group consisting of
hydrogen,
$C_{1-8}$ alkyl,
$(CH_2)_n$-aryl,
$(CH_2)_n C_{3-6}$ cycloalkyl,
$(CH_2)_n$-heteroaryl,
$(CH_2)_n$-heterocyclyl,
$COC(R^7)_2 NH_2$,
$COR^7$,
$(CH_2)_n OR^7$,
$(CH_2)_n CO_2 R^7$,
$CH_2 C{\equiv}CH$,
$CO_2 R^7$,
$CH_2 CHF_2$,
$CONR^7 R^7$, and
$SO_2 R^7$;
in which aryl and heteroaryl are unsubstituted or substituted with one to three groups independently selected from $R^6$; and alkyl, cycloalkyl, and heterocyclyl are unsubstituted or substituted with one to three groups independently selected from $R^6$ and oxo;
$R^{5a}$ and $R^{5b}$ are each independently selected from the group consisting of
hydrogen,
$C_{1-8}$ alkyl,
$C_{3-8}$ cycloalkyl, and
$(CH_2)_n$-aryl;
wherein alkyl and cycloalkyl are unsubstituted or substituted with one to three groups independently selected from $R^6$ and oxo; and aryl is unsubstituted or substituted with one to three groups independently selected from $R^6$;
$R^6$ is selected from the group consisting of
hydrogen,
$C_{1-8}$ alkyl,
$(CH_2)_n$-aryl,
$(CH_2)_n C_{3-7}$ cycloalkyl,
$(CH_2)_n$-heteroaryl,
halogen,
$OR^7$,
$NHSO_2 R^7$,
$N(R^7)_2$,
$C{\equiv}N$,
$CO_2 R^7$,
$C(R^7)(R^7)N(R^7)_2$,
$NO_2$,
$SO_2 N(R^7)_2$,
$S(O)_{0-2} R^7$,
$CF_3$, and
$OCF_3$;
or two $R^6$ substituents, when on the same carbon atom, can be taken together together with the carbon atom to which they are attached to form a cyclopropyl group;
each $R^7$ is independently selected from the group consisting of
hydrogen,
$C_{1-8}$ alkyl,
$(CH_2)_n$-aryl, and
$(CH_2)_n C_{3-7}$ cycloalkyl;
each $R^8$ is independently selected from the group consisting of
hydrogen,
$C_{1-8}$ alkyl,
$(CH_2)_n$-aryl,
$(CH_2)_n$-heteroaryl,
$(CH_2)_n$-heterocyclyl, and
$(CH_2)_n C_{3-7}$ cycloalkyl;
wherein aryl and heteroaryl are unsubstituted or substituted with one to three groups independently selected from $R^6$; and alkyl, cycloalkyl, heterocyclyl, and $(CH_2)_n$ are unsubstituted or substituted with one to three groups independently selected from $R^6$ and oxo; or two $R^8$ groups together with the atoms to which they are attached form a 5- to 8-membered mono- or bi-cyclic ring system optionally having an additional heteroatom selected from O, S, $NR^7$, NBoc, and NCbz;
each $R^9$ is independently selected from the group consisting of
hydrogen,
$C_{1-8}$ alkyl,
$(CH_2)_n$-aryl,
$(CH_2)_n C_{3-6}$ cycloalkyl,
$(CH_2)_n$-heteroaryl,
halogen,
$OR^7$,
$NHSO_2 R^7$,
$N(R^7)_2$,
$C{\equiv}N$,
$CO_2 R^7$,
$C(R^7)(R^7)N(R^7)_2$,
$NO_2$, $SO_2N(R^7)_2$,
$S(O)_{0-2}R^7$,
$CF_3$, and
$OCF_3$;

X is selected from the group consisting of
$C_{1-8}$ alkyl,
$(CH_2)_nC_{3-8}$ cycloalkyl,
$(CH_2)_n$aryl,
$(CH_2)_n$heteroaryl,
$(CH_2)_n$heterocyclyl,
$(CH_2)_nC\equiv N$,
$(CH_2)_nCONR^8R^8$,
$(CH_2)_nCO_2R^8$,
$(CH_2)_nCOR^8$,
$(CH_2)_nNR^8C(O)R^8$,
$(CH_2)_nNR^8CO_2R^8$,
$(CH_2)_nNR^8C(O)N(R^8)_2$,
$(CH_2)_nNR^8SO_2R^8$,
$(CH_2)_nS(O)_{0-2}R^8$,
$(CH_2)_nSO_2N(R^8)(R^8)$,
$(CH_2)_nOR^8$,
$(CH_2)_nOC(O)R^8$,
$(CH_2)_nOC(O)OR^8$,
$(CH_2)_nOC(O)N(R^8)_2$,
$(CH_2)_nN(R^8)(R^8)$, and
$(CH_2)_nNR^8SO_2N(R^8)(R^8)$;
wherein aryl and heteroaryl are unsubstituted or substituted with one to three groups selected from $R^6$; and alkyl, $(CH_2)_n$, cycloalkyl, and heterocyclyl are unsubstituted or substituted with one to three groups independently selected from $R^6$ and oxo;

Y is selected from the group consisting of
hydrogen,
$C_{1-8}$ alkyl,
$(CH_2)_nC_{3-8}$ cycloalkyl,
$(CH_2)_n$aryl,
$(CH_2)_n$heterocyclyl, and
$(CH_2)_n$heteroaryl;
wherein aryl and heteroaryl are unsubstituted or substituted with one to three groups selected from $R^6$; and alkyl, $(CH_2)_n$, cycloalkyl, and heterocyclyl are optionally substituted with one to three groups selected from $R^6$ and oxo.

2. The compound of claim 1 wherein Z is O or $NR^{4b}$.

3. The compound of claim 2 wherein Z is $NR^{4b}$.

4. The compound of claim 3 wherein $R^{4a}$ and $R^{4b}$ are each independently selected from the group consisting of
hydrogen,
$C_{1-8}$ alkyl,
$(CH_2)_n$-aryl,
$(CH_2)_n$-heteroaryl,
$(CH_2)_n$-heterocyclyl,
$(CH_2)_nC_{3-6}$ cycloalkyl,
$(CH_2)_nCO_2R^7$
$(CH_2)_nOR^7$,
$COC(R^7)_2NH_2$,
$CH_2C\equiv CH$, and
$CH_2CHF_2$; and
$R^3$, $R^{5a}$, and $R^{5b}$ are each independently hydrogen, $C_{1-4}$ alkyl, $C_{3-6}$ cycloalkyl, or aryl; wherein aryl is unsubstituted or substituted with one to three groups independently selected from $R^6$.

5. The compound of claim 4 wherein $R^{4a}$ and $R^{4b}$ are each independently selected from the group consisting of
hydrogen,
$C_{1-4}$ alkyl,
$CH_2$-aryl,
$CH_2$-heteroaryl,
$CH_2$-heterocyclyl,
$(CH_2)_{0-1}C_{3-6}$ cycloalkyl,
$CH_2CO_2R^7$
$(CH_2)_2OR^7$,
$COC(R^7)_2NH_2$,
$CH_2C\equiv CH$, and
$CH_2CHF_2$; and
$R^3$, $R^{5a}$, and $R^{5b}$ are each independently hydrogen, $C_{1-4}$ alkyl, $C_{3-6}$ cycloalkyl, or phenyl; wherein phenyl is unsubstituted or substituted with one to three groups independently selected from $R^6$.

6. The compound of claim 1 wherein $R^1$ is $CHR^7$-aryl, $CHR^7OCHR^7$-aryl, or $CHR^7$-heteroaryl wherein aryl and heteroaryl are optionally substituted with one or two groups independently selected from $R^6$.

7. The compound of claim 6 wherein $R^1$ is benzyl optionally substituted with one or two groups selected from halogen, $C_{1-4}$ alkyl, $C_{1-4}$ alkoxy, CN, $CF_3$, and $OCF_3$.

8. The compound of claim 7 wherein $R^1$ is 4-chlorobenzyl; 4-fluorobenzyl; 3,4-difluorobenzyl; 3,5-difluorobenzyl; 2-cyano-4-fluorobenzyl; or 4-methoxybenzyl.

9. The compound of claim 1 wherein $R^2$ is H or $CH_3$.

10. The compound of claim 1 wherein X is $C_{1-6}$ alkyl, $(CH_2)_n$-aryl, $(CH_2)_n$-heteroaryl, $(CH_2)_n$-heterocyclyl, $(CH_2)_nC(O)N(R^8)(R^8)$, $(CH_2)_nCO_2R^8$, $(CH_2)_nOR^8$, $(CH_2)_nS(O)_{0-2}R^8$, $(CH_2)_nNHC(O)R^8$, $(CH_2)_nOC(O)NR^8R^8$, or $(CH_2)_nNR^8SO_2R^8$; wherein aryl and heteroaryl are optionally substituted with one to three groups selected from $R^6$; heterocyclyl is optionally substituted with one to three groups selected from $R^6$ and oxo; the $(CH_2)_n$ group is optionally substituted with one to three groups selected from $R^7$, halogen, $S(O)_{0-2}R^7$, $N(R^7)_2$, and $OR^7$; and $R^8$ is each independently selected from H, $C_{1-8}$ alkyl, and $C_{3-6}$ cycloalkyl optionally substituted with one to three groups selected from $R^6$ and oxo; or two $R^8$ groups together with the atoms to which they are attached form a 5- to 8-membered mono- or bi-cyclic ring system optionally having an additional heteroatom selected from O, S, $NR^7$, NBoc, and NCbz.

11. The compound of claim 10 wherein X is C 1–6 alkyl, $(CH_2)_{0-1}$-heteroaryl, $CH_2$-heterocyclyl, $CO_2R^8$, $CH_2OR^8$, $CH_2S(O)_{0-2}R^8$, $NHC(O)R^8$, $CH_2NR^8SO_2R^8$, $CH_2OC(O)NR^8R^8$, $CH_2NR^8SO_2R^8$, or $C(O)N(R^8)(R^8)$; wherein heteroaryl is optionally substituted with one to three groups selected from $R^6$; heterocyclyl is optionally substituted with one to three groups selected from $R^6$ and oxo; and $R^8$ is each independently selected from H, $C_{1-8}$ alkyl, and $C_{3-6}$ cycloalkyl optionally substituted with one to three groups selected from $R^6$ and oxo; or two $R^8$ groups together with the atoms to which they are attached form a 5- to 8-membered mono- or bi-cyclic ring system optionally having an additional heteroatom selected from O, S, $NR^7$, NBoc, and NCbz.

12. The compound of claim 1 wherein Y is $C_{1-8}$ alkyl, $(CH_2)_nC_{3-7}$ cycloalkyl, $(CH_2)_n$-aryl, $(CH_2)_n$-heteroaryl, or $(CH_2)_n$-heterocyclyl; wherein aryl and heteroaryl are optionally substituted with one to three groups selected from $R^6$; and $(CH_2)_n$, alkyl, cycloalkyl, and heterocyclyl are optionally substituted with one to three groups selected from $R^6$ and oxo.

13. The compound of claim 12 wherein Y is cyclohexyl, cycloheptyl, cyclopentyl, or $C_{1-6}$ alkyl; wherein alkyl and cycloalkyl are unsubstituted or substituted with one to three groups selected from $R^6$ and oxo.

14. The compound of claim 13 wherein Y is cyclohexyl or $C_{1-6}$ alkyl, wherein the cyclohexyl and alkyl groups are unsubstituted or substituted with one to three groups selected from $R^6$ and oxo.

15. The compound of claim 1 wherein the carbon atom marked with * has the R configuration.

16. The compound of claim 1 wherein X is selected from the group consisting of:

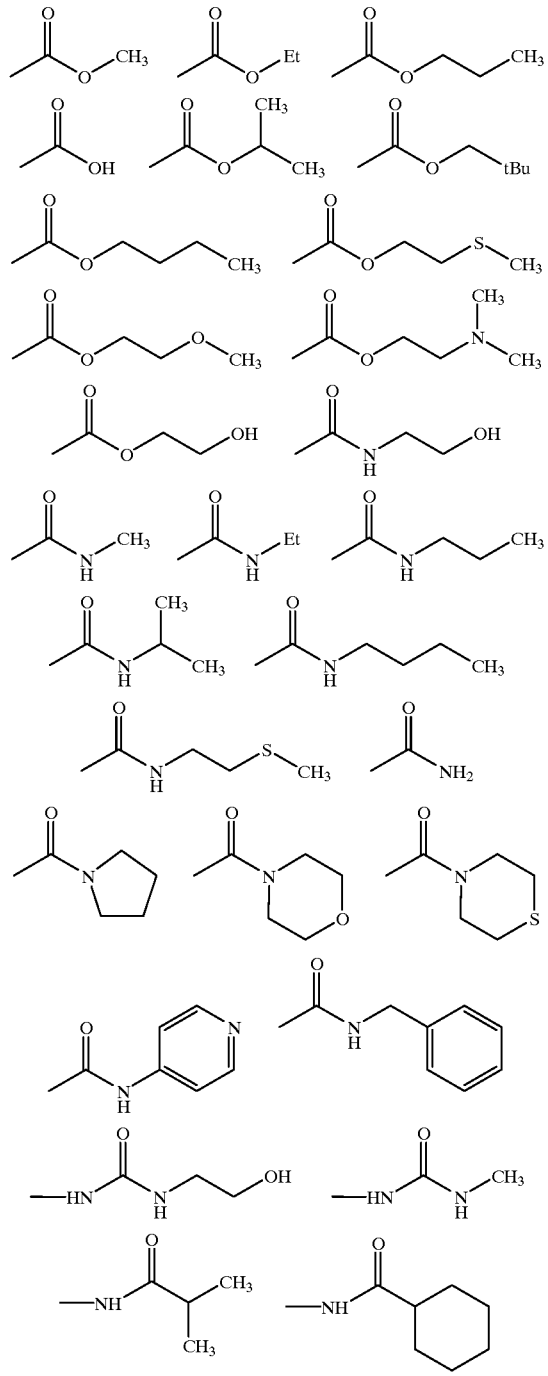

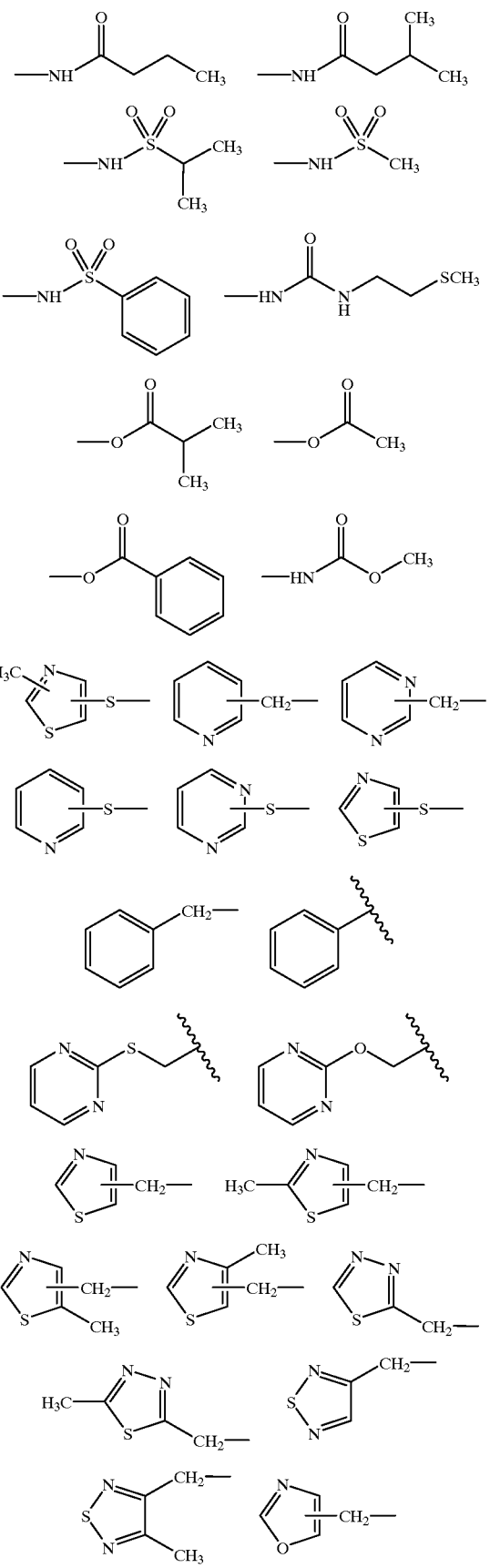

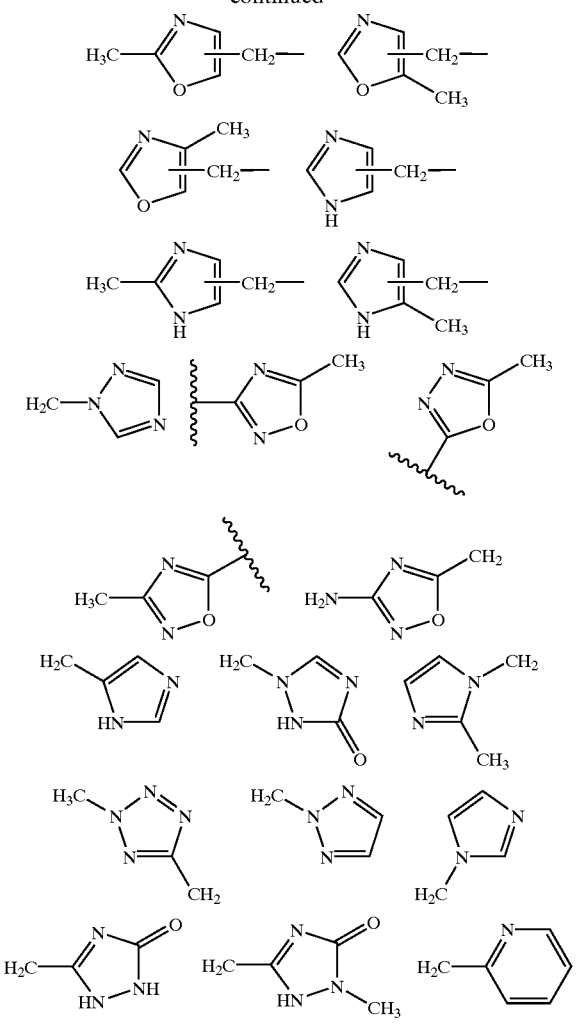

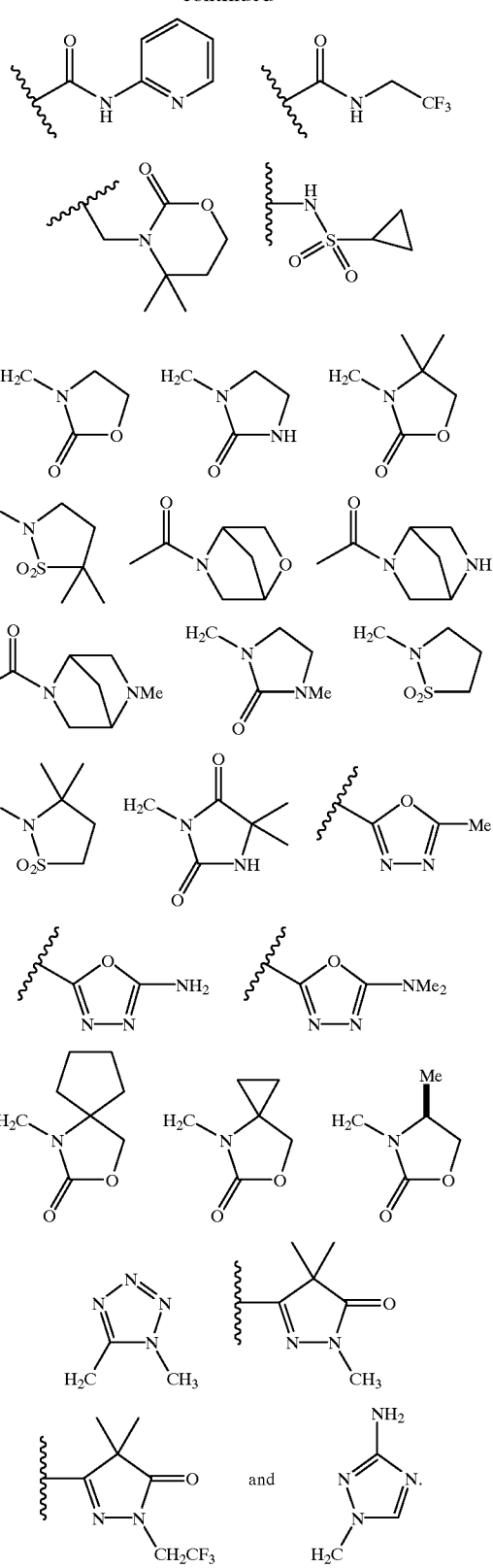

—NH—C(O)CH₃  —C(O)N(CH₃)₂  —C(O)NH-t-Bu
—NHC(O)tBu;  —C(O)NHCH(Et)₂;  —C(O)NHCH₂tBu;
—CH₂SCH(CH₃)₂;  —CH₂S(O)CH(CH₃)₂;  —CH₂S(O)₂CH(CH₃)₂;  —C(O)NHCH₂CH₂N(CH₃)₂;  C(O)CH(CH₃)₂;
—CH₂NHCOtBu;  —CH₂OC(O)NMe₂;  —CH₂C(O)NEt₂;
—CH₂OC(Me)₂CO₂H;  —C(O)NHC(Me)₂CO₂Me;  —C(O)NHC(Me)₂CO₂H;  —CH₂N(CH₃)COtBu;  —CH₂N(iPr)COMe;  —CH₂N(iPr)SO₂Me;  C(O)NHC(Me)₂CH₂OMe;  C(O)NHC(Me)₂CH₂OH;  —CH₂CH₂C(Me)₂OH;

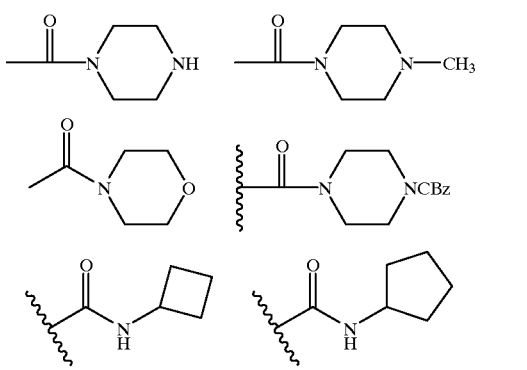

17. The compound of claim 16 of structural formula Ia selected from the group consisting of

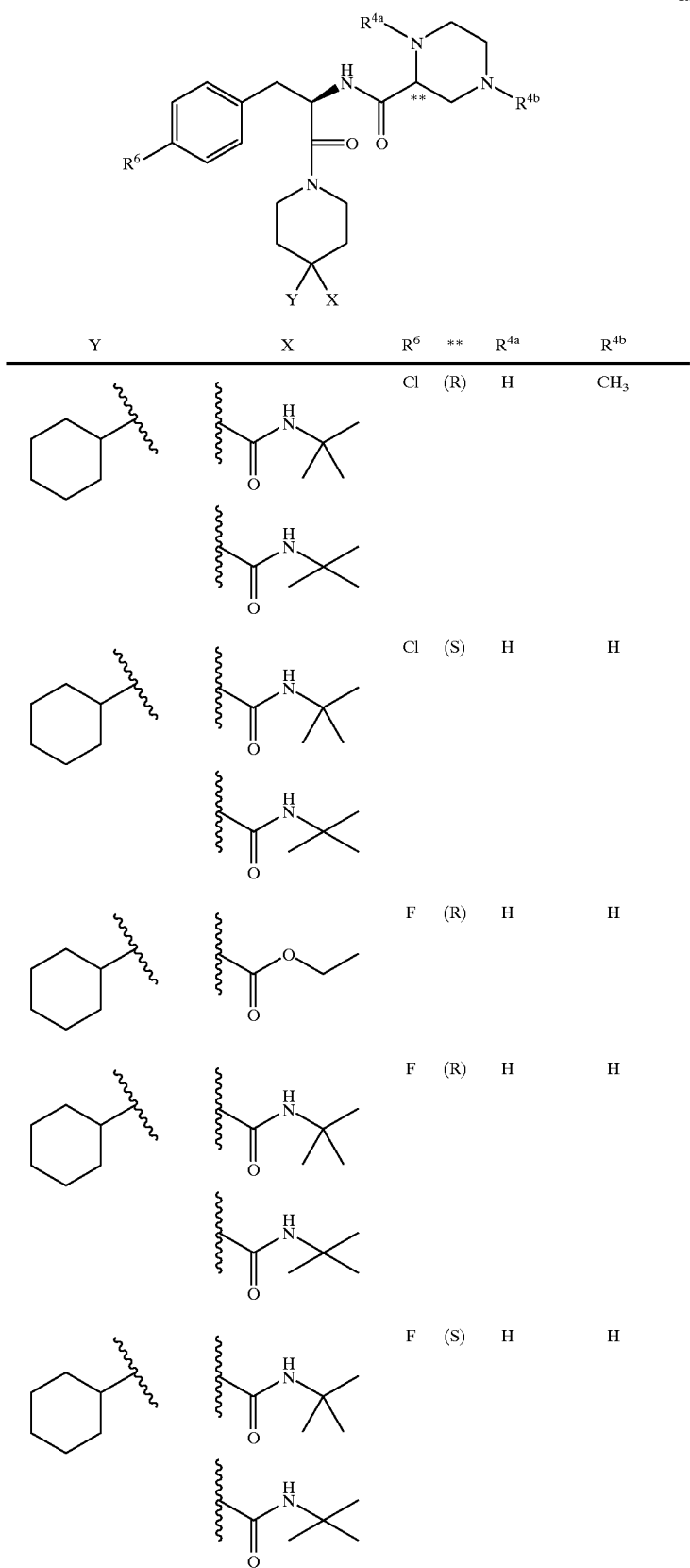

-continued
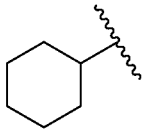
Ia
| Y | X | R⁶ | ** | R⁴ᵃ | R⁴ᵇ |
|---|---|---|---|---|---|
| 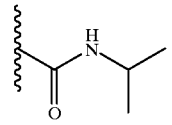 | 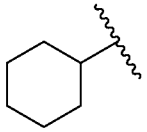 | Cl | (S) | H | H |
| 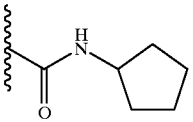 | 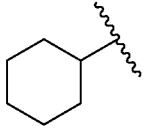 | Cl | (S) | H | H |
| 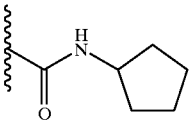 | 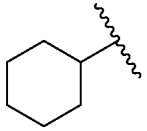 | Cl | (R) | H | H |
| 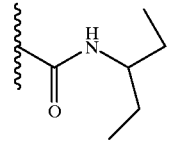 | 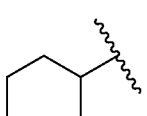 | Cl | (S) | H | H |
| 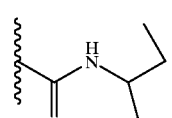 | 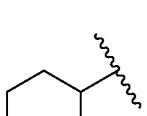 | Cl | (R) | H | H |
| 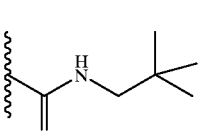 | 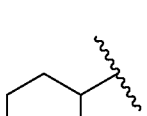 | Cl | (R) | H | H |
| 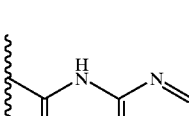 | | Cl | (S) | H | H |

-continued

| Y | X | R6 | ** | R4a | R4b |
|---|---|---|---|---|---|
| cyclohexyl | -NH-C(O)-CH2-CF3 | Cl | (S) | H | H |
| cyclohexyl | -C(O)-piperazine-NH | F | (S) | H | H |
| cyclohexyl | -C(O)-N-methylpiperazine | F | (S) | H | H |
| cyclohexyl | -NH-C(O)-C(CH3)3 and -NH-C(O)-C(CH3)3 | Cl | (S) | H | H |
| cyclohexyl | -NH-C(O)-C(CH3)3 and -NH-C(O)-C(CH3)3 | Cl | (R) | H | H |
| cyclohexyl | -CH2-(4,4-dimethyloxazolidin-2-one-3-yl) | F | (S) | H | H |

-continued
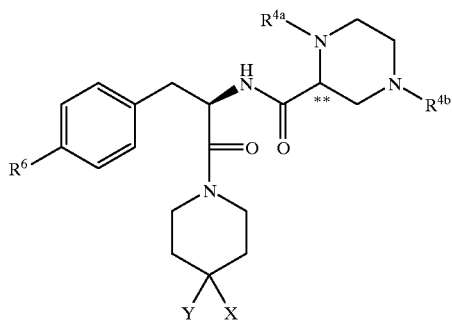
Ia
| Y | X | R⁶ | ** | R⁴ᵃ | R⁴ᵇ |
|---|---|---|---|---|---|
| 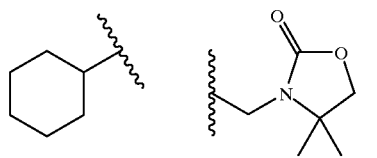 | 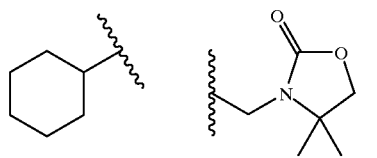 | F | (R) | H | H |
| 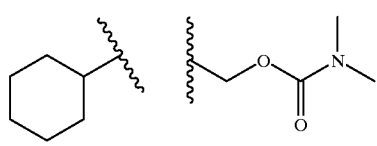 | 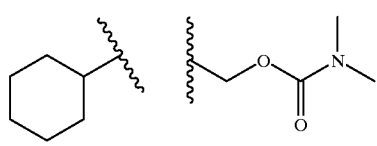 | Cl | (S) | H | H |
| 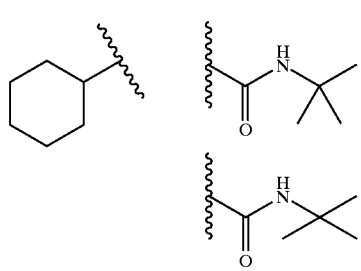 | 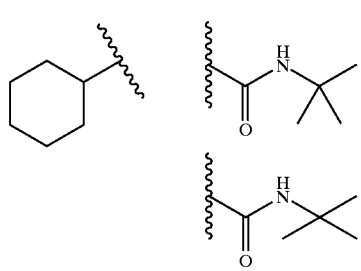 | Cl | (S) | CH₃ | H |
| 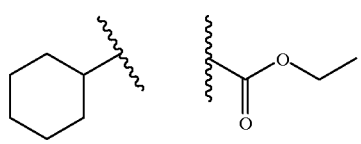 | 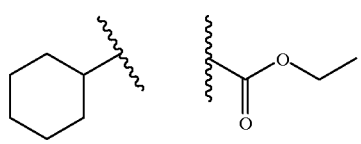 | F | (R) | CH₃ | H |
| 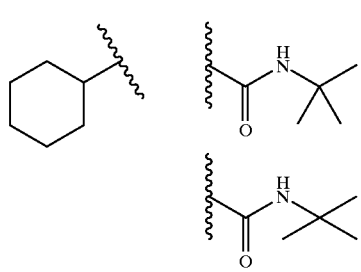 | 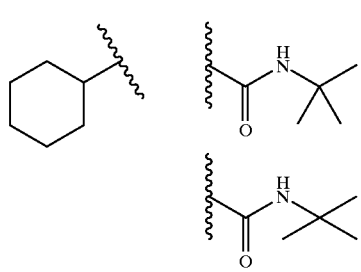 | Cl | (S) | CH₃ | H |

-continued
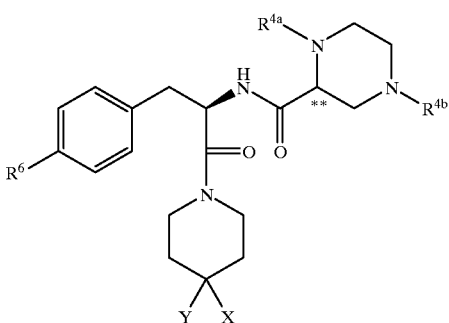
Ia
| Y | X | R⁶ | ** | R⁴ᵃ | R⁴ᵇ |
|---|---|---|---|---|---|
| 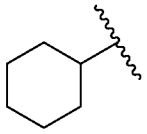 | 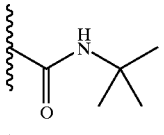 | F | (S) | CH₃ | H |
| 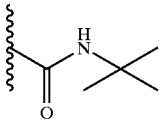 | 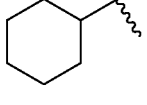 | Cl | (R) | CH₃ | H |
| 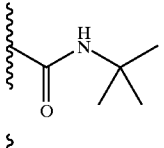 | 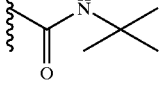 | F | (R) | CH₃ | H |
| 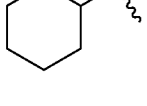 | 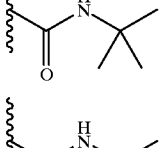 | Cl | (S) | CH₃ | H |
| 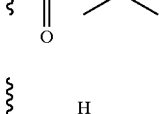 | 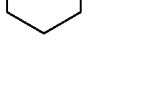 | Cl | (S) | CH₃ | H |

-continued
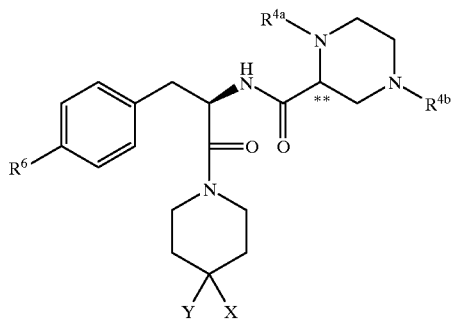
| Y | X | R⁶ | ** | R⁴ᵃ | R⁴ᵇ |
|---|---|---|---|---|---|
| cyclohexyl | -C(O)NH-cyclobutyl | Cl | (R) | CH₃ | H |
| cyclohexyl | -C(O)NH-cyclopentyl | Cl | (S) | CH₃ | H |
| cyclohexyl | -C(O)NH-cyclopentyl | Cl | (R) | CH₃ | H |
| cyclohexyl | -C(O)NH-CH(Et)₂ | Cl | (S) | CH₃ | H |
| cyclohexyl | -C(O)NH-CH(Et)₂ | Cl | (R) | CH₃ | H |
| cyclohexyl | -C(O)NH-CH₂C(CH₃)₃ | Cl | (R) | CH₃ | H |
| cyclohexyl | -C(O)NH-(2-pyridyl) | Cl | (S) | CH₃ | H |

-continued

| Y | X | R⁶ | ** | R⁴ᵃ | R⁴ᵇ |
|---|---|---|---|---|---|
| cyclohexyl | -NH-C(O)-CH₂-CF₃ | Cl | (S) | CH₃ | H |
| cyclohexyl | -C(O)-N(piperazine)-NH | F | (S) | CH₃ | H |
| cyclohexyl | -C(O)-N(piperazine)-N-CH₃ | F | (S) | CH₃ | H |
| cyclohexyl | -NH-C(O)-C(CH₃)₃ and -NH-C(O)-C(CH₃)₃ | Cl | (S) | CH₃ | H |
| cyclohexyl | -NH-C(O)-C(CH₃)₃ and -NH-C(O)-C(CH₃)₃ | Cl | (R) | CH₃ | H |
| cyclohexyl | -CH₂-N(4,4-dimethyloxazolidin-2-one) | Cl | (S) | CH₃ | H |

-continued
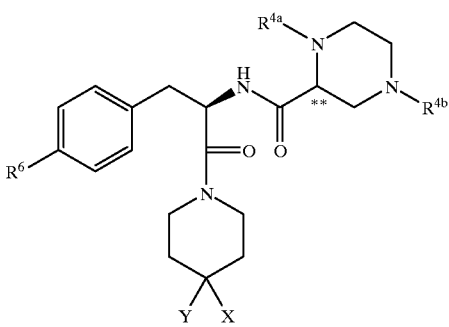
Ia
| Y | X | R⁶ | ** | R⁴ᵃ | R⁴ᵇ |
|---|---|---|---|---|---|
| 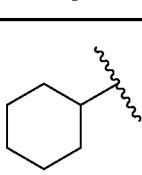 | 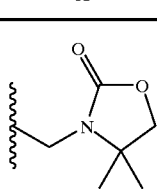 | F | (S) | CH₃ | H |
| 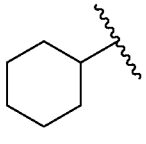 | 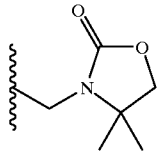 | Cl | (R) | CH₃ | H |
| 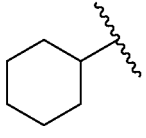 | 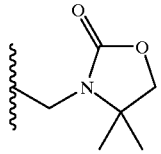 | F | (R) | CH₃ | H |
| 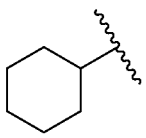 | 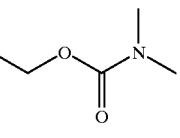 | Cl | (S) | CH₃ | H |
| 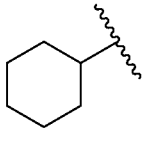 | 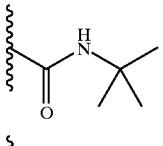 | Cl | (S) | CH₃ | CH₃ |
|  | 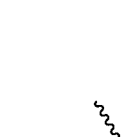 |  |  |  |  |
| 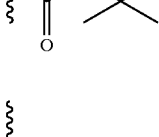 |  | Cl | (S) | CH₃ | CH₃ |

-continued
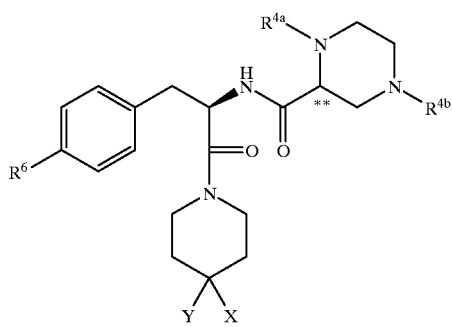
| Y | X | R⁶ | ** | R⁴ᵃ | R⁴ᵇ |
|---|---|---|---|---|---|
| cyclohexyl | -C(O)NH-t-Bu / -C(O)NH-t-Bu | Cl | (S) | $CH_3$ | $CH_3$ |
| cyclohexyl | -C(O)NH-t-Bu / -C(O)NH-t-Bu | Cl | (R) | $CH_3$ | $CH_3$ |
| cyclohexyl | -C(O)NH-cyclopentyl | Cl | (R) | $CH_3$ | $CH_3$ |
| cyclohexyl | -C(O)NH-CH(Et)₂ | Cl | (R) | $CH_3$ | $CH_3$ |
| cyclohexyl | -NHC(O)-C(CH₃)₃ / -NHC(O)-C(CH₃)₃ | Cl | (S) | $CH_3$ | $CH_3$ |

-continued
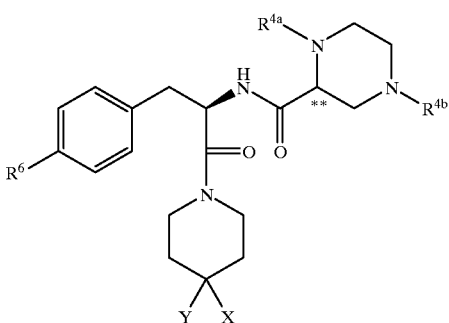
Ia
| Y | X | R⁶ | ** | R⁴ᵃ | R⁴ᵇ |
|---|---|---|---|---|---|
| 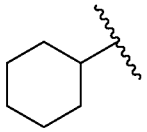 | 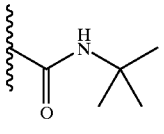 <br> 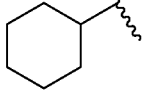 | Cl | (S) | H | CH₃ |
| 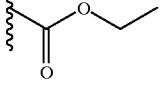 | 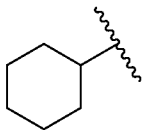 | Cl | (S) | H | i-Pr |
| 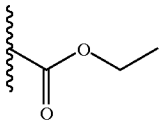 | 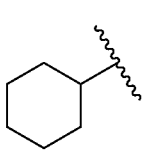 | F | (S) | H | 2-hydroxyethyl |
| 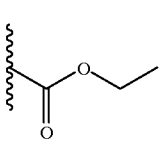 |  | F | (S) | H | 2-methoxyethyl |
|  |  | F | (S) | H | CH₂CO₂Et |
|  |  | F | (R) | H | CH₃ |
|  | | F | (R) | H | 2-methoxyethyl |

-continued
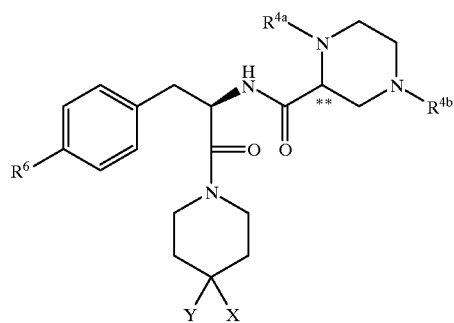
Ia
| Y | X | R⁶ | ** | R⁴ᵃ | R⁴ᵇ |
|---|---|---|---|---|---|
| | | Cl | (S) | H | CH₃ |
| | | Cl | (S) | H | i-Pr |
| | | Cl | (S) | H | 2,2-difluoroethyl |
| | | F | (S) | H | CH₃ |
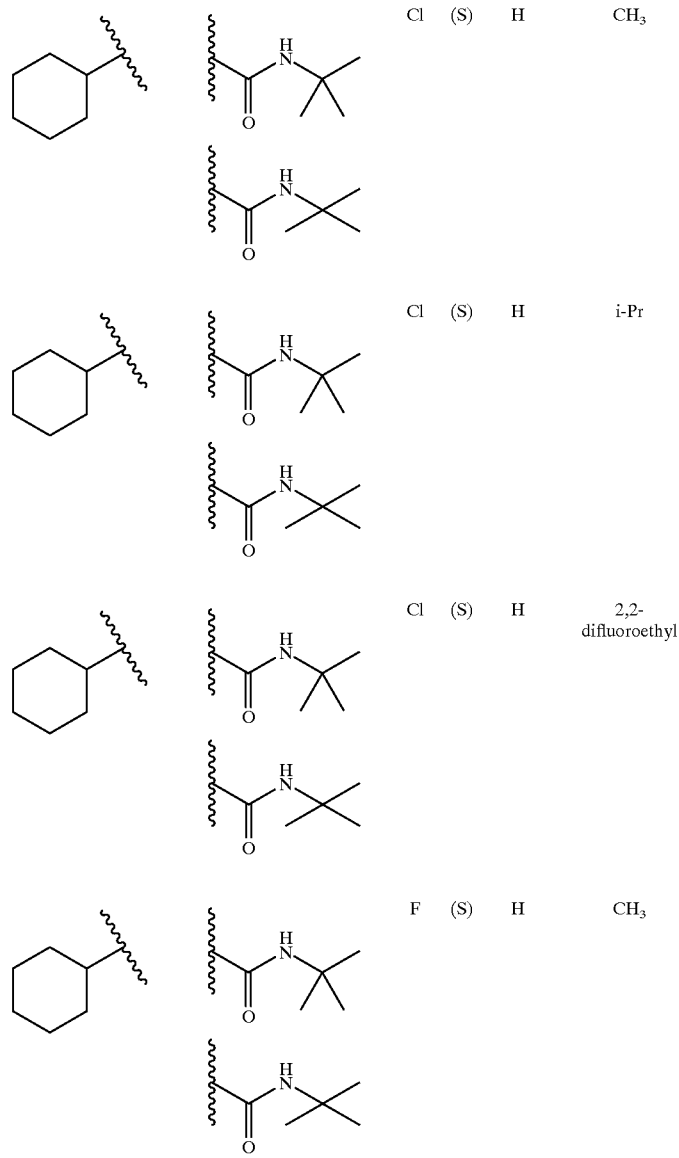

-continued
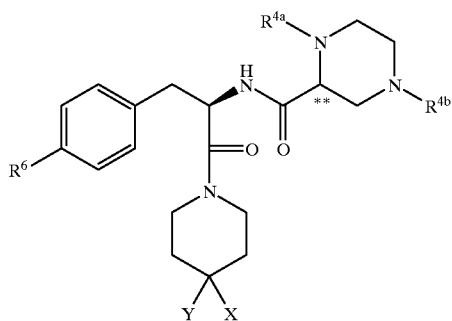
Ia
| Y | X | R6 | ** | R4a | R4b |
|---|---|---|---|---|---|
| cyclohexyl | -C(O)NH-t-Bu / -C(O)NH-t-Bu | F | (S) | H | i-Pr |
| cyclohexyl | -C(O)NH-t-Bu / -C(O)NH-t-Bu | F | (S) | H | 2,2-difluoroethyl |
| cyclohexyl | -C(O)NH-t-Bu / -C(O)NH-t-Bu | Cl | (R) | H | CH3 |
| cyclohexyl | -C(O)NH-t-Bu / -C(O)NH-t-Bu | Cl | (R) | H | i-Pr |

-continued
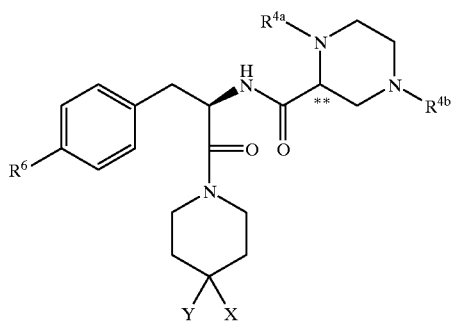
Ia
| Y | X | R6 | ** | R4a | R4b |
|---|---|----|----|-----|-----|
| cyclohexyl | -C(O)NH-tBu / -C(O)NH-tBu | Cl | (R) | H | cyclopropyl-methyl |
| cyclohexyl | -C(O)NH-tBu / -C(O)NH-tBu | Cl | (R) | H | benzyl |
| cyclohexyl | -C(O)NH-tBu / -C(O)NH-tBu | Cl | (R) | H | 2-propynyl |
| cyclohexyl | -C(O)NH-tBu / -C(O)NH-tBu | Cl | (R) | H | cyclobutyl |

-continued
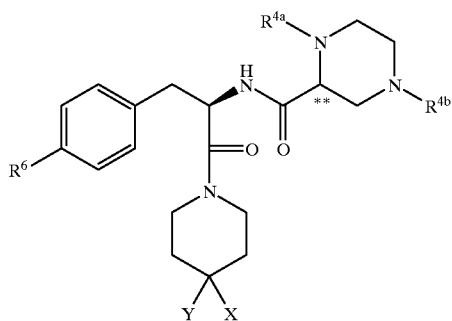
| Y | X | R⁶ | ** | R⁴ᵃ | R⁴ᵇ |
|---|---|---|---|---|---|
| cyclohexyl | -C(O)NH-t-Bu / -C(O)NH-t-Bu | Cl | (R) | H | 2,2-difluoroethyl |
| cyclohexyl | -C(O)NH-t-Bu / -C(O)NH-t-Bu | F | (R) | H | CH₃ |
| cyclohexyl | -C(O)NH-t-Bu / -C(O)NH-t-Bu | F | (R) | H | i-Pr |
| cyclohexyl | -C(O)NH-t-Bu / -C(O)NH-t-Bu | F | (R) | H | cyclopropyl-methyl |

-continued

Ia

| Y | X | R⁶ | ** | R⁴ᵃ | R⁴ᵇ |
|---|---|----|----|-----|-----|
| cyclohexyl | -C(O)NH-tBu | F | (R) | H | 2,2-difluoroethyl |
|  | -C(O)NH-tBu |  |  |  |  |
| cyclohexyl | -C(O)NH-tBu | Cl | (S) | H | CH₃ |
|  | -C(O)NH-tBu |  |  |  |  |
| cyclohexyl | -C(O)NH-cyclobutyl | Cl | (S) | H | CH₃ |
| cyclohexyl | -C(O)NH-cyclobutyl | Cl | (R) | H | CH₃ |
| cyclohexyl | -C(O)NH-cyclopentyl | Cl | (S) | H | CH₃ |
| cyclohexyl | -C(O)NH-cyclopentyl | Cl | (R) | H | CH₃ |

-continued
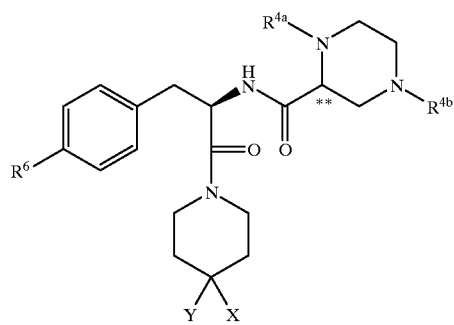
Ia
| Y | X | R⁶ | ** | R⁴ᵃ | R⁴ᵇ |
|---|---|----|----|-----|------|
| cyclohexyl | -C(O)NH-CH(Et)₂ | Cl | (S) | H | CH₃ |
| cyclohexyl | -C(O)NH-CH(Et)₂ | Cl | (R) | H | CH₃ |
| cyclohexyl | -C(O)NH-CH₂C(CH₃)₃ | Cl | (R) | H | CH₃ |
| cyclohexyl | -C(O)NH-(2-pyridyl) | Cl | (S) | H | CH₃ |
| cyclohexyl | -C(O)-(4-methylpiperazinyl) | F | (S) | H | CH₃ |
| cyclohexyl | -NHC(O)C(CH₃)₃ | Cl | (S) | H | CH₃ |
| | -NHC(O)C(CH₃)₃ | | | | |

-continued
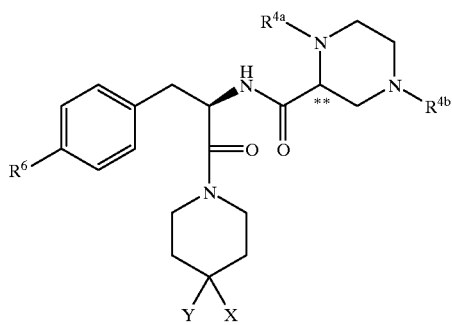
| Y | X | R⁶ | ** | R⁴ᵃ | R⁴ᵇ |
|---|---|---|---|---|---|
| cyclohexyl | -NHC(O)C(CH₃)₃ | Cl | (R) | H | CH₃ |
|  | -NHC(O)C(CH₃)₃ |  |  |  |  |
| cyclohexyl | 4,4-dimethyl-oxazolidinone-CH₂- | Cl | (S) | H | CH₃ |
| cyclohexyl | 4,4-dimethyl-oxazolidinone-CH₂- | Cl | (R) | H | CH₃ |
| cyclohexyl | 4,4-dimethyl-oxazolidinone-CH₂- | F | (S) | H | CH₃ |
| cyclohexyl | 4,4-dimethyl-oxazolidinone-CH₂- | F | (R) | H | CH₃ |
| cyclohexyl | 4,4-dimethyl-oxazolidinone-CH₂- | F | (R) | H | i-Pr |

-continued

Ia

| Y | X | R⁶ | ** | R⁴ᵃ | R⁴ᵇ |
|---|---|---|---|---|---|
| cyclohexyl | -C(O)NH-t-Bu ; -C(O)NH-t-Bu | F | (S) | H | -C(O)CH(NH₂)CH₃ |
| cyclohexyl | -C(O)NH-t-Bu ; -C(O)NH-t-Bu | Cl | (S) | CH₃ | i-Pr |
| cyclohexyl | -C(O)OEt | Cl | (S) | CH₃ | i-Pr |
| cyclohexyl | -C(O)NH-t-Bu ; -C(O)NH-t-Bu | F | (S) | H | Et |
| cyclohexyl | -CH₂CH₂C(CH₃)₂OH | F | (R) | H | H |

-continued

Ia

| Y | X | R⁶ | ** | R⁴ᵃ | R⁴ᵇ |
|---|---|----|----|----|----|
| cyclohexyl | -CH₂CH₂C(CH₃)₂OH | F | (S) | H | H |
| cyclohexyl | -CH₂CH₂C(CH₃)₂OH | F | (R) | H | Me |
| cyclohexyl | -CH₂CH₂C(CH₃)₂OH | F | (S) | H | Me |
| cyclohexyl | -CH₂OC(CH₃)₂CO₂Et | F | (S) | H | Me |
| cyclohexyl | -CH₂OC(CH₃)₂CO₂H | F | (S) | H | Me |
| cyclohexyl | -C(O)NHC(CH₃)₂CO₂H | F | (S) | H | Me |
| cyclohexyl | -C(O)NHC(CH₃)₂CO₂Me | F | (S) | H | Me |

-continued

| Y | X | R⁶ | ** | R⁴ᵃ | R⁴ᵇ |
|---|---|---|---|---|---|
| cyclohexyl | -NH-S(O)₂-cyclopropyl | F | (S) | H | Me |
| cyclohexyl | -CH₂-N(3-oxo-5,5-dimethylmorpholinyl) | F | (S) | H | Me |
| 1-methylcyclohexyl | -C(O)NH-tBu | F | (S) | H | Me |
| | -C(O)NH-C(Me)₂Et | | | | |
| 1,1-dimethylpropyl (tert-amyl) | -C(O)NH-tBu | F | (S) | H | Me |
| | -C(O)NH-C(Me)₂Et | | | | |
| 4,4-dimethylcyclohexyl | -C(O)NH-tBu | F | (S) | H | Me |
| | -C(O)NH-C(Me)₂Et | | | | |

-continued
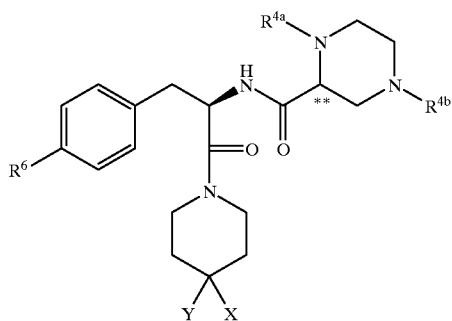
Ia
| Y | X | R⁶ | ** | R⁴ᵃ | R⁴ᵇ |
|---|---|---|---|---|---|
| 4,4-dimethylcyclohexyl | -C(O)NH-tBu | F | (S) | H | H |
| | -C(O)NH-tBu | | | | |
| 4,4-difluorocyclohexyl | -C(O)NH-tBu | F | (S) | H | Me |
| | -C(O)NH-tBu | | | | |
| 4-methylcyclohexyl | -C(O)NH-tBu | F | (S) | H | Me |
| | -C(O)NH-tBu | | | | |
| 4-methylcyclohexyl | -C(O)NH-tBu | F | (S) | H | H |
| | -C(O)NH-tBu | | | | |

-continued

| Y | X | R⁶ | ** | R⁴ᵃ | R⁴ᵇ |
|---|---|---|---|---|---|
| CH₂-cyclopropyl | C(O)NH-tBu | F | (S) | H | Me |
| CH₂-cyclopropyl | C(O)NH-tBu | | | | |
| CH₂-cyclobutyl | C(O)NH-tBu | F | (S) | H | Me |
| CH₂-cyclobutyl | C(O)NH-tBu | | | | |
| CH₂-cyclopropyl | CH₂-S-iPr | F | (S) | H | H |
| cyclohexyl | CH₂-N(iPr)(SO₂Me) | Cl | (R) | H | Me |
| cyclohexyl | 2-methyl-1,3,4-oxadiazol-5-yl | Cl | (S) | H | H |
| cyclohexyl | CH₂-(4,4-dimethyl-2-oxo-oxazolidin-3-yl) | F | (S) | iPr | Me |

-continued
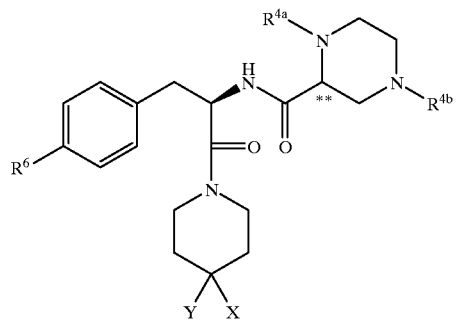
Ia
| Y | X | R⁶ | ** | R⁴ᵃ | R⁴ᵇ |
|---|---|---|---|---|---|
| 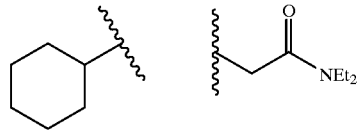 | | F | (S) | H | Me |
or a pharmaceutically acceptable salt thereof.
18. The compound of claim 16 of structural formula Ib selected from the group consisting of
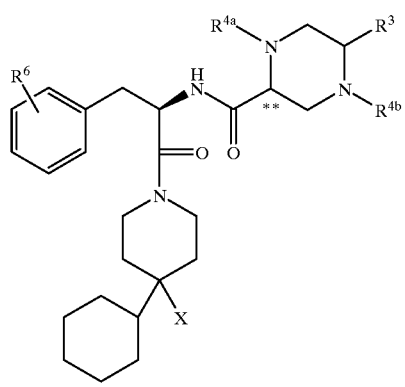
Ib
| R⁶ | ** | X | R³ | R⁴ᵃ | R⁴ᵇ | Diastereomer |
|---|---|---|---|---|---|---|
| 4-fluoro | (R) | 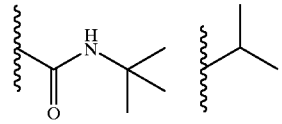 | | H | H | D₁ + D₂ |
| 4-fluoro | (R) | 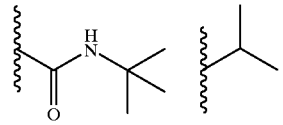 | | H | H | D₁ |

-continued
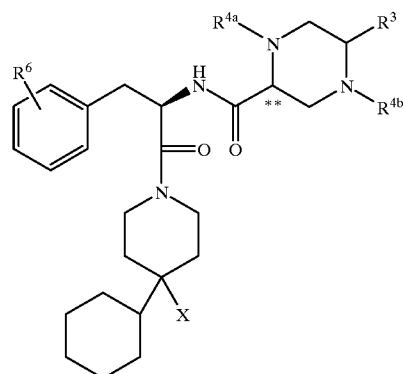
Ib
| R⁶ | ** | X | R³ | R⁴ᵃ | R⁴ᵇ | Diastereomer |
|---|---|---|---|---|---|---|
| 4-fluoro | (R) | -C(O)NH-C(CH₃)₃ | -iPr | H | H | D₂ |
| 4-chloro | (R) | -C(O)NH-C(CH₃)₃ | -iPr | H | H | D₁ + D₂ |
| 4-chloro | (R) | -C(O)NH-C(CH₃)₃ | -iPr | H | H | D₁ |
| 4-chloro | (R) | -C(O)NH-C(CH₃)₃ | -iPr | H | H | D₂ |
| 4-fluoro | (R) | 4,4-dimethyl-2-oxo-oxazolidin-3-ylmethyl | -iPr | H | H | D₁ + D₂ |
| 4-fluoro | (R) | -C(O)OEt | -iPr | H | H | D₁ + D₂ |
| 4-fluoro | (R) | -CH₂-S-iPr | -iPr | H | H | D₁ + D₂ |

-continued
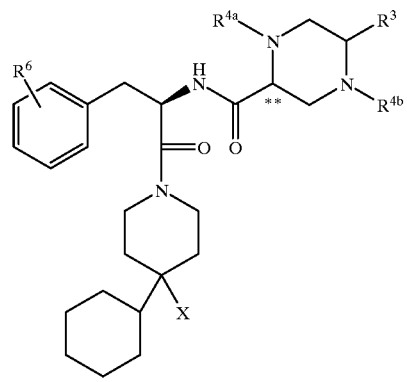
Ib
| R[6] | ** | X | R[3] | R[4a] | R[4b] | Diastereomer |
|---|---|---|---|---|---|---|
| 4-fluoro | (R) | ~S(O)CH(CH3)2 via CH2 | isobutyl | H | H | |
| 4-chloro | (R) | ~C(O)NH-tBu | Ph | H | H | D1 + D2 |
| 4-fluoro | (R) | ~C(O)NH-tBu | Ph | H | H | D1 + D2 |
| 4-fluoro | (R) | ~CH2-N(oxazolidinone-4,4-dimethyl) | Ph | H | H | D1 + D2 |
| 4-fluoro | (S) | ~C(O)NH-tBu | isobutyl | H | H | D1 + D2 |
| 4-fluoro | (S) | ~C(O)NH-tBu | isobutyl | H | H | D1 |
| 4-fluoro | (S) | ~C(O)NH-tBu | isobutyl | H | H | D2 |

-continued
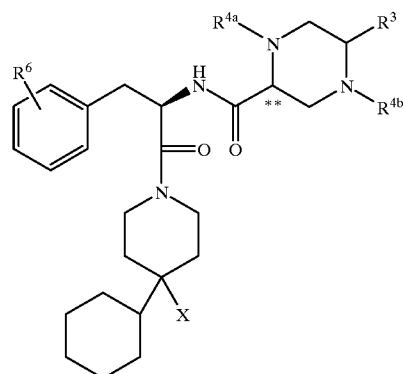
Ib
| R⁶ | ** | X | R³ | R⁴ᵃ | R⁴ᵇ | Diastereomer |
|---|---|---|---|---|---|---|
| 4-fluoro | (S) | -C(O)NH-C(CH₃)₃ | cyclopropyl | H | H | D₁ + D₂ |
| 4-fluoro | (S) | -C(O)NH-C(CH₃)₃ | cyclopropyl | H | H | D₁ |
| 4-fluoro | (S) | -C(O)NH-C(CH₃)₃ | cyclopropyl | H | H | D₂ |
| 4-fluoro | (R) | -C(O)NH-C(CH₃)₃ | cyclopropyl | H | H | D₁ + D₂ |
| 4-fluoro | (R) | -C(O)NH-C(CH₃)₃ | cyclopropyl | H | H | D₁ |
| 4-fluoro | (R) | -C(O)NH-C(CH₃)₃ | cyclopropyl | H | H | D₂ |
| 4-fluoro | (S) | -C(O)NH-C(CH₃)₃ | -C(CH₃)₃ | H | H | D₁ + D₂ |

-continued
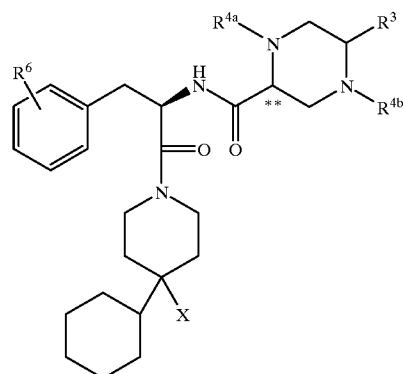
Ib
| R6 | ** | X | R3 | R4a | R4b | Diastereomer |
|---|---|---|---|---|---|---|
| 4-fluoro | (S) | -C(O)NH-C(CH3)3 | t-Bu | H | H | D1 |
| 4-fluoro | (S) | -C(O)NH-C(CH3)3 | t-Bu | H | H | D2 |
| 4-fluoro | (R) | -C(O)NH-C(CH3)3 | t-Bu | H | H | D1 + D2 |
| 4-fluoro | (R) | -C(O)NH-C(CH3)3 | t-Bu | H | H | D1 |
| 4-fluoro | (R) | -C(O)NH-C(CH3)3 | t-Bu | H | H | D2 |
| 4-fluoro | (S) | -C(O)NH-C(CH3)3 | cyclopropyl | H | H | D1 + D2 |
| 4-fluoro | (S) | -C(O)NH-C(CH3)3 | cyclopropyl | H | H | D1 |

-continued
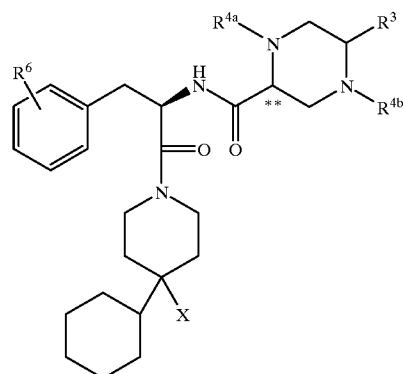
Ib
| R[6] | ** | X | R[3] | R[4a] | R[4b] | Diastereomer |
|---|---|---|---|---|---|---|
| 4-fluoro | (S) | ⸺C(O)NH-C(CH₃)₃ | cyclopropyl | H | H | D₂ |
| 4-fluoro | (R) | ⸺C(O)NH-C(CH₃)₃ | cyclopropyl | H | H | D₁ + D₂ |
| 4-fluoro | (R) | ⸺C(O)NH-C(CH₃)₃ | cyclopropyl | H | H | D₁ |
| 4-fluoro | (R) | ⸺C(O)NH-C(CH₃)₃ | cyclopropyl | H | H | D₂ |
| 4-chloro | (R) | ⸺C(O)NH-C(CH₃)₃ | cyclopropyl | H | H | D₁ + D₂ |
| 4-chloro | (R) | ⸺C(O)NH-C(CH₃)₃ | cyclopropyl | H | H | D₁ |
| 4-chloro | (R) | ⸺C(O)NH-C(CH₃)₃ | cyclopropyl | H | H | D₂ |

-continued
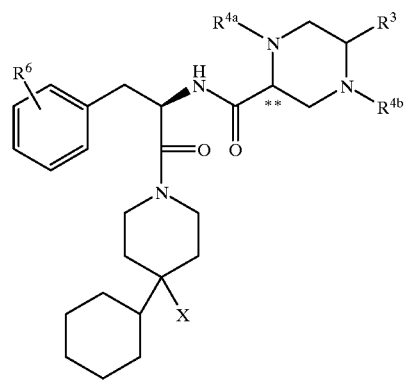
Ib
| R⁶ | ** | X | R³ | R⁴ᵃ | R⁴ᵇ | Diastereomer |
|---|---|---|---|---|---|---|
| 4-chloro | (S) | -C(O)NH-tBu | Ph | H | H | D₁ + D₂ |
| 4-fluoro | (S) | -C(O)NH-tBu | Ph | H | H | D₁ + D₂ |
| 4-fluoro | (S) | -CH₂-(4,4-dimethyl-2-oxo-oxazolidin-3-yl) | Ph | H | H | D₁ + D₂ |
| 4-chloro | (S) | -C(O)NH-tBu | Ph | Me | Me | D₁ |
| 4-chloro | (S) | -C(O)NH-tBu | Ph | Me | Me | D₂ |
| 4-fluoro | (S) | -C(O)NH-tBu | Ph | Me | Me | D₁ |
| 4-fluoro | (S) | -C(O)NH-tBu | Ph | Me | Me | D₂ |

-continued
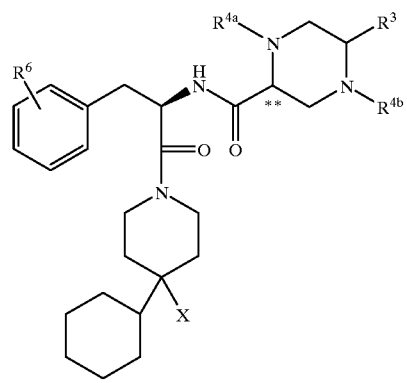
Ib
| R6 | ** | X | R3 | R4a | R4b | Diastereomer |
|---|---|---|---|---|---|---|
| 4-fluoro | (S) | oxazolidinone-CH2- (4,4-dimethyl) | Ph | Me | Me | $D_1$ |
| 4-chloro | (R) | -C(O)NH-tBu | Ph | Me | Me | $D_1$ |
| 4-chloro | (R) | -C(O)NH-tBu | Ph | Me | Me | $D_2$ |
| 4-fluoro | (R) | -C(O)NH-tBu | Ph | Me | Me | $D_1$ |
| 4-fluoro | (R) | -C(O)NH-tBu | Ph | Me | Me | $D_2$ |
| 4-fluoro | (R) | oxazolidinone-CH2- (4,4-dimethyl) | Ph | Me | Me | $D_1$ |
| 3,4-difluoro | (S) | -C(O)NH-tBu | H | H | H | |

-continued
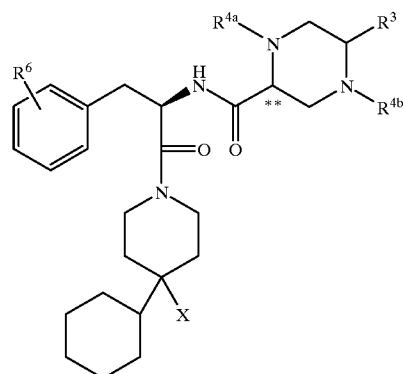
Ib
| $R^6$ | ** | X | $R^3$ | $R^{4a}$ | $R^{4b}$ | Diastereomer |
|---|---|---|---|---|---|---|
| 3,4-difluoro | (S) | -C(O)NH-tBu | H | H | Me | |
| 3,4-difluoro | (S) | -C(O)NH-tBu | iPr | H | H | $D_1 + D_2$ |
| 3,4-difluoro | (S) | -C(O)NH-tBu | iPr | H | H | $D_1$ |
| 3,4-difluoro | (S) | -C(O)NH-tBu | iPr | H | H | $D_2$ |
| 3,5-difluoro | (S) | -C(O)NH-tBu | H | H | Me | |
| 3,5-difluoro | (S) | -C(O)NH-tBu | iPr | H | H | |
| 4-fluoro | (S) | -C(O)NH-tBu | iPr | Me | H | $D_1 + D_2$ |

-continued
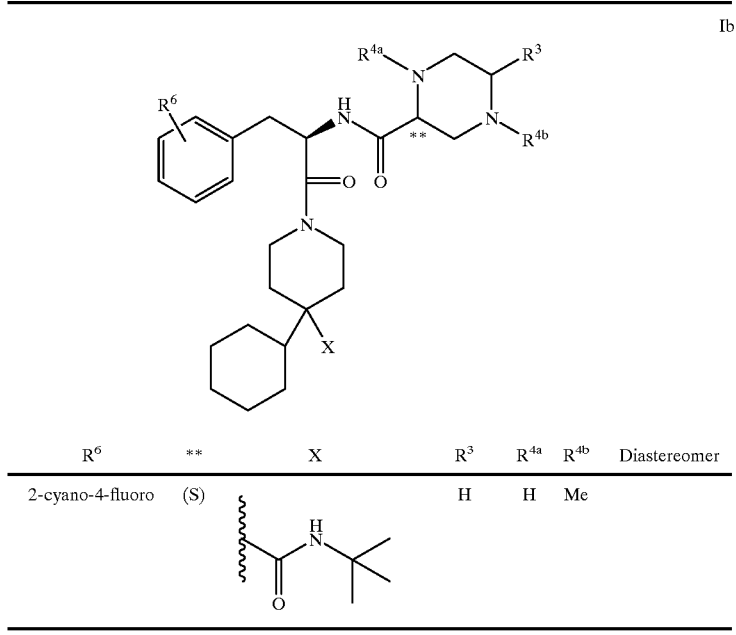
| R⁶ | ** | X | R³ | R⁴ᵃ | R⁴ᵇ | Diastereomer |
|---|---|---|---|---|---|---|
| 2-cyano-4-fluoro | (S) | | H | H | Me | |
or a pharmaceutically acceptable salt thereof.
19. The compound of claim 16 selected from the group consisting
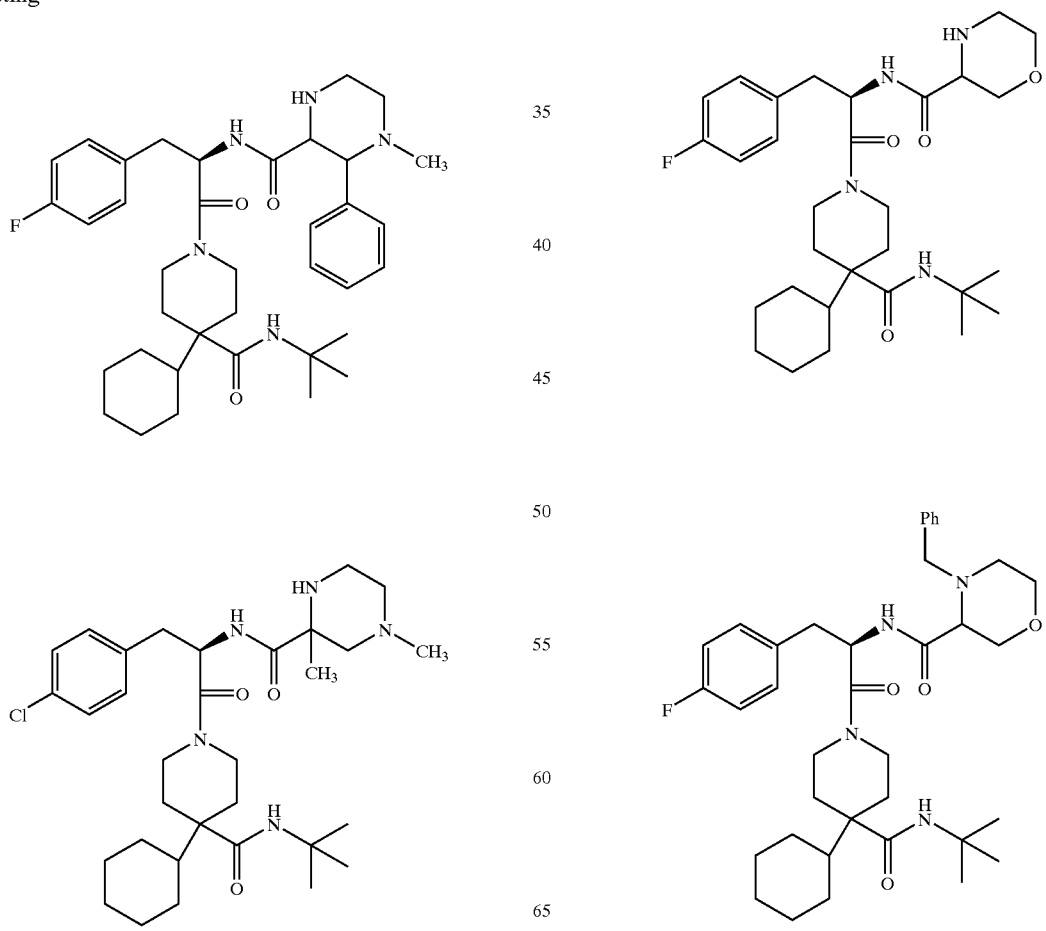

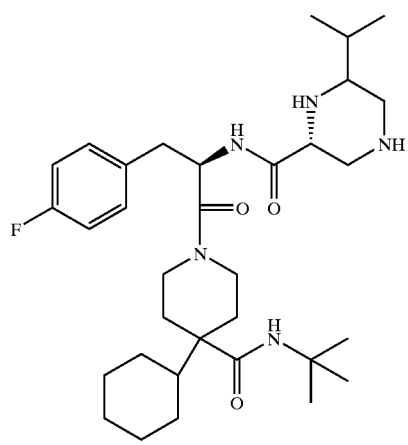
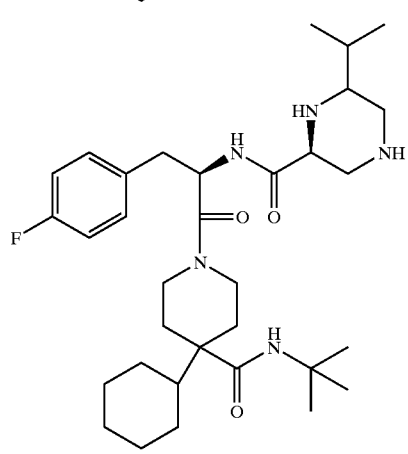
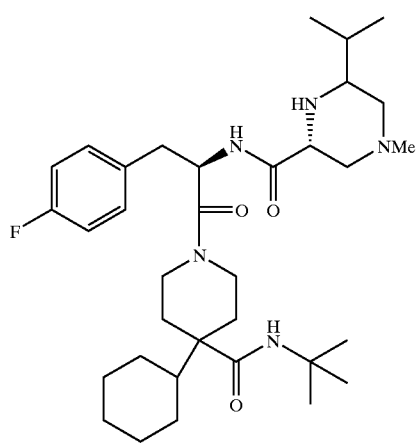
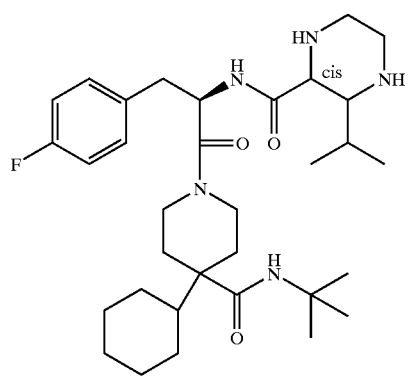
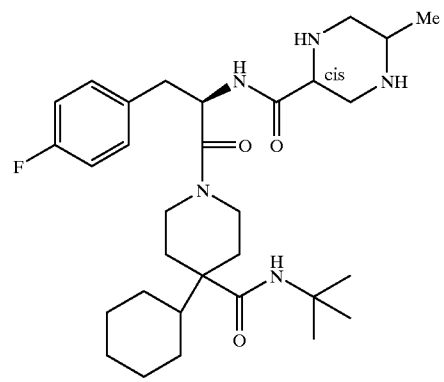
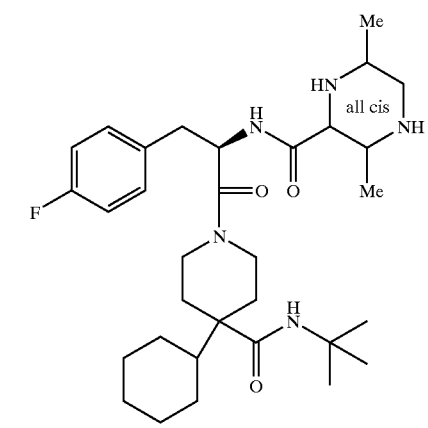
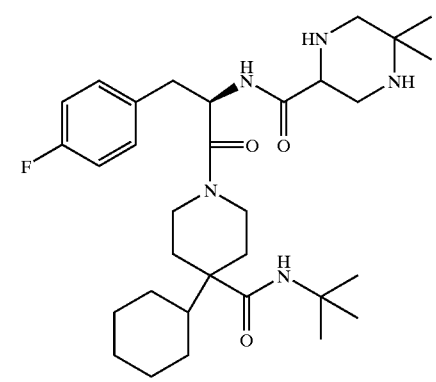
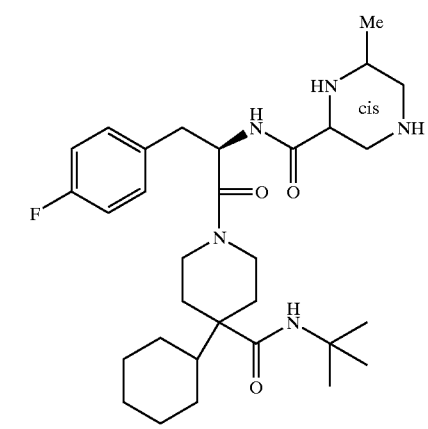

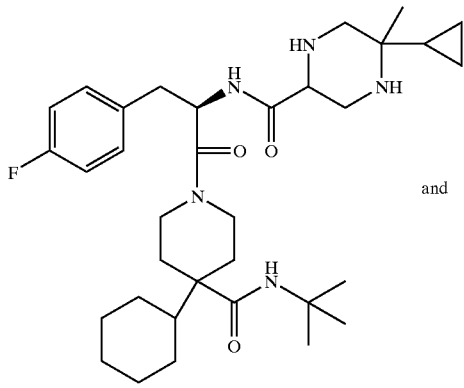
and
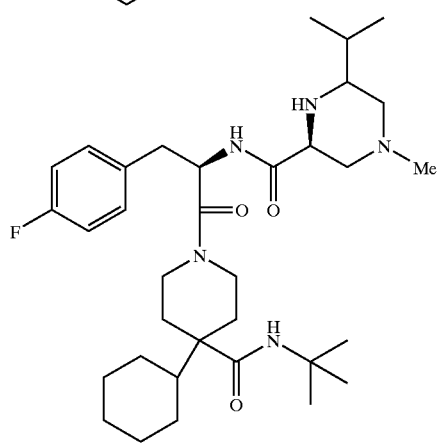
or a pharmaceutically acceptable salt thereof.
20. The compound of claim 16 of structural formula Ic selected from the group consisting of
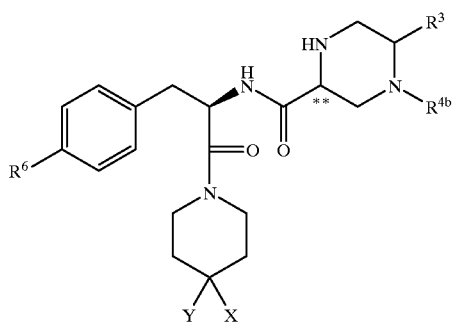
| Y | X | R⁶ | ** | R³ | R⁴ᵇ |
|---|---|---|---|---|---|
| 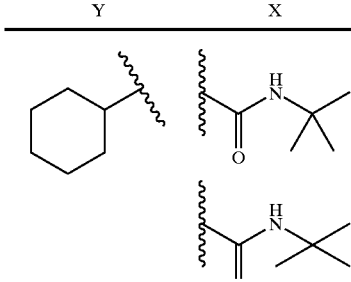 | 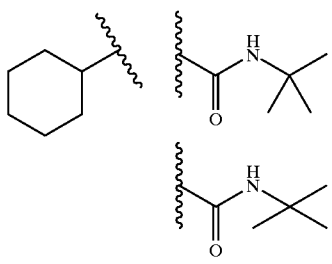 | F | (S) | H | CH₃ |
| 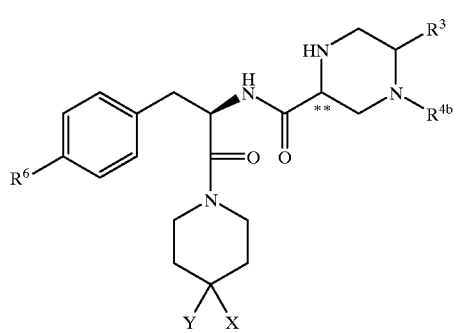 | 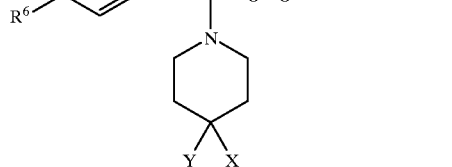 | F | (S) | H | CH₃ |
| 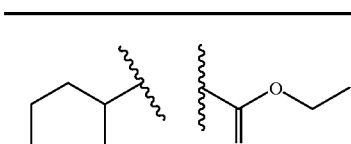 | 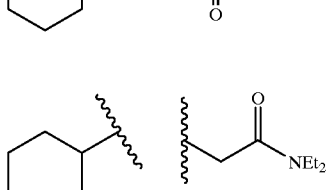 | F | (R) | H | CH₃ |
| 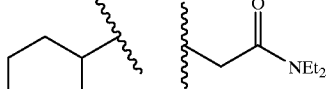 |  | F | (S) | H | CH₃ |
| 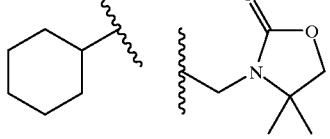 | 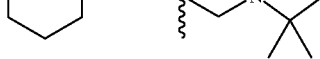 | Cl | (R) | H | CH₃ |

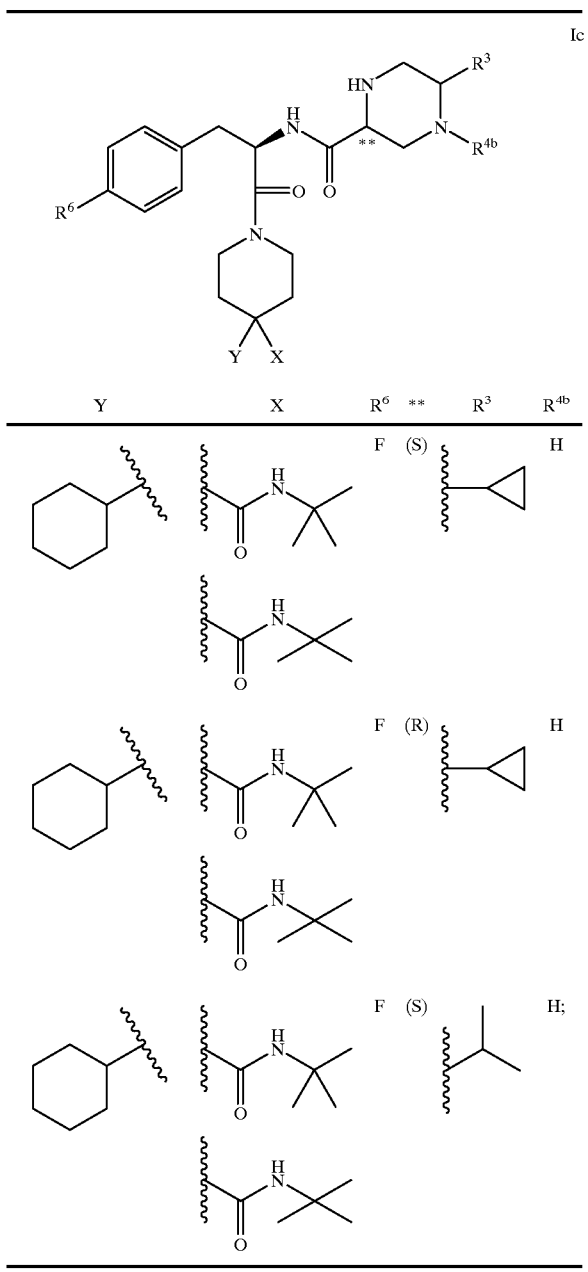

or a pharmaceutically acceptable salt thereof.

21. A method for the treatment of disorders, diseases or conditions responsive to the activation of the melanocortin receptor in a mammal in need thereof which comprises administering to the mammal a therapeutically effective amount of a compound according to claim 1.

22. The method of claim 21 wherein the melanocortin receptor is the melanocortin-4 receptor.

23. A method for the treatment of obesity in a mammal in need thereof which comprising administering to a mammal a therapeutically effective amount of a compound according to claim 1.

24. A method for the treatment of diabetes mellitus in a mammal in need thereof comprising administering to a mammal a therapeutically effective amount of a compound according to claim 1.

25. A method for the treatment of male or female sexual dysfunction in a mammal in need thereof comprising administering to a mammal a therapeutically effective amount of a compound according to claim 1.

26. A method for the treatment of erectile dysfunction in a mammal in need thereof comprising administering to a mammal a therapeutically effective amount of a compound according to claim 1.

27. A pharmaceutical composition which comprises a compound of claim 1 and a pharmaceutically acceptable carrier.

28. A method of treating male or female sexual dysfunction in a mammal in need thereof, comprising administering to the mammal a therapeutically effective amount of the composition of claim 27.

29. The method of claim 31 wherein the male sexual dysfunction is erectile dysfunction.

* * * * *